United States Patent
Nampally et al.

(10) Patent No.: US 11,684,625 B2
(45) Date of Patent: Jun. 27, 2023

(54) COMPOUNDS FOR THE TREATMENT, ALLEVIATION OR PREVENTION OF DISORDERS ASSOCIATED WITH TAU AGGREGATES

(71) Applicant: AC Immune SA, Lausanne (CH)

(72) Inventors: Sreenivasachary Nampally, Ecublens (CH); Emanuele Gabellieri, Lausanne (CH); Jerome Molette, Prevessin Moens (FR)

(73) Assignee: AC Immune SA, Lausanne (CH)

( * ) Notice: Subject to any disclaimer, the term of this patent is extended or adjusted under 35 U.S.C. 154(b) by 33 days.

(21) Appl. No.: 17/053,459

(22) PCT Filed: May 30, 2019

(86) PCT No.: PCT/EP2019/064144
§ 371 (c)(1),
(2) Date: Nov. 6, 2020

(87) PCT Pub. No.: WO2019/233883
PCT Pub. Date: Dec. 12, 2019

(65) Prior Publication Data
US 2021/0267989 A1 Sep. 2, 2021

(30) Foreign Application Priority Data
Jun. 4, 2018 (EP) .................... 18175845

(51) Int. Cl.
| C07D 413/14 | (2006.01) |
| A61K 31/496 | (2006.01) |
| A61K 31/5377 | (2006.01) |
| A61P 25/28 | (2006.01) |
| A61K 31/145 | (2006.01) |
| A61K 31/185 | (2006.01) |
| A61K 31/27 | (2006.01) |
| A61K 31/437 | (2006.01) |
| A61K 31/444 | (2006.01) |
| A61K 31/445 | (2006.01) |
| A61K 31/473 | (2006.01) |
| A61K 31/497 | (2006.01) |
| A61K 31/501 | (2006.01) |
| A61K 31/5386 | (2006.01) |
| A61K 31/55 | (2006.01) |
| A61K 31/5513 | (2006.01) |
| A61K 45/06 | (2006.01) |
| C07D 471/04 | (2006.01) |
| C07D 471/14 | (2006.01) |
| C07D 471/18 | (2006.01) |
| C07D 519/00 | (2006.01) |

(52) U.S. Cl.
CPC ........ *A61K 31/5377* (2013.01); *A61K 31/145* (2013.01); *A61K 31/185* (2013.01); *A61K 31/27* (2013.01); *A61K 31/437* (2013.01); *A61K 31/444* (2013.01); *A61K 31/445* (2013.01); *A61K 31/473* (2013.01); *A61K 31/496* (2013.01); *A61K 31/497* (2013.01); *A61K 31/501* (2013.01); *A61K 31/5386* (2013.01); *A61K 31/55* (2013.01); *A61K 31/5513* (2013.01); *A61K 45/06* (2013.01); *A61P 25/28* (2018.01); *C07D 471/04* (2013.01); *C07D 471/14* (2013.01); *C07D 471/18* (2013.01); *C07D 519/00* (2013.01)

(58) Field of Classification Search
CPC .. C07D 413/14; C07D 471/04; A61K 31/496; A61K 31/437; A61P 25/28
USPC .............. 544/361; 514/253.03, 292; 546/85
See application file for complete search history.

(56) References Cited

FOREIGN PATENT DOCUMENTS

| CN | 107216327 A | 9/2017 |
| EP | 1 136 493 A1 | 9/2001 |
| WO | 2007/096743 A1 | 8/2007 |
| WO | 2014/207240 A1 | 12/2014 |

OTHER PUBLICATIONS

Wei, G. et al.: Enantioselective aerobic oxidative olefination of amines via cooperative photoredox and asymmetric catalysis. ACS Catalysis, vol. 6, pp. 3708-3712, 2016.*
Database Registry, 2016, RN 1948199-62-9, Retrieved from STN international [online]; retrieved on Nov. 18, 2021.
Database Registry, 2015,RN 1794307-60-0, 1497619-59-6, 1497557-11-5, 1371825-00-1, 1371004-32-8, 1356709-09-5, 1333974-37-0, 1333927-61-9, 1324386-72-2, 1320983-04-7, 1318103-95-5, 1316764-23-4, 1316264-49-9, 1269256-52-1, 1269193-44-3, 1223061-06-0, 1211728-75-4, 1211206-57-3, 1209092-09-0, 1147315-08-9, 1111571-99-3, 1090836-41-1, 1090836-38-6,1090781-52-4,1089996-99-5, 1089615-89-3, 949198-56-5, 929988-03-4, Retrieved from STN international [online]; retrieved on Aug. 18, 2021.
(Continued)

*Primary Examiner* — Charanjit Aulakh
(74) *Attorney, Agent, or Firm* — Robert D. Shereda

(57) ABSTRACT

The present invention relates to novel compounds of formula (I) that can be employed in the treatment, alleviation or prevention of a group of disorders and abnormalities associated with Tau (Tubulin associated unit) protein aggregates including, but not limited to, Neurofibrillary Tangles (NFTs), such as Alzheimer's disease (AD).

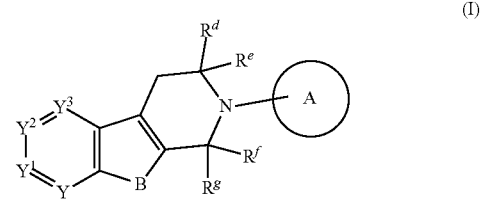

(I)

12 Claims, 1 Drawing Sheet

(56) References Cited

OTHER PUBLICATIONS

International Searching Authority, International Search Report for PCT/EP2019/064144, dated Aug. 12, 2019, AC Immune SA.
Written Opinion of the International Searching Authority for PCT/2019/064144, dated Jun. 4, 2018, AC Immune SA.
Hongbo Zheng et al; "Design and synthesis of furyl/thineyl pyrroloquinolones based on natural alkaloid perlolyrine, lead to the discovery of potent and selective PDE5 inhibitors", European Journal of Medicinal Chemistry, vol. 150, Feb. 16, 2018 (Feb. 16, 2018), pp. 30-38, XP055605397, Scheme S3; compounds 9k, 9m.
Hongbo Zheng et al; "S1 Supporting Information Design and Synthesis of Furyl/Thineyl Pyrroloquinolones Based on Natural Alkaloid Perlolyrine, Lead to the Discovery of Potent and Selective PDE5 Inhibitors", European Journal of Medicinal Chemistry, vol. 150, Feb. 16, 2018 (Feb. 16, 2018), pp. 30-38, XP055605612, compounds 9k, 9m.
Bohang Zhou et al; "New 2-Aryl-9-methyl-[beta]-carbolinium salts as Potential Acetylcholinesterase Inhibitor agents: Synthesis, Bioactivity and Structure-Activity Relationship", Scientific Reports, vol. 8, No. 1, Jan. 24, 2018 (Jan. 24, 2018), XP055605537, DOI: 10.1038/s41598-018-19999-3, tables 1-2; compound C1.
Kinthada Ramakumar et al; "Synthesis of Spirooxindoles via the tert-Amino Effect", Organic Letters, vol. 19, No. 15, Jul. 24, 2017 (Jul. 24, 2017), pp. 4014-4017, XP055605614, US, ISSN: 1523-7060, DOI: 10.1021/acs.orglett.7b01752, Scheme 4, starting material for 5q and 5r.

* cited by examiner

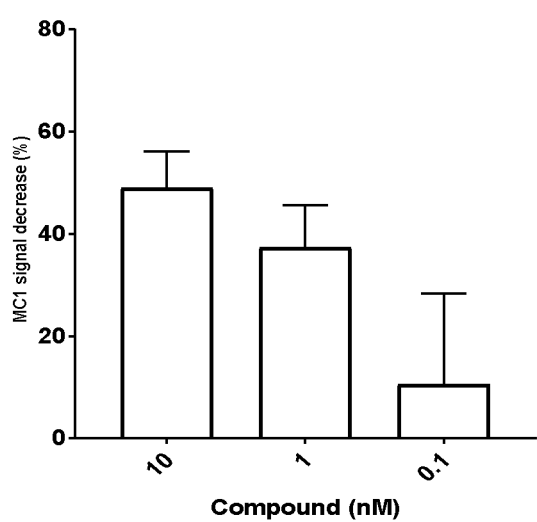

COMPOUNDS FOR THE TREATMENT, ALLEVIATION OR PREVENTION OF DISORDERS ASSOCIATED WITH TAU AGGREGATES

CROSS-REFERENCE TO RELATED APPLICATIONS

This application is a national stage entry under 35 U.S.C. § 371 of International Application No. PCT/EP2019/064144, filed May 30, 2019, which is entitled to the benefit of European Patent Application No. 18175845.9, filed Jun. 4, 2018, the disclosures of which are incorporated herein in their entireties by reference.

FIELD OF THE INVENTION

The present invention relates to novel compounds that can be employed in the treatment, alleviation or prevention of a group of disorders and abnormalities associated with Tau (Tubulin associated unit) protein aggregates including, but not limited to, Neurofibrillary Tangles (NFTs), such as Alzheimer's disease (AD).

BACKGROUND OF THE INVENTION

Many aging diseases are based on or associated with extracellular or intracellular deposits of amyloid or amyloid-like proteins that contribute to the pathogenesis as well as to the progression of the disease. The best characterized amyloid protein that forms extracellular aggregates is amyloid beta (Aβ). Other examples of amyloid proteins that form extracellular aggregates are prion, ATTR (transthyretin) or ADan (ADanPP). Amyloid-like proteins, that form mainly intracellular aggregates, include, but are not limited to Tau, alpha-synuclein, TAR DNA-binding protein 43 (TDP-43), and huntingtin (htt). Diseases involving Tau aggregates are generally listed as tauopathies such as AD.

Amyloid or amyloid-like deposits result from misfolding of proteins followed by aggregation to give β-sheet assemblies in which multiple peptides or proteins are held together by inter-molecular hydrogen-bonds. While amyloid or amyloid-like proteins have different primary amino acid sequences, their deposits often contain many shared molecular constituents, in particular the presence of β-sheet quaternary structures. The association between amyloid deposits and diseases remains largely unclear. A diverse range of protein aggregates, including both those associated and not associated with disease pathologies, have been found to be toxic suggesting that the common molecular features of amyloid are implicated or responsible for disease on-set (Bucciantini et al., Nature, 2002, 416, 507-11). Various multimers of β-sheet aggregated peptides or proteins have also been associated with toxicity for different peptides or proteins ranging from dimers, through to soluble low molecular weight oligomers, protofibrils or insoluble fibrillar deposits.

Alzheimer's disease (AD) is a neurological disorder primarily thought to be caused by amyloid plaques, an extracellular accumulation of abnormal deposit of (amyloid-beta) Aβ aggregates in the brain. The other major neuropathological hallmarks in AD are the intracellular neurofibrillary tangles (NFT) that originate by the aggregation of the hyperphosphorylated Tau protein, misfolded Tau or pathological Tau and its conformers. AD shares its etiopathology with many neurodegenerative tauopathies, in particular with specified types of frontotemporal dementia (FTD). The Tau protein is a freely soluble, "naturally unfolded" protein that binds avidly to microtubuli (MT) to promote their assembly and stability. MT are of major importance for the cytoskeletal integrity of neurons—and thereby for the proper formation and functioning of neuronal circuits, hence for learning and memory. The binding of Tau to MT is controlled by dynamic phosphorylation and de-phosphorylation, as demonstrated mainly in vitro and in non-neuronal cells. In AD brain, Tau pathology (tauopathy) develops later than amyloid pathology, but it is still discussed controversially if Aβ protein is the causative agent in AD which constitutes the essence of the so-called amyloid cascade hypothesis (Hardy et al., Science 1992, 256, 184-185; Musiek et al., Nature Neurosciences 2015, 18(6), 800-806). The exact mechanisms that link amyloid to Tau pathology remain largely unknown, but are proposed to involve activation of neuronal signaling pathways that act on or by GSK3 and cdk5 as the major "Tau-kinases" (Muyllaert et al., Rev. Neurol. (Paris), 2006, 162, 903-7; Muyllaert et al., Genes Brain and Behav. 2008, Suppl 1, 57-66). Even if the tauopathy develops later than amyloid, it is not just an innocent side-effect but a major pathological executer in AD. In experimental mouse models the cognitive defects caused by amyloid pathology are nearly completely alleviated by the absence of Tau protein (Roberson et al., Science, 2007, 316(5825), 750-4) and the severity of cognitive dysfunction and dementia correlates with the tauopathy, not with amyloid pathology.

Diseases involving Tau aggregates are generally listed as tauopathies and they include, but are not limited to, Alzheimer's disease (AD), familial AD, PART (primary age-related Tauopathy), Creutzfeldt-Jacob disease, dementia pugilistica, Down's Syndrome, Gerstmann-Straussler-Scheinker disease (GSS), inclusion-body myositis, prion protein cerebral amyloid angiopathy, traumatic brain injury (TBI), amyotrophic lateral sclerosis (ALS), Parkinsonism-dementia complex of Guam, non-Guamanian motor neuron disease with neurofibrillary tangles, argyrophilic grain disease, corticobasal degeneration (CBD), diffuse neurofibrillary tangles with calcification, frontotemporal dementia with Parkinsonism linked to chromosome 17 (FTDP-17), Hallervorden-Spatz disease, multiple system atrophy (MSA), Niemann-Pick disease type C, pallido-ponto-nigral degeneration, Pick's disease (PiD), progressive subcortical gliosis, progressive supranuclear palsy (PSP), subacute sclerosing panencephalitis, tangle predominant dementia, postencephalitic Parkinsonism, myotonic dystrophy, subacute sclerosis panencephalopathy, mutations in LRRK2, chronic traumatic encephalopathy (CTE), familial British dementia, familial Danish dementia, other frontotemporal lobar degenerations, Guadeloupean Parkinsonism, neurodegeneration with brain iron accumulation, SLC9A6-related mental retardation, white matter tauopathy with globular glial inclusions, epilepsy, Lewy body dementia (LBD), mild cognitive impairment (MCI), multiple sclerosis, Parkinson's disease, HIV-related dementia, adult onset diabetes, senile cardiac amyloidosis, glaucoma, ischemic stroke, psychosis in AD and Huntington's disease. (Williams et al., Intern. Med. J., 2006, 36, 652-60; Kovacs et al., J Neuropathol Exp Neurol. 2008; 67(10): 963-975; Higuchi et al., Neuropsychopharmacology—5th Generation of Progress, 2002, Section 9, Chapter 94: 1339-1354; Hilton et al., Acta Neuropathol. 1995; 90(1):101-6; Iqbal et al., Biochimica et Biophysica Acta 1739 (2005) 198-210; McQuaid et al., Neuropathol Appl Neurobiol. 1994 April; 20(2):103-10; Vossel et al., Lancet Neurol 2017; 16: 311-22; Stephan et al., Molecular Psychiatry (2012) 17, 1056-1076; Anderson et al., Brain (2008), 131, 1736-1748; Savica et al., JAMA Neurol. 2013; 70(7):859-866; Brown et al. Molecular Neurodegeneration 2014, 9:40; El Khoury et al., Front. Cell. Neurosci., 2014, Volume 8, Article 22: 1-18; Tanskanen et al., Ann. Med. 2008; 40(3):232-9; Gupta et al., CAN J OPHTHALMOL—VOL. 43, NO. 1, 2008: 53-60; Dickson et al., Int J Clin Exp Pathol 2010; 3(1):1-23; Fernández-Nogales et al., Nature Medicine, 20, 881-885 (2014); Bi et al., Nature Communications volume 8, Article number: 473 (2017); Murray et al., Biol Psychiatry. 2014 Apr. 1; 75(7): 542-552).

Of all the agents in clinical trials for the treatment of Alzheimer's disease in 2017, the ones targeting Tau are very scarce and represent only 8% of the Phase II clinical trials (Cummings et al., Alzheimer's & Dementia: Translational Research & Clinical Interventions 3 (2017) 367-384). Current therapeutic approaches that target Tau protein comprise mainly antibody-based approaches with the main limitation of targeting only extracellular Tau. Among the approaches using small molecules, several Tau kinase inhibitors have been developed, despite being very challenging with respect to toxicity and specificity. Nevertheless, currently only one kinase inhibitor, Nilotinib, is tested in clinical trials. Lastly, among the Tau aggregation inhibitors only one, LMTX, is currently in clinical trials (Cummings et al., 2017). Although in recent years, Tau-based treatments have become a point of increasing focus, there is still a big need for additional therapeutic agents that target the pathological Tau conformers that are known or presumed to cause tauopathies.

WO2011/128455 refers to specific compounds which are suitable for treating disorders associated with amyloid proteins or amyloid-like proteins.

DESCRIPTION OF THE FIGURES

FIG. 1: Reduction of intracellular Tau misfolding by immunocytochrmistry in differentiated neuroblastoma cells with Example 44. Data are shown as mean+SD.

SUMMARY OF THE INVENTION

It was an object of the present invention to provide compounds that can be employed in the treatment, alleviation or prevention of a group of disorders and abnormalities associated with Tau protein aggregates including, but not limited to, NFTs, such as Alzheimer's disease (AD). Furthermore, there exists a need in the art for compounds which can be used as therapeutic agents for (a) decreasing Tau aggregates/NFTs, by recognizing aggregated Tau and disaggregating Tau, for example by changing the Tau aggregate molecular conformation, and/or (b) preventing the formation of Tau aggregates, and/or (c) interfering intracellularly with Tau aggregates. The present inventors have surprisingly found that these objects can be achieved by the compounds of formula (I) as described hereinafter.

The compounds of formula (I) display a high capability in decreasing Tau aggregates by, recognizing aggregated Tau and disaggregating Tau, for example by changing the Tau aggregate molecular conformation. Some compounds of formula (I) prevent the formation of Tau aggregates, and/or interfere intracellularly with Tau aggregates. While not wishing to be bound by theory, it is assumed that the compounds of formula (I) inhibit the Tau aggregation or disaggregate preformed Tau aggregates including when present intracellularly. Due to their unique design features, these compounds display properties such as appropriate lipophilicity and molecular weight, brain uptake and pharmacokinetics, cell permeability, solubility and metabolic stability, in order to be a successful medicament for the treatment, alleviation or prevention of tauopathies.

Ultrastructural analyses have shown that Tau inclusions are composed of paired helical filaments (PHF) or straight filaments (SF). High resolution structural analyses have shown that these filaments are composed of a core region comprising amino acids 306-378 of Tau which adapt a cross beta/beta-helix structure. The compounds of this invention can recognize aggregated Tau and disaggregate Tau, for example by changing the Tau aggregate molecular conformation, and can therefore be expected to facilitate Tau clearance.

In addition, it has been shown that Tau is able to both propagate from cell-to-cell and that certain forms of Tau (acting as seeds) are able to induce the structural change of native Tau protein within the healthy cell to undergo misfolding and aggregation. It is considered that aggregated Tau is responsible for the seeding and thus of the Tau pathology spreading. The compounds of this invention can interfere intracellularly with aggregated Tau and can therefore be expected to reduce Tau pathology spreading and finally prevent or reduce the associated cognitive deficits in AD.

The present invention discloses novel compounds of formula (I) having capabilities to decrease Tau aggregates, recognize aggregated Tau and disaggregate Tau, for example by changing the Tau aggregate molecular conformation.

The present invention discloses some novel compounds of formula (I) having capabilities to prevent the formation of Tau aggregates, and/or to interfere intracellularly with Tau aggregates.

The present invention provides methods for the treatment of disorders and abnormalities associated with Tau protein aggregates including, but not limited to, NFTs, using a compound of formula (I) or a pharmaceutical composition thereof. The present invention further provides a pharmaceutical composition comprising a compound of formula (I) and a pharmaceutically acceptable carrier or excipient.

The present invention is summarized in the following items:

1. A compound of formula (I):

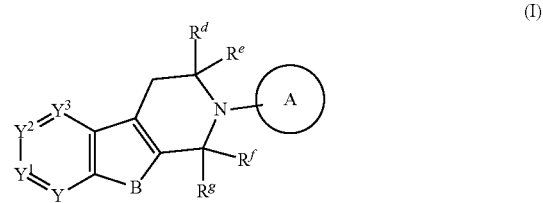

or stereoisomers, racemic mixtures, tautomers, pharmaceutically acceptable salts, prodrugs, hydrates, solvates and polymorphs thereof;
wherein
A is selected from the group consisting wherein

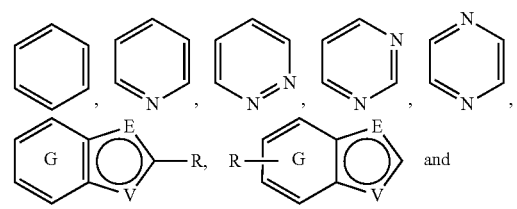

-continued

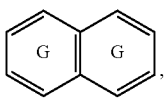

wherein

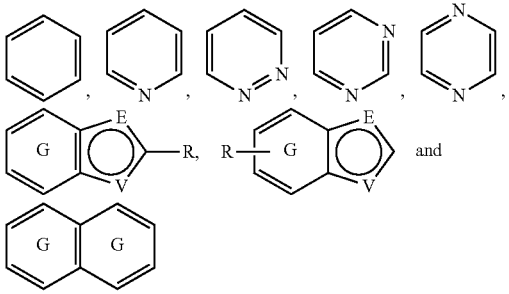

can be attached to the N atom at any available position, wherein the 5-membered ring containing E and V is unsaturated, and wherein

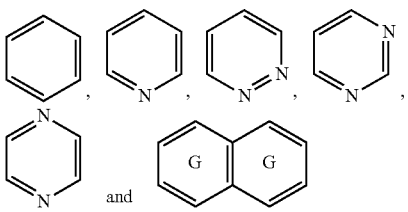

is substituted by one or more substituents

B is selected from the group consisting of O and $NR^a$;

E and V are independently selected from the group consisting of N, $NR^5$, O and S;

G is selected from the group consisting of a benzene ring and a pyridine ring;

J is selected from the group consisting of O, N—$R^1$ and $CH_2$ or J is selected from the group consisting of CH or C if J is attached to $R^2$;

Y, $Y^1$, $Y^2$ and $Y^3$ are CZ;

Z is independently selected from the group consisting of H, halogen, O-alkyl, alkyl and CN;

R is independently selected from the group consisting of and

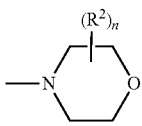

—$NR^3R^4$;

$R^a$ is selected from the group consisting of H and alkyl;

$R^d$, $R^e$, $R^f$, and $R^g$ are independently selected from the group consisting of H and alkyl, or any two of $R^d$, $R^e$, $R^f$, and $R^g$ may be joined to form a 3 to 8-membered ring;

$R^j$ is independently selected from the group consisting of -halogen, —O-alkyl, —$NR^3R^4$, —CN,

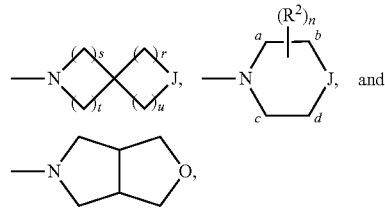

wherein a $C_{1-2}$ carbon atom-containing bridge or a bond can be present between the a carbon atom and the c or d carbon atom or wherein a $C_{1-2}$ carbon atom-containing bridge or a bond can be present between the b carbon atom and the c or d carbon atom;

$R^1$ is selected from the group consisting of H and alkyl;

$R^2$ is independently selected from the group consisting of alkyl, or —O-alkyl and wherein if two $R^2$ are geminal they can be joined to form a 3 to 6-membered ring;

$R^3$ and $R^4$ are independently selected from the group consisting of H and alkyl;

$R^5$ is selected from the group consisting of H and alkyl;

n is 0, 1, 2, 3 or 4;

r and s are independently 0, 1, 2 or 3; and t and u are independently 1, 2 or 3.

2. The compound according to item 1, which is a compound of formula (Ia):

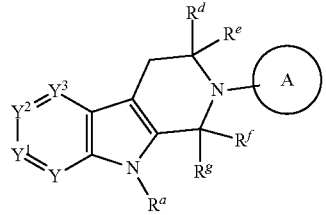

(Ia)

wherein A, $R^a$, $R^d$, $R^e$, $R^f$, $R^g$, Y, $Y^1$, $Y^2$ and $Y^3$ are as defined in item 1.

3. The compound according to any one of items 1 and 2, wherein A is wherein

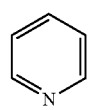

can be attached to the N atom at any available position, wherein A is substituted by one or more substituents $R^j$, and wherein $R^j$ is as defined in item 1.

4. The compound according to any one of items 1 to 3, which is a compound of the formula (Ib):
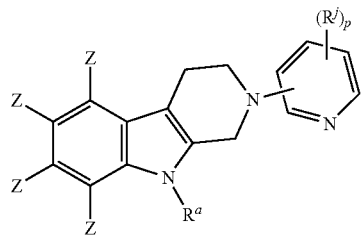
wherein $R^a$, $R^j$ and Z are as defined in item 1 and p is 1 or 2.
5. The compound according to any one of items 1 to 4, wherein the compound is selected from the group consisting of
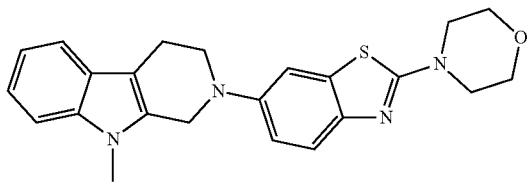
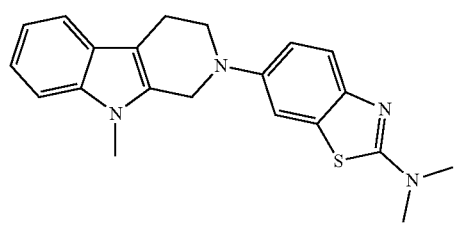
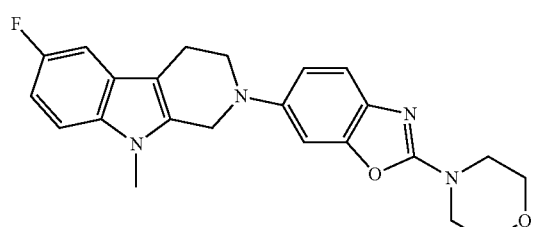
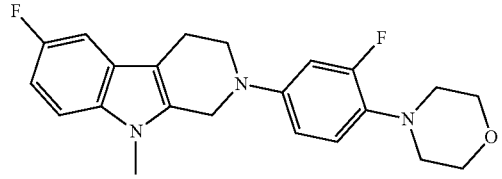
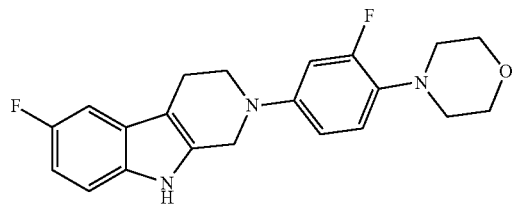
-continued
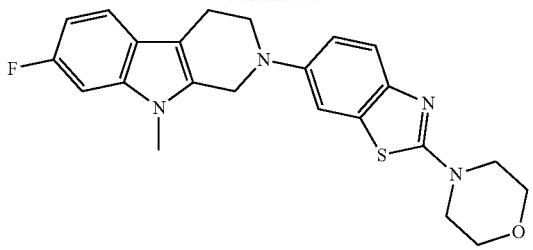
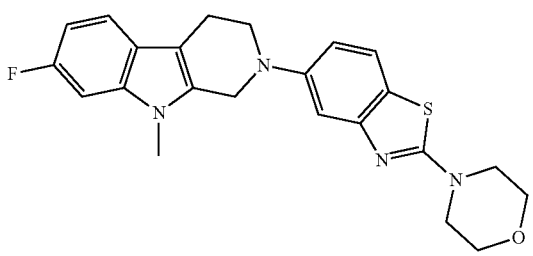
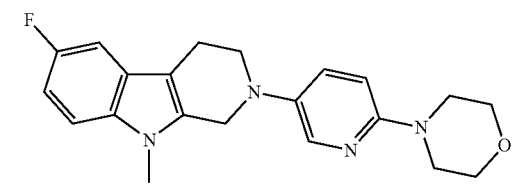
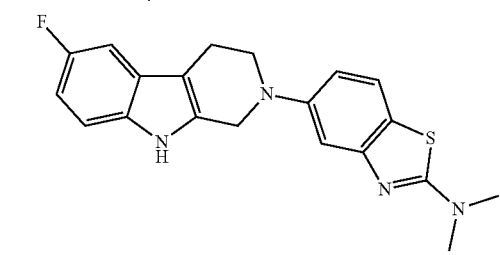
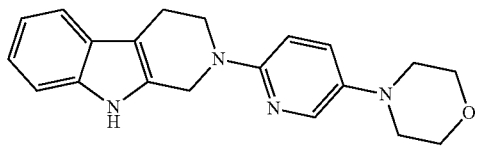
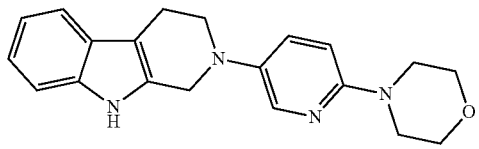
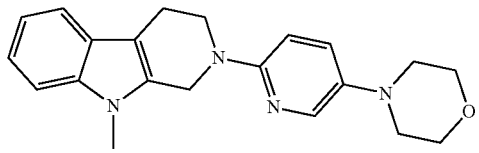
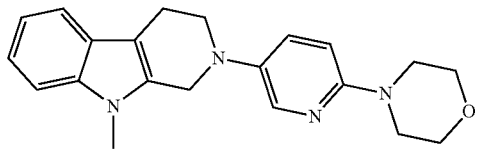
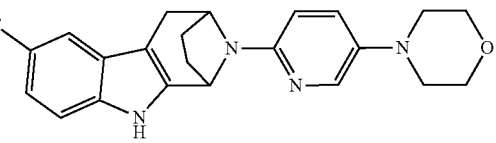

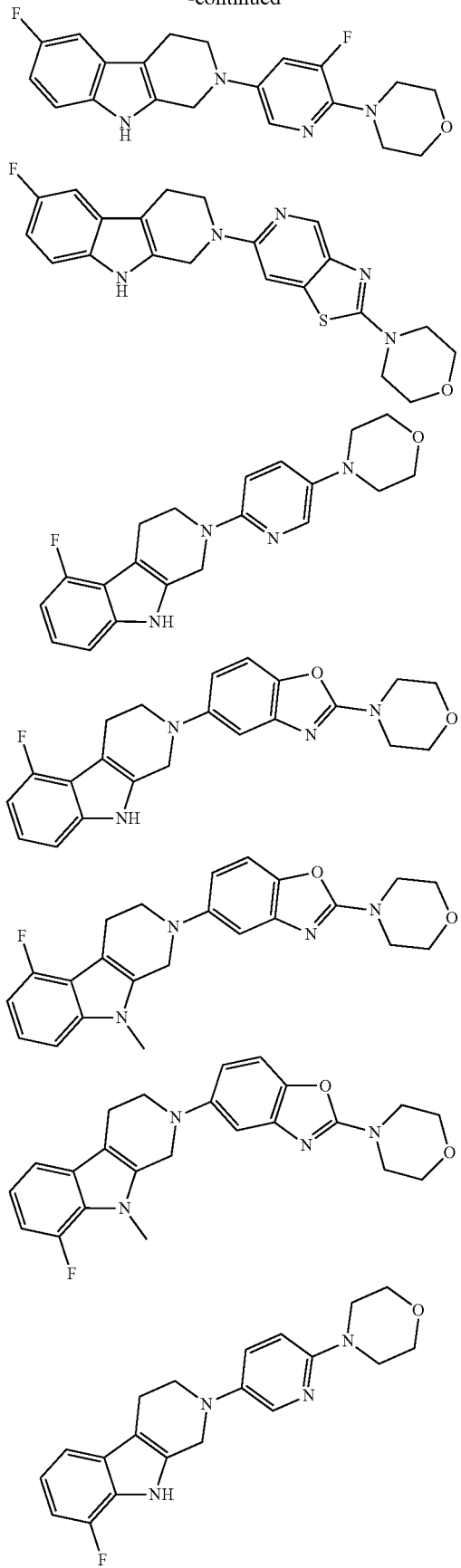
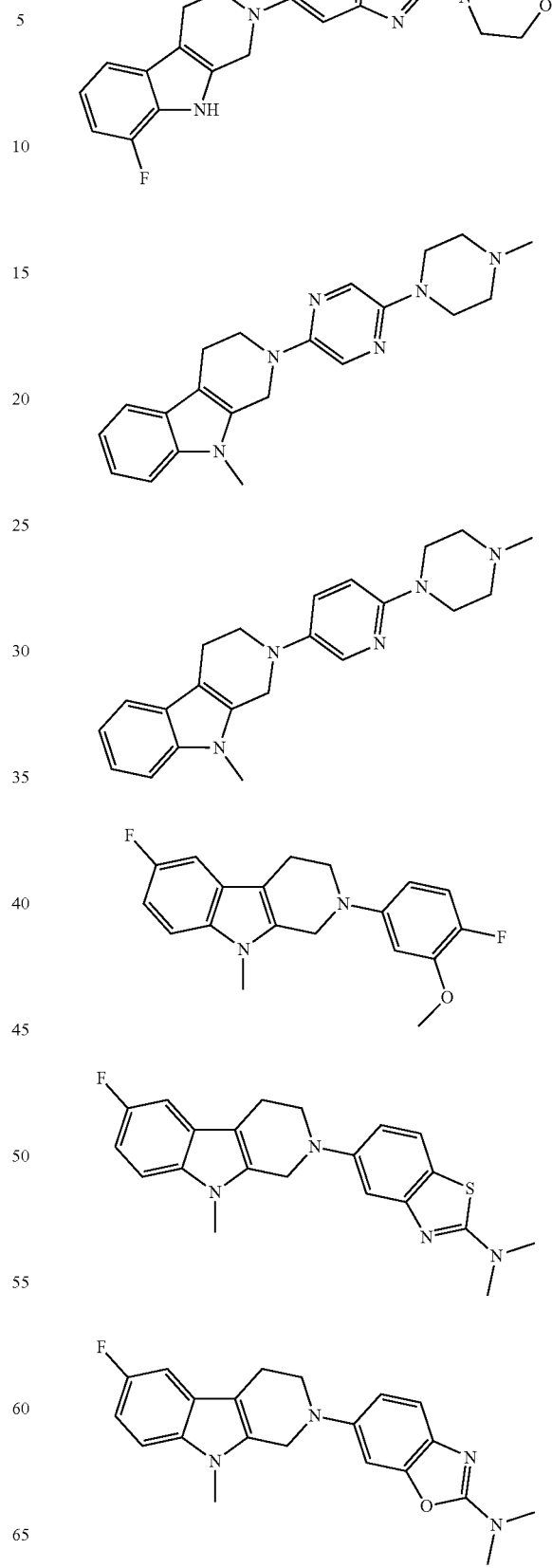

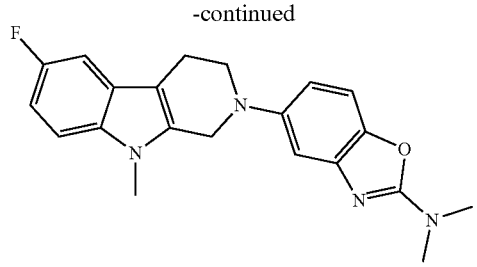
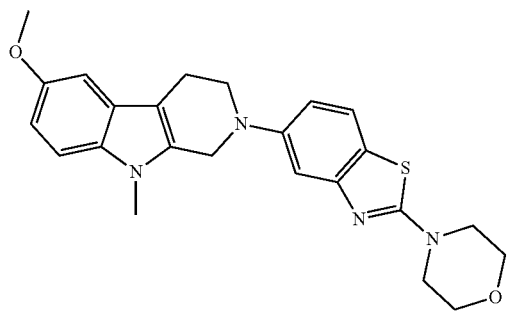
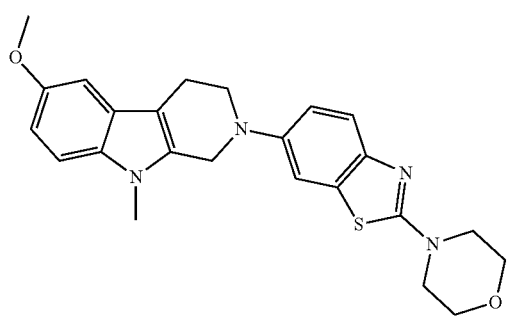
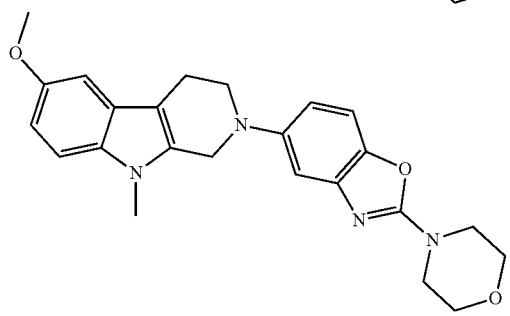
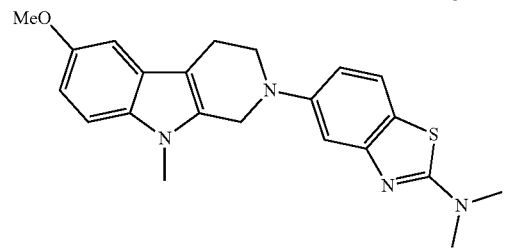
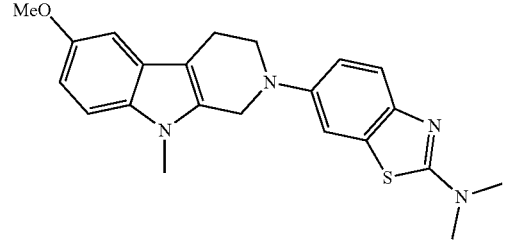
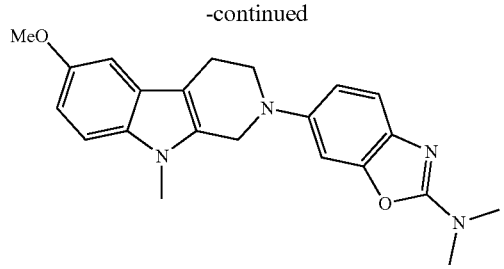
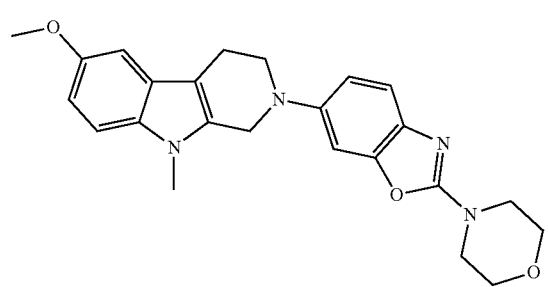
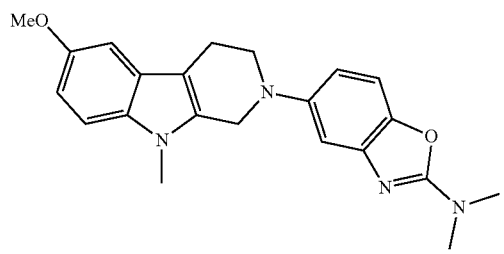
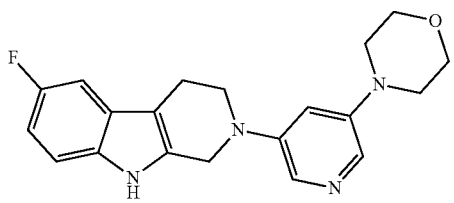
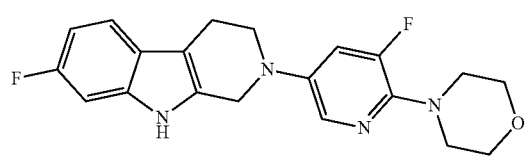
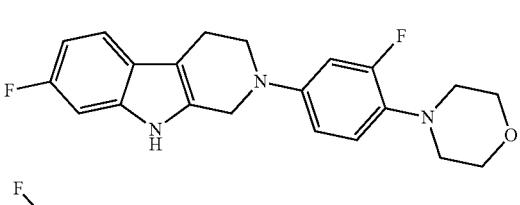
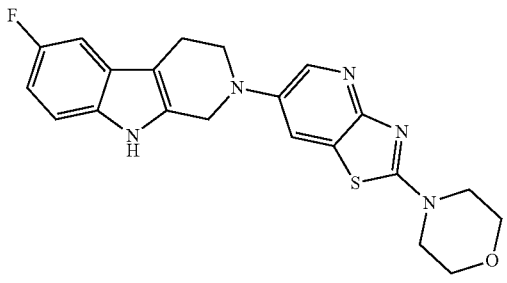

-continued
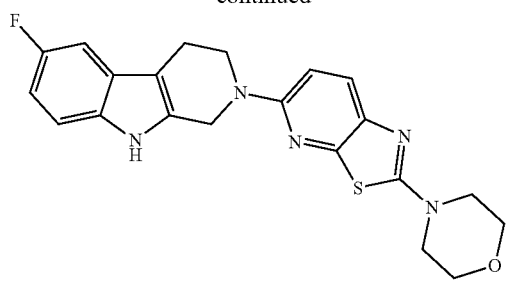
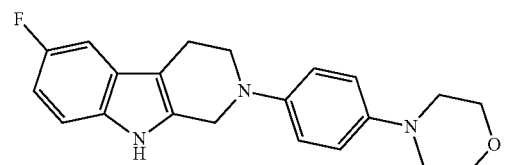
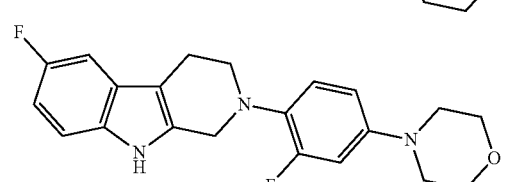
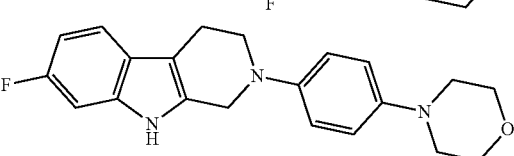
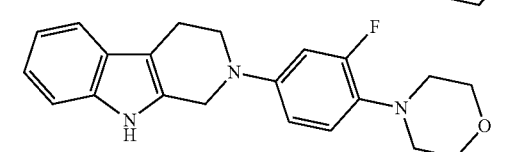
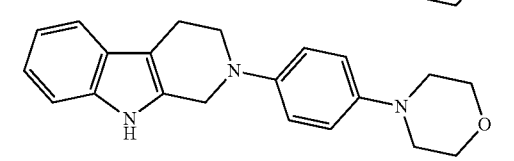
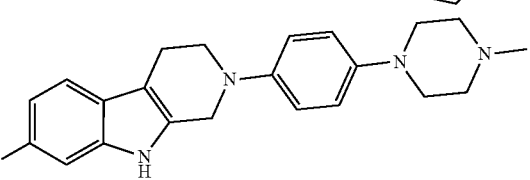
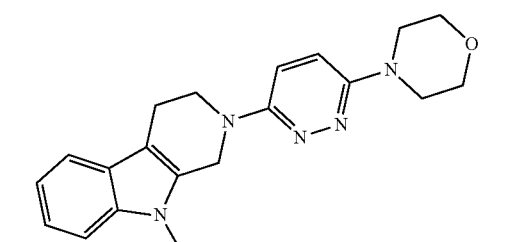
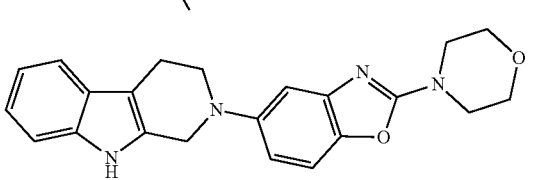
-continued
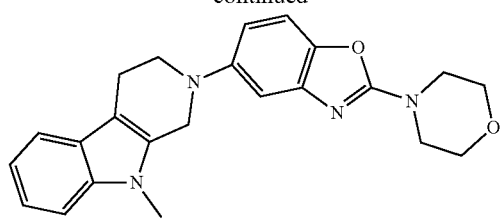
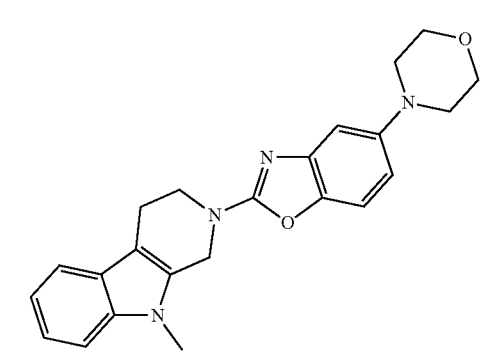
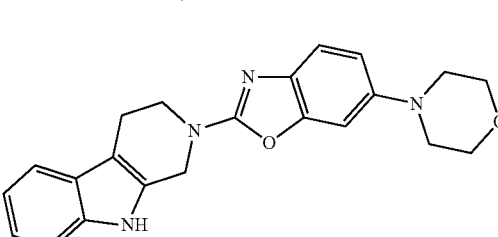
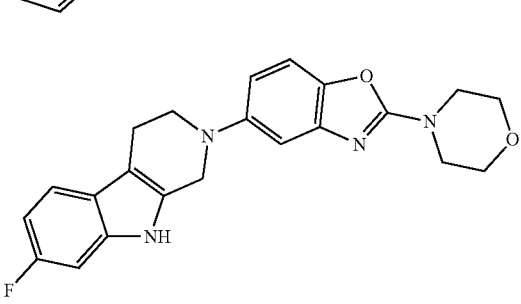
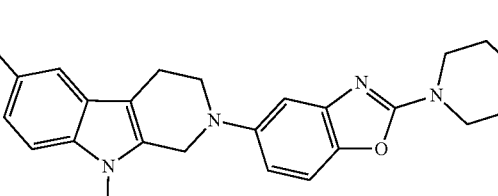
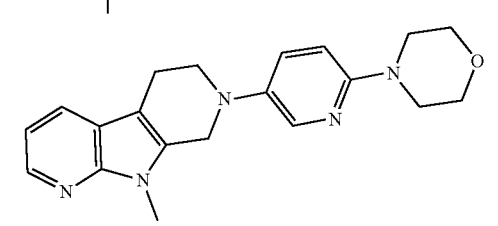
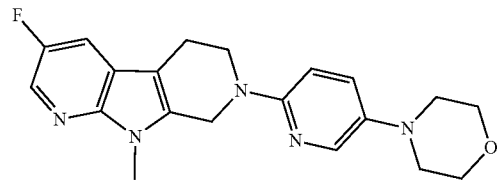

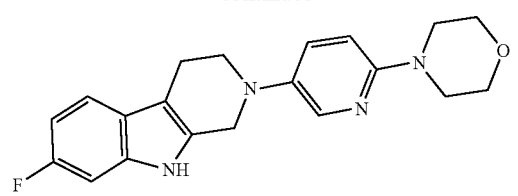
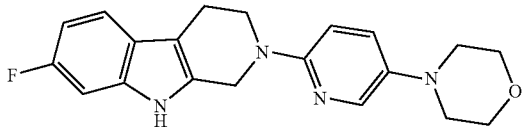
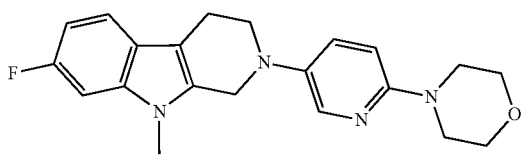
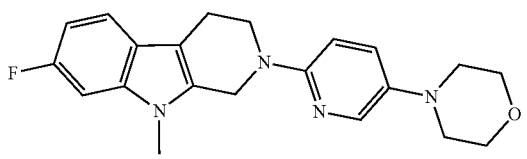
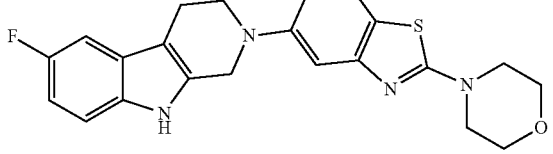
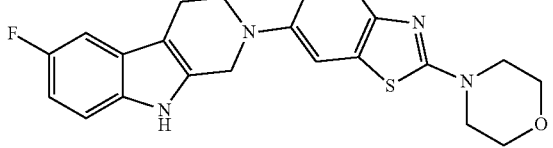
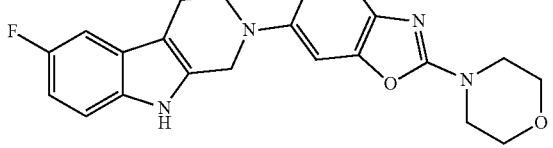
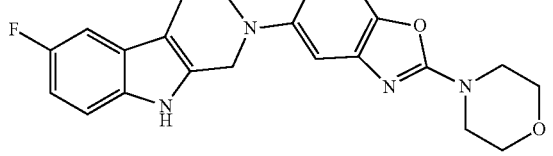
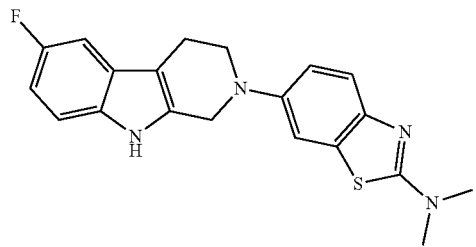
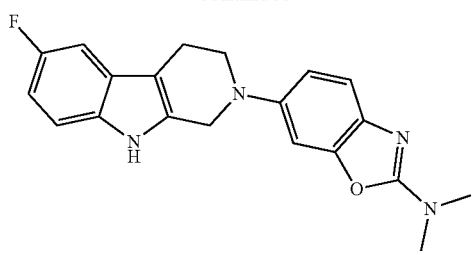
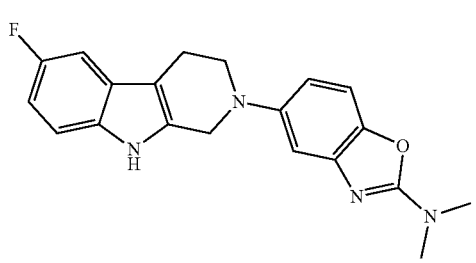
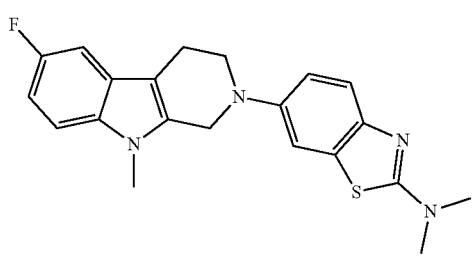
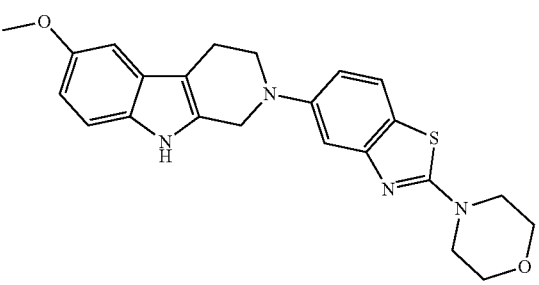
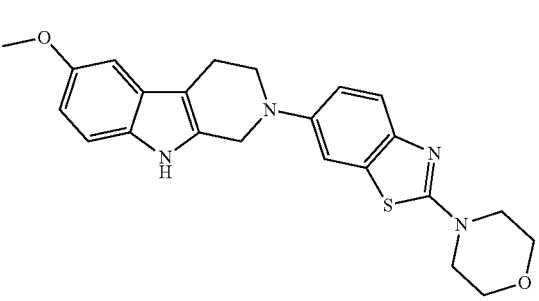
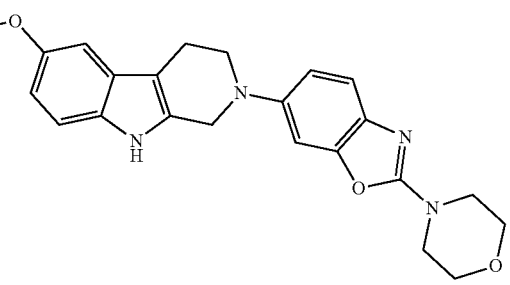

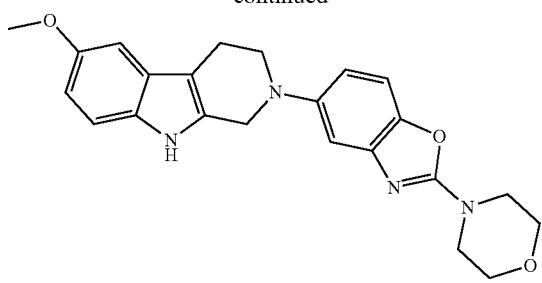
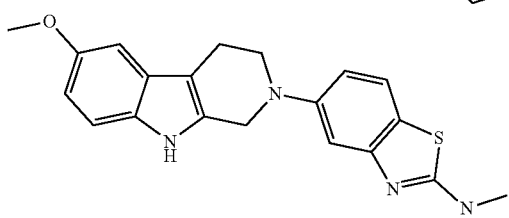
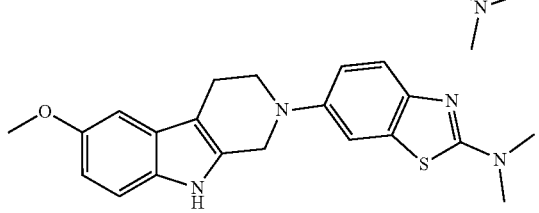
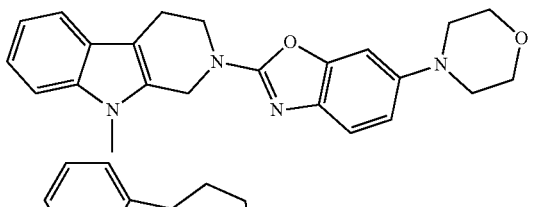
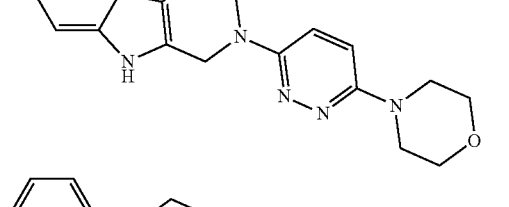
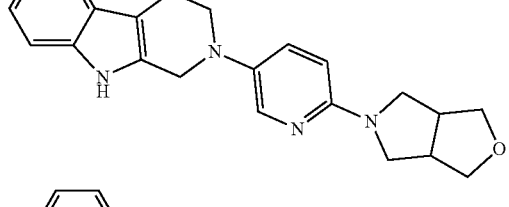
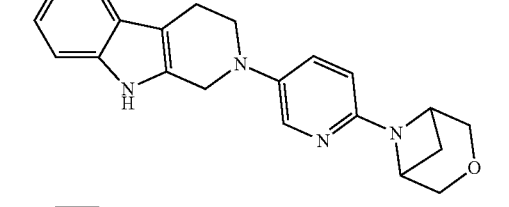
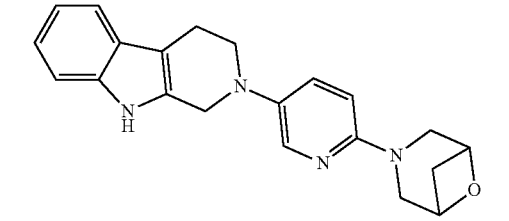
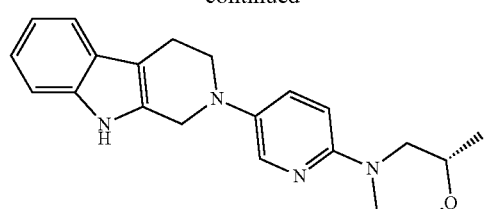
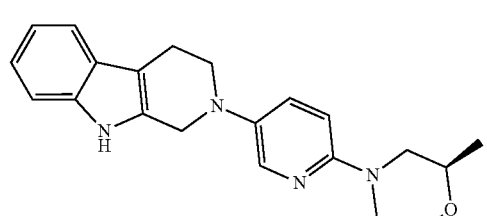
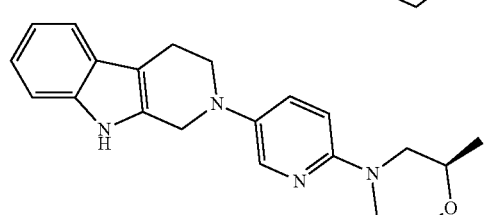
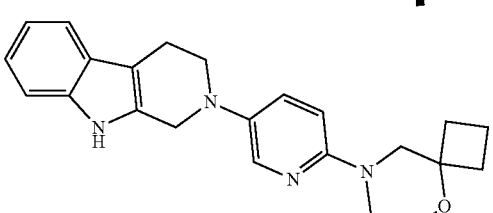
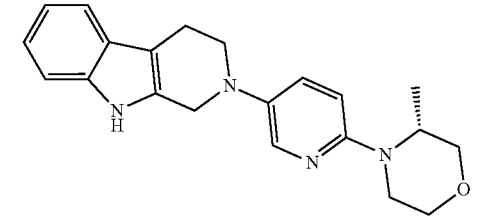
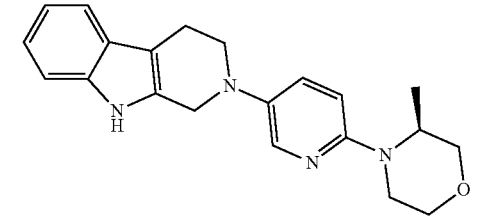
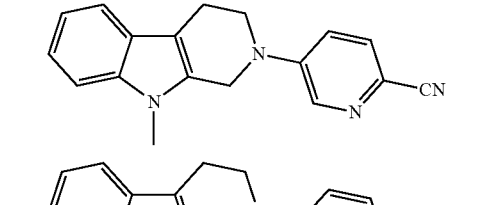
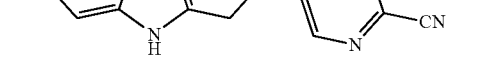

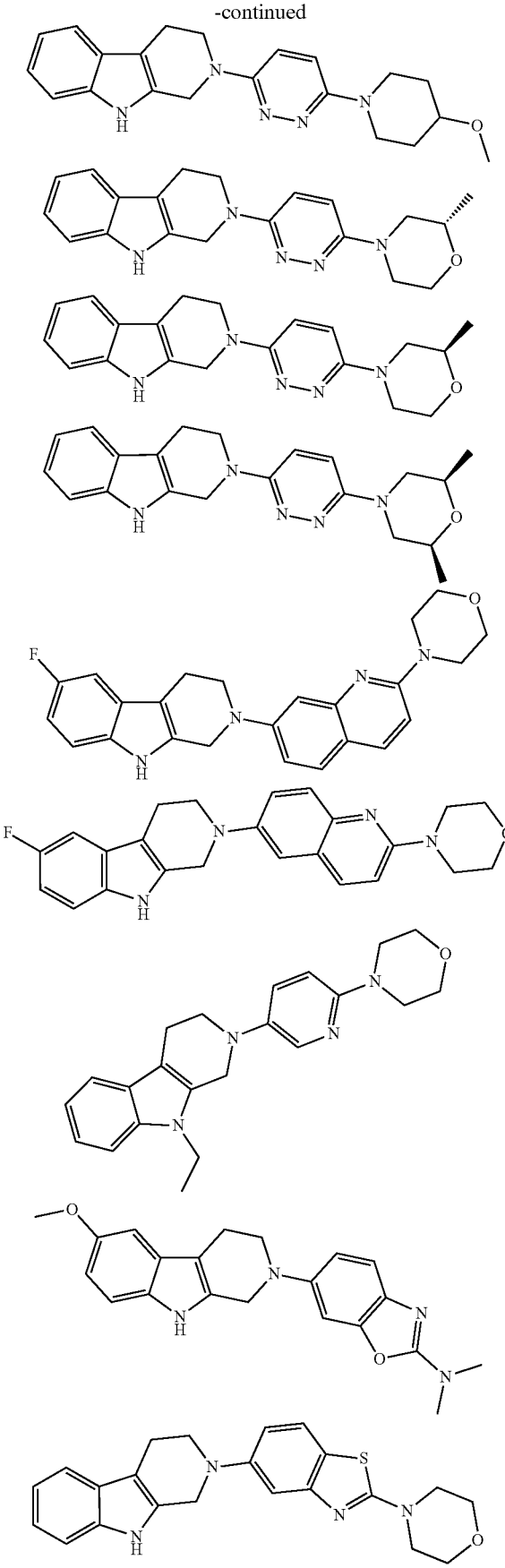
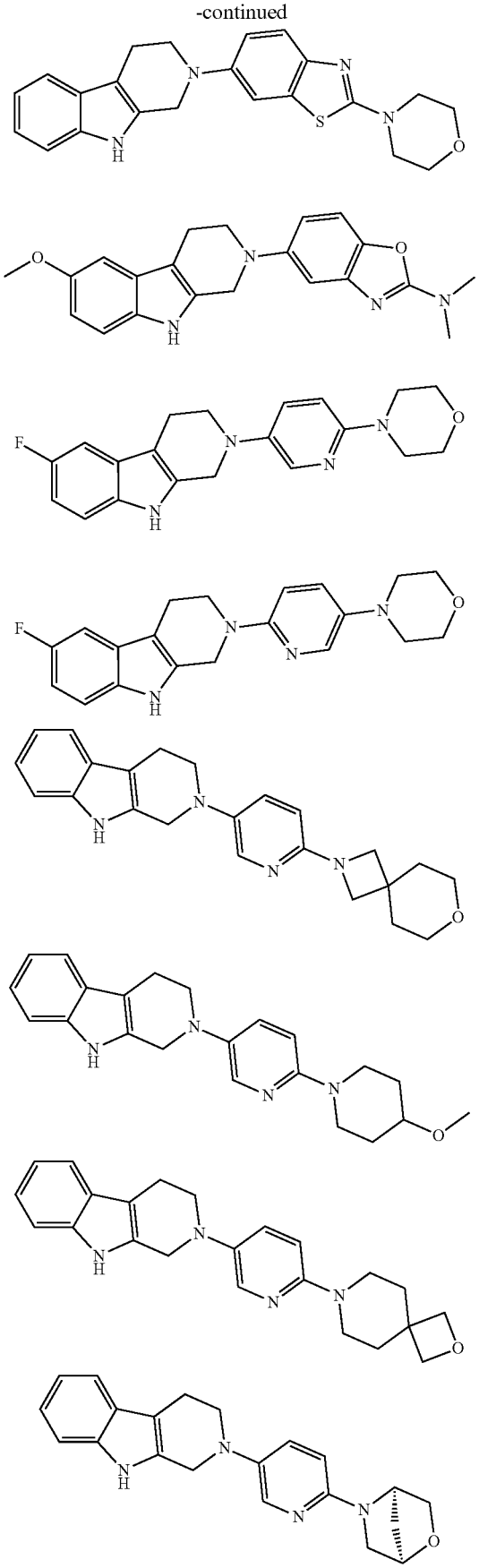

-continued

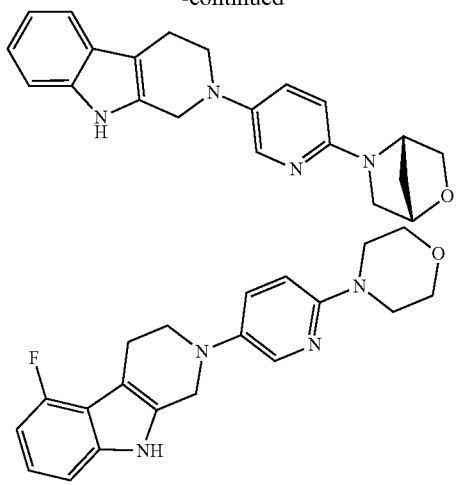

6. A pharmaceutical composition comprising a compound as defined in any one of items 1 to 5 and optionally a pharmaceutically acceptable carrier or excipient.
7. The compound as defined in any one of items 1 to 5 for use as a medicament.
8. The compound as defined in any one of items 1 to 5 for use in the treatment, alleviation or prevention of a disorder or abnormality associated with Tau protein aggregates.
9. The compound as defined in any one of items 1 to 5 for use in decreasing tau aggregation.
10. The compound as defined in any one of items 1 to 5 for use in preventing the formation of Tau aggregates and/or for use in inhibiting Tau aggregation.
11. The compound as defined in any one of items 1 to 5 for use in interfering intracellularly with Tau aggregates.
12. A method of treating, preventing or alleviating a disorder associated with Tau protein aggregates, the method comprising administering an effective amount of a compound as defined in any one of items 1 to 5 to a subject in need thereof.
13. A method of decreasing tau aggregation, the method comprising administering an effective amount of a compound as defined in any one of items 1 to 5 to a subject in need thereof.
14. A method of preventing the formation of Tau aggregates and/or of inhibiting Tau aggregation, the method comprising administering an effective amount of a compound as defined in any one of items 1 to 5 to a subject in need thereof.
15. A method of interfering intracellularly with Tau aggregates, the method comprising administering an effective amount of a compound as defined in any one of items 1 to 5 to a subject in need thereof.
16. The use of a compound as defined in any of items 1 to 5 in the manufacture of a medicament for the treatment of a disorder or abnormality associated with Tau protein aggregates.
17. The use of a compound as defined in any one of items 1 to 5 in the manufacture of a medicament for decreasing tau aggregation.
18. The use of a compound as defined in any one of items 1 to 5 in the manufacture of a medicament for preventing the formation of Tau aggregates and/or for use in inhibiting Tau aggregation.
19. The use of a compound as defined in any of items 1 to 5 in the manufacture of a medicament for interfering intracellularly with Tau aggregates.
20. A mixture comprising a compound as defined in any one of items 1 to 5 and at least one further biologically active compound selected from a therapeutic agent different from the compound as defined in any one of items 1 to 5, a pharmaceutically acceptable carrier, a diluent and an excipient.
21. The mixture according to item 20, wherein the further biologically active compound is a compound used in the treatment of amyloidosis.
22. The mixture according to item 20 or 21, wherein the further biologically active compound is selected from the group consisting of compounds against oxidative stress, anti-apoptotic compounds, metal chelators, inhibitors of DNA repair such as pirenzepine and metabolites, 3-amino-1-propanesulfonic acid (3APS), 1,3-propanedisulfonate (1,3PDS), α-secretase activators, β- and γ-secretase inhibitors, Tau proteins, neurotransmitter, β-sheet breakers, attractants for amyloid beta clearing/depleting cellular components, inhibitors of N-terminal truncated amyloid beta including pyroglutamated amyloid beta 3-42, anti-inflammatory molecules, or cholinesterase inhibitors (ChEIs) such as tacrine, rivastigmine, donepezil, and/or galantamine, M1 agonists, other drugs including any amyloid or Tau modifying drug and nutritive supplements, an antibody, including any functionally equivalent antibody or functional parts thereof or a vaccine.
23. The mixture according to item 22, wherein the further biologically active compound is a cholinesterase inhibitor (ChEI).
24. The mixture according to item 22, wherein the further biologically active compound is selected from the group consisting of tacrine, rivastigmine, donepezil, galantamine, niacin and memantine.
25. The mixture according to item 22, wherein the further biologically active compound is an antibody, particularly a monoclonal antibody, including any functionally equivalent antibody or functional parts thereof.
26. The mixture according to any one of items 20 to 25, wherein the compound and/or the further biologically active compound is/are present in a therapeutically effective amount.
27. The compound for use according to item 8, the method according to item 12, or the use according to item 16, wherein the disorder is selected from Alzheimer's disease (AD), familial AD, Primary Age-Related Tauopathy (PART), Creutzfeldt-Jacob disease, dementia pugilistica, Down's Syndrome, Gerstmann-Straussler-Scheinker disease (GSS), inclusion-body myositis, prion protein cerebral amyloid angiopathy, traumatic brain injury (TBI), amyotrophic lateral sclerosis (ALS), Parkinsonism-dementia complex of Guam, non-Guamanian motor neuron disease with neurofibrillary tangles, argyrophilic grain disease, corticobasal degeneration (CBD), diffuse neurofibrillary tangles with calcification, frontotemporal dementia with Parkinsonism linked to chromosome 17 (FTDP-17), Hallervorden-Spatz disease, multiple system atrophy (MSA), Niemann-Pick disease type C, pallidoponto-nigral degeneration, Pick's disease (PiD), progressive subcortical gliosis, progressive supranuclear palsy (PSP), subacute sclerosing panencephalitis, tangle predominant dementia, postencephalitic Parkinsonism, myotonic dystrophy, subacute sclerosis panencephalopathy, mutations in LRRK2, chronic traumatic encephalopathy (CTE), familial British dementia, familial Danish dementia, other frontotemporal lobar degenerations, Guadeloupean Parkinsonism, neurodegeneration with brain iron accumulation, SLC9A6-related mental retardation, white matter tauopathy with globular glial inclusions, epilepsy, Lewy body dementia (LBD), mild cognitive impairment (MCI), multiple sclerosis, Parkinson's disease, HIV-related dementia, adult onset diabetes, senile cardiac amyloidosis, glaucoma, ischemic stroke, psychosis in AD and Huntington's disease, preferably Alzheimer's disease (AD), corticobasal degeneration (CBD), Pick's disease (PiD), and progressive supranuclear palsy (PSP).

28. Use of the compound as defined in any of items 1 to 5 as an analytical reference or an in vitro screening tool.

29. A compound of the formula:

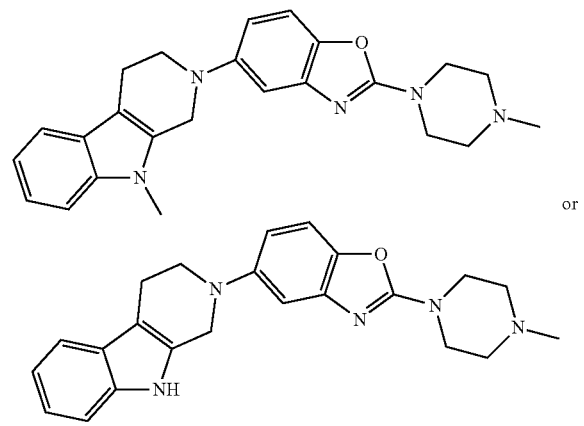

or a pharmaceutically acceptable salt thereof.

Definitions

Within the meaning of the present application the following definitions apply:

"Alkyl" refers to a saturated straight or branched organic moiety consisting of carbon and hydrogen atoms. Examples of suitable alkyl groups have 1 to 6 carbon atoms, preferably 1 to 4 carbon atoms, and include methyl, ethyl, propyl, isopropyl, n-butyl, t-butyl and isobutyl.

"Hal" or "halogen" refers to F, Cl, Br, and I, preferably F.

"3- to 8-membered ring" refers to a three-, four-, five-, six-, seven- or eight-membered ring wherein none, one or more of the carbon atoms in the ring have been replaced by 1 or 2 (for the three-membered ring), 1, 2 or 3 (for the four-membered ring), 1, 2, 3, or 4 (for the five-membered ring) or 1, 2, 3, 4, or 5 (for the six-membered ring) 1, 2, 3, 4, 5 or 6 (for the seven-membered ring), or 1, 2, 3, 4, 5, 6 or 7 (for the eight-membered ring) of the same or different heteroatoms, whereby the heteroatoms are selected from O, N and S.

Compounds of the present invention having one or more optically active carbons can exist as racemates and racemic mixtures (including mixtures in all ratios), stereoisomers (including diastereomeric mixtures and individual diastereomers, enantiomeric mixtures and single enantiomers, mixtures of conformers and single conformers), tautomers, atropisomers, and rotamers. All isomeric forms are included in the present invention. Compounds described in this invention containing olefinic double bonds include E and Z geometric isomers. Also included in this invention are all pharmaceutically acceptable salts, prodrugs, polymorphs, hydrates and solvates.

The term "polymorphs" refers to the various crystalline structures of the compounds of the present invention. This may include, but is not limited to, crystal morphologies (and amorphous materials) and all crystal lattice forms. Salts of the present invention can be crystalline and may exist as more than one polymorph.

Solvates, hydrates as well as anhydrous forms of the salt are also encompassed by the invention. The solvent included in the solvates is not particularly limited and can be any pharmaceutically acceptable solvent. Examples include water and $C_{1-4}$ alcohols (such as methanol or ethanol).

"Pharmaceutically acceptable salts" are defined as derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as, but not limited to, hydrochloric, hydrobromic, sulfuric, sulfamic, phosphoric, nitric acid and the like; and the salts prepared from organic acids such as, but not limited to, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic acid, and the like. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Organic solvents include, but are not limited to, nonaqueous media like ethers, ethyl acetate, ethanol, isopropanol, or acetonitrile. Lists of suitable salts can be found in Remington's Pharmaceutical Sciences, 18$^{th}$ ed., Mack Publishing Company, Easton, Pa., 1990, p. 1445, the disclosure of which is hereby incorporated by reference.

The compounds of the present invention can also be provided in the form of a prodrug, namely a compound which is metabolized in vivo to the active metabolite. As used hereinafter in the description of the invention and in the claims, the term "prodrug" means any covalently bonded compound which releases the active parent pharmaceutical due to in vivo biotransformation. The reference by Goodman and Gilman (The Pharmacological Basis of Therapeutics, 8 ed, McGraw-Hill, Int. Ed. 1992, "Biotransformation of Drugs", p 13-15) describing prodrugs generally is hereby incorporated herein by reference.

"Pharmaceutically acceptable" is defined as those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The patients or subjects in the present invention are typically animals, particularly mammals, more particularly humans.

"Tau" as used herein refers to a highly soluble microtubule binding protein mostly found in neurons and includes the major 6 isoforms, cleaved or truncated forms, and other modified forms such as arising from phosphorylation, glycosylation, glycation, prolyl isomerization, nitration, acetylation, polyamination, ubiquitination, sumoylation and oxidation.

"Aggregated Tau" refers to aggregated monomers of Tau peptides or proteins which are folded into the oligomeric or polymeric structures.

"Neurofibrillary Tangles" (NFTs) as used herein refer to insoluble aggregates of the hyperphosphorylated Tau protein containing paired helical filaments (PHF) and straight filaments. Their presence is a hallmark of AD and other diseases known as tauopathies.

The definitions and preferred definitions given in the "Definition"-section apply to all of the embodiments described below unless stated otherwise.

DETAILED DESCRIPTION OF THE INVENTION

The compounds of the present invention will be described in the following. It is to be understood that all possible combinations of the following definitions are also envisaged.

In one embodiment, the present invention relates to a compound of formula (I):

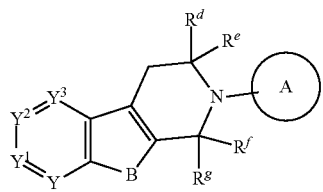

(I)

or stereoisomers, racemic mixtures, tautomers, pharmaceutically acceptable salts, prodrugs, hydrates, solvates and polymorphs thereof.

A preferred embodiment of the compound of formula (I) is

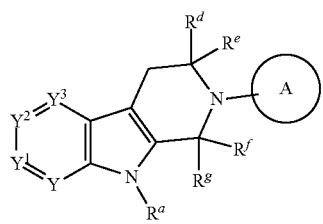

(Ia)

A further preferred embodiment of the compound of formula (I) is

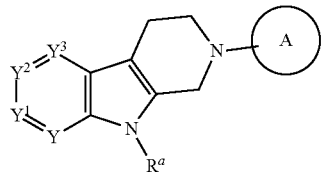

More preferably the compound of formula (I) is

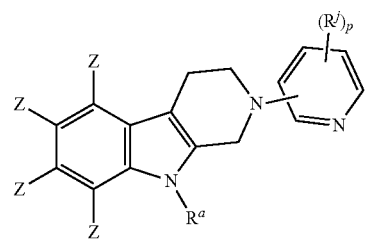

(Ib)

The following definitions of A apply to the compounds of formula (I) and its preferred embodiments.

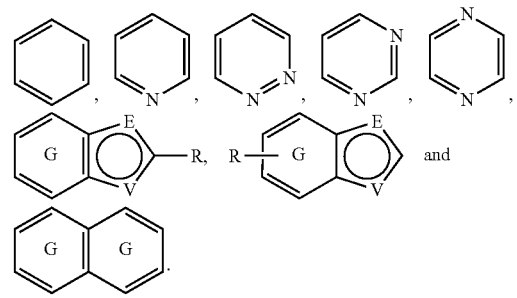

A is selected from the group consisting of
In the formula

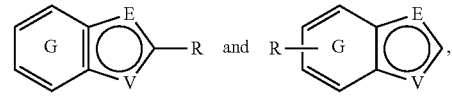

G is selected from a benzene ring and a

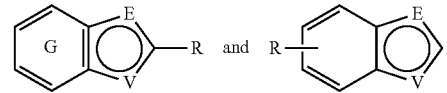

pyridine ring. Therefore, cover the following embodiments

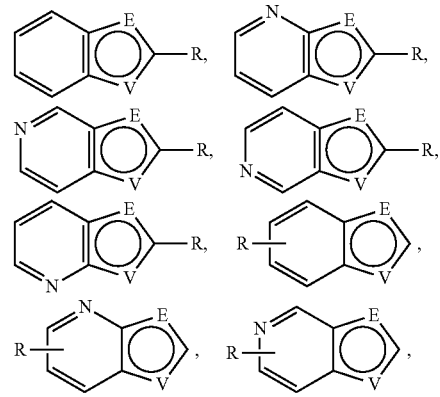

-continued

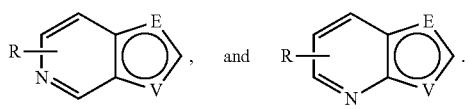

In a preferred embodiment,

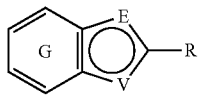

is selected from

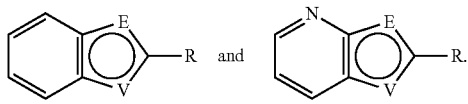

In a further preferred embodiment

In one preferred embodiment, A is

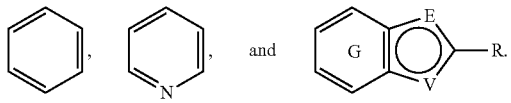

In a more preferred embodiment, A is selected from

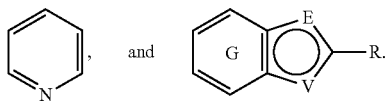

In a further preferred embodiment, A is selected from

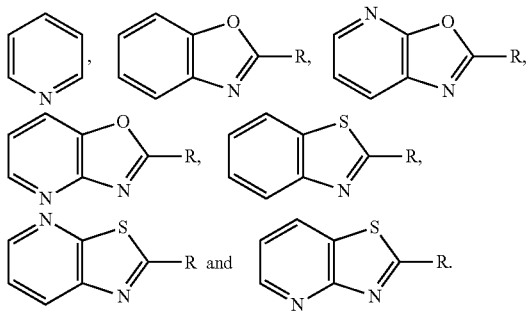

In an even more preferred embodiment, A is

In the above definitions of A and the preferred embodiments thereof,

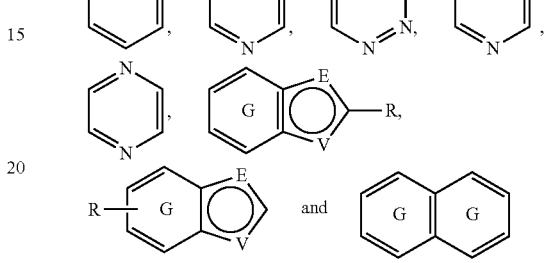

can be attached to the N atom at any available position.

In the above definitions of A and the preferred embodiments thereof, A is substituted by one or more substituents $R^j$, for instance, $R^j$ can be present one or two times. If A is phenyl ring, then 1 or 2 substituents can be preferably present. If A is a pyridine ring, then 1 substituent can be preferably present.

The following definitions apply to the formula (I) and their preferred embodiments, as appropriate.

B is selected from the group consisting of O and $NR^a$. More preferably B is $NR^a$.

E and V are independently selected from the group consisting of N, $NR^5$, O and S, so that

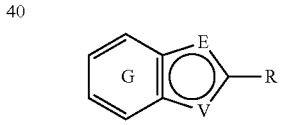

is selected from

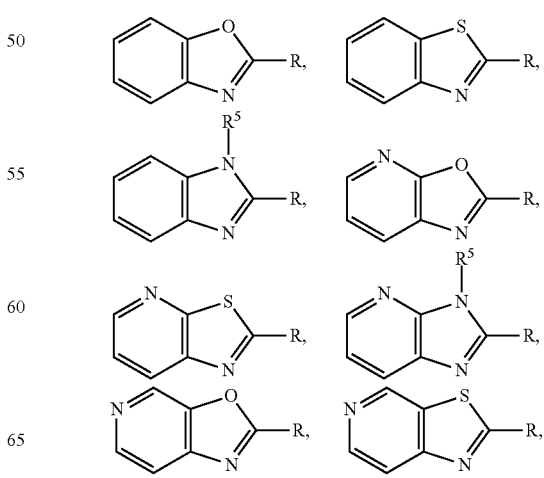

-continued

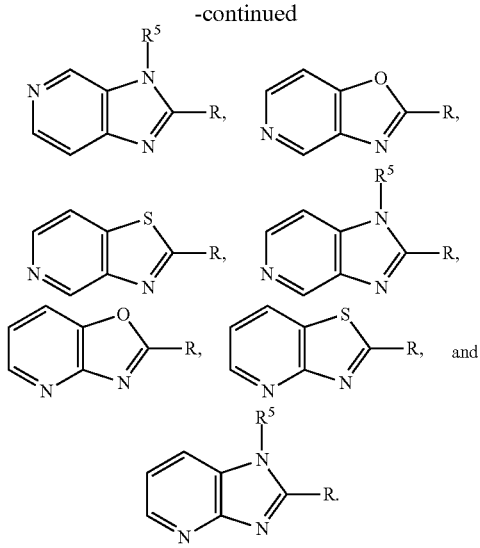

Preferably

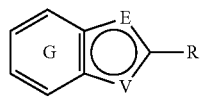

is selected from

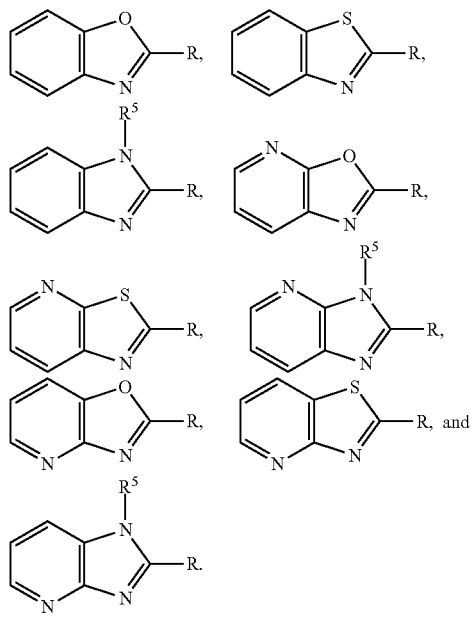

The same combinations of E, V and G can be considered for

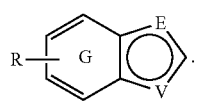

J is selected from the group consisting of O, N—R¹ and CH₂ or J is selected from the group consisting of CH or C if J is attached to R². In one embodiment J is O, in another embodiment J is N—R¹ (preferably N-Me) and in a further embodiment J is CH₂, CH or C.

Y, Y¹, Y² and Y³ are CZ, more preferably Y, Y¹, Y² and Y³ are CH.

Z is independently selected from the group consisting of H, halogen (preferably F), O-alkyl, alkyl and CN, preferably H, halogen (preferably F), and O-alkyl. In one preferred embodiment, one Z is halogen (preferably F), or O-alkyl and the other Z are H. In a more preferred embodiment, one Z is halogen (preferably F) and the other Z are H.

R is independently selected from the group consisting of

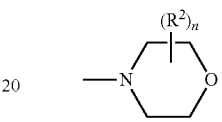

and —NR³R⁴, preferably R is

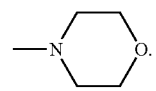

$R^a$ is selected from the group consisting of H and alkyl, more preferably H and Me.

$R^d$, $R^e$, $R^f$, and $R^g$ are independently selected from the group consisting of H and alkyl, or any two of $R^d$, $R^e$, $R^f$, and $R^g$ may be joined to form a 3 to 8-membered ring. Preferably $R^d$, $R^e$, $R^f$, $R^g$ are independently H or $R^d$ and $R^f$ can be joined together to form a $C_{1-2}$ carbon atom-containing bridge. More preferably $R^d$, $R^e$, $R^f$, and $R^g$ are H.

$R^j$ is independently selected from the group consisting of -halogen, —O-alkyl, —NR³R⁴, —CN,

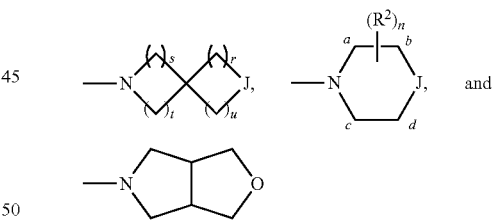

wherein a $C_{1-2}$ carbon atom-containing bridge or a bond can be present between the a carbon atom and the c or d carbon atom or wherein a $C_{1-2}$ carbon atom-containing bridge or a bond can be present between the b carbon atom and the c or d carbon atom. More preferably $R^j$ is selected from the group consisting of -halogen (preferably —F), —O-alkyl (preferably —O-Me) and

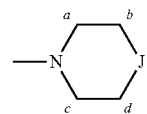

(preferably

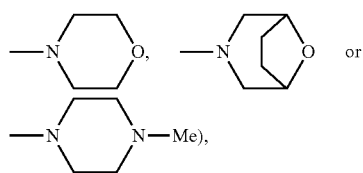

even more preferably $R^j$ is

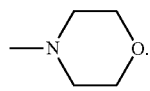

$R^1$ is selected from the group consisting of H and alkyl, preferably alkyl, more preferably $CH_3$.

$R^2$ is independently selected from the group consisting of alkyl, or —O-alkyl and wherein if two $R^2$ are geminal they can be joined to form a 3 to 6-membered ring. In one embodiment $R^2$ is alkyl, in another embodiment $R^2$ is —O-alkyl, in a further embodiment two $R^2$ that are geminal can be joined to form a 3 to 6-membered ring.

$R^3$ and $R^4$ are independently selected from the group consisting of H and alkyl. In one embodiment $R^3$ or $R^4$ is alkyl and the other is H. In another embodiment $R^3$ is alkyl and $R^4$ is alkyl. In a further embodiment $R^3$ and $R^4$ are H.

$R^5$ is selected from the group consisting of H and alkyl. In one embodiment $R^5$ is H. In another embodiment $R^5$ is alkyl.

n is 0, 1, 2, 3 or 4, more preferably 0, 1 or 2, even more preferably n is 0.

p is 1 or 2, more preferably 1.

r and s are independently 0, 1, 2 or 3.

t and u are independently 1, 2 or 3.

Preferred compounds of formula (I) are

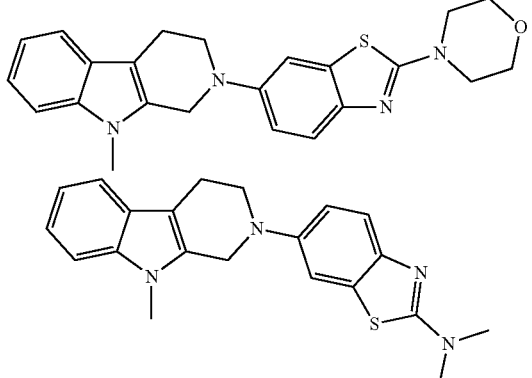

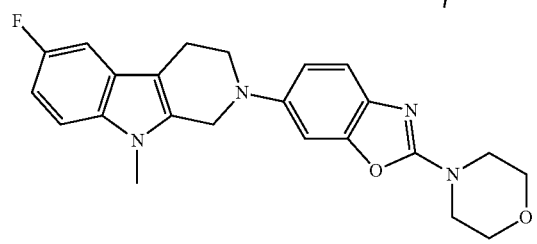

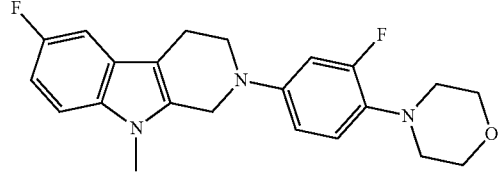

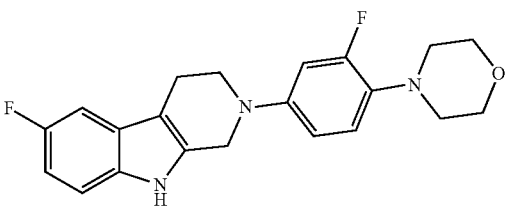

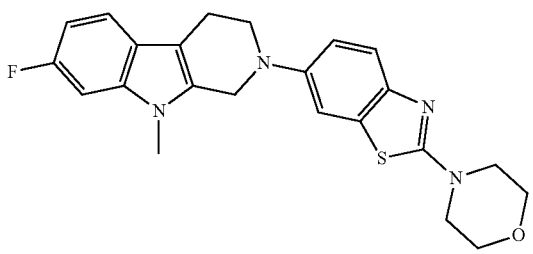

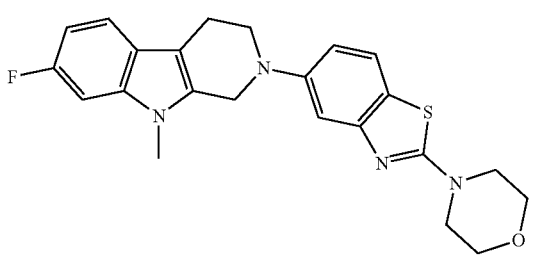

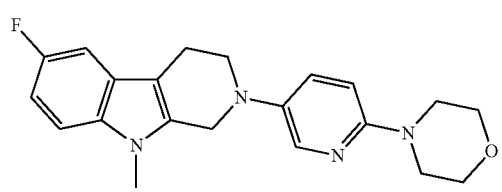 [SMILES: Cn1c2c(c3cc(F)ccc31)CCN(c1ccc(N3CCOCC3)nc1)C2]

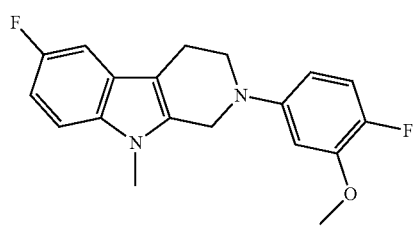 [SMILES: COc1cc(N2CCc3c(n(C)c4ccc(F)cc34)C2)ccc1F]

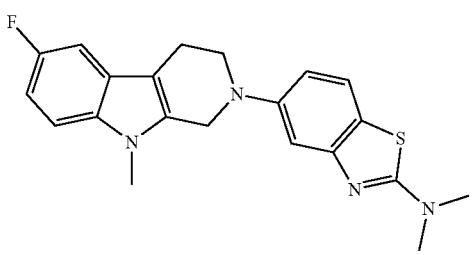 [SMILES: CN(C)c1nc2cc(N3CCc4c(n(C)c5ccc(F)cc45)C3)ccc2s1]

-continued
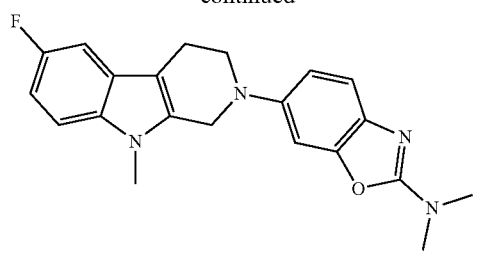
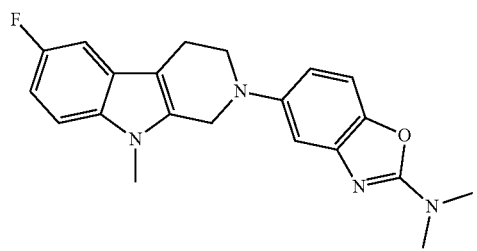
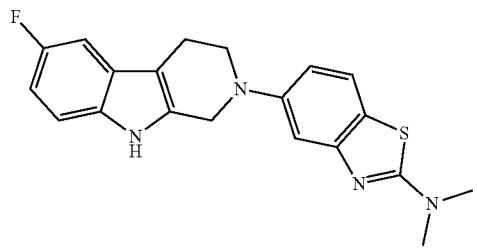
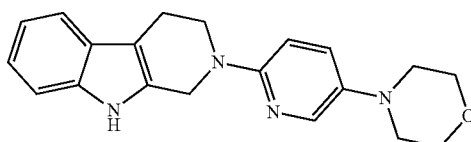
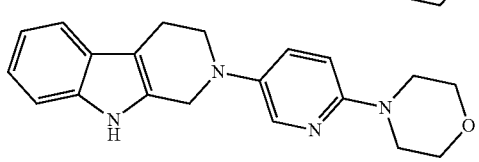
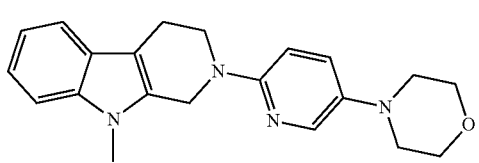
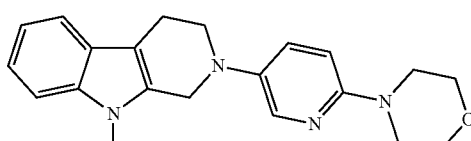
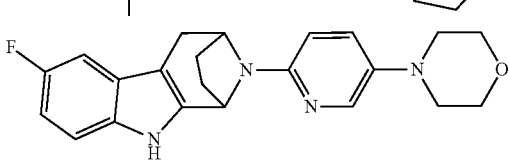
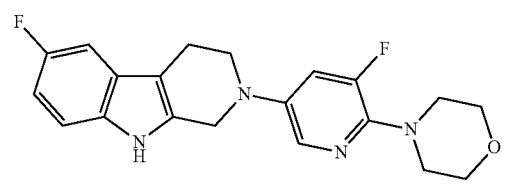
-continued
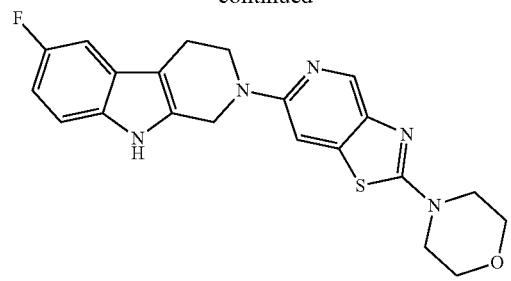
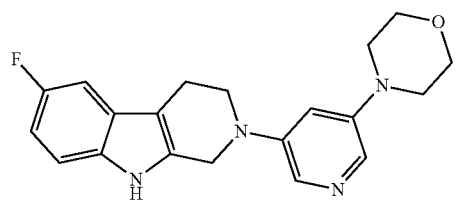
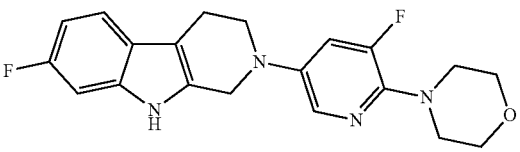
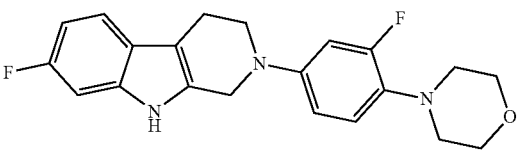
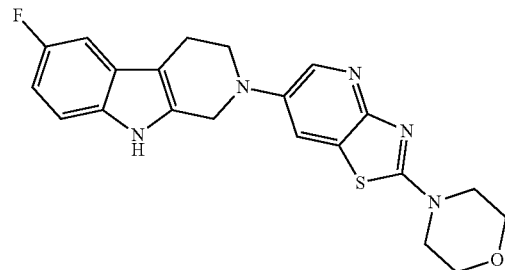
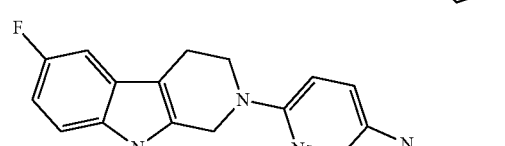
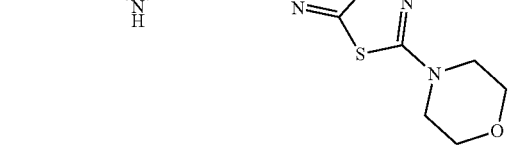
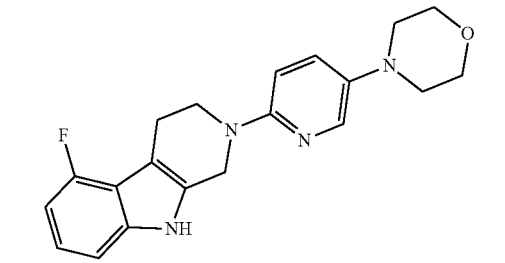

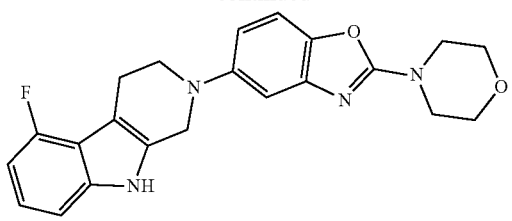
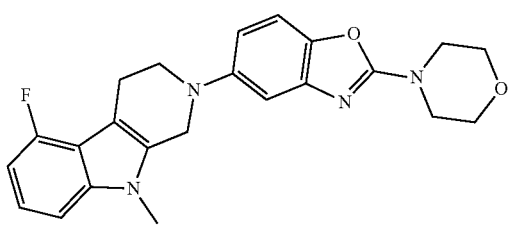
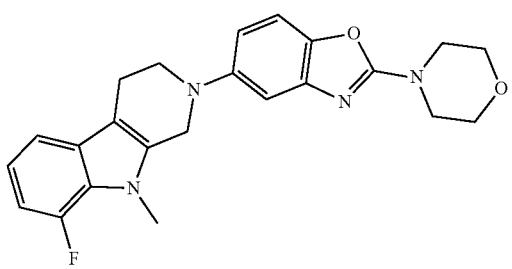
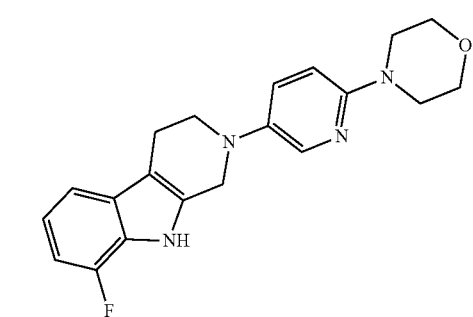
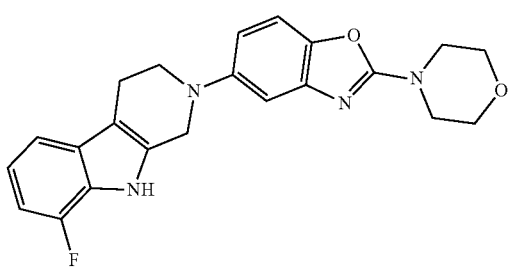
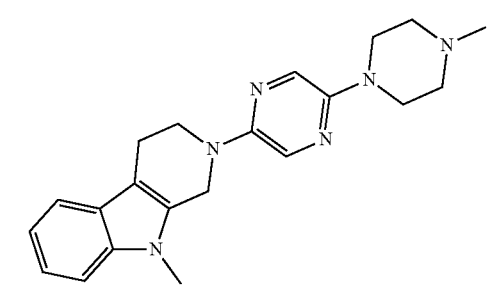
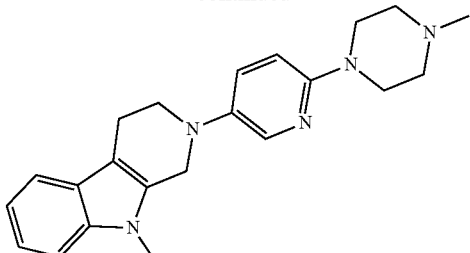
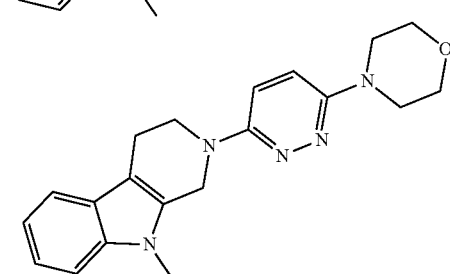
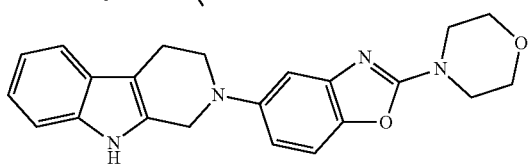
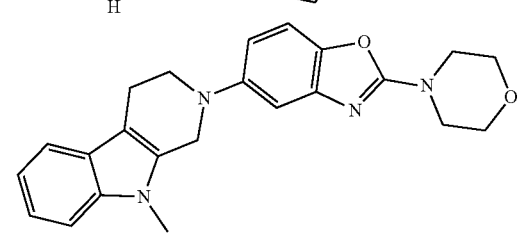
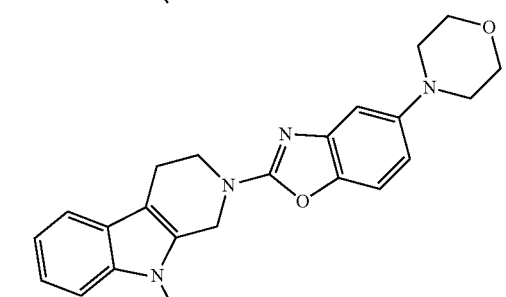
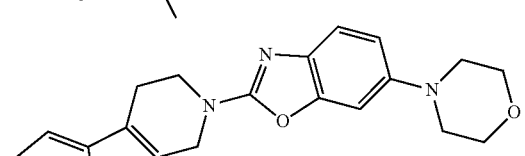
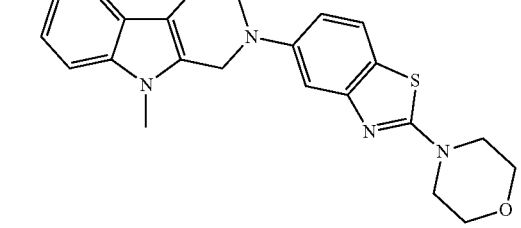

37
-continued
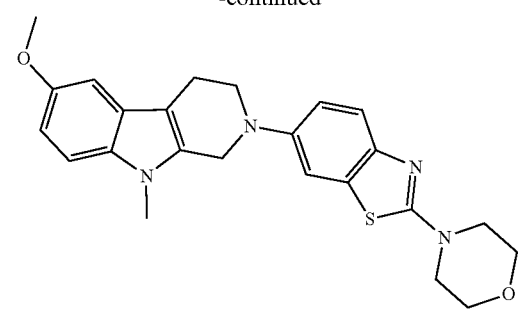
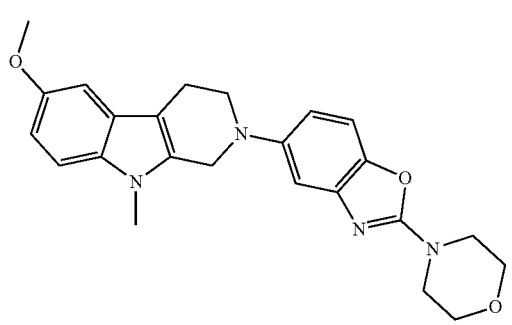 [SMILES: COc1ccc2c(c1)c1c(n2C)CN(c2ccc3oc(N4CCOCC4)nc3c2)CC1]
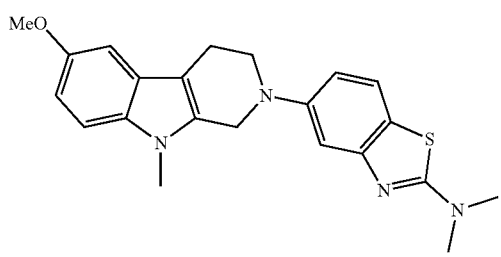
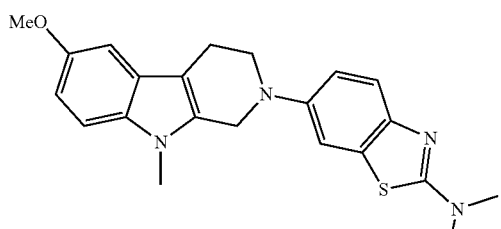
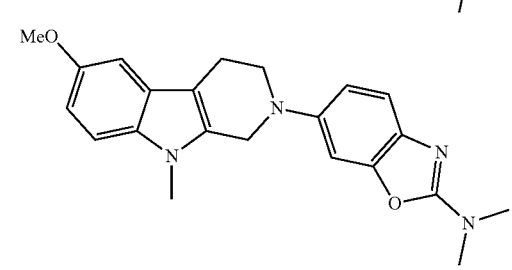
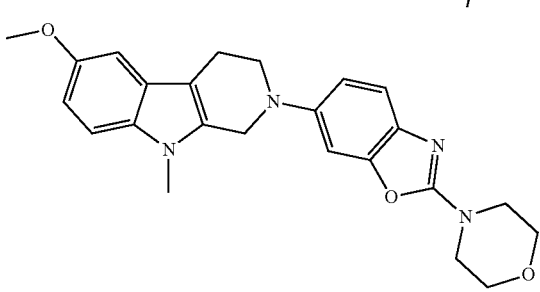
38
-continued
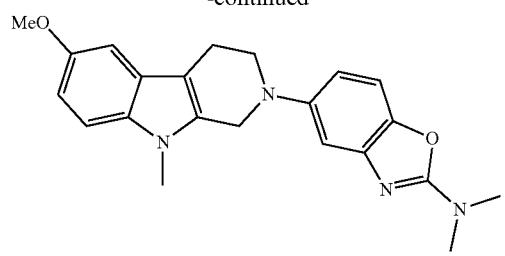
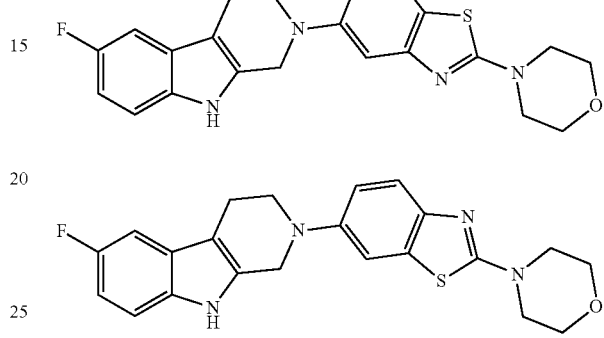
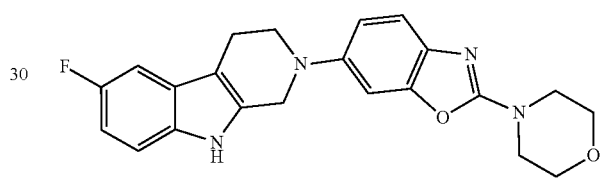
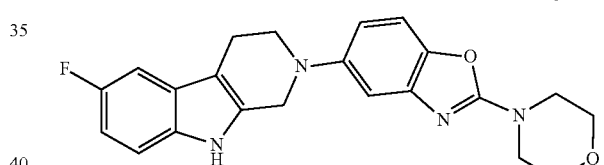
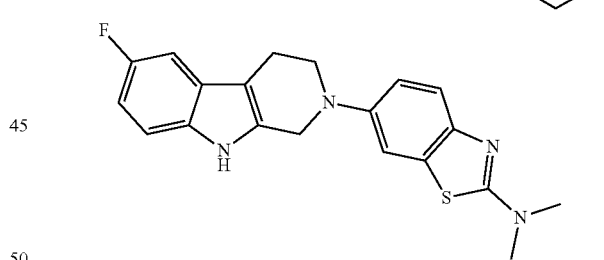
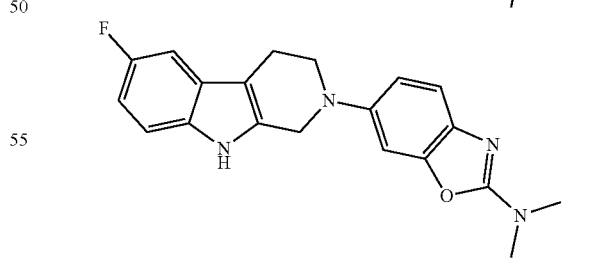
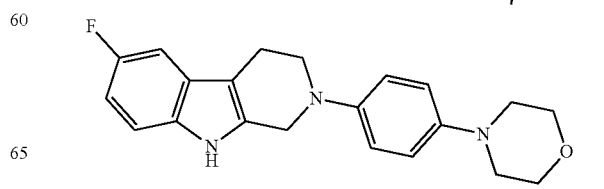

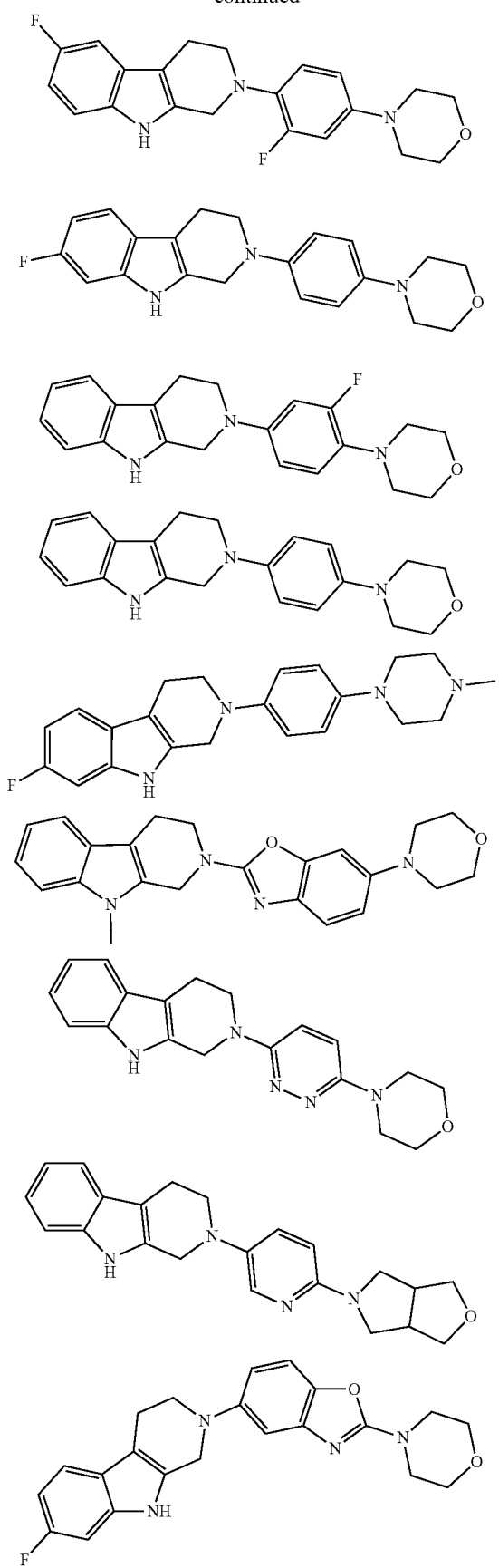
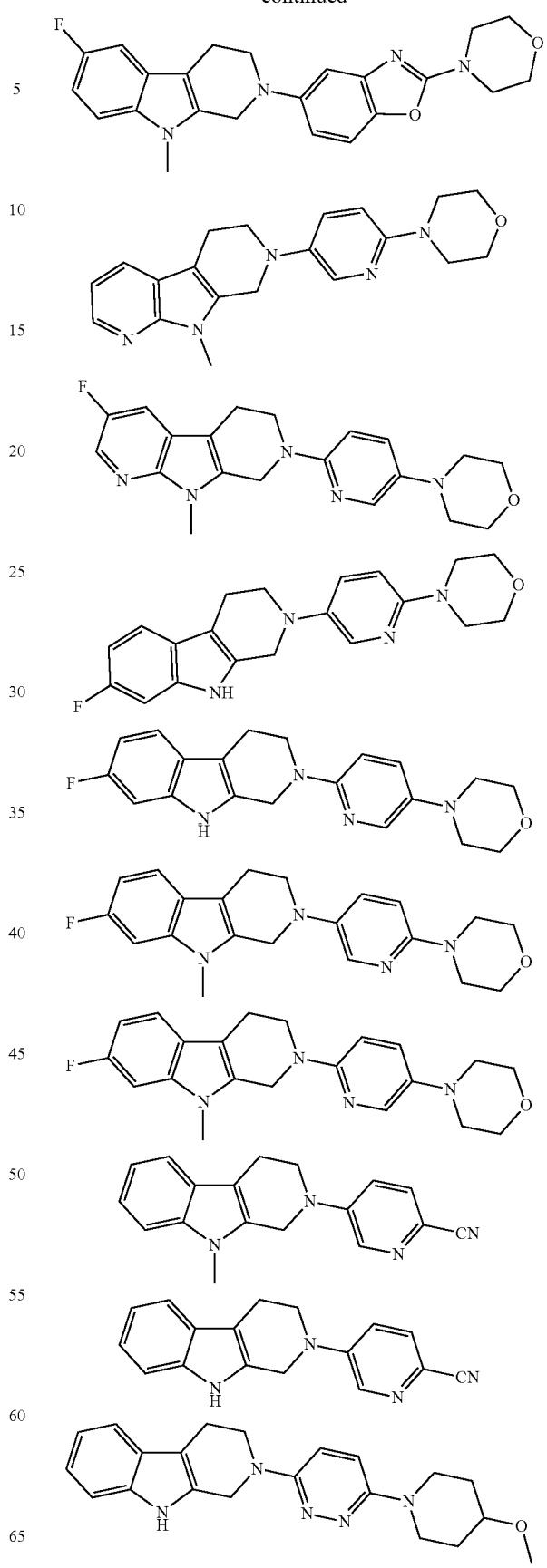

41
-continued
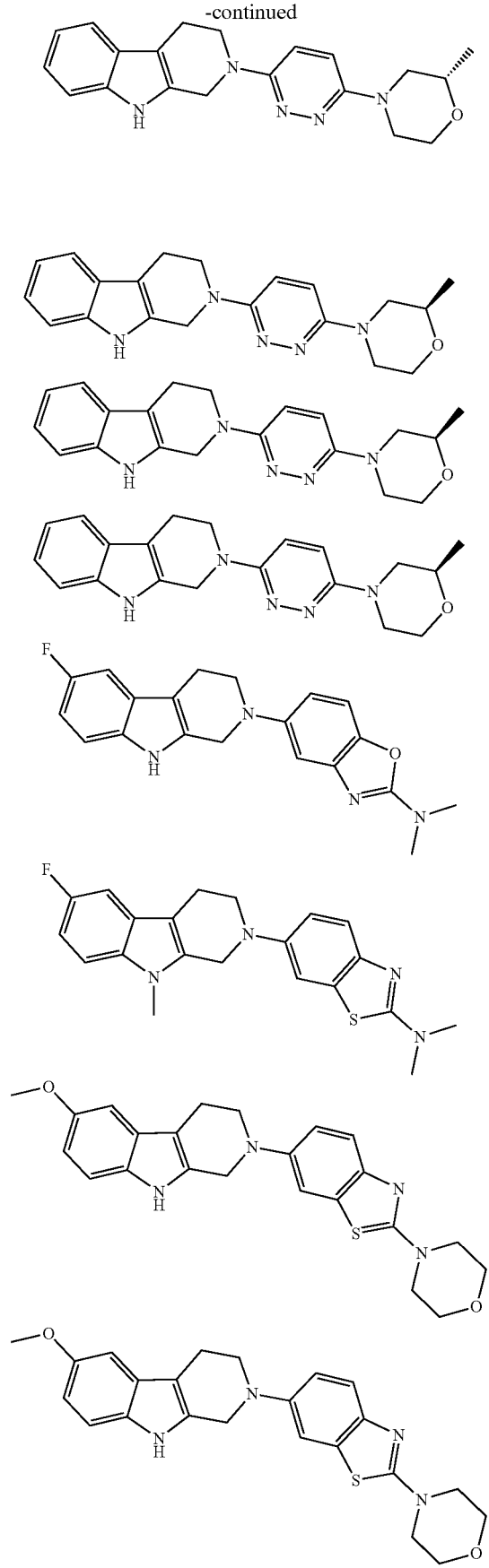
42
-continued
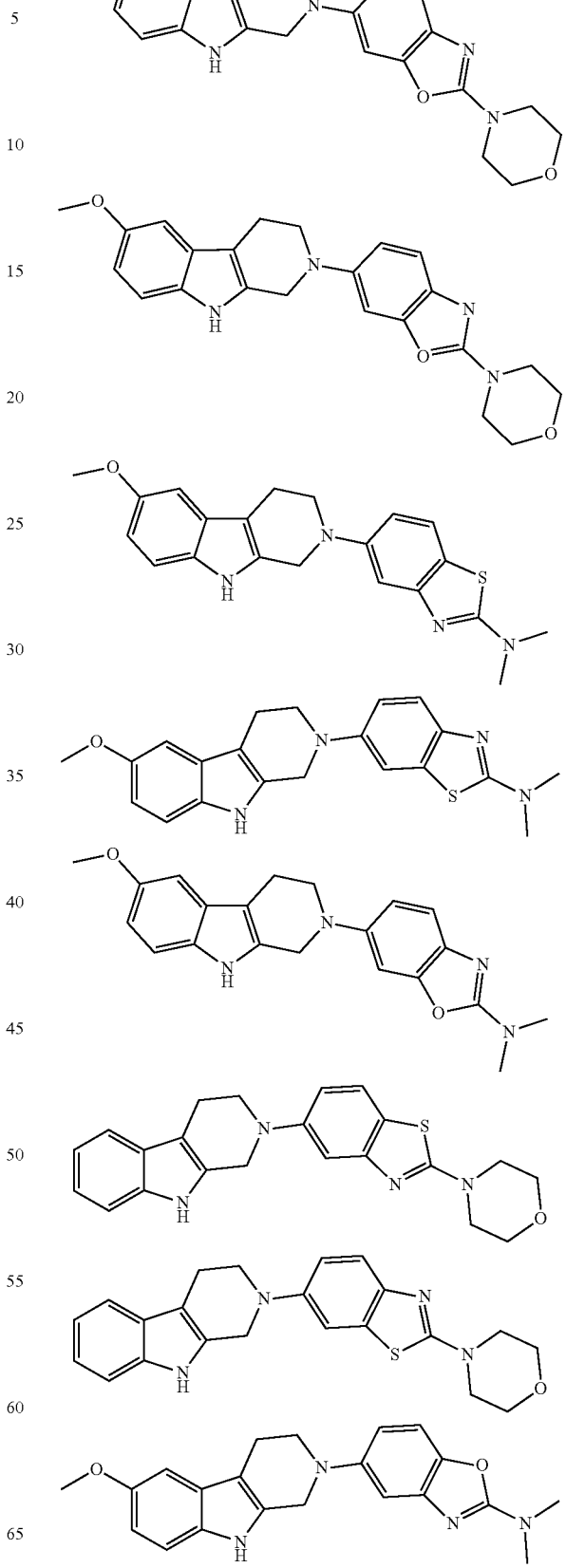

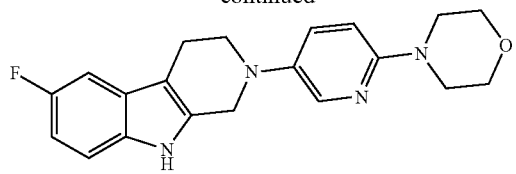
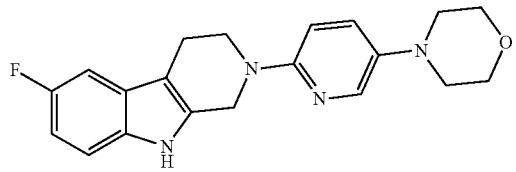
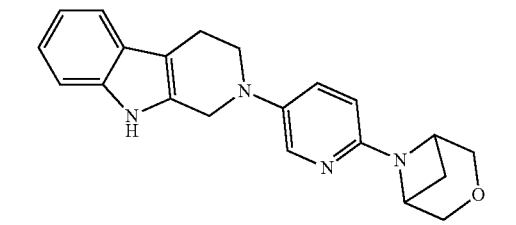
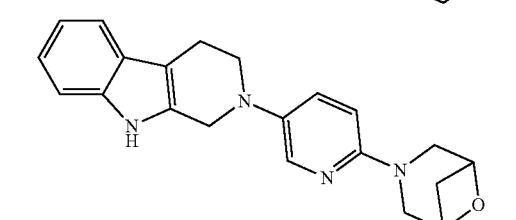
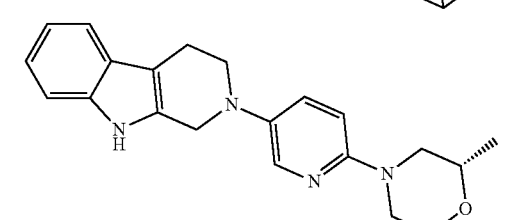
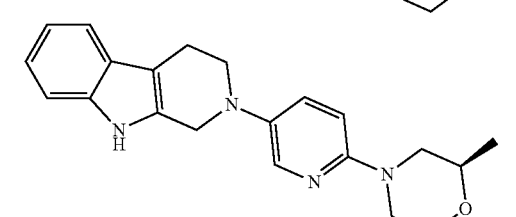
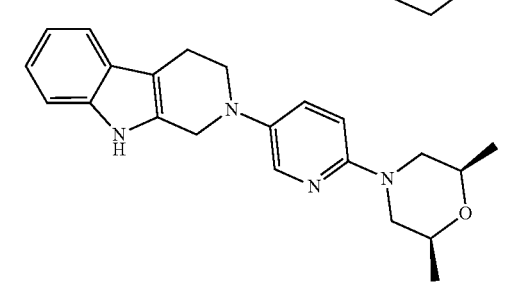
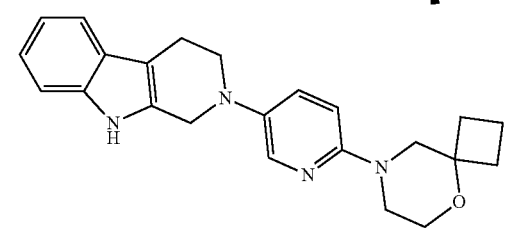
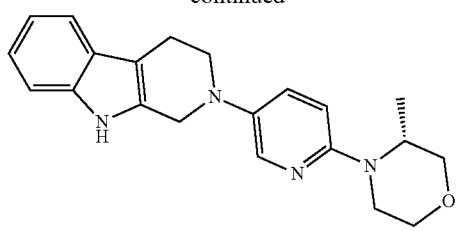
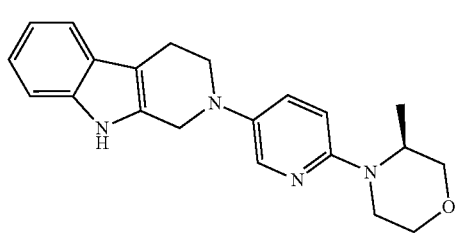
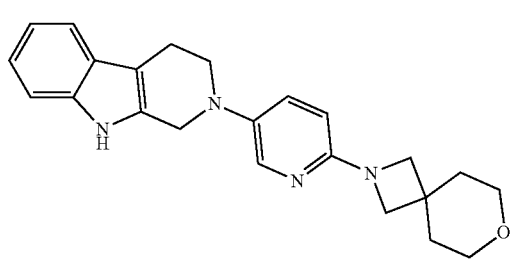
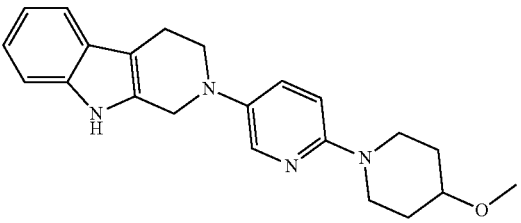
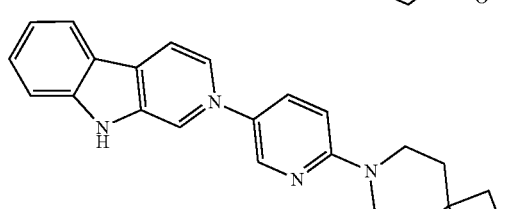
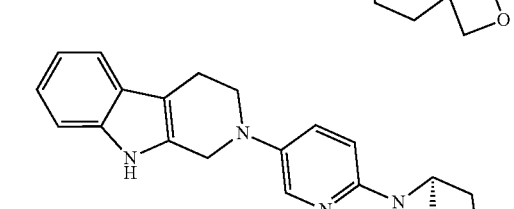
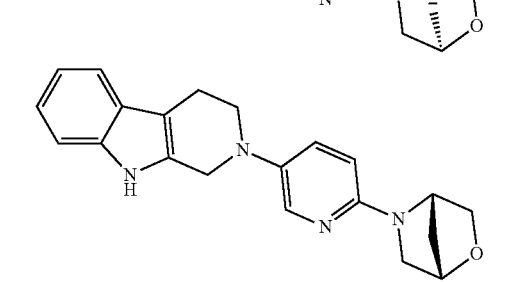

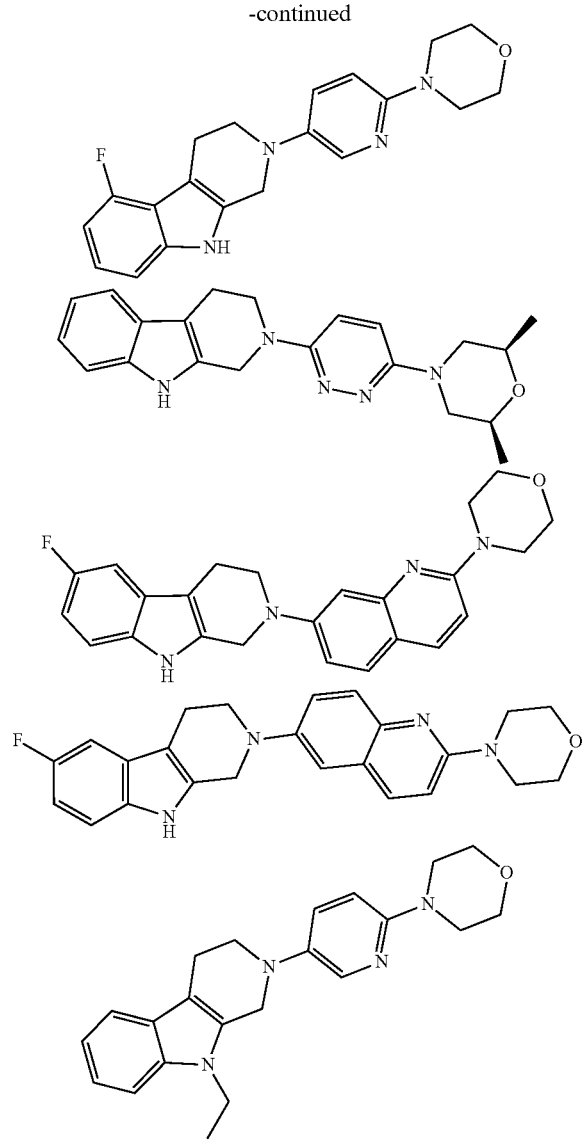

Preferred compounds are also illustrated in the examples.

Any combination of the embodiments, preferred embodiments and more preferred embodiments disclosed herein is also envisaged in the present invention.

Pharmaceutical Compositions

While it is possible for the compounds of the present invention to be administered alone, it is preferable to formulate them into a pharmaceutical composition in accordance with standard pharmaceutical practice. Thus, the invention also provides a pharmaceutical composition which comprises a therapeutically effective amount of a compound of formula (I) optionally in admixture with a pharmaceutically acceptable carrier, diluent, adjuvant or excipient.

Pharmaceutically acceptable excipients are well known in the pharmaceutical art, and are described, for example, in Remington's Pharmaceutical Sciences, 15$^{th}$ Ed., Mack Publishing Co., New Jersey (1975). The pharmaceutical excipient can be selected with regard to the intended route of administration and standard pharmaceutical practice. The excipient must be acceptable in the sense of being not deleterious to the recipient thereof.

Pharmaceutically useful excipients that may be used in the formulation of the pharmaceutical composition of the present invention may comprise, for example, carriers, vehicles, diluents, solvents such as monohydric alcohols such as ethanol, isopropanol and polyhydric alcohols such as glycols and edible oils such as soybean oil, coconut oil, olive oil, safflower oil cottonseed oil, oily esters such as ethyl oleate, isopropyl myristate, binders, adjuvants, solubilizers, thickening agents, stabilizers, disintegrants, glidants, lubricating agents, buffering agents, emulsifiers, wetting agents, suspending agents, sweetening agents, colorants, flavors, coating agents, preservatives, antioxidants, processing agents, drug delivery modifiers and enhancers such as calcium phosphate, magnesium stearate, talc, monosaccharides, disaccharides, starch, gelatin, cellulose, methylcellulose, sodium carboxymethyl cellulose, dextrose, hydroxypropyl-R-cyclodextrin, polyvinylpyrrolidone, low melting waxes, and ion exchange resins.

The routes for administration (delivery) of the compounds of the invention include, but are not limited to, one or more of: oral (e. g. as a tablet, capsule, or as an ingestible solution), topical, mucosal (e. g. as a nasal spray or aerosol for inhalation), nasal, parenteral (e. g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual.

For example, the compounds can be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

If the compounds of the present invention are administered parenterally, then examples of such administration include one or more of: intravenously, intraarterially, intraperitoneally, intrathecally, intraventricularly, intraurethrally, intrasternally, intracranially, intramuscularly or subcutaneously administering the compounds; and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

As indicated, the compounds of the present invention can be administered intranasally or by inhalation and are conveniently delivered in the form of a dry powder inhaler or an aerosol spray presentation from a pressurized container, pump, spray or nebulizer with the use of a suitable propellant, e. g. dichlorodifluoromethane, trichlorofluoromethane, dichlorotetrafluoroethane, a hydrofluoroalkane such as 1,1,1,2-tetrafluoroethane (HFA134AT) or 1,1,1,2,3,3,3-heptafluoropropane (HFA 227EA), carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e. g. using a mixture of ethanol and the propellant as the solvent, which may additionally contain a lubricant, e. g. sorbitan trioleate. Capsules and cartridges (made, for example, from gelatin) for use in an inhaler or insufflator may be formulated to contain a powder mix of the compound and a suitable powder base such as lactose or starch.

Alternatively, the compounds of the present invention can be administered in the form of a suppository or pessary, or it may be applied topically in the form of a gel, hydrogel, lotion, solution, cream, ointment or dusting powder. The compounds of the present invention may also be dermally or transdermally administered, for example, by the use of a skin patch.

They may also be administered by the pulmonary or rectal routes. They may also be administered by the ocular route. For ophthalmic use, the compounds can be formulated as micronized suspensions in isotonic, pH was adjusted, sterile saline, or, preferably, as solutions in isotonic, pH was adjusted, sterile saline, optionally in combination with a preservative such as a benzylalkonium chloride. Alternatively, they may be formulated in an ointment such as petrolatum.

For application topically to the skin, the compounds of the present invention can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Typically, a physician will determine the actual dosage which will be most suitable for an individual subject. The specific dose level and frequency of dosage for any particular individual may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

A proposed dose of the compounds according to the present invention for administration to a human (of approximately 70 kg body weight) is 0.1 mg to 1 g, preferably 1 mg to 500 mg of the active ingredient per unit dose. The unit dose may be administered, for example, 1 to 4 times per day. The dose will depend on the route of administration. It will be appreciated that it may be necessary to make routine variations to the dosage depending on the age and weight of the patient as well as the severity of the condition to be treated. The precise dose and route of administration will ultimately be at the discretion of the attendant physician or veterinarian.

The compounds of the invention may also be used in combination with other therapeutic agents. When a compound of the invention is used in combination with a second therapeutic agent active against the same disease, the dose of each compound may differ from that when the compound is used alone.

The combinations referred to above may conveniently be presented for use in the form of a pharmaceutical formulation. The individual components of such combinations may be administered either sequentially or simultaneously in separate or combined pharmaceutical formulations by any convenient route. When administration is sequential, either the compound of the invention or the second therapeutic agent may be administered first. When administration is simultaneous, the combination may be administered either in the same or different pharmaceutical composition. When combined in the same formulation it will be appreciated that the two compounds must be stable and compatible with each other and the other components of the formulation. When formulated separately they may be provided in any convenient formulation, conveniently in such manner as are known for such compounds in the art.

The pharmaceutical compositions of the invention can be produced in a manner known per se to the skilled person as described, for example, in Remington's Pharmaceutical Sciences, $15^{th}$ Ed., Mack Publishing Co., New Jersey (1975).

The diseases or conditions that can be treated, alleviated or prevented with the compounds of the present invention are disorders or abnormalities associated with Tau protein aggregates such as neurodegenerative disorders. Examples of diseases and conditions which can be treated, alleviated or prevented are caused by or associated with the formation of neurofibrillary lesions. This is the predominant brain pathology in tauopathy. The diseases and conditions comprise a heterogeneous group of neurodegenerative diseases or conditions including diseases or conditions which show co-existence of Tau and amyloid pathologies.

Examples of the diseases and conditions which can be treated, alleviated or prevented include, but are not limited, to Alzheimer's disease (AD), familial AD, PART (Primary Age-Related Tauopathy), Creutzfeldt-Jacob disease, dementia pugilistica, Down's Syndrome, Gerstmann-Straussler-Scheinker disease (GSS), inclusion-body myositis, prion protein cerebral amyloid angiopathy, traumatic brain injury (TBI), amyotrophic lateral sclerosis (ALS), Parkinsonism-dementia complex of Guam, non-Guamanian motor neuron disease with neurofibrillary tangles, argyrophilic grain disease, corticobasal degeneration (CBD), diffuse neurofibrillary tangles with calcification, frontotemporal dementia with Parkinsonism linked to chromosome 17 (FTDP-17), Hallervorden-Spatz disease, multiple system atrophy (MSA), Niemann-Pick disease type C, pallido-ponto-nigral degeneration, Pick's disease (PiD), progressive subcortical gliosis, progressive supranuclear palsy (PSP), subacute sclerosing panencephalitis, tangle predominant dementia, postencephalitic Parkinsonism, myotonic dystrophy, subacute sclerosis panencephalopathy, mutations in LRRK2, chronic traumatic encephalopathy (CTE), familial British dementia, familial Danish dementia, other frontotemporal lobar degenerations, Guadeloupean Parkinsonism, neurodegeneration with brain iron accumulation, SLC9A6-related mental retardation, white matter tauopathy with globular glial inclusions, epilepsy, Lewy body dementia (LBD), mild cognitive impairment (MCI), multiple sclerosis, Parkinson's disease, HIV-related dementia, adult onset diabetes, senile cardiac amyloidosis, glaucoma, ischemic stroke, psychosis in AD and Huntington's disease. Preferably the diseases and conditions which can be treated, alleviated or prevented include Alzheimer's disease (AD), as well as other neurodegenerative tauopathies such as Creutzfeldt-Jacob disease, dementia pugilistica, amyotrophic lateral sclerosis (ALS), argyrophilic grain disease, corticobasal degeneration (CBD), frontotemporal dementia with Parkinsonism linked to chromosome 17 (FTDP-17), Pick's disease (PiD), progressive supranuclear palsy (PSP), tangle predominant dementia, Parkinson dementia complex of Guam, Hallervorden-Spatz disease, chronic traumatic encephalopathy (CTE), traumatic brain injury (TBI), and other frontotemporal lobar degeneration. More preferably Alzheimer's disease (AD), corticobasal degeneration (CBD), Pick's disease (PiD), and progressive supranuclear palsy (PSP).

The compounds of the present invention can also be employed to decrease protein aggregation, in particular Tau aggregation. The ability of a compound to decrease of Tau aggregation can, for example, be determined using the ThT assay (Hudson et al., FEBS J., 2009, 5960-72).

The compounds of the invention can be used in the treatment of a wide range of disorders in which the neuroinflammation process is associated with misfolding and/or pathologic aggregation of Tau protein.

The compounds of the present invention can be used as an analytical reference or an in vitro screening tool for characterization of tissue with Tau pathology and for testing of compounds targeting Tau pathology on such tissue.

The compounds according to the present invention can also be provided in the form of a mixture with at least one further biologically active compound and/or a pharmaceutically acceptable carrier and/or a diluent and/or an excipient. The compound and/or the further biologically active compound are preferably present in a therapeutically effective amount.

The nature of the further biologically active compound will depend on the intended use of the mixture. The further biologically active substance or compound may exert its biological effect by the same or a similar mechanism as the compound according to the invention or by an unrelated mechanism of action or by a multiplicity of related and/or unrelated mechanisms of action.

Generally, the further biologically active compound may include neutron-transmission enhancers, psychotherapeutic drugs, acetylcholineesterase inhibitors, calcium-channel blockers, biogenic amines, benzodiazepine tranquillizers, acetylcholine synthesis, storage or release enhancers, acetylcholine postsynaptic receptor agonists, monoamine oxidase-A or -B inhibitors, N-methyl-D-aspartate glutamate receptor antagonists, non-steroidal anti-inflammatory drugs, antioxidants, and serotonergic receptor antagonists. In particular, the further biologically active compound can be selected from the group consisting of a compound used in the treatment of amyloidosis, compounds against oxidative stress, anti-apoptotic compounds, metal chelators, inhibitors of DNA repair such as pirenzepine and metabolites, 3-amino-1-propanesulfonic acid (3APS), 1,3-propanedisulfonate (1,3PDS), α-secretase activators, β- and β-secretase inhibitors, Tau proteins, neurotransmitter, β-sheet breakers, attractants for amyloid beta clearing/depleting cellular components, inhibitors of N-terminal truncated amyloid beta including pyroglutamated amyloid beta 3-42, anti-inflammatory molecules, or cholinesterase inhibitors (ChEIs) such as tacrine, rivastigmine, donepezil, and/or galantamine, M1 agonists, other drugs including any amyloid or Tau modifying drug and nutritive supplements, an antibody, including any functionally equivalent antibody or functional parts thereof, or a vaccine.

In a further embodiment, the mixtures according to the invention may comprise niacin or memantine together with a compound according to the present invention and, optionally, a pharmaceutically acceptable carrier and/or a diluent and/or an excipient.

In still another embodiment of the invention mixtures are provided that comprise as a further biologically active compound "atypical antipsychotics" such as, for example clozapine, ziprasidone, risperidone, aripiprazole or olanzapine for the treatment of positive and negative psychotic symptoms including hallucinations, delusions, thought disorders (manifested by marked incoherence, derailment, tangentiality), and bizarre or disorganized behavior, as well as anhedonia, flattened affect, apathy, and social withdrawal, together with a compound according to the invention and, optionally, a pharmaceutically acceptable carrier and/or a diluent and/or an excipient.

Other compounds that can be suitably used in mixtures in combination with the compound according to the present invention are, for example, described in WO 2004/058258 (see especially pages 16 and 17) including therapeutic drug targets (pages 36 to 39), alkanesulfonic acids and alkanolsulfuric acids (pages 39 to 51), cholinesterase inhibitors (pages 51 to 56), NMDA receptor antagonists (pages 56 to 58), estrogens (pages 58 to 59), non-steroidal anti-inflammatory drugs (pages 60 and 61), antioxidants (pages 61 and 62), peroxisome proliferators-activated receptor (PPAR) agonists (pages 63 to 67), cholesterol-lowering agents (pages 68 to 75), amyloid inhibitors (pages 75 to 77), amyloid formation inhibitors (pages 77 to 78), metal chelators (pages 78 and 79), anti-psychotics and anti-depressants (pages 80 to 82), nutritional supplements (pages 83 to 89) and compounds increasing the availability of biologically active substances in the brain (see pages 89 to 93) and prodrugs (pages 93 and 94), which document is incorporated herein by reference.

The invention also includes all suitable isotopic variations of the compounds of the invention. An isotopic variation of the compound of the invention is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, sulphur, fluorine and chlorine such as $^{2}H$, $^{3}H$, $^{13}V$, $^{14}V$, $^{15}N$, $^{17}O$, $^{18}O$, $^{35}S$, $^{18}F$ and $^{36}Cl$ respectively. Certain isotopic variations of the invention, for example, those in which a radioactive isotope such as $^{3}H$ or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and delectability. $^{18}F$-labeled compounds are particularly suitable for imaging applications such as PET. Further, substitution with isotopes such as deuterium, i.e., $^{2}H$, may afford certain therapeutic advantages resulting from greater metabolic stability, for example, increased in vivo half-life or reduced dosage requirements and hence may be preferred in some circumstances. Isotopic variations of the compounds of the invention can generally be prepared by conventional procedures such as by the illustrative methods or by the preparations described in the Examples and Preparations hereafter using appropriate isotopic variations of suitable reagents.

The compounds of the present invention can be synthesized by one of the general methods shown in the following schemes. These methods are only given for illustrative purposes and should not to be construed as limiting.

General Synthetic Schemes for the Preparation of Building Blocks of this Invention:

Scheme 1

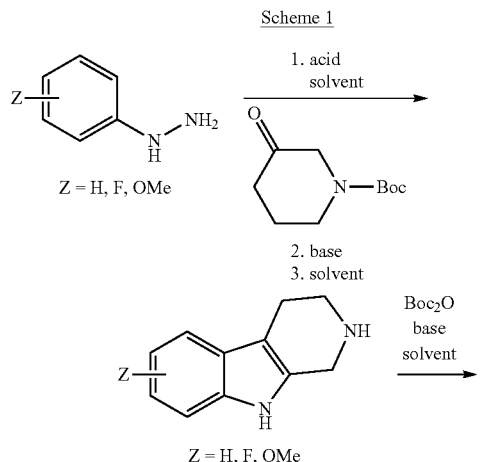

Z = H, F, OMe

Heating of commercially available phenylhydrazine derivatives (Z=H, F or OMe) with commercially available tert-butyl 3-oxopiperidine-1-carboxylate in a suitable solvent under acidic conditions (Fischer-Indole synthesis) afforded the tricyclic derivatives (regiomer formation possible for Z=F or OMe) after purification. In case regioisomers were formed, they were separated by supercritical fluid chromatography (SFC) to obtain the desired tetrahydro-1H-pyrido[3,4-b]indole derivatives. The aliphatic, secondary NH-moiety of the tricyclic building blocks was further protected with the Boc-protecting group using an appropriate solvent and base to afford the desired Boc-protected building blocks after purification.

Scheme 2

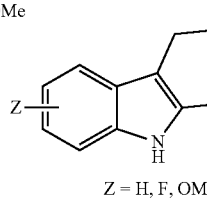

Z = H, F, OMe
T = CH₃, tosyl

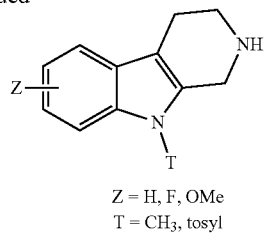

Z = H, F, OMe
T = CH₃, tosyl

The NH-moiety of the tricyclic building blocks was treated with either methyl iodide or tosyl chloride in an appropriate solvent using a suitable base to afford the N-methyl or N-tosyl derivatives after purification. The Boc-protecting group was cleaved by acid treatment in an appropriate solvent to afford the desired N-methyl or N-tosyl tricyclic building blocks after purification. In case there was no base treatment after cleavage of the Boc-protecting group, the corresponding salts were obtained.

Scheme 3

Heating of commercially available phenylhydrazine derivatives (Z=F) with commercially available tert-butyl 2-oxo-8-azabicyclo[3.2.1]octane-8-carboxylate in a suitable solvent under acidic conditions (Fischer indole synthesis) afforded the tricyclic derivatives. In case of 2- or 3-substituted phenylhydrazine derivatives, the regioisomers were separated by supercritical fluid chromatography (SFC). The aliphatic, secondary amine moiety was then Boc-protected using appropriate solvents and base to afford the desired building block after purification. The NH-moiety of the indole moiety was then treated with tosyl chloride in an appropriate solvent using a suitable base to afford the N-tosyl derivatives after purification. The Boc-protecting group was cleaved by acid treatment in an appropriate solvent to afford the tricyclic building blocks containing a secondary amine after purification. In case there was no base treatment after cleavage of the Boc-protecting group, the corresponding salts were obtained.

Scheme 4

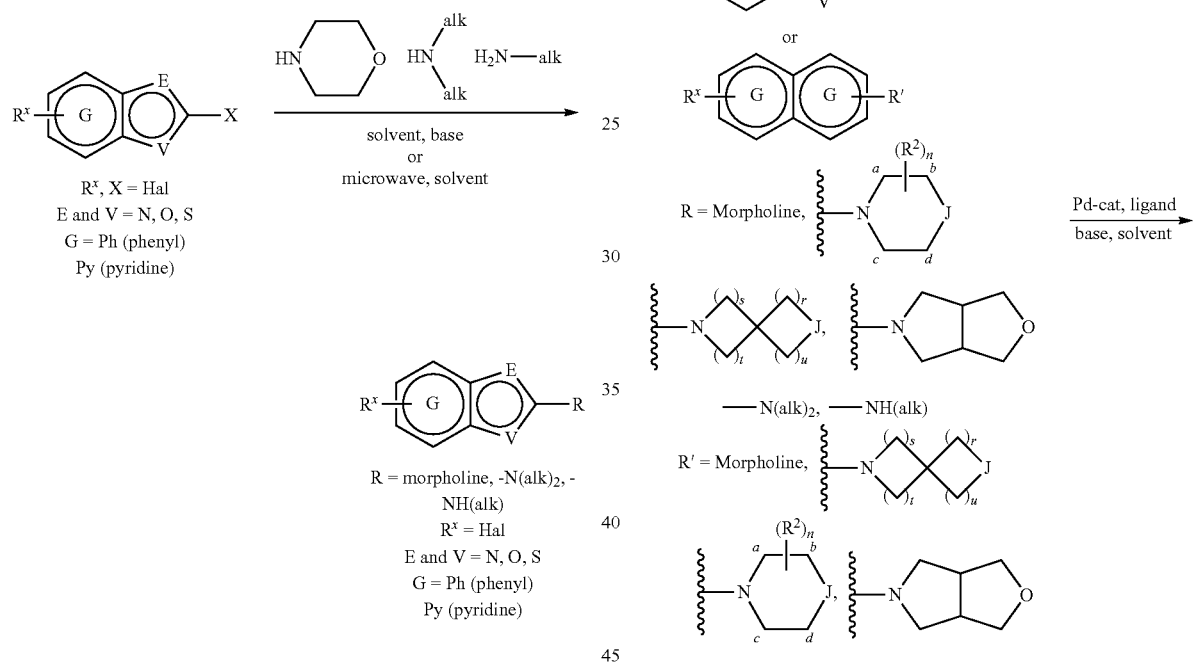

Scheme 5

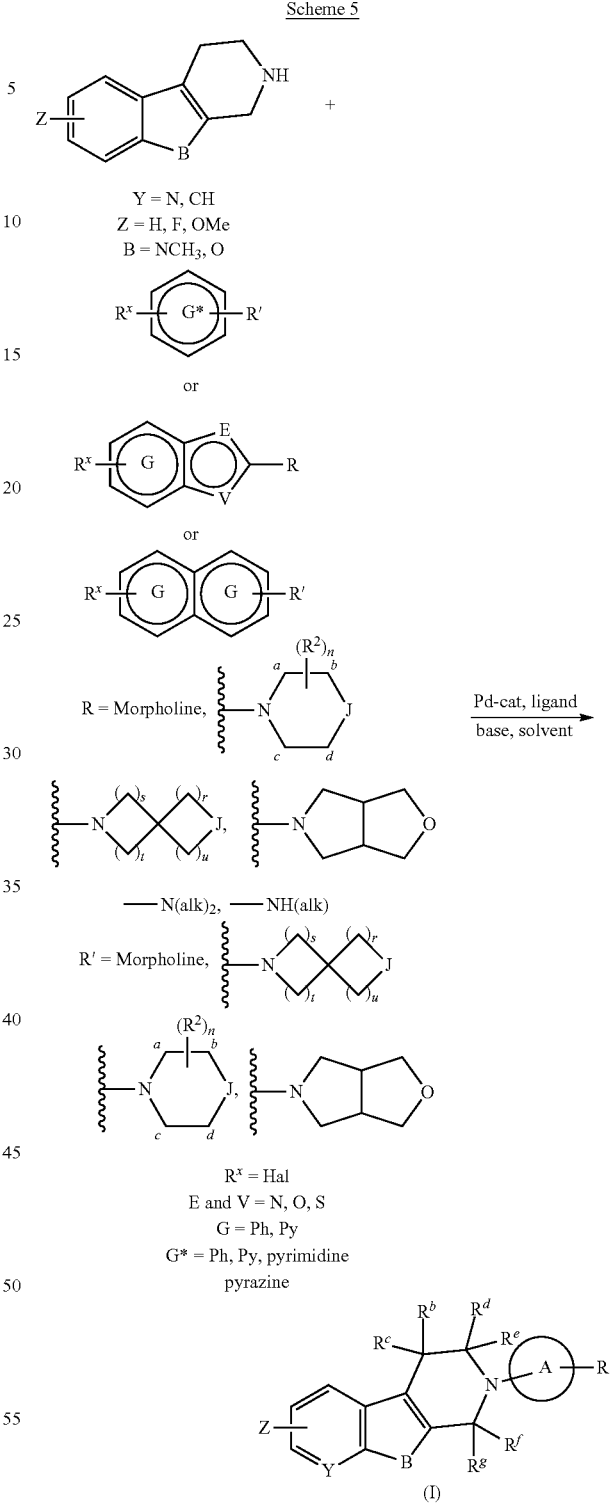

Commercially available benzo[d]thiazole (G=Ph) or benzo[d]oxazole (G=Ph) derivatives containing two halogen (Br or Cl) atoms were treated with primary or secondary amines in an appropriate solvent and with an additional base. The leaving group X was replaced via nucleophilic substitution by the primary or secondary amines to afford the corresponding amino-substituted benzo[d]thiazole or benzo[d]oxazole derivatives after purification. In case of less reactive amines, the desired benzo[d]thiazole or benzo[d]oxazole derivatives were obtained by performing the nucleophilic substitution reaction under microwave conditions. The corresponding thiazolo[5,4-b]pyridine (G=Py) and thiazolo[4,5-b]pyridine (G=Py) derivatives containing two halogen (Br or Cl) atoms were treated with morpholine in an appropriate solvent and with an additional base and the corresponding nucleophilic displacement products (morpholino-thiazolo[5,4-b]pyridine (G=Py) and morpholino-thiazolo[4,5-b]pyridine (G=Py) derivatives) were obtained after purification.

General Synthetic Schemes for the Preparation of Compounds of this Invention:

The tricyclic building blocks with B=NCH$_3$, O were coupled with substituted benzo[d]thiazole or benzo[d]oxazole derivatives, or substituted phenyl or pyridine derivatives, via palladium chemistry with a suitable palladium source like Palladium(II) acetate (Pd(OAc)$_2$), Tris(dibenzylideneacetone)dipalladium(0) (Pd$_2$(dba)$_3$) a suitable ligand like 2-dicyclohexylphosphino-2',6'-diisopropoxybiphenyl (RuPhos), 4,5-Bis(diphenylphosphino)-9,9-dimethylxanthene (Xantphos), 2-Dicyclohexylphosphino-2',4',6'-triisopropylbiphenyl (Xphos) and a suitable base like Cesium carbonate (Cs$_2$CO$_3$) and Sodium tert-butoxide (NaOtBu) in a suitable solvent like Dioxane to afford the desired compounds of formula (I) after purification.

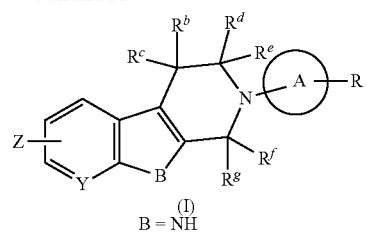

The tricyclic building blocks containing a N-tosyl group at the indole moiety, were coupled with substituted benzo[d]thiazole or benzo[d]oxazole derivatives, or substituted phenyl or pyridine derivatives, via palladium chemistry with a suitable palladium source like Palladium(II) acetate (Pd(OAc)$_2$), Tris(dibenzylideneacetone)dipalladium(0) (Pd$_2$(dba)$_3$) a suitable ligand like 2-dicyclohexylphosphino-2',6'-diisopropoxybiphenyl (RuPhos), 4,5-Bis(diphenylphosphino)-9,9-dimethylxanthene (Xantphos), 2-Dicyclohexylphosphino-2',4',6'-triisopropylbiphenyl (Xphos) and a suitable base like Cesium carbonate (Cs$_2$CO$_3$) and Sodium tert-butoxide (NaOtBu) in a suitable solvent like Dioxane to afford the desired compounds of formula (I) after purification. In case the tosyl-group is not cleaved during the palladium coupling, the tosyl protected compounds were generally treated with a suitable base like Sodium tert-butoxide (NaOtBu) in appropriate solvents mixture like Dioxane and Methanol to afford the desired compounds of formula (I) after purification.

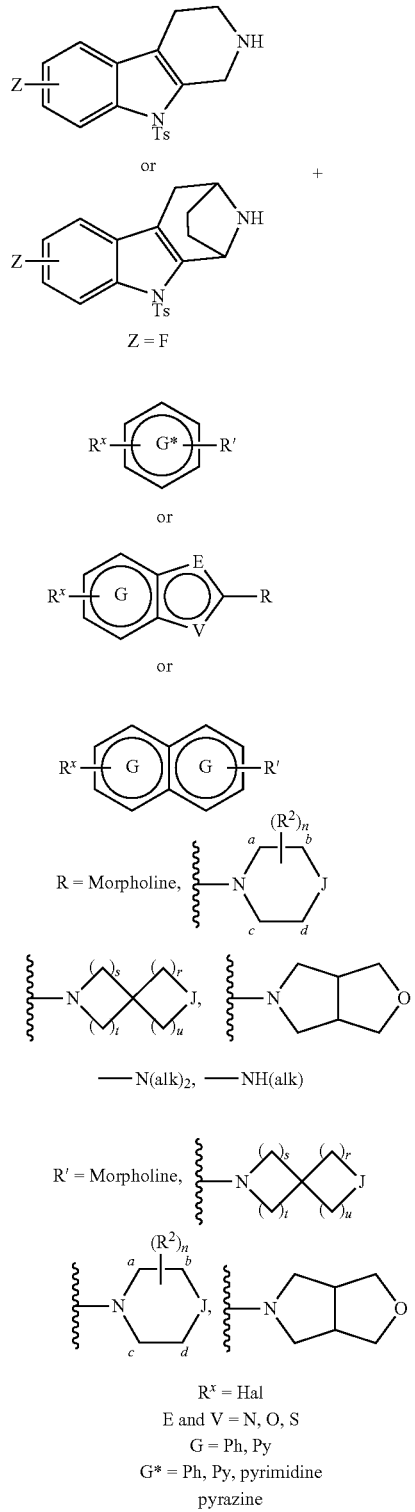

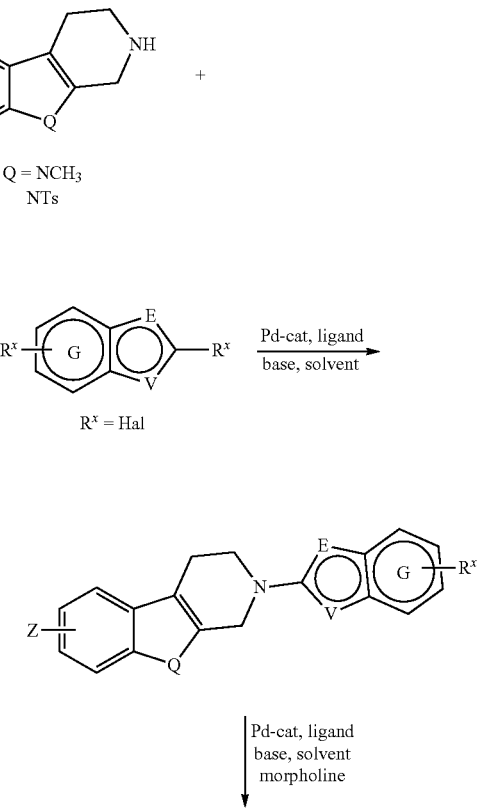

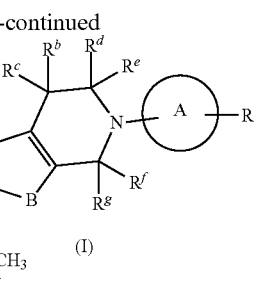

B = NCH₃ (I)
NH

The tricyclic building blocks containing a N-tosyl- or NCH₃-group at the indole moiety, were coupled with halogen-substituted benzo[d]thiazole or benzo[d]oxazole derivatives via palladium chemistry with a suitable palladium source like Palladium(II) acetate (Pd(OAc)₂), Tris(dibenzylideneacetone)dipalladium(0) (Pd₂(dba)₃) a suitable ligand like 2-dicyclohexylphosphino-2',6'-diisopropoxybiphenyl (RuPhos), 4,5-Bis(diphenylphosphino)-9,9-dimethylxanthene (Xantphos), 2-Dicyclohexylphosphino-2',4',6'-thisopropylbiphenyl (Xphos) and a suitable base like Cesium carbonate (Cs₂CO₃) and Sodium tert-butoxide (NaOtBu) in a suitable solvent like Dioxane to afford the desired intermediates. Subsequent palladium coupling of the mono-halogenated intermediates with morpholine using similar conditons was described for the first step, afforded the desired compounds of formula (I) after purification. In case the tosyl-group is not cleaved during the final palladium coupling, the tosyl protected compounds were generally treated with a suitable base like Sodium tert-butoxide (NaOtBu) in appropriate solvents mixture like Dioxane and Methanol to afford the desired compounds of formula (I) after purification.

EXAMPLES

All reagents and solvents were obtained from commercial sources and used without further purification. 1H NMR spectra were recorded on Bruker AV 300 and 400 MHz spectrometers in deuterated solvents. Chemical shifts (δ) are reported in parts per million and coupling constants (J values) in hertz. Spin multiplicities are indicated by the following symbols: s (singlet), d (doublet), t (triplet), q (quartet), m (multiplet), bs (broad singlet). Mass spectra were obtained on an Agilent 1290 Infinity II spectrometer with a 6130 Chemstation and an Agilent 1200 Infinity II spectrometer with a 6130 Chemstation. GC-MS data were collected using an Agilent 7890B gas chromatograph and 5977B mass spectrometer. Infrared spectra were obtained on a PerkinElmer spectrometer. Chromatography was performed using silica gel (Fluka: Silica ge10l 60, 0.063-0.2 mm) and suitable solvents as indicated in specific examples. Flash purification was conducted with a Biotage Isolera with HP-Sil or KP-NH SNAP cartridges (Biotage) and the solvent gradient indicated in specific examples. Thin layer chromatography (TLC) was carried out on silica gel plates with UV detection.

Preparative Example 1

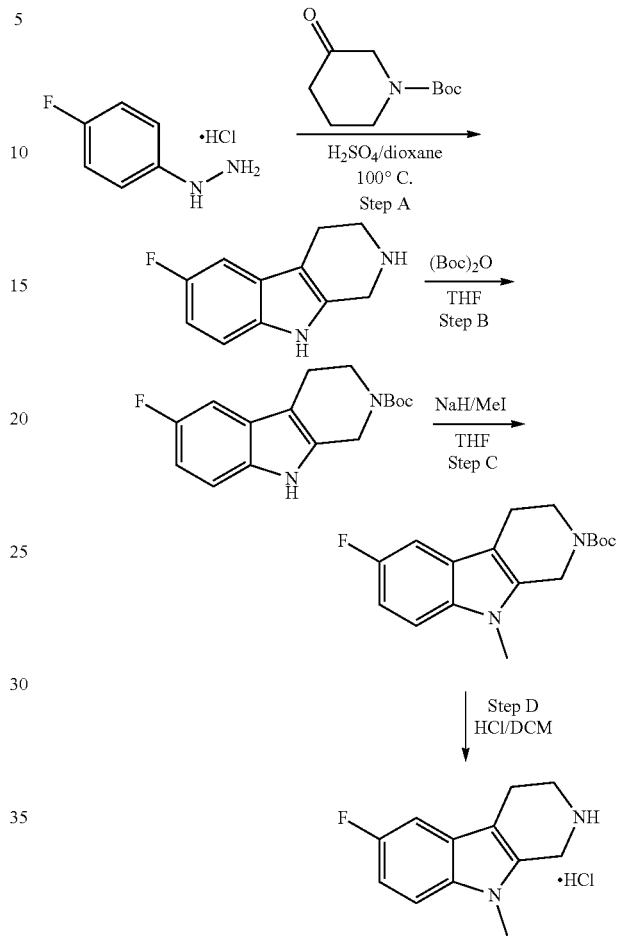

Step A

To a solution of (4-fluorophenyl)hydrazine HCl-salt (1 g, 6.1 mmol) and tert-butyl 3-oxopiperidine-1-carboxylate (1.2 g, 6.1 mmol) in 1,4-dioxane (10 mL) was added conc. H₂SO₄ (1 mL), 0° C. Then the reaction mixture was heated at 110° C. for 3 h. The reaction mixture was cooled to 25° C. and the precipitate was filtered off. The solid was dissolved in water basified with NaOH solution and extracted with dichloromethane. The organic phase was separated, dried over Na₂SO₄, filtered and the solvent was removed under reduced pressure to afford the cyclized title compound as a pale yellow solid (0.6 g, 54%).

¹H-NMR (400 MHz, DMSO-d₆) δ=10.73 (br-s, 1H), 7.21-7.22 (m, 1H), 7.06-7.07 (m, 1H), 6.78-6.79 (m, 1H), 3.83 (s, 2H), 2.94-2.95 (m, 2H), 2.49-2.50 (m, 2H).

MS: 191 (M+H)⁺.

Step B

To a solution of the title compound from Step A above (0.6 g, 3.15 mmol) in THF (10 mL) was added triethylamine (1.3 mL, 9.47 mmol) and di-tert-butyl dicarbonate (0.757 g, 3.46 mmol) and the reaction mixture was stirred for 12 h. After the completion of the reaction as evidenced by TLC, the solvent was removed under reduced pressure and the crude reaction mixture was purified by flash column chromatography using hexane/ethyl acetate (80:20) to afford the title compound as a pale yellow solid (0.55 g, 60%).

$^1$H-NMR (400 MHz, DMSO-d$_6$) δ=10.94 (br-s, 1H), 7.26-7.28 (m, 1H), 7.12-7.13 (m, 1H), 6.83-6.84 (m, 1H), 4.55 (s, 2H), 3.64-3.66 (m, 2H), 2.65 (s, 2H), 1.47 (s, 9H).

MS: 191 (M-Boc)$^+$.

Step C

To a solution of the title compound from Step B above (0.55 g, 1.89 mmol) in THF (5 mL) was added sodium hydride (0.136 g, 5.6 mmol), and followed by methyl iodide (0.13 mL, 2.07 mmol). The reaction mixture was stirred at room temperature for 2 h. The mixture was dissolved in ethyl acetate (20 mL) and washed with water and brine. The organic phase was separated, dried over Na$_2$SO$_4$, filtered and the solvent removed under reduced pressure. The crude reaction mixture was purified by flash column chromatography using hexane/ethyl acetate (70:30) to afford the methylated title compound (0.42 g, 73%).

$^1$H-NMR (400 MHz, DMSO-d$_6$) δ=7.40-7.42 (m, 1H), 7.18-7.19 (m, 1H), 6.92-6.93 (m, 1H), 4.61 (s, 2H), 3.64-3.65 (m, 5H), 2.67 (br-s, 2H), 1.47 (s, 9H).

MS: 305.0 (M+H)$^+$.

Step D

To a solution of the title compound from Step C above (0.42 g, 1.38 mmol) in dichloromethane (10 mL) was added 2N HCl (5 mL) in 1,4-dioxane. The reaction mixture was stirred overnight. After the completion of the reaction, the reaction mixture was evaporated to remove the solvent and washed with diethyl ether to afford the title compound as an off white solid (0.25 g, 80%).

$^1$H-NMR (400 MHz, DMSO-d$_6$) δ=9.83 (br-s, 1H), 7.47-7.50 (m, 1H), 7.30 (d, J=9.60 Hz, 1H), 7.02 (bs, 1H), 4.42 (s, 2H), 3.67 (s, 3H), 3.40 (br-s, 2H), 2.92 (br-s, 2H).

MS: 205.2 (M+H)$^+$.

Preparative Example 2

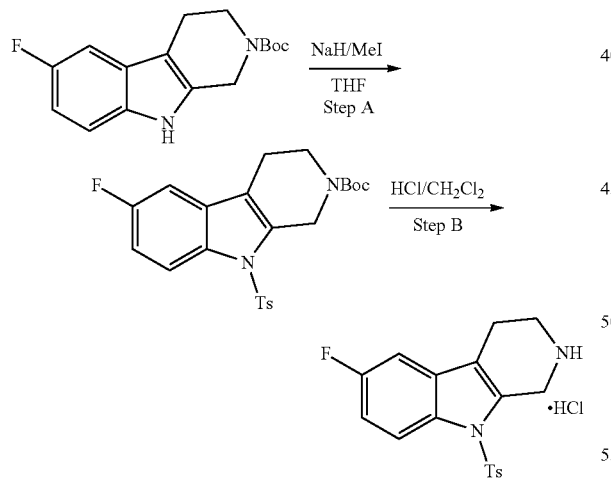

Step A

To a solution of the title compound from Preparative Example 1 Step B (0.55 g, 1.89 mmol) in THF (5 mL) was added sodium hydride (0.136 g, 5.6 mmol), and followed by p-toluenesulfonyl chloride (0.396 g, 2.07 mmol). The reaction mixture was stirred for 30 minutes at room temperature. The mixture was dissolved in ethyl acetate (20 mL) and washed with water and brine. The organic phase was separated, dried over Na$_2$SO$_4$, filtered and the solvent removed under reduced pressure. The crude reaction mixture was purified by flash column chromatography using hexane/ethyl acetate (70:30) to afford the title compound (0.4 g, 47%).

$^1$H-NMR (400 MHz, DMSO-d$_6$) δ=8.00 (s, 1H), 7.77 (s, 2H), 7.30-7.32 (m, 3H), 7.16-7.18 (m, 1H), 4.87 (s, 2H), 3.64 (s, 2H), 2.62 (br-s, 2H), 2.32 (s, 3H), 1.39 (s, 9H).

MS: 445.2 (M+H)$^+$.

Step B

To a solution of the title compound from Step A above (0.4 g, 0.9 mmol) in dichloromethane (10 mL) was added 2N HCl (5 mL) in 1,4-dioxane. The reaction mixture was stirred at room temperature for 12 h. After the completion of the reaction, the reaction mixture was evaporated to remove the solvent and washed with diethyl ether to afford the title compound as an off white solid (0.25 g, 80%). The crude product was taken as such for next step.

MS: 345.0 (M+H)$^+$.

Preparative Example 3

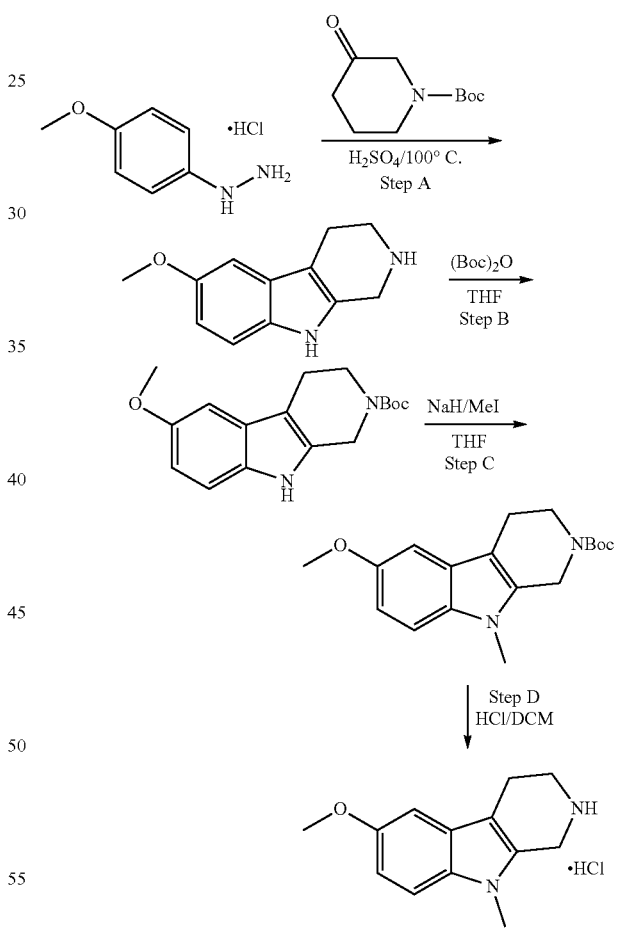

Step A

To a solution of (4-methoxyphenyl)hydrazine HCl-salt (10 g, 57.5 mmol) and tert-butyl 3-oxopiperidine-1-carboxylate (11.4 g, 57.5 mmol) in 1,4-dioxane (100 mL) was added conc. H$_2$SO$_4$ (10 mL), 0° C. Then the reaction mixture was heated at 110° C. for 3 h. The reaction mixture was cooled to 25° C. and the precipitate was filtered off. The solid was dissolved in water basified with NaOH solution and extracted with dichloromethane. The organic phase was separated, dried over Na₂SO₄, filtered and the solvent was removed under reduced pressure to afford the cyclized title compound as a brown, gummy solid (10 g, crude). The product was taken as such for next step.

MS: 203.2 (M+H)⁺.

Step B

To a solution of the title compound from Step A above (10 g, 49.5 mmol) in THF (10 mL) was added triethylamine (20 mL, 148.5 mmol) and di-tert-butyl dicarbonate (11.8 g, 54 mmol) and the reaction mixture was stirred for 12 h. After the completion of the reaction as evidenced by TLC, the solvent was removed under reduced pressure and the crude reaction mixture was purified by flash column chromatography using hexane/ethyl acetate (80:20) to afford the title compound as a white solid (4 g, 26.7%).

¹H-NMR (400 MHz, DMSO-d₆) δ=10.67 (br-s, 1H), 7.19 (d, J=8.40 Hz, 1H), 6.89 (d, J=2.00 Hz, 1H), 6.66-6.67 (m, 1H), 4.54 (s, 2H), 3.75 (s, 3H), 3.65-3.66 (m, 2H), 2.64-2.66 (m, 2H), 1.44 (s, 9H).

MS: 303.2 (M+H)⁺.

Step C

To a solution of the title compound from Step B above (2 g, 6.6 mmol) in THF (10 mL) was added sodium hydride (0.317 g, 13.2 mmol), and followed by methyl iodide (0.4 mL, 7.26 mmol). The reaction mixture was stirred at room temperature for 2 h. The mixture was dissolved in ethyl acetate (200 mL) and washed with water and brine. The organic phase was separated, dried over Na₂SO₄, filtered and the solvent removed under reduced pressure. The crude reaction mixture was purified by flash column chromatography using hexane/ethyl acetate (80:20) to afford the methylated title compound (0.65 g, 30%).

¹H-NMR (400 MHz, DMSO-d₆) δ=7.30 (d, J=8.80 Hz, 1H), 6.92 (s, 1H), 6.73-6.73 (m, 1H), 4.59 (s, 2H), 3.76 (s, 3H), 3.60-3.64 (m, 5H), 2.66-2.68 (m, 2H), 1.45 (s, 9H).

MS: 317.2 (M+H)⁺.

Step D

To a solution of the title compound from Step C above (0.65 g, 2.05 mmol) in dichloromethane (10 mL) was added 4N HCl (5 mL) in 1,4-dioxane. The reaction mixture was stirred overnight. After the completion of the reaction, the reaction mixture was evaporated to remove the solvent and washed with diethyl ether to afford the title compound as an off white solid (0.5 g, 98%).

¹H-NMR (400 MHz, DMSO-d₆) δ=9.80 (s, 2H), 7.35 (d, J=8.80 Hz, 1H), 6.99 (d, J=2.00 Hz, 1H), 6.79-6.80 (m, 1H), 4.39 (s, 2H), 3.77 (s, 3H), 3.63 (s, 3H), 3.38-3.40 (m, 2H), 2.90-2.92 (m, 2H).

MS: 217.3 (M+H)⁺.

Preparative Example 4

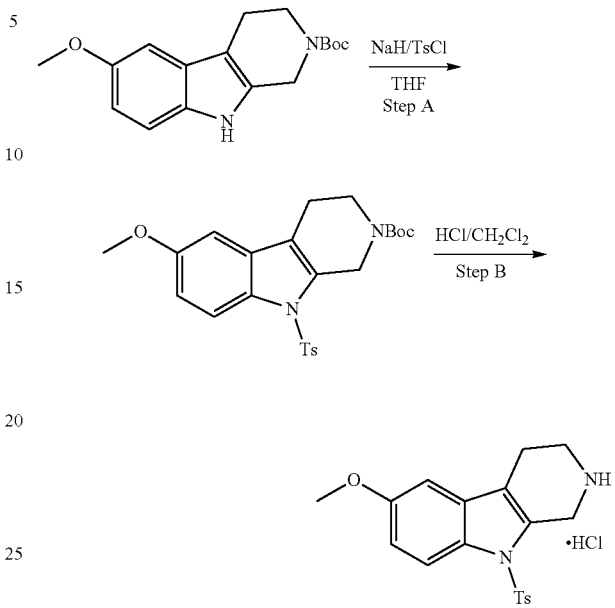

Step A

To a solution of the title compound from Preparative Example 3 Step B (2 g, 6.6 mmol) in THF (10 mL) was added sodium hydride (0.317 g, 13.2 mmol), and followed by p-toluenesulfonyl chloride (1.5 g, 7.9 mmol). The reaction mixture was stirred for 2 h at room temperature. The mixture was dissolved in ethyl acetate (200 mL) and washed with water and brine. The organic phase was separated, dried over Na₂SO₄, filtered and the solvent removed under reduced pressure to afford the title compound (1.5 g, 50%). The crude product was taken as such for next step.

MS: 357.2 (M-Boc)⁺.

Step B

To a solution of the title compound from Step A above (1.5 g, 3.28 mmol) in dichloromethane (15 mL) was added 2N HCl (10 mL) in 1,4-dioxane. The reaction mixture was stirred at room temperature for 12 h. After the completion of the reaction, the reaction mixture was evaporated to remove the solvent and washed with diethyl ether to afford the title compound as an off white solid (1 g, 77%).

¹H-NMR (400 MHz, DMSO-d₆) δ=9.91 (br-s, 2H), 7.83 (d, J=8.40 Hz, 3H), 7.35 (d, J=8.40 Hz, 2H), 7.06 (d, J=2.00 Hz, 1H), 6.93-6.94 (m, 1H), 4.61 (s, 2H), 3.76 (s, 3H), 3.57 (s, 4H), 3.44 (s, 4H), 2.89 (br-s, 2H), 2.32 (s, 3H).

MS: 357.2 (M+H)⁺.

Preparative Example 5

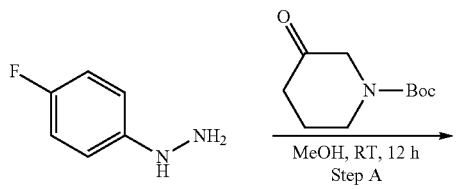

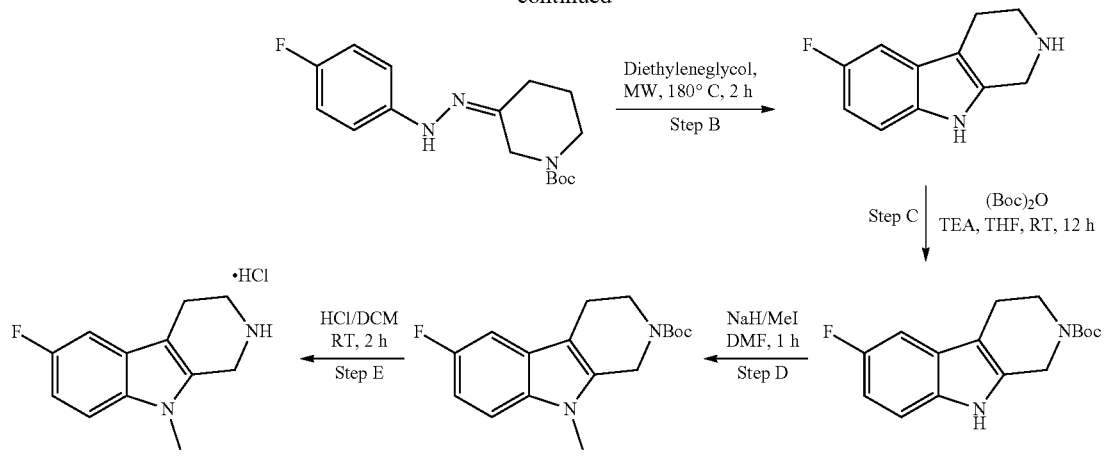

Step A

A solution of 5-fluoro-2-hydrazineylpyridine (5 g) and tert-butyl 3-oxopiperidine-1-carboxylate (5 g) in methanol (50 mL) was stirred at 25° C. for 12 h. After completion of the reaction by TLC, the reaction mixture was concentrated and the dark brown crude product (10 g) was directly to the next step without further purification.

MS: 309.1 (M+H)$^+$.

Step B

A solution of the crude title compound from Step A above (10 g) in diethyleneglycol (20 ml) was heated at 180° C. using a microwave for 90 min (4 batch). After completion of the reaction by LCMS, the reaction mixture was poured into water, followed by extraction using dichloromethane. The organic layer was separated, concentrated to get the crude product which was washed with diethyl ether and dried under vacuum to afford the title compound as a pale brown solid (1 g, 16%).

MS: 192.2 (M+H)$^+$.

Step C

To a solution of the title compound from Step B above (1 g, 5.23 mmol) in THF (10 ml) was added triethylamine (2.2 ml, 15.39 mmol), followed by di-tert-butyl dicarbonate (1.36 g, 6.28 mmol). The reaction mixture was then stirred at room temperature for 12 h. After the completion of the reaction as evidenced by TLC, the solvent was removed and the crude reaction mixture was purified by flash column chromatography using hexane/ethyl acetate (60:40) to afford the title compound as a yellow solid (1.1 g, 72%).

$^1$H-NMR (400 MHz, DMSO-d$_6$) δ=11.54 (s, 1H), 8.08 (s, 1H), 7.65 (d, J=12.40 Hz, 1H), 3.65-3.66 (m, 2H), 2.82 (t, J=8.80 Hz, 2H), 1.95 (t, J=6.40 Hz, 2H), 1.46 (s, 9H).

MS: 292.2 (M+H)$^+$.

Step D

To a solution of the title compound from Step C above (1.1 g, 3.78 mmol) in N,N'-dimethylformamide (10 mL) was added sodium hydride (0.226 g, 5.67 mmol) at 0° C. The reaction mixture was stirred at 0° C. for 30 min, followed by the addition of methyl iodide (0.25 mL, 4.15 mmol) at 0° C. The reaction mixture was then stirred at 0° C. for 30 min. After completion of the reaction by TLC, the reaction mixture was quenched with ice water followed by extraction using ethyl acetate (20 mL). The organic layer was concentrated to get the crude product as yellow solid (1 g) which was directly taken to next step without further purification.

MS: 306.1 (M+H)$^+$.

Step E

To a solution of the title compound from Step D above (1 g) in dichloromethane (10 ml) was added 2N HCl (5 mL) in 1,4-dioxane. The reaction mixture was stirred at room temperature for 3 h. After the completion of the reaction, the reaction mixture was evaporated to remove the solvent and washed with diethyl ether to afford the title compound as a pale yellow solid (0.25, 37%).

$^1$H-NMR (400 MHz, DMSO-d$_6$) δ=11.32 (t, J=6.92 Hz, 2H), 8.32 (s, 1H), 7.87 (d, J=9.12 Hz, 1H), 3.73 (s, 3H), 3.45 (s, 2H), 2.94 (t, J=5.88 Hz, 2H), 2.17 (t, J=4.80 Hz, 2H).

MS: 206.1 (M+H)$^+$.

Preparative Example 6

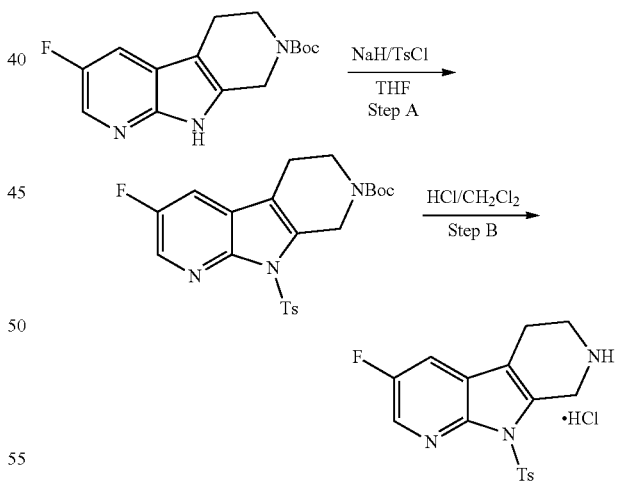

Step A

To a solution of the title compound from Preparative Example 5 Step C (1.1 g, 3.78 mmol) in N,N'-dimethylformamide (10 mL) was added sodium hydride (0.226 g, 5.67 mmol) at 0° C., The reaction mixture was stirred at 0° C. for 30 min, followed by p-toluenesulfonyl chloride (0.788 g, 4.15 mmol). The reaction mixture was stirred for 30 min at 0° C. The mixture was quenched with ice water and extracted with ethyl acetate (20 mL). The organic phase was separated, dried over Na$_2$SO$_4$, filtered and the solvent removed under reduced pressure to afford the crude title compound as pale brown solid (1 g). The crude product was taken as such for next step.

MS: 446.1 (M+H)$^+$.

Step B

To a solution of the title compound from Step A above (1 g) in dichloromethane (10 mL) was added 2N HCl (5 mL) in 1,4-dioxane. The reaction mixture was stirred at room temperature for 3 h. After the completion of the reaction, the reaction mixture was evaporated to remove the solvent and washed with diethyl ether to afford the title compound as a pale yellow solid (0.75 g, 65%).

$^1$H-NMR (400 MHz, DMSO-d$_6$) δ=8.40 (d, J=1.24 Hz, 1H), 7.97 (d, J=8.24 Hz, 2H), 7.88 (q, J=2.64 Hz, 1H), 7.40 (d, J=8.24 Hz, 2H), 3.37 (q, J=5.20 Hz, 2H), 3.22 (t, J=6.12 Hz, 2H), 2.33 (d, J=12.52 Hz, 3H), 2.09 (t, J=5.00 Hz, 2H).

MS: 346.1 (M+H)$^+$.

Preparative Example 7 compounds as a pale brown solid (23 g). The crude mixture of regioisomers was taken as such for next step.

MS: 191 (M+H)$^+$.

Step B

To a solution of the title compound from Step A above (23 g, 121.05 mmol) in THF (250 mL) was added triethylamine (33.7 mL, 242.1 mmol) and di-tert-butyl dicarbonate (32 g, 145.2 mmol) and the reaction mixture was stirred for 12 h. After the completion of the reaction as evidenced by TLC, the solvent was removed under reduced pressure and the crude reaction mixture was purified by flash column chromatography using hexane/ethyl acetate (80:20) to afford the title compounds as a pale yellow solids (7 g, 20%).

MS: 191.2 (M-Boc)$^+$.

Step C

The mixture of regioisomers from Step B above (7.0 g, ratio: 95/5) was separated by SFC Chiral column (YMC Amylose-SA) to afford the desired major regioisomer as a pale yellow solid with 100% Regioisomer purity (3 g, 43%).

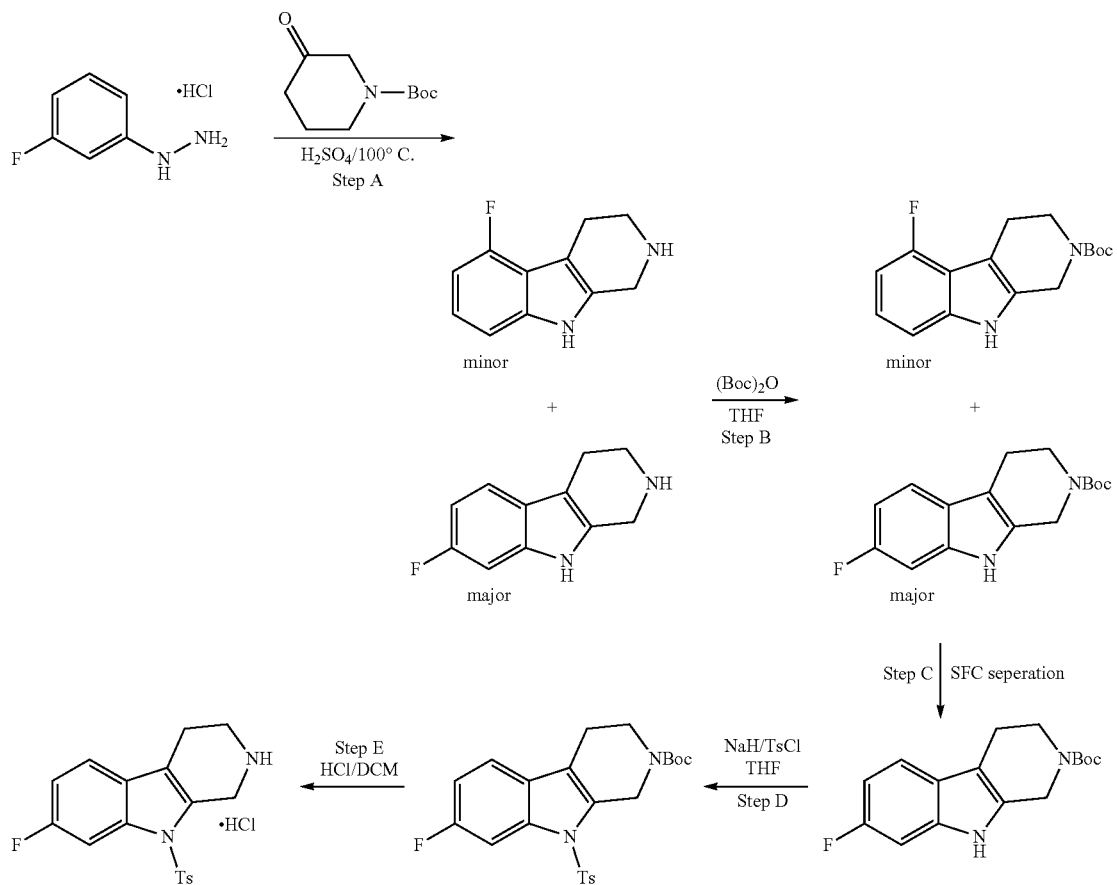

Step A

To a solution of (3-fluorophenyl)hydrazine HCl-salt (25 g, 153.7 mmol) and tert-butyl 3-oxopiperidine-1-carboxylate (30.59 g, 153.7 mmol) in 1,4-dioxane (250 mL) was added conc. H$_2$SO$_4$ (25 mL), 0° C. Then the reaction mixture was heated at 110° C. for 3 h. The reaction mixture was cooled to 25° C. and the precipitate was filtered off. The solid was dissolved in water basified with NaOH solution and extracted with dichloromethane. The organic phase was separated, dried over Na$_2$SO$_4$, filtered and the solvent was removed under reduced pressure to afford the cyclized title $^1$H-NMR (400 MHz, DMSO-d$_6$) δ=10.95 (br-s, 1H), 7.35-7.37 (m, 1H), 7.09-7.12 (m, 1H), 6.80-6.85 (m, 1H), 4.54 (s, 2H), 3.66 (t, J=5.64 Hz, 2H), 2.67 (t, J=5.48 Hz, 2H), 1.44 (s, 9H).

MS: 191.2 (M-Boc)$^+$.

The minor regioisomer was isolated as well (0.3 g, 4.3%).

$^1$H-NMR (400 MHz, DMSO-d$_6$) δ=11.16 (s, 1H), 7.13 (d, J=8.12 Hz, 1H), 6.96-7.01 (m, 1H), 6.68-6.70 (m, 1H), 4.56 (s, 2H), 3.67 (t, J=5.64 Hz, 2H), 2.78 (t, J=5.24 Hz, 2H), 1.44 (s, 9H).

MS: 191.2 (M-Boc)$^+$.

Step D

To a solution of the major regioisomer from Step C above (1.5 g, 5.16 mmol) in N,N'-dimethylformamide (15 mL) was added sodium hydride (0.3 g, 7.74 mmol), followed by p-toluenesulfonyl chloride (1.17 g, 6.19 mmol). The reaction mixture was stirred for 30 min at room temperature. The mixture dissolved in ethyl acetate (50 mL) and washer with water and brine. The organic phase was separated, dried over $Na_2SO_4$, filtered and the solvent removed under reduced pressure. The crude material was purified by flash column chromatography using hexane/ethyl acetate (80:20) to afford the title compound (2 g, 87%).

$^1$H-NMR (400 MHz, DMSO-$d_6$) δ=7.75-7.78 (m, 3H), 7.47-7.48 (m, 1H), 7.38-7.40 (m, 2H), 7.16-7.17 (m, 1H), 4.84 (s, 2H), 3.61-3.62 (m, 2H), 2.63-2.66 (m, 2H), 2.32 (s, 3H), 1.44 (s, 9H).

MS: 345.2 (M-Boc)$^+$.

Step E

To a solution of the title compound from Step D above (2 g, 4.5 mmol) in dichloromethane (120 mL) was added 2N HCl (10 mL) in 1,4-dioxane. The reaction mixture was stirred at room temperature for 12 h. After the completion of the reaction, the reaction mixture was evaporated to remove the solvent and washed with diethyl ether to afford the title compound as an off-white solid (1.6 g 94%).

$^1$H-NMR (400 MHz, DMSO-$d_6$) δ=9.65 (br-s, 2H), 7.93 (d, J=7.92 Hz, 2H), 7.72-7.72 (m, 1H), 7.58-7.59 (m, 1H), 7.40 (d, J=8.24 Hz, 2H), 7.19-7.24 (m, 1H), 4.65 (s, 2H), 3.36 (bs, 2H), 2.91 (br-s, 2H), 2.35 (s, 3H).

MS: 345.2 (M+H)$^+$.

Preparative Example 8

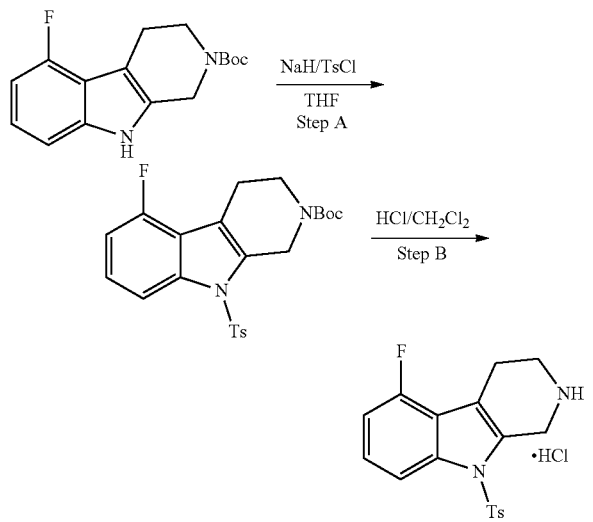

Step A

To a solution of the minor regiosiomer from Preparative Example 7 Step C (0.3 g, 1.034 mmol) in THF (10 mL) was added sodium hydride (0.082 g, 2.06 mmol), and followed by p-toluenesulfonyl chloride (0.294 g, 1.55 mmol). The reaction mixture was stirred for 30 min at room temperature. The mixture dissolved in ethyl acetate (30 mL) and washer with water and brine. The organic phase was separated, dried over $Na_2SO_4$, filtered and the solvent removed under reduced pressure to afford the crude title compound (0.25 g, 55%). The crude product was taken as such for next step.

MS: 345.1 (M+H)$^+$.

Step B

To a solution of the title compound from Step A above (0.25 g, 0.56 mmol) in dichloromethane (10 mL) was added 2N HCl (2 mL) in 1,4-dioxane. The reaction mixture was stirred at room temperature for 12 h. After the completion of the reaction, the reaction mixture was evaporated to remove the solvent and washed with diethyl ether to afford the crude title compound as an off white solid (0.2 g).

MS: 345.1 (M+H)$^+$.

Preparative Example 9

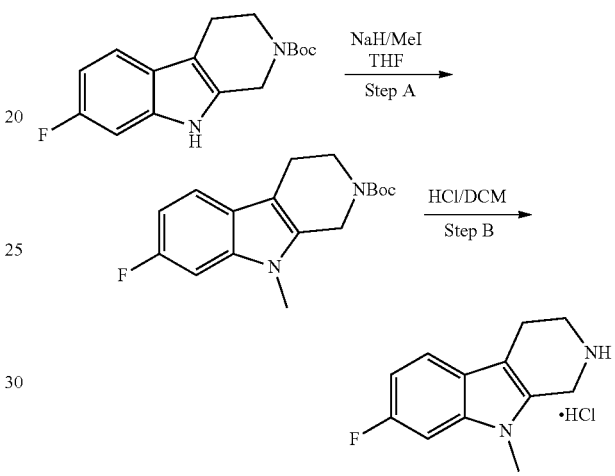

Step A

To a solution of the major regiosiomer from Preparative Example 7 Step C (1.0 g, 3.44 mmol) in THF (15 mL) was added sodium hydride (0.275 g, 6.89 mmol), and followed by methyl iodide (10.3 mL, 4.14 mmol). The reaction mixture was stirred at room temperature for 30 min. The mixture was dissolved in ethyl acetate (40 ml) and washed with water, brine and dried over $Na_2SO_4$. The crude reaction mixture was purified by flash column chromatography using hexane/ethyl acetate (70:30) to afford the title compound (1.0 g, 96%).

$^1$H-NMR (400 MHz, DMSO-$d_6$) δ=7.38-7.40 (m, 1H), 7.28-7.29 (m, 1H), 6.87 (d, J=12.80 Hz, 1H), 4.59 (s, 2H), 3.61-3.63 (m, 5H), 2.68 (s, 2H), 1.45 (s, 9H).

MS: 305.1 (M+H)$^+$.

Step B

To a solution of the title compound from Step A above (1.0 g, 3.28 mmol) in dichloromethane (10 mL) was added 2N HCl (5 mL) in 1,4-dioxane.

The reaction mixture was stirred at room temperature for 12 h. After the completion of the reaction, the reaction mixture was evaporated to remove the solvent and washed with diethyl ether to afford the title compound as an off-white solid (0.75 g 96%).

$^1$H-NMR (400 MHz, DMSO-$d_6$) δ=9.86 (br-s, 2H), 7.46-7.47 (m, 1H), 7.34-7.37 (m, 1H), 6.89-6.90 (m, 1H), 4.39 (s, 2H), 3.63 (s, 3H), 3.37 (d, J=6.04 Hz, 2H), 2.91-2.93 (m, 2H).

MS: 205.1 (M+H)$^+$.

Preparative Example 10

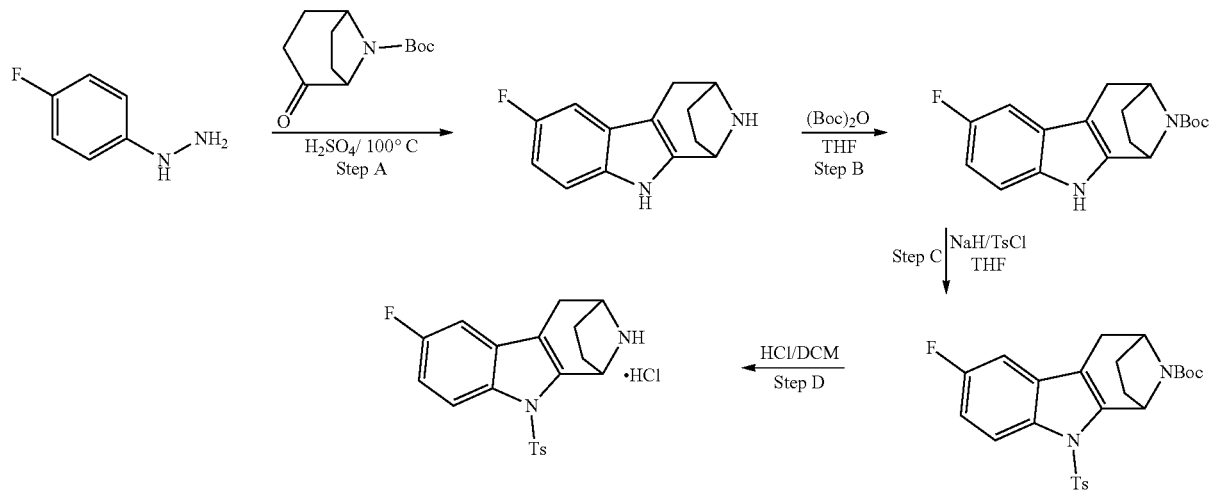

Step A

To a solution of (4-fluorophenyl)hydrazine HCl-salt (2 g, 12.3 mmol) and tert-butyl 2-oxo-8-azabicyclo[3.2.1]octane-8-carboxylate (2.7 g, 12.3 mmol) in 1,4-dioxane (30 mL) was added conc. $H_2SO_4$ (2 mL), 0° C. Then the reaction mixture was heated at 100° C. for 12 h. After completion of the reaction, the reaction mixture was cooled to room temperature and the solvent was removed by high vacuum to get the crude material. The crude material was basified by using 30% sodium hydroxide solution, followed by extraction using ethyl acetate (50 mL). The ethyl acetate layer was washed with water (20 mL) and brine solution (10 mL). The organic layer was dried over $Na_2SO_4$, filtered and evaporated to afford the crude title compound as a pale brown gummy mass (1.6 g, 83%). The crude product was taken as such for next step.

MS: 217.2 $(M+H)^+$.

Step B

To a solution of the title compound from Step A above (2 g, 5.1 mmol) in THF (20 mL) was added triethylamine (2.56 mL, 18 mmol) and di-tert-butyl dicarbonate (2.21 g, 10 mmol) and the reaction mixture was stirred for 12 h. After the completion of the reaction as evidenced by TLC, the solvent was removed under reduced pressure and the crude reaction mixture was purified by flash column chromatography using 40% to 50% ethyl acetate in petrol ether to afford the title compound as a pale yellow solid (0.9 g, 31%).

$^1$H-NMR (400 MHz, DMSO-$d_6$) δ=10.94 (br-s, 1H), 7.22-7.23 (m, 2H), 6.80-6.81 (m, 1H), 5.09 (d, J=5.20 Hz, 2H), 4.46 (br-s, 1H), 3.22 (br-s, 1H), 2.50-2.51 (m, 1H), 2.22 (br-s, 1H), 2.06 (br-s, 1H), 1.79 (br-s, 1H), 1.58-1.60 (m, 1H), 1.42 (s, 9H).

MS: 261.2 (M-t-butyl)$^+$.

Step C

To a solution of the title compound from Step B above (1 g, 3.16 mmol) in THF (15 mL) was added sodium hydride (60% in mineral oil; 0.25 g, 6.32 mmol) in small in portions at 0° C. After the addition was completed, the reaction mixture was allowed to stir at room temperature for 30 min, and then the reaction mixture was again cooled to 0° C. To the reaction mixture was then dropwise added at 0° C. a solution of p-toluenesulfonyl chloride (0.72 g, 3.79 mmol) in THF (5 mL). After the addition was completed, the reaction mixture was allowed to stir at room temperature for 2 h. After completion of the reaction by TLC, the reaction mixture was cooled to 0° C. and quenched with ice water, followed by extraction using ethyl acetate (50 mL). The ethyl acetate layer was washed with water (10 mL) and brine solution (10 mL). The organic layer was dried over $Na_2SO_4$, filtered and evaporated to afford the crude product, which was purified by silica gel column using 15% to 25% of ethyl acetate in petrol ether to afford the title compound as an off-white solid (0.9 g, 61%).

$^1$H-NMR (400 MHz, DMSO-$d_6$) δ=8.01-8.02 (m, 1H), 7.58-7.60 (m, 2H), 7.50-7.51 (m, 1H), 7.50-7.51 (m, 2H), 7.15-7.16 (m, 1H), 5.06 (br-s, 1H), 4.46 (br-s, 1H), 3.35 (br-s, 1H), 2.91 (br-s, 1H), 2.44 (br-s, 3H), 1.77-1.79 (m, 3H), 1.56-1.58 (m, 1H), 1.27-1.33 (m, 9H).

MS: 371.1 (M-Boc)$^+$.

Step D

To a solution of the title compound from Step C above (0.9 g, 1.91 mmol) in dichloromethane (5 mL) at 0° C. was added 4N HCl (10 mL) in 1,4-dioxane. The reaction mixture was allowed to stir at ambient temperature for 12 h. After the completion of the reaction, the reaction mixture was evaporated to remove the solvent and washed with diethyl ether (10 mL) to afford the crude title compound as an off-white solid (0.65 g, 93%).

MS: 371.1 $(M+H)^+$.

Preparative Example 11

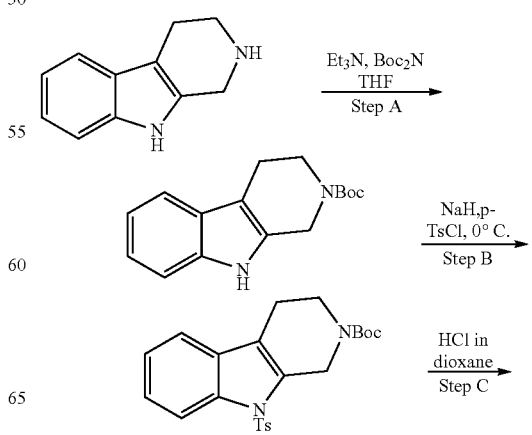

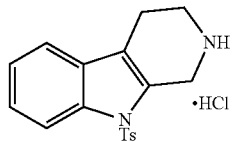

Step A

To a stirred solution of tryptoline (2,3,4,9-tetrahydro-1H-pyrido[4,3-b]indole) (150 g, 0.871 mol) in THF (1.5 L) at 0° C., triethylamine (243 mL, 1.74 mol) and di-tert-butyl dicarbonate (228 g, 1.04 mol) were added and the reaction mixture was stirred at 25° C. for 12 h. After the completion of the reaction (monitored by TLC), water was added to the reaction mixture under ice-cooling and extracted with ethyl acetate (2×500 mL). The combined organic extracts were washed with brine (1×250 mL), dried over anhydrous $Na_2SO_4$, filtered and evaporated under reduced pressure to get the crude product. The crude material was stirred with diethyl ether (200 mL) and the solid thus obtained was filtered, washed with diethyl ether (2×100 mL) and dried to afford the title compound as brown solid (200 g, 84%).

$^1$H-NMR (400 MHz, $CDCl_3$) δ=7.94 (br-s, 1H), 7.51 (d, J=7.60 Hz, 1H), 7.33-7.34 (m, 1H), 7.11-7.13 (m, 2H), 4.67 (s, 2H), 3.79 (br-s, 2H), 2.83 (br-s, 2H), 1.53 (s, 9H).

MS: 273.2 $(M+H)^+$.

Step B

To a stirred suspension of sodium hydride (15.86 g, 60% mineral oil, 1.10 mol) in dry THF (400 mL) at 0° C., a solution of the title compound from Step A above (100 g, 0.367 mol) in dry THF (1 L) was added slowly and stirred at the same temperature for 30 min. Then a solution of p-toluene sulfonyl chloride (105 g, 0.55 mol) in dry THF (100 mL) was added dropwise at 0° C., and the reaction mixture was allowed to stir at 0° C. for 1 h. After completion of the reaction (monitored by TLC), the reaction mixture was cooled to 0° C. and quenched with ice water (500 mL), followed by extraction using ethyl acetate (3×500 mL). The combined organic extracts were washed with water (2×500 mL), brine (1×250 mL) and dried over $Na_2SO_4$, filtered and evaporated under reduced pressure to afford the crude product which was triturated with hexane (250 mL). The solid thus obtained was filtered, washed with hexane (2×100 mL) and dried to afford the title compound as pale brown solid (130 g, 83%).

$^1$H-NMR (400 MHz, DMSO-$d_6$) δ=8.01 (d, J=10.40 Hz, 1H), 7.77 (br-s, 2H), 7.45-7.48 (m, 1H), 7.13-7.24 (m, 4H), 4.88 (s, 2H), 3.63-3.65 (m, 2H), 2.65 (br-s, 2H), 2.31 (s, 3H), 1.46 (s, 9H).

MS: 327.1 $(M^+$-Boc).

Step C

To a solution of the title compound from Step B above (130 g, 0.30 mol) in 1,4-dioxane (1.3 L) was added 4M HCl in 1,4-dioxane (500 mL) at 0° C. The reaction mixture was stirred at 25° C. for 12 h. After the completion of the reaction, the reaction mixture was evaporated under reduced pressure and the residue was washed with diethyl ether to afford the title compound as pale brown solid (95 g, 94%).

$^1$H-NMR (400 MHz, DMSO-$d_6$) δ=9.64 (br-s, 2H), 7.86-7.89 (m, 3H), 7.55 (d, J=10.40 Hz, 1H), 7.27-7.30 (m, 4H), 4.67 (s, 2H), 3.47 (br-s, 2H), 2.92 (br-s, 2H), 2.33 (s, 3H).

MS: 327.1 $(M+H)^+$.

Preparative Example 12

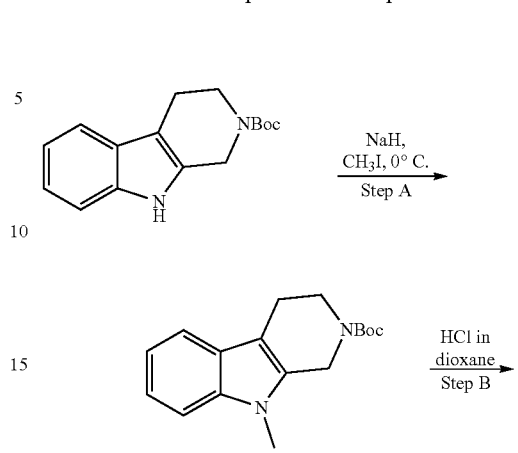

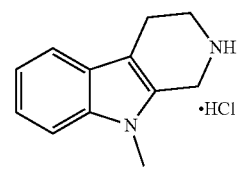

Step A

To a stirred suspension of sodium hydride (15.86 g, 60% mineral oil, 1.10 mol) in dry THF (400 mL) at 0° C., a solution of the title compound from Preparative Example 11 Step A (100 g, 0.367 mol) in dry THF (1 L) was added slowly and stirred at the same temperature for 30 min. Then a solution of methyl iodide (10 mL, 0.55 mol) in dry THF (100 mL) was added dropwise at 0° C., and the reaction mixture was allowed to stir at 0° C. for 1 h. After completion of the reaction (monitored by TLC), the reaction mixture was cooled to 0° C. and quenched with ice water (500 mL), followed by extraction using ethyl acetate (3×500 mL). The combined organic extracts were washed with water (2×300 mL), brine (1×250 mL) and dried over $Na_2SO_4$, filtered and evaporated under reduced pressure to afford the crude product which was triturated with hexane (250 mL). The solid thus obtained was filtered, washed with hexane (2×100 mL) and dried to afford the title compound as brown solid (93 g, 88%).

$^1$H-NMR (400 MHz, DMSO-$d_6$) δ=7.39-7.41 (m, 2H), 7.09-7.11 (m, 1H), 6.98-7.00 (m, 1H), 4.58 (s, 2H), 3.64-3.66 (m, 5H), 2.69 (s, 2H), 1.45 (s, 9H).

MS: 287.2 $(M+H)^+$.

Step B

To a solution of the title compound from Step A above (93 g, 0.32 mol) in 1,4-dioxane (1.0 L) was added 4M HCl in 1,4-dioxane (400 mL) at 0° C. The reaction mixture was stirred at 25° C. for 12 h. After the completion of the reaction, the reaction mixture was evaporated under reduced pressure and the residue was washed with diethyl ether to afford the title compound as pale brown solid (58 g, 80%).

$^1$H-NMR (400 MHz, DMSO-$d_6$) δ=9.81 (br-s, 1H), 7.44-7.47 (m, 2H), 7.15-7.18 (m, 1H), 7.03-7.06 (m, 1H), 4.42 (s, 1H), 3.66 (s, 3H), 3.41-3.45 (m, 2H), 2.95 (br-s, 2H).

MS: 187.1 $(M+H)^+$.

Preparative Example 13

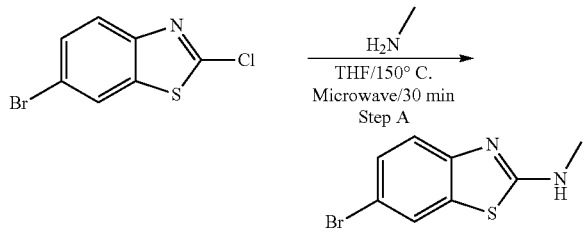

Step A

To a solution of 6-bromo-2-chlorobenzo[d]thiazole (1 g, 4.0 mmol) in ethanol (6 mL), was added 4 M methyl amine solution (1.5 mL) and the reaction mixture was heated at 150° C. for 45 min using Biotage microwave. The reaction mixture was cooled to room temperature. The solvent was removed under reduced pressure, the crude product was dissolved in dichloromethane (150 mL) and washed with 1 M NaOH solution, water, brine and dried over $Na_2SO_4$. The solvent was removed under reduced pressure, to give the crude reaction mixture which was purified by flash column chromatography using hexane:ethyl acetate (50:50) to afford the title compound as a solid (0.35 g, 36%).

$^1$H-NMR (400 MHz, $CDCl_3$) δ=7.72 (s, 1H), 7.41 (s, 1H), 7.29 (d, J=3.3 Hz, 1H), 5.40 (s, 1H), 3.13 (s, 3H).

Preparative Example 14

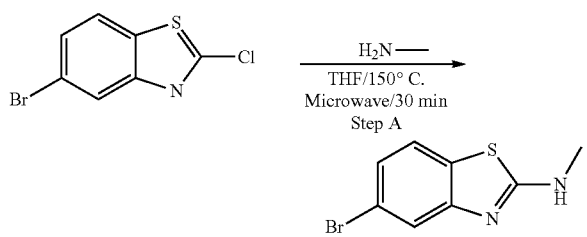

Step A

To a solution of 5-bromo-2-chlorobenzo[d]thiazole (0.9 g, 3.62 mmol) in ethanol (12 ml), was added 4 M methyl amine solution (1 mL) and the reaction mixture was heated at 150° C. for 45 min using a Biotage microwave. The reaction mixture was cooled to room temperature. The solvent was removed under reduced pressure, and the crude reaction mixture was purified by flash column chromatography using hexane:ethyl acetate (50:50) to afford the title compound as a solid (0.57 g, 65%).

$^1$H-NMR (400 MHz, $CDCl_3$) δ=7.68 (t, J=2.0 Hz, 1H), 7.46 (d, J=8.3 Hz, 1H), 7.29 (d, J=0.7 Hz, 1H), 7.22 (dd, J=8.4, 1.9 Hz, 1H), 5.90 (s, 1H), 3.13 (s, 3H).

Preparative Example 15

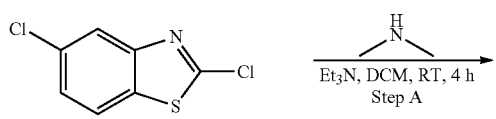

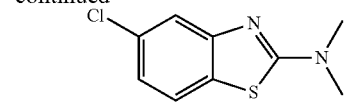

Step A

To a solution of 2,5-dichlorobenzo[d]thiazole (5 g, 24.5 mmol) in dry dichloromethane (50 mL) was added a 2 M solution of dimethylamine in THF (18.37 mL, 36.65 mmol), and the reaction mixture was cooled to 0° C. To this cold reaction mixture was added triethylamine (6.8 mL, 49 mmol) drop-wise. After the addition was completed, the reaction mixture was allowed to stir at room temperature for 4 h. After the completion of the reaction, the reaction mixture was treated with water (2×20 mL) and extracted with dichloromethane. The organic layer was separated, dried over $Na_2SO_4$, filtered and evaporated to afford a white solid which was used triturated with diethyl ether to afford the title compound (4.5 g, 88%).

$^1$H-NMR (400 MHz, DMSO-$d_6$) δ=7.77 (d, J=11.20 Hz, 1H), 7.46 (d, J=2.40 Hz, 1H), 7.05-7.05 (m, 1H), 3.14 (s, 6H).

MS: 213.4 $(M+H)^+$.

Preparative Example 16

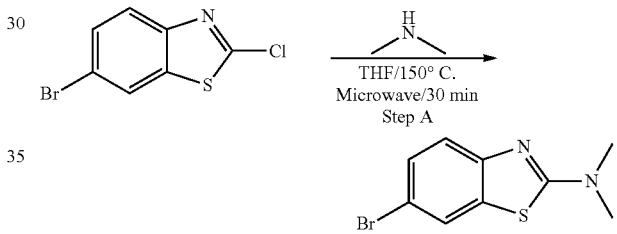

Step A

To a solution of 6-bromo-2-chlorobenzo[d]thiazole (0.45 g, 1.81 mmol) in ethanol (12 mL), was added a 2 M solution of dimethyl amine solution in THF (3 mL) and the reaction mixture was heated at 150° C. for 45 min using a Biotage microwave. The reaction mixture was cooled to room temperature. The solvent was removed under reduced pressure, and the crude reaction mixture was purified by flash column chromatography using hexane:ethyl acetate (50:50) to afford the title compound as a solid (0.441 g 95%) as solid.

$^1$H-NMR (400 MHz, DMSO-$d_6$) δ=7.70 (d, J=1.9 Hz, 1H), 7.43-7.35 (m, 2H), 3.20 (s, 6H).

Preparative Example 17

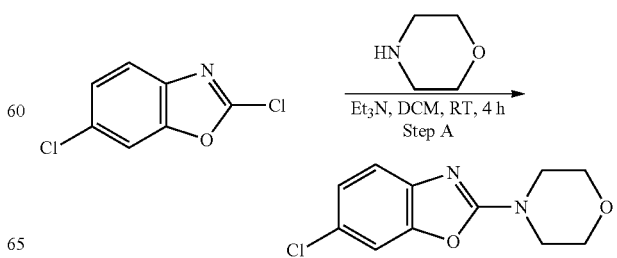

Step A

To a solution of 2,6-dichlorobenzo[d]oxazole (5 g, 26.8 mmol) in dry dichloromethane (50 mL) was added morpholine (3.50 g, 40.3 mmol), and the reaction mixture was cooled to 0° C. To this cold reaction mixture was added triethylamine (4.0 g, 39.6 mmol) dropwise. After the addition was completed, the reaction mixture was allowed to stir at room temperature for 4 h. After the completion of the reaction, the reaction mixture was treated with water (2×20 mL) and extracted with dichloromethane. The organic layer was separated, dried over $Na_2SO_4$, filtered and evaporated to afford a white solid which was triturated with diethyl ether to afford the title compound (5 g, 78%).

$^1$H-NMR (400 MHz, DMSO-$d_6$) δ=7.59 (d, J=2.80 Hz, 1H), 7.30 (d, J=11.20 Hz, 1H), 7.21 (dd, J=2.80, 11.20 Hz, 1H), 3.71-3.74 (m, 4H), 3.57-3.60 (m, 4H).

MS: 239.2 (M+H)$^+$.

Preparative Example 18

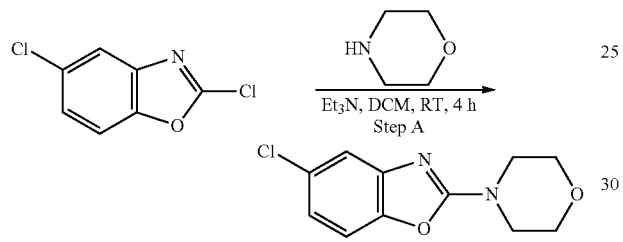

Step A

To a solution of 2,5-dichlorobenzo[d]oxazole (5 g, 26.8 mmol) in dry dichloromethane (50 mL) was added morpholine (3.50 g, 40.3 mmol), and the reaction mixture was cooled to 0° C. To this cold reaction mixture was added triethylamine (4.0 g, 39.6 mmol) drop-wise. After the addition was completed, the reaction mixture was allowed to stir at room temperature for 4 h. After the completion of the reaction, the reaction mixture was treated with water (2×20 mL) and extracted with dichloromethane. The organic layer was separated, dried over $Na_2SO_4$, filtered and evaporated to afford a white solid which was triturated with diethyl ether to afford the title compound (5.2 g, 81%).

$^1$H-NMR (400 MHz, DMSO-$d_6$) δ=7.44 (d, J=8.40 Hz, 1H), 7.36 (d, J=2.40 Hz, 1H), 7.06 (dd, J=2.00, 8.40 Hz, 1H), 3.71-3.73 (m, 4H), 3.59-3.61 (m, 4H).

MS: 239.2 (M+H)$^+$.

Preparative Example 19

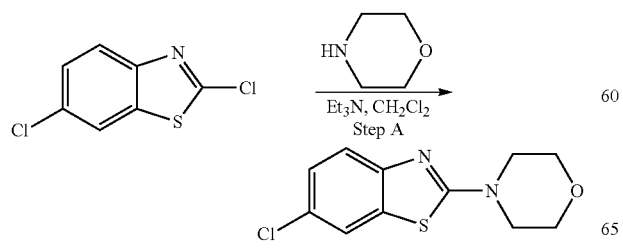

Step A

To a stirred solution of commercially available 2,6-2,6-dichlorobenzo[d]thiazole (500 g, 2.45 mol) in dichloromethane (4 L) was added triethylamine (1031 mL, 7.35 mol) and morpholine (290 mL, 3.67 mol) at 0° C. Then the reaction mixture was stirred at 25° C. for 48 h. After completion of the reaction (monitored by TLC), water was added to the reaction mixture, followed by extraction using dichloromethane (2×2.5 L). The organic layer was dried over $Na_2SO_4$, filtered and evaporated under reduced pressure to afford the crude product. To the crude material was added methyl tert-butyl ether (1 L), and the mixture was stirred for 2 h. The solid was collected by filtration, and dried under line vacuum for 6 h to afford the title compound as a pale brown solid (530 g, 85%).

$^1$H-NMR (400 MHz, DMSO-$d_6$) δ=7.93-7.94 (m, 1H), 7.43-7.44 (m, 1H), 7.28-7.29 (m, 1H), 3.72-3.74 (m, 4H), 3.54-3.55 (m, 4H).

MS: 255.1 (M+H)$^+$.

Preparative Example 20

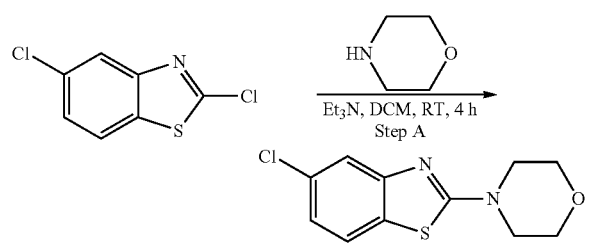

Step A

To a solution of 2,5-dichlorobenzo[d]thiazole (5 g, 24.5 mmol) in dry dichloromethane (50 mL) was added morpholine (3.19 g, 36.6 mmol), and the reaction mixture was cooled to 0° C. To this cold reaction mixture was added triethylamine (3.71 g, 36.7 mmol) drop-wise and the reaction mixture was allowed to stir at room temperature for 4 h. After the completion of the reaction, the reaction mixture was treated with water (2×20 mL) and extracted with dichloromethane. The organic layer was separated, dried over $Na_2SO_4$, filtered and evaporated under reduced pressure to afford a white solid which was triturated with diethyl ether to afford the title compound (4.5 g, 86%).

$^1$H-NMR (400 MHz, DMSO-$d_6$) δ=7.82 (d, J=8.00 Hz, 1H), 7.50 (d, J=2.00 Hz, 1H), 7.11-7.11 (m, 1H), 3.72-3.73 (m, 4H), 3.55-3.56 (m, 4H).

MS: 255.4 (M+H)$^+$.

Preparative Example 21

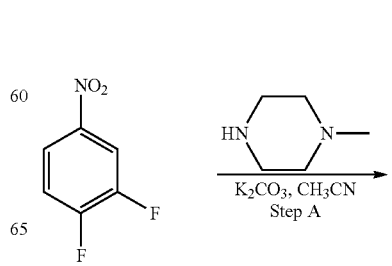

-continued

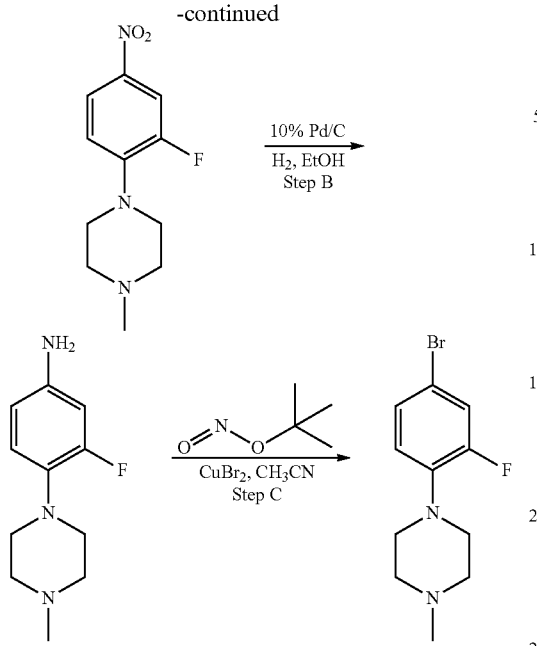

Step A
To a solution of 3,4-difluoro nitrobenzene (5 g, 31.4 mmol) in acetonitrile (50 mL), was added N-methyl piperazine (3.7 g, 37.7 mmol) and potassium carbonate (12.8 g, 94.3 mmol). The reaction mixture was then heated to reflux for 3 hours. The reaction mixture was filtered, concentrated under vacuum, and the solid obtained was washed with ether to afford the title compound as yellow solid (5.2 g, 69%).

$^1$H-NMR (300 MHz, CDCl$_3$) δ=7.89-8.03 (m, 2H), 6.90-6.91 (m, 1H), 3.33-3.34 (m, 4H), 2.60-2.61 (m, 4H), 2.38 (s, 3H).

MS: 240.1 (M+H)$^+$.

Step B
To a solution of the title compound from Step A above (5.2 g, 21.7 mmol) in ethanol (100 mL), was added 10% Pd/C (0.5 g) and the reaction mixture was hydrogenated for 16 hours. The reaction mixture was filtered through celite pad and concentrated under vacuum to afford the title compound as brown solid (4.0 g, 88%).

$^1$H-NMR (400 MHz, DMSO-d$_6$) δ=6.75 (t, J=9.20 Hz, 1H), 6.31 (t, J=9.20 Hz, 2H), 4.97 (s, 2H), 2.82 (br-s, 4H), 2.43 (br-s, 4H), 2.21 (s, 3H).

MS: 210.2 (M+H)$^+$.

Step C
To a suspension of the title compound from Step B above (3.0 g, 14.33 mmol) in acetonitrile (30 mL) at 0° C., was added tert-butyl nitrite (2.5 mL, 21.5 mmol) over a period of 10 min with a syringe. Then, copper (II) bromide (3.8 g, 17.2 mmol) was added portion wise at 0° C. and stirred for 30 min. The reaction mixture was allowed to warm to 25° C. for 1 h and heated to 60° C. for 4 h. After completion of the reaction (monitored by TLC), the reaction mixture was filtered through celite pad, and washed with ethyl acetate to yield the crude product. The crude material was purified by silica-gel (60-120) column chromatography using dichloromethane/methanol (99:1) to afford the title compound as a brown solid (1 g, 25%).

$^1$H-NMR (400 MHz, DMSO-d$_6$) δ=7.40-7.41 (m, 1H), 7.28-7.31 (m, 1H), 6.96-6.98 (m, 1H), 2.98-2.99 (m, 4H), 2.46-2.47 (m, 4H), 2.22 (s, 3H).

MS: 275.1 (M+H)$^+$.

Preparative Example 22

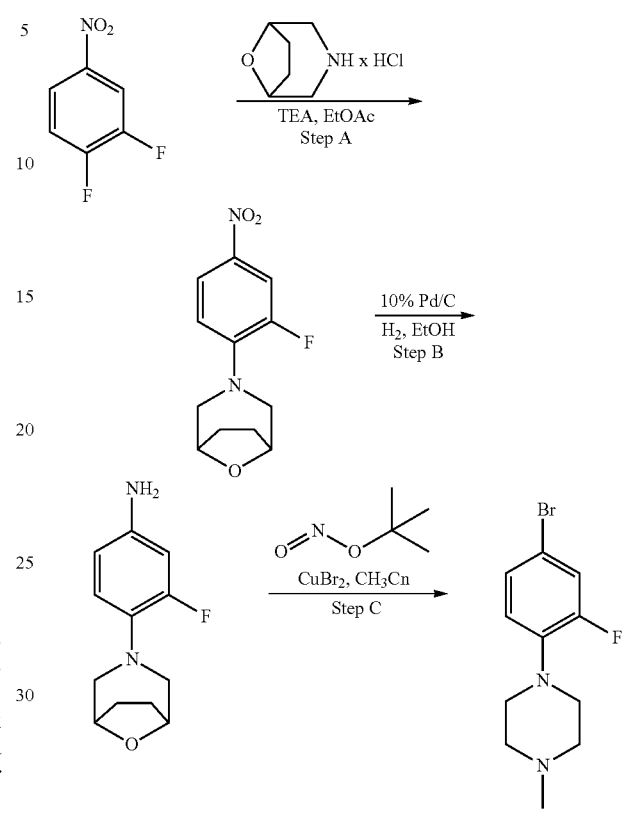

Step A
To a solution of 3,4-difluoro nitrobenzene (0.5 g, 3.14 mmol) in ethyl acetate (10 mL), was added trimethylamine 81.3 mL, 9.42 mmol) followed by 8-oxa-3-azabicyclo[3.2.1]octane hydrochloride (0.56 g, 3.77 mmol). The reaction mixture was then stirred at room temperature for 16 h. The reaction mixture was filtered, concentrated under vacuum, and the solid obtained was washed with ether to afford the title compound as yellow solid (0.7 g, 88%).

$^1$H-NMR (400 MHz, DMSO-d$_6$) δ=7.99-8.02 (m, 2H), 7.10 (t, J=8.88 Hz, 1H), 4.41 (br-s, 2H), 3.40 (d, J=11.80 Hz, 2H), 3.13 (d, J=10.64 Hz, 2H), 1.89 (br-s, 4H).

MS: 253.1 (M+H)$^+$.

Step B
To a solution of the title compound from Step A above (0.7 g, 2.77 mmol) in ethanol (20 mL), was added 10% Pd/C (0.1 g) and the reaction mixture was hydrogenated for 16 hours. The reaction mixture was filtered through celite pad and concentrated under vacuum to afford the title compound as pale brown gummy solid (0.6 g, 96%).

$^1$H-NMR (400 MHz, DMSO-d$_6$) δ=6.71 (t, J=9.64 Hz, 1H), 6.27-6.28 (m, 2H), 4.96 (s, 2H), 4.29 (br-s, 2H), 2.80 (br-s, 4H), 1.92-1.93 (m, 2H), 1.77-1.78 (m, 2H).

MS: 223.1 (M+H)$^+$.

Step C
To a suspension of the title compound from Step B above (0.50 g, 2.24 mmol) in acetonitrile (10 mL) at 0° C., was added tert-butyl nitrite (0.4 mL, 3.35 mmol) over a period of 10 min with a syringe. Then, copper (II) bromide (0.6 g, 2.68 mmol) was added portion wise at 0° C. and stirred for 30 min. The reaction mixture was allowed to warm to 25° C. for 1 h and heated to 60° C. for 4 h. After completion of the reaction (monitored by TLC), the reaction mixture was filtered through celite pad, and washed with ethyl acetate to yield the crude product. The crude material was purified by silica-gel (60-120) column chromatography using dichloromethane/methanol (99:1) to afford the title compound as a pale brown solid (0.27 g, 42%).

$^1$H-NMR (300 MHz, CDCl$_3$) δ=7.17-7.19 (m, 2H), 6.75 (t, J=8.68 Hz, 1H), 4.43 (br-s, 2H), 3.03-3.06 (m, 4H), 2.09 (br-s, 2H), 1.98 (br-s, 2H).

MS: 288.0 (M+H)$^+$.

Preparative Example 23

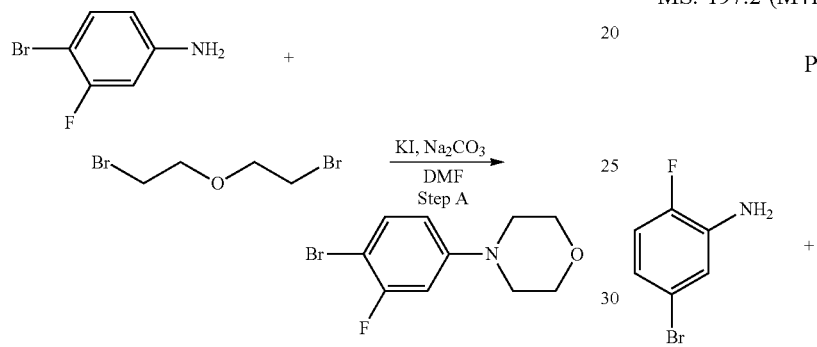

Step A

To a solution of 4-bromo-3-fluoroaniline (1 g, 5.26 mmol) in N,N'-dimethylformamide (10 ml), potassium iodide (2.18 g, 13.1 mmol), and sodium carbonate (1.95 g, 18.4 mmol) were added and the reaction mixture was heated to 150° C. Then 1-bromo-2-(2-bromoethoxy)ethane (1.34 g, 5.77 mmol) was added and heating was continued for 16 h. After completion of the reaction (monitored by TLC), the reaction mixture was diluted with water (25 mL) and extracted with ethyl acetate (2×15 mL). The combined organic extracts were dried over Na$_2$SO$_4$, filtered and concentrated under reduced pressure to yield the crude product. The crude material was purified by flash column chromatography using hexane/ethyl acetate (80:20) to afford the title compound (0.6 g, 43%).

$^1$H-NMR (400 MHz, DMSO-d$_6$) δ=7.43-7.44 (m, 1H), 6.93-6.94 (m, 1H), 6.73-6.74 (m, 1H), 3.70-3.72 (m, 4H), 3.13-3.14 (m, 4H).

MS: 261.9 (M+H)$^+$.

Preparative Example 24

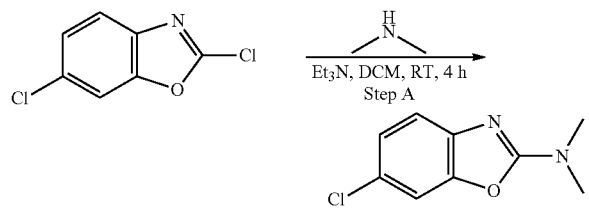

Step A

To a solution of 2,6-dichlorobenzo[d]oxazole (5 g, 26.6 mmol) in dry dichloromethane (50 mL) at 0° C., a 2 M solution of dimethylamine in THF (26.6 mL, 53.2 mmol) and triethylamine (5.6 mL, 39.9 mmol) were added. The reaction mixture was then stirred at 25° C. for 4 h. After the completion of the reaction (monitored by TLC), the reaction mixture was diluted with water (20 mL) and extracted with dichloromethane (2×20 mL). The combined organic extracts were dried over Na$_2$SO$_4$, filtered and evaporated under reduced pressure to afford the crude product. The crude material was triturated with diethyl ether, filtered, washed with diethyl ether and dried to afford the title compound as a solid (5 g, 96%)

$^1$H-NMR (400 MHz, DMSO-d$_6$) δ=7.56 (s, 1H), 7.23-7.24 (m, 1H), 7.16-7.16 (m, 1H), 3.13 (s, 6H).

MS: 197.2 (M+H)$^+$.

Preparative Example 25

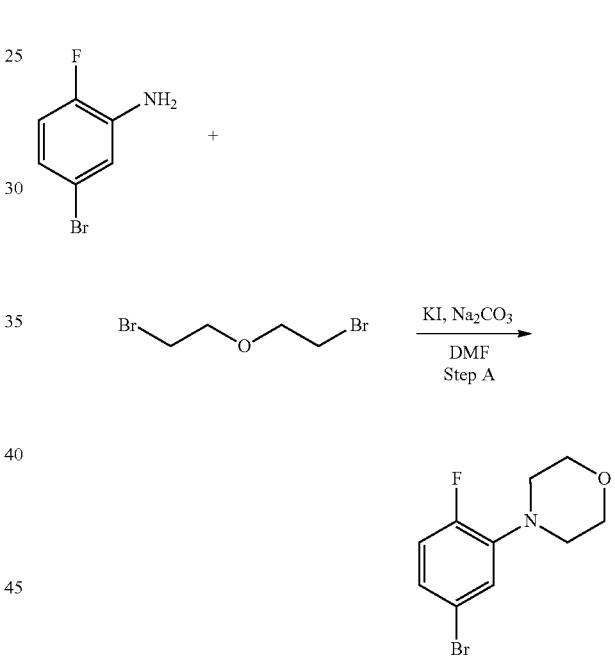

Step A

To a solution of 5-bromo-2-fluoroaniline (1 g, 5.26 mmol) in N,N'-dimethylformamide (10 ml), potassium iodide (2.18 g, 13.1 mmol), and sodium carbonate (1.95 g, 18.4 mmol) were added and the reaction mixture was heated to 150° C. Then 1-bromo-2-(2-bromoethoxy)ethane (1.34 g, 5.77 mmol) was added and heating was continued for 16 h. After completion of the reaction (monitored by TLC), the reaction mixture was diluted with water (25 mL) and extracted with ethyl acetate (2×15 mL). The combined organic extracts were dried over Na$_2$SO$_4$, filtered and concentrated under reduced pressure to yield the crude product. The crude material was purified by flash column chromatography using hexane/ethyl acetate (80:20) to afford the title compound (0.8 g, 58%). $^1$H-NMR (400 MHz, CDCl$_3$) δ=7.03-7.04 (m, 2H), 6.90-6.92 (m, 1H), 3.87-3.88 (m, 4H), 3.08-3.10 (m, 4H).

Preparative Example 26

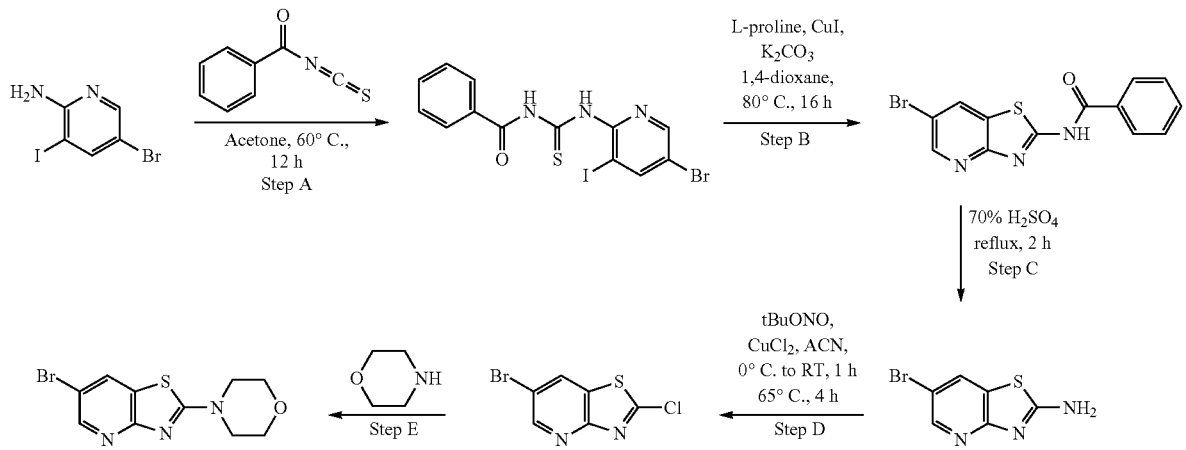

Step A

A solution of 5-bromo-3-iodopyridin-2-amine (5 g, 16.73 mmol) and benzoyl isothiocyanate (3.29, 20.16 mmol) in acetone (10 mL) was stirred at 60° C. for 12 h. After completion of the reaction (monitored by TLC), the reaction mixture was evaporated under reduced pressure and the solid was filtered, washed with hexane (200 mL) and dried to afford the title compound as an off-white solid (4 g, 52%).

$^1$H-NMR (400 MHz, DMSO-$d_6$) δ=12.35 (s, 1H), 11.86 (s, 1H), 8.64-8.65 (m, 2H), 7.99-7.99 (m, 2H), 7.67 (s, 1H), 7.56 (d, J=9.40 Hz, 2H).

MS: 461.5 (M+H)$^+$.

Step B

To a solution of the title compound from Step A above (4 g, 8.67 mmol) in 1,4-dioxane (60 mL) at 25° C., potassium carbonate (2.5 g, 18.1 mmol), L-proline (0.28 g, 2.43 mmol) and copper(I) iodide (0.462 g, 2.42 mmol) were added and the reaction mixture was stirred at 80° C. for 16 h, After completion of the reaction (monitored by TLC) the reaction mixture was poured into water (100 mL) and aqueous saturated NH$_4$Cl (100 mL) and stirred at 25° C. for 1 h. The solid thus obtained was filtered, washed with aqueous saturated NH$_4$Cl (2×25 mL), water (2×25 mL) and dried to give afford the crude title compound as an off-white solid (2.5 g).

MS: 336.0 (M+H)$^+$.

Step C

A suspension of the crude title compound from Step B above (2 g, 5.98 mmol) in H$_2$SO$_4$ (70%, 6 mL) was heated at 120° C. for 2 h. After completion of the reaction (monitored by TLC), the reaction mixture was cooled to 25° C. and slowly poured into 100 mL of cold water. Then, the reaction mixture was basified using aqueous NaOH (50%) and extracted with ethyl acetate (6×25 mL).

The combined organic layers were dried over with Na$_2$SO$_4$, filtered and the solvent was concentrated under reduced pressure, to afford the title compound as a light yellow solid (0.3 g, 23%).

$^1$H-NMR (400 MHz, DMSO-$d_6$) δ=8.27-8.31 (m, 2H), 8.11 (s, 2H).

MS: 230.4 (M+H)$^+$.

Step D

To a suspension of the title compound from Step C above (0.3 g, 1.3 mmol) in acetonitrile (5 mL) at 0° C., was added tert-butyl nitrite (0.2 g, 1.95 mmol) over a period of 10 min with a syringe. Then, copper (II) chloride (0.2 g, 1.48 mmol) was added portion wise at 0° C. and the reaction mixture was stirred for 30 min. The reaction mixture was allowed to warm to 25° C. for 1 h and heated to 65° C. for 4 h. After completion of the reaction (monitored by TLC), the solvent was evaporated under reduced pressure and the residue obtained was diluted with water (20 mL) and extracted with dichloromethane/methanol (95:5) (3×20 mL). The combined organics were washed with brine (10 mL), dried over Na$_2$SO$_4$, filtered and concentrated under reduced pressure to yield the crude product. The crude material was purified by silica-gel (60-120) column chromatography using dichloromethane/methanol (99:1) to afford the title compound as an off white solid (0.15 g, 46%).

$^1$H-NMR (400 MHz, DMSO-$d_6$) δ=8.91 (d, J=2.40 Hz, 1H), 8.82 (d, J=1.60 Hz, 1H).

MS: 250.9 (M+H)$^+$.

Step E

To a solution of the title compound from Step D above (0.18 g, 0.72 mmol) in dry dichloromethane (5 mL) at 0° C., triethylamine (0.3 mL, 2.16 mmol) and morpholine (74 mg, 0.85 mmol) were added and the reaction mixture was stirred at 25° C. for 6 h. After completion of the reaction (monitored by TLC), the reaction mixture was concentrated under reduced pressure to yield the crude product which was purified by silica-gel (60-120 mesh) column chromatography using hexane/ethyl acetate (70:30) to afford the title compound as an off yellow solid (0.18 g, 83%).

$^1$H-NMR (400 MHz, DMSO-$d_6$) δ=8.49 (d, J=2.00 Hz, 1H), 8.38 (d, J=1.60 Hz, 1H), 3.72-3.74 (m, 4H), 3.61-3.62 (m, 4H).

MS: 302.0 (M+H)$^+$.

Preparative Example 27

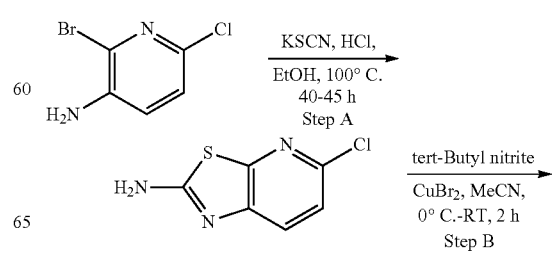

-continued

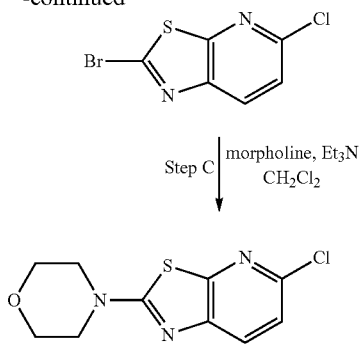

Step C | morpholine, Et₃N, CH₂Cl₂

Step A

A solution of 2-bromo-6-chloropyridin-3-amine (5 g, 24.1 mmol) and potassium thiocyanate (7 g, 72.3 mmol) in ethanol (50 mL), hydrochloric acid (37%, 100 mL) was added and the reaction mixture was stirred at 100° C. for 40-45 h. The completion of the reaction was confirmed by TLC. The reaction mixture was cooled to room temperature and concentrated to provide a brown solid, which was partitioned in dichloromethane (150 mL) and aqueous 1 N NaOH (50 mL). The solid was filtered and dried to provide the crude title compound as a light yellow solid (3.5 g, 79%). The product was taken as such for next step.

MS: 186.1 (M+H)⁺.

Step B

To a suspension of the title compound from Step A above (1.5 g, 8.08 mmol) in acetonitrile (25 mL) at 0° C. was added tert-butyl nitrite (1.4 ml, 12.12 mmol) over a period of 10 min with a syringe. Then, copper(II) bromide (2.16 g, 9.69 mmol) was added portion wise. After 30 minutes at 0° C., the reaction mixture was allowed to warm to room temperature for 2 h. The progress of the reaction was monitored by TLC. After completion of the reaction, solvent was evaporated and diluted with water (20 mL) and dichloromethane/methanol (95:5) (3×20 mL). The combined organics were washed with brine (10 mL), dried over Na₂SO₄, filtered and concentrated under reduced pressure. The crude compound was purified by silica-gel (60-120) column chromatography, eluted with dichloromethane/methanol (99:1) to afford the title compound as an pale yellow solid (0.65 g, 32%). The product was taken as such for next step.

MS: 248.5 (M+H)⁺.

Step C

To a solution of the crude title compound from Step B above (0.65 g, 2.61 mmol) in dry dichloromethane (5 mL), were added triethylamine (1.1 mL, 7.83 mmol) and morpholine (0.34 g, 3.91 mmol). The reaction mixture was then stirred at room temperature for 6 h. The reaction mixture was concentrated under in vacuum. The crude compound was purified by silica-gel (60-120) column chromatography, eluted with petrol ether/ethyl acetate (50/50) to afford the title compound as an off yellow solid (0.6 g, 90%).

¹H-NMR (400 MHz, DMSO-d₆) δ=7.83 (d, J=8.40 Hz, 1H), 7.41 (d, J=8.44 Hz, 1H), 3.72-3.74 (m, 2H), 3.59-3.60 (m, 2H).

MS: 256.0 (M+H)⁺.

Preparative Example 28

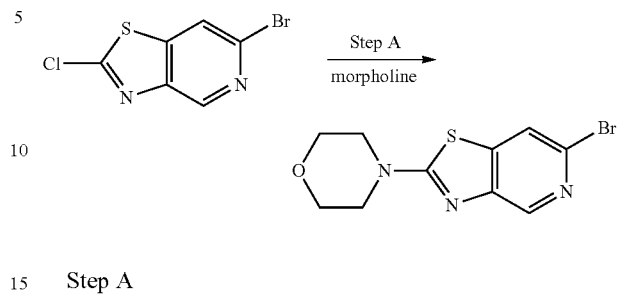

Step A

In a microwave tube commercially available 6-bromo-2-chlorothiazolo[4,5-c]pyridine (50 mg, 0.20 mmol) and morpholine (3.5 mL, 40.1 mmol) were added. The tube was sealed and stirred at room temperature for 10 minutes and then at 150° C. for 10 minutes in a microwave reactor (Biotage). The solvent was removed under reduce pressure to afford the title compound (0.60 g, 78%).

¹H NMR (400 MHz, DMSO-d₆) δ=8.48 (s, 1H), 8.05 (s, 1H), 3.61 (dd, 4H), 3.17-3.03 (m, 4H).

Preparative Example 29

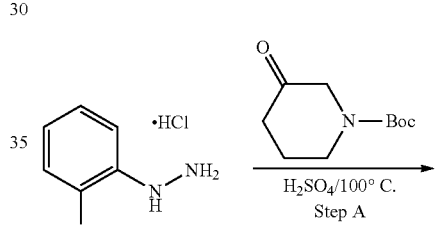

H₂SO₄/100° C.
Step A

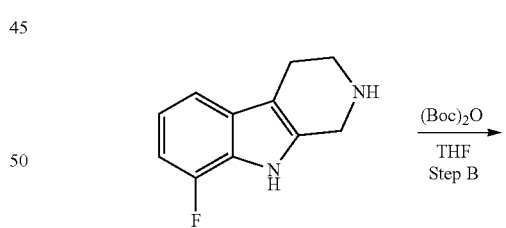

(Boc)₂O
THF
Step B

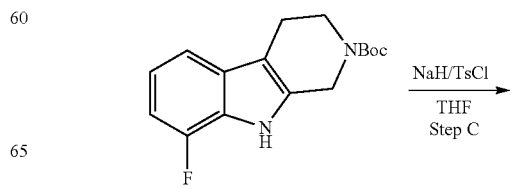

NaH/TsCl
THF
Step C

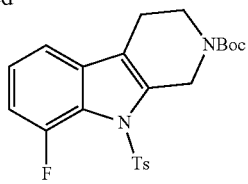

Step D
HCl/DCM

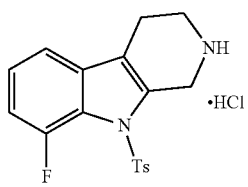

Step A

To a stirred solution of commercially available (2-fluorophenyl)hydrazine; hydrochloride (10.0 g, 0.0615 mol) and tert-butyl 3-oxopiperidine-1-carboxylate (12.3 g, 0.0615 mol) in 1,4-Dioxane (100.0 mL) concentrated $H_2SO_4$ (10.0 mL) was added (at 0° C.), then heated to 100° C. for 12 h under nitrogen atmosphere.

The reaction mixture was concentrated and the crude product was basified by using 30% NaOH water solution (pH=9-10) followed by dichloromethane extraction. The dichloromethane layer was concentrated under reduced pressure to afford the title compound (10.0 g, Crude) as a brown oil.

The crude compound was used for the next step without further purifications.

MS: 191.1 $(M+H)^+$.

Step B

To a solution of the crude title compound from Step A above (10.0 g, Crude) in tetrahydrofuran (100.0 mL) was added triethylamine (2.83 mL, 0.0205 mol) and Di-tert-butyl dicarbonate (1.88 mL, 0.00820 mol) at 0° C., then stirred at room temperature for 12 h under nitrogen. The reaction was monitored by TLC and LCMS. The reaction mixture was diluted with ethyl acetate (50 mL) and water (100 mL). The organic phase was separated and the aqueous phase was extracted with ethyl acetate two more times. The combined organic phase was dried over $Na_2SO_4$, filtered and the solvents were evaporated under reduced pressure. The crude purified on HP-Sil column (Biotage), by employing a petroleum ether/ethyl acetate gradient (100/0→90/10) to afford to afford the title compound (1.5 g, 10%) as a pale yellow solid.

$^1$H-NMR (400 MHz, DMSO-$d_6$) δ 11.32 (bs, 1H), 7.22 (d, J=7.64 Hz, 1H), 6.86-6.88 (m, 2H), 4.58 (s, 2H), 3.68 (t, J=5.60 Hz, 2H), 2.69 (t, J=5.00 Hz, 2H), 1.44 (s, 9H).

MS: 235.1 (M+H)-t-butyl.

Step C

To a suspension of Sodium hydride (0.575 g, 15.0 mmol) in THF (10.0 mL), was added dropwise a THF solution (10.0 mL) of the title compound from Step B above (1.50 g, 5.00 mmol) at 0° C. and the mixture was stirred at room temperature for 60 min. Tosyl chloride (1.20 g, 6.00 mol) was added at 0° C. dropwise and then stirred at room temperature for 3 h under nitrogen atmosphere.

After completion of the reaction by TLC, the reaction mixture was quenched with ice water followed by extraction using ethyl acetate (50.0 mL). The organic layer was separated, dried over sodium sulphate, filtered and then concentrated under reduced pressure. The crude purified on HP-Sil column (Biotage), by employing a petroleum ether/ethyl acetate gradient (100/0→80/20) to afford the title compound (1.6 g, 71.8%) as an off white solid.

$^1$H-NMR (400 MHz, DMSO-$d_6$) δ 7.76 (d, J=7.52 Hz, 2H), 7.42 (d, J=8.08 Hz, 2H), 7.31 (d, J=7.20 Hz, 1H), 7.22-7.24 (m, 1H), 7.07-7.09 (m, 1H), 4.94 (s, 2H), 3.69 (bs, 2H), 2.69 (bs, 2H), 2.35 (s, 3H), 1.46 (s, 9H).

MS: 345.1 $(M+H)^+$-Boc.

Step D

To a stirred solution of the title compound from Step C above (1.6 g, 3.59 mmol) in dichloromethane (10.0 mL) was added 4M HCl in 1,4-dioxane (10.00 mL) at 0° C., then stirred for 2 h at 0° C. and warmed up to room temperature.

After completion of the reaction by TLC, the reaction mixture was concentrated to afford the title compound (1.3 g, 94.6%) as a grey solid.

The crude compound was used for the next step without further purifications

MS: 345.1 $(M+H)^+$

Preparative Example 30

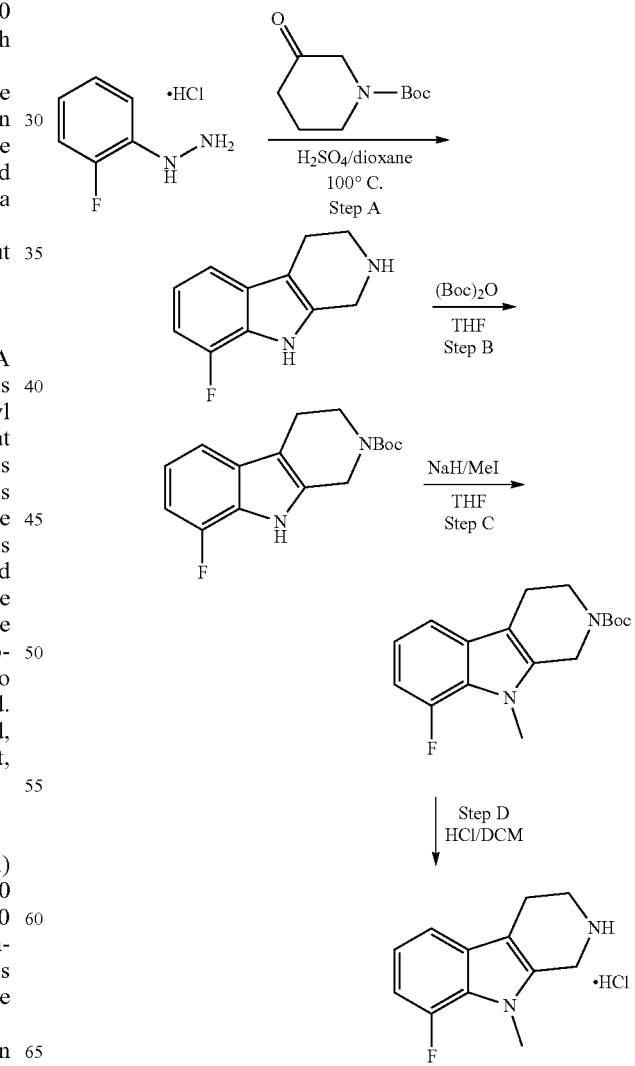

Step A

To a stirred solution of commercially available (2-fluorophenyl)hydrazine; hydrochloride (10.0 g, 0.0615 mol) and tert-butyl 3-oxopiperidine-1-carboxylate (12.3 g, 0.0615 mol) in 1,4-Dioxane (100.0 mL) was added Concentrated $H_2SO_4$ (10.0 mL) at 0° C. The reaction was then heated at 100° C. for 12 h under nitrogen atmosphere.

The reaction mixture was concentrated and the crude product was basified by using 30% NaOH water solution (pH=9-.10) followed by dichloromethane extraction. The dichloromethane layer was concentrated under reduced pressure to afford the title compound (10.0 g, Crude) as a brown oil.

The crude compound was used for the next step without further purifications.

MS: 191.1 $(M+H)^+$.

Step B

To a stirred solution of the title compound from Step A (10.0 g, Crude) in tetrahydrofuran (100.0 mL) was added triethylamine (2.83 mL, 0.0205 mol) and Di-tert-butyl dicarbonate (1.88 mL, 8.20 mmol) at 0° C. The mixture was stirred at room temperature for 12 h under nitrogen atmosphere. The reaction was monitored by TLC and LCMS. The reaction mixture was diluted with ethyl acetate (50 mL) and water (100 mL). The organic phase was separated and the aqueous phase was extracted with ethyl acetate two more times. The combined organic phase was dried over $Na_2SO_4$, filtered and the solvents were evaporated under reduced pressure. The crude purified on HP-Sil column (Biotage), by employing a petroleum ether/ethyl acetate gradient (100/0→90/10) to afford the title compound (1.5 g, 10%) as a pale yellow solid.

$^1$H-NMR (400 MHz, DMSO-$d_6$) δ 11.32 (bs, 1H), 7.22 (d, J=7.64 Hz, 1H), 6.86-6.88 (m, 2H), 4.58 (s, 2H), 3.68 (t, J=5.60 Hz, 2H), 2.69 (t, J=5.00 Hz, 2H), 1.44 (s, 9H).

MS: 235.1 (M+H)-t-butyl.

Step C

To a suspension of Sodium hydride (0.421 g, 0.0110 mol) in THF (10.0 mL), was added dropwise a THF solution (10 mL) of the title compound from Step B (1.1 g, 3.66 mol) at 0° C., The mixture was then stirred at room temperature for 60 min. Iodomethane (0.624 g, 4.39 mmol) was added at 0° C. and the mixture was then stirred at room temperature for 3 h under nitrogen atmosphere. After completion of the reaction by TLC, the reaction mixture was quenched with ice water followed by extraction using ethyl acetate (50.0 mL). The organic layer was separated, dried over sodium sulphate, filtered and then concentrated to afford the title compound (1.10 g, 96.2%) as a pale brown solid.

The crude compound was used for the next step without further purifications.

MS: 305.3 $(M+H)^+$.

Step D

To a stirred solution of of the title compound from Step C (1.10 g, 3.52 mol) in dichloromethane (5.0 mL) was added a solution of 4N HCl in dioxane (10.00 mL) at 0° C. The misture was stirred for 2 h at 0° and warmed up to room temperature.

The reaction mixture was concentrated and the crude product was washed with diethyl ether (10.00 mL), dried under vacuum to afford the title compound (750 mg, 78.8%) as a grey solid.

$^1$H-NMR (400 MHz, DMSO-$d_6$) δ 9.94 (bs, 2H), 7.29 (d, J=7.60 Hz, 1H), 6.97-6.98 (m, 2H), 4.41 (s, 2H), 3.82 (s, 3H), 3.37-3.38 (m, 2H), 2.92-2.93 (m, 2H).

MS: 205.0 $(M+H)^+$.

Preparative Example 31

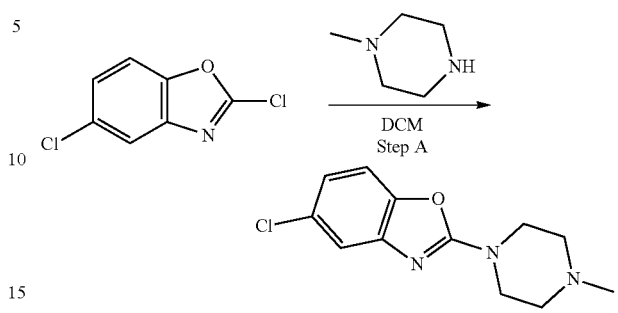

Step A

To a solution of commercially available 2,5-dichloro-1,3-benzoxazole (1.00 g, 5.32 mmol) in dichloromethane (50.0 mL), triethylamine (1.61 g, 1.60 mol) and 1-methylpiperazine (0.693 g, 6.38 mmol) were added slowly at 0° C. The mixture was then stirred at 25° C. for 12 hr. The reaction mixture was diluted with water (50.0 mL) and dichloromethane (50.0 mL). The organic phase was separated and the aqueous phase was extracted with dichloromethane two more times. The combined organic phase was dried over $Na_2SO_4$, filtered and the solvents were evaporated under reduced pressure. The crude purified on HP-Sil column (Biotage), by employing a DCM/MeOH gradient (100/0→90/10) to afford the title compound (1.0 g, 73.9%) as a white solid.

$^1$H-NMR (400 MHz, DMSO-$d_6$) δ 7.41 (d, J=8.44 Hz, 1H), 7.33 (s, 1H), 7.02-7.03 (m, 1H), 3.59-3.61 (m, 4H), 2.41-2.42 (m, 4H), 2.23 (s, 3H).

MS: 252.1 $(M+H)^+$.

Preparative Example 32

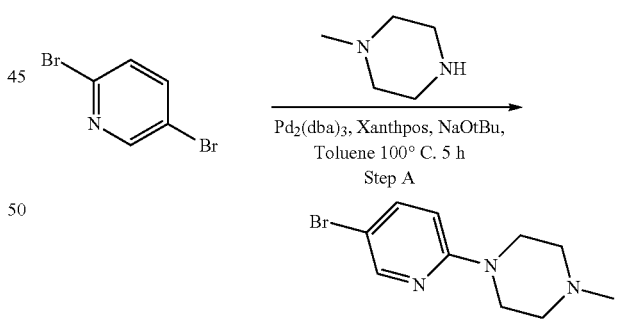

Step A

Commercially available 2,5 dibromo pyridine (1.0 g, 4.22 mmol) and N-methyl piperazine (0.55 g, 5.49 mmol) were dissolved in toluene degassed and filled with nitrogen atmosphere. Then Tris(dibenzylideneacetone)dipalladium(0) (0.077 g, 0.084 mmol), xantphos (0.147 g, 0.253 mmol) and sodium t-butoxide (0.609 g, 6.33 mmol) were added and the mixture was heated to 100° C. for 5 h.

The reaction mixture was filtered with celite, washed with dichloromethane and methanol and the solvents were evaporated under reduced pressure. The crude purified on HP-Sil column (Biotage), by employing a DCM/MeOH gradient (100/0→96/04) to afford the title compound (0.46 g, 37%) as a pale yellow solid.

¹H-NMR (400 MHz, MeOD) δ 8.14-8.14 (m, 1H), 7.63-7.64 (m, 1H), 6.79 (d, J=9.08 Hz, 1H), 3.54-3.56 (m, 4H), 2.55-2.56 (m, 4H), 2.36 (s, 3H).

MS: 258.1 (M+2H)⁺.

Preparative Example 33

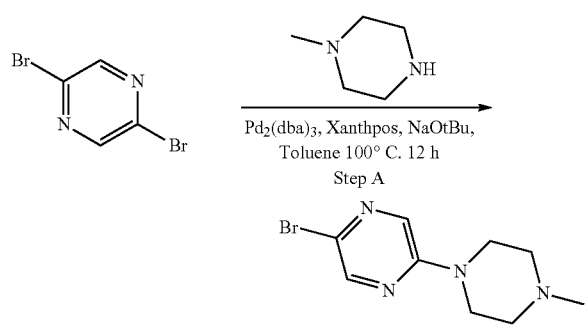

Step A

Commercially available 2,5-dibromopyrazine (0.500 g, 2.10 mmol) and 1-methylpiperazine (0.105 g, 1.05 mmol), Xantphos (0.073 g, 0.126 mmol), Tris(dibenzylideneacetone)dipalladium(0) (0.0385 g, 0.126 mmol) and sodium tert-butoxide (0.404 g, 4.20 mmol) were added into a degaessed and dry Toluene (15.0 ml) was added. The vial was filled with Argon gas, sealed, and heated at 100° C. for 12 hours. The reaction mixture was filtered through celite and the filtrate was concentrated under reduced pressure to afford the title compound (0.165 g, 28%) as a pale brown gummy solid. The crude compound was used for the next step without further purifications.

MS: 259.0 (M+2H)⁺.

Preparative Example 34

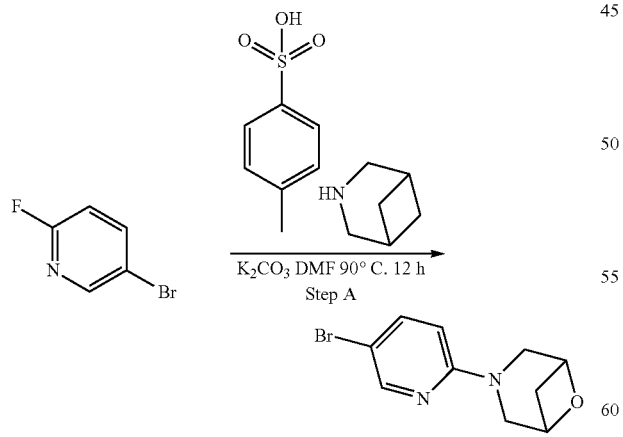

Step A

To a solution of commercially available 5-bromo-2-fluoropyridine (0.3 g, 1.70 mmol) and 6-oxa-3-azabicyclo[3.1.1]heptane 4-methylbenzenesulfonate (0.463 g, 1.7 mmol) in DMF potassium carbonate was added (0.707 g, 5.11 mmol). The reaction heated to 90° C. for 12 h. The reaction mixture was diluted with ethyl acetate (30 mL) and water (30 mL). The organic phase was separated and the aqueous phase was extracted with ethyl acetate two more times. The combined organic phase was dried over Na₂SO₄, filtered and the solvents were evaporated under reduced pressure. The crude purified on HP-Sil column (Biotage), by employing an ethyl acetate/petroleum ether gradient (30/70) to afford the title compound (0.14 g, 31%) as a white solid.

¹H-NMR (400 MHz, DMSO-d₆) δ 8.20 (d, J=3.20 Hz, 1H), 7.71-7.73 (m, 1H), 6.63 (d, J=11.60 Hz, 1H), 4.69-4.71 (m, 2H), 3.64-3.68 (m, 2H), 3.54-3.55 (m, 2H), 1.89-1.90 (m, 2H).

MS: 255.1 (M+H)⁺.

Preparative Example 35

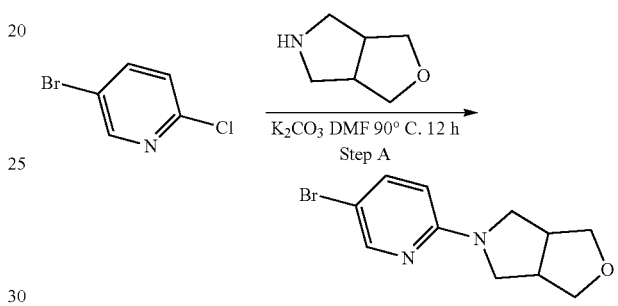

Step A

To a solution of commercially available 5-bromo-2-chloro-pyridine (0.25 g, 2.451 mmol) and hexahydro-1H-furo[3,4-c]pyrrole (0.647 g, 3.676 mmol) in DMF (5 mL) and potassium carbonate (0.677 g, 4.902 mmol) was added and the mixture was heated at 90° C. for 12 h. The reaction mixture was diluted with ethyl acetate (30 mL) and water (30 mL). The organic phase was separated and the aqueous phase was extracted with ethyl acetate two more times. The combined organic phase was dried over Na₂SO₄, filtered and the solvents were evaporated under reduced pressure. The crude purified on HP-Sil column (Biotage), by employing an ethyl acetate/petroleum ether gradient (30/70) to afford the title compound (0.25 g, 60%).

MS: 271.1 (M+2H)⁺.

Preparative Example 36

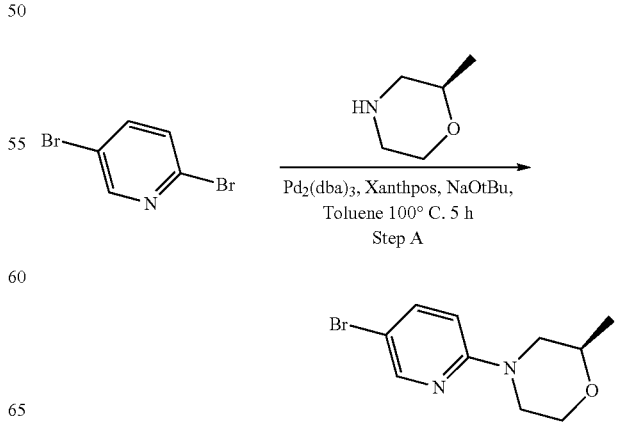

Step A

Commercially available 2,5-dibromopyridine (0.5 g, 2.2 mmol) and (R)-2-methylmorpholine (0.234 g, 2.9 mmol) were added to a reaction tube and degassed toluene (10.0 ml) was added. Then Xantphos (0.073 g, 2.1 mol), Tris(dibenzylideneacetone)dipalladium(0) (0.024 g, 0.4 mmol) and Sodium tert-butoxide (0.608 g, 6.3 mmol) were added and the solution was heated at 100° C. for 5 hours in sealed tube filled with Argon gas.

The reaction mixture was filtered through celite and the filtrate was concentrated under reduced pressure. The crude purified on HP-Sil column (Biotage), by employing a Petroleum ether/ethyl acetate gradient (100/0→70/30) to afford title compound (0.3 g, 55%) as an off white solid.

$^1$H-NMR (400 MHz, DMSO-d$_6$) δ 8.18 (d, J=3.20 Hz, 1H), 7.69-7.70 (m, 1H), 6.84 (d, J=12.00 Hz, 1H), 3.87-3.88 (m, 3H), 3.48-3.49 (m, 2H), 2.74-2.76 (m, 1H), 1.14 (d, J=8.00 Hz, 3H).

MS: 257.1 (M+H)$^+$.

Preparative Example 37

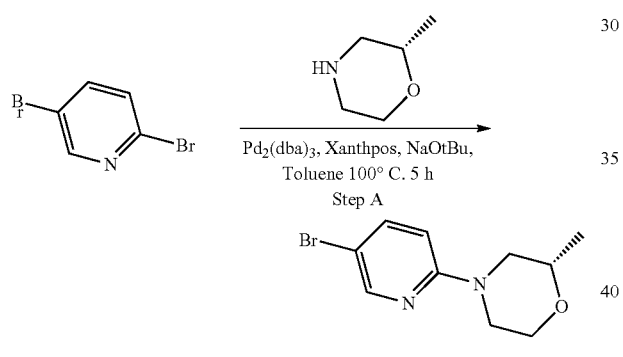

Step A

Commercially available 2,5-dibromopyridine (0.5 g, 2.2 mmol) and (S)-2-methylmorpholine (0.234 g, 2.9 mmol) were added to a reaction tube and degassed toluene (10.0 ml) was added. Then Xantphos (0.073 g, 2.1 mol), Tris(dibenzylideneacetone)dipalladium(0) (0.024 g, 0.4 mmol) and Sodium tert-butoxide (0.608 g, 6.3 mmol) were added and the solution was heated at 100° C. for 5 hours in sealed tube filled with Argon gas.

The reaction mixture was filtered through celite and the filtrate was concentrated under reduced pressure. The crude purified on HP-Sil column (Biotage), by employing a Petroleum ether/ethyl acetate gradient (100/0→70/30) to afford title compound (0.37 g, 68%) as an off white solid.

$^1$H-NMR (400 MHz, DMSO-d$_6$) δ 8.18 (d, J=2.32 Hz, 1H), 7.70-7.71 (m, 1H), 6.84 (d, J=9.04 Hz, 1H), 3.90-3.91 (m, 3H), 3.52-3.53 (m, 2H), 2.52-2.53 (m, 1H), 1.15 (d, J=6.24 Hz, 3H).

MS: 257.1 (M+H)$^+$.

Preparative Example 38

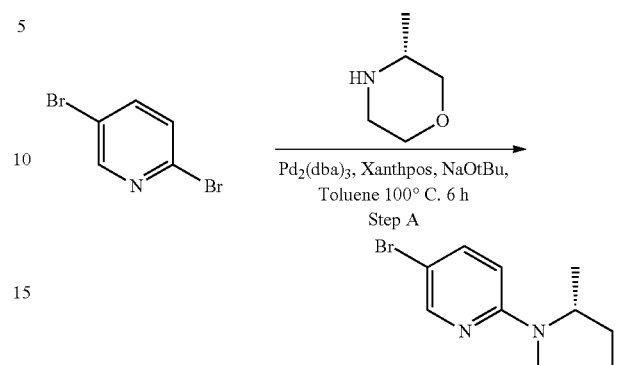

Step A

Commercially available 2,5-dibromopyridine (1 g, 4.22 mmol) and (R)-3-methyl morpholine (0.234 g, 2.9 mmol) were added to a reaction tube and degassed toluene (10.0 ml) was added. Then Xantphos (0.146 g, 0.253 mmol), Tris (dibenzylideneacetone)dipalladium(0) (0.048 g, 0.84 mmol) and Sodium tert-butoxide (1.21 g, 12.66 mmol) were added and the solution was heated at 100° C. for 6 hours in sealed tube filled with Argon gas. The reaction mixture was filtered through celite and the filtrate was concentrated under reduced pressure. The crude purified on HP-Sil column (Biotage), by employing a Petroleum ether/ethyl acetate gradient (100/0→70/30) to afford title compound (0.17 g, 15%) as an off white solid. The crude compound was used for the next step without further purifications.

MS: 257.1 (M+H)$^+$.

Preparative Example 39

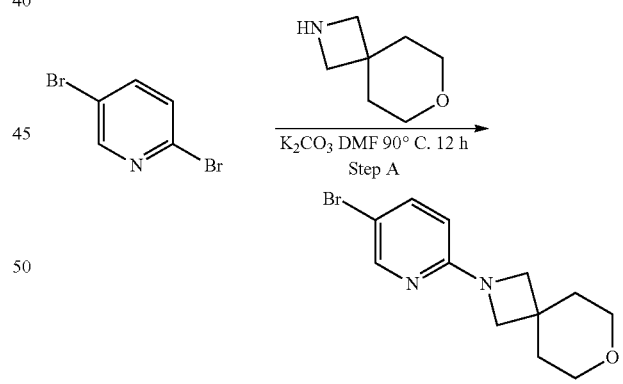

Step A

To a solution of commercially available 5-bromo-2-fluoro-pyridine (0.5 g, 2.84 mmol) and 7-oxa-2-azaspiro[3.5]nonane (0.36 g, 2.84 mol) in DMF (5 mL) potassium carbonate (1.17 g, 8.52 mmol) and the mixture was heated to 90° C. for 12 h. The reaction mixture was diluted with ethyl acetate (30 mL) and water (30 mL). The organic phase was separated and the aqueous phase was extracted with ethyl acetate two more times. The combined organic phase was dried over Na$_2$SO$_4$, filtered and the solvents were evaporated under reduced pressure to afford title compound (0.44 g, 55%).

¹H-NMR (400 MHz, DMSO-d₆) δ 8.12 (d, J=2.40 Hz, 1H), 7.64-7.65 (m, 1H), 6.36 (d, J=11.60 Hz, 1H), 3.66-3.69 (m, 4H), 3.52-3.54 (m, 4H), 1.71-1.73 (m, 4H).

MS: 285.0 (M+H)⁺.

Preparative Example 40

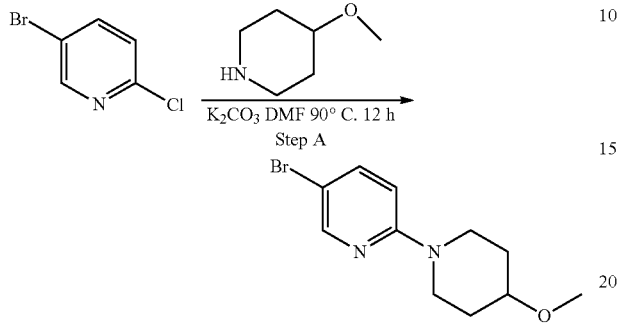

Step A

To a solution of commercially available 5-bromo-2-chloro-pyridine (0.83 g, 4.34 mmol) and 4-methoxy piperidine (0.5 g, 4.34 mmol) in DMF (5 mL) potassium carbonate (1.79 g, 13.02 mmol) was added and the mixture was heated to 90° C. for 12 h. The reaction mixture was diluted with ethyl acetate (50 mL) and water (30 mL). The organic phase was separated and the aqueous phase was extracted with ethyl acetate two more times. The combined organic phase was dried over Na₂SO₄, filtered and the solvents were evaporated under reduced pressure. The crude purified on HP-Sil column (Biotage), by employing a ethyl acetate/petroleum ether gradient (30/70) to afford title compound (0.5 g, 42%).

¹H-NMR (400 MHz, DMSO-d₆) δ 8.14-8.15 (m, 1H), 7.63-7.64 (m, 1H), 6.85 (d, J=9.12 Hz, 1H), 3.86-3.87 (m, 2H), 3.39-3.40 (m, 1H), 3.27 (s, 3H), 3.14-3.15 (m, 2H), 1.84-1.85 (m, 2H), 1.35-1.36 (m, 2H).

MS: 273.1 (M+2H)⁺.

Preparative Example 41

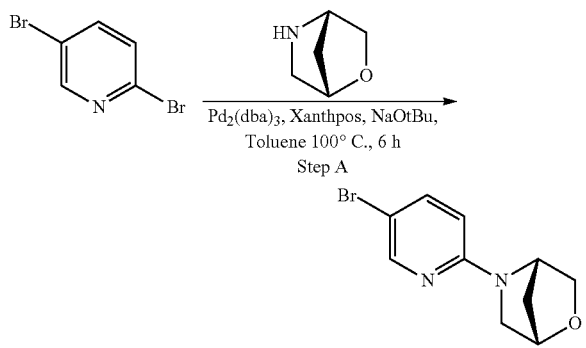

Step A

To a solution of commercially available 2,5-dibromopyridine (0.5 g, 2.11 m mol) and ((1S,4S)-2-oxa-5-azabicyclo[2.2.1]heptane (0.25 g, 2.53 mmol) were added to a reaction tube and degassed toluene (10.0 ml) was added. Then Xantphos (0.073 g, 0.127 mmol), Tris(dibenzylideneacetone)dipalladium(0) (0.024 g, 0.042 m mol) and Sodium tert-butoxide (0.61 g, 6.3 mmol) were added and the solution was heated at 100° C. for 6 hours in sealed tube filled with Argon gas. The reaction mixture was filtered through celite and the filtrate was concentrated under reduced pressure. The crude purified on HP-Sil column (Biotage), by employing a Petroleum ether/ethyl acetate gradient (100/0→70/30) to afford title compound (0.3 g, 57%) as an off white solid.

¹H-NMR (400 MHz, DMSO-d₆) δ 8.13 (s, 1H), 7.64-7.65 (m, 1H), 6.54 (d, J=8.80 Hz, 1H), 4.80 (s, 1H), 4.65 (s, 1H), 3.76 (d, J=7.20 Hz, 1H), 3.61 (d, J=6.80 Hz, 1H), 3.42 (d, J=10.00 Hz, 1H), 3.19 (d, J=10.00 Hz, 1H), 1.86-1.89 (m, 2H).

MS: 255.1 (M+H)⁺.

Preparative Example 42

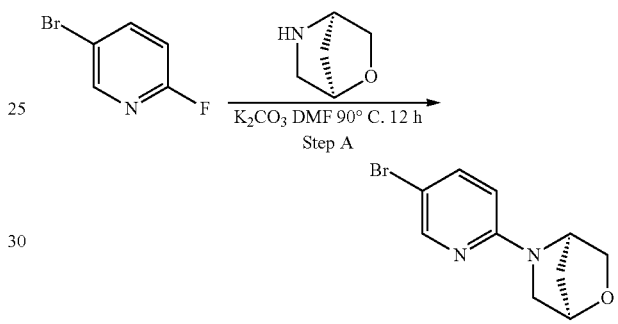

Step A

To a solution of commercially available 5-bromo-2-fluoro-pyridine (0.23 g, 1.30 mmol) and ((1R,4R)-2-oxa-5-azabicyclo[2.2.1]heptane (0.18 g, 1.30 mmol) in DMF (5 mL) potassium carbonate (0.54 g, 3.9 mmol) was added and the mixture was heated to 90° C. for 12 h. The reaction mixture was diluted with ethyl acetate (30 mL) and water (30 mL). The organic phase was separated and the aqueous phase was extracted with ethyl acetate two more times. The combined organic phase was dried over Na₂SO₄, filtered and the solvents were evaporated under reduced pressure to afford title compound (0.32 g, 96%).

¹H-NMR (400 MHz, DMSO-d₆) δ 8.13 (d, J=2.80 Hz, 1H), 7.64-7.64 (m, 1H), 6.54 (d, J=11.60 Hz, 1H), 4.81 (s, 1H), 4.65 (s, 1H), 3.76 (d, J=10.00 Hz, 1H), 3.61 (d, J=10.00 Hz, 1H), 3.43 (d, J=13.20 Hz, 1H), 3.20 (d, J=13.60 Hz, 1H), 1.83-1.86 (m, 2H).

MS: 257.0 (M+2H)⁺.

Preparative Example 43

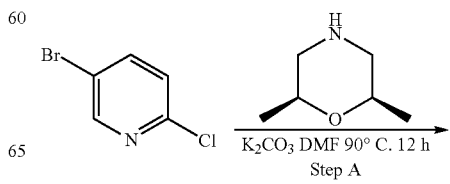

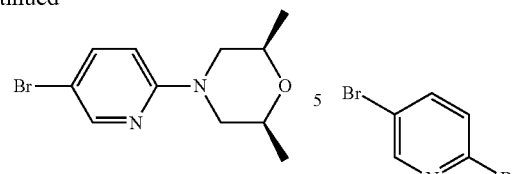

Step A

To a solution of commercially available 5-bromo-2-chloro-pyridine (1 g, 5.19 mmol) and ((2S,6R)-2,6-dimethylmorpholine (0.778 g, 6.75 mmol) in DMF (5 mL) potassium carbonate (1.57 g, 11.43 mmol) was added and the mixture was heated to 90° C. for 12 h. The reaction mixture was diluted with ethyl acetate (50 mL) and water (30 mL). The organic phase was separated and the aqueous phase was extracted with ethyl acetate two more times. The combined organic phase was dried over $Na_2SO_4$, filtered and the solvents were evaporated under reduced pressure. The crude purified on HP-Sil column (Biotage), by employing a ethyl acetate/petroleum ether gradient (30/70) to afford title compound (0.17 g, 12%).

$^1$H-NMR (400 MHz, $CDCl_3$) δ 8.20 (d, J=2.00 Hz, 1H), 7.54-7.54 (m, 1H), 6.54 (d, J=8.80 Hz, 1H), 3.97-3.97 (m, 2H), 3.69-3.70 (m, 2H), 2.49-2.51 (m, 2H), 1.27 (d, J=6.40 Hz, 6H).

MS: 271.1 $(M+H)^+$.

Preparative Example 44

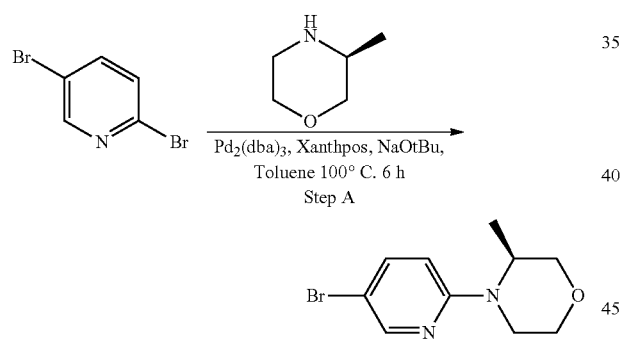

Step A

To a solution of commercially available 2,5-dibromopyridine (0.5 g, 2.11 mmol) and ((S)-3-methylmorpholine (0.213 g, 2.11 mmol) were added to a reaction tube and degassed toluene (10.0 ml) was added. Then Xantphos 0.073 g, 0.12 mmol), Tris(dibenzylideneacetone)dipalladium(0) (0.038 g, 0.042 mmol) and Sodium tert-butoxide (0.608 g, 6.33 mmol) were added and the solution was heated at 100° C. for 6 hours in sealed tube filled with Argon gas. The reaction mixture was filtered through celite and the filtrate was concentrated under reduced pressure. The crude purified on HP-Sil column (Biotage), by employing a Petroleum ether/ethyl acetate gradient (100/0→70/30) to afford title compound (0.23 g, 42%) as pale yellow solid.

$^1$H-NMR (400 MHz, $CDCl_3$) δ 8.22-8.23 (m, 1H), 7.55-7.56 (m, 1H), 6.50 (d, J=9.04 Hz, 1H), 4.23-4.24 (m, 1H), 4.01-4.02 (m, 1H), 3.76-3.77 (m, 3H), 3.59-3.60 (m, 1H), 3.16-3.17 (m, 1H), 1.24 (d, J=6.72 Hz, 3H).

MS: 259.1 $(M+H)^+$.

Preparative Example 45

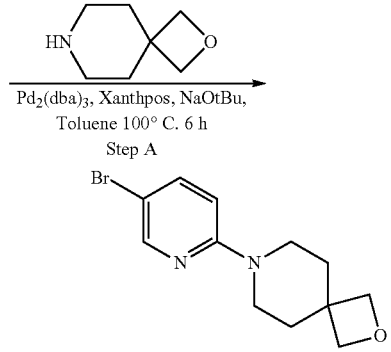

Step A

To a solution of commercially available 2,5-dibromopyridine (0.5 g, 2.11 mmol) and 2-oxa-7-azaspiro[3.5]nonane (0.268 g, 2.11 mmol) were added to a reaction tube and degassed toluene (10.0 ml) was added. Then Xantphos (0.073 g, 0.12 mmol), Tris(dibenzylideneacetone)dipalladium(0) (0.038 g, 0.042 mmol) and Sodium tert-butoxide (0.608 g, 6.33 mmol) were added and the solution was heated at 100° C. for 6 hours in sealed tube filled with Argon gas. The reaction mixture was filtered through celite and the filtrate was concentrated under reduced pressure to afford title compound (0.37 g, 62%) as an off white solid.

$^1$H-NMR (400 MHz, $CDCl_3$) δ 8.19-8.19 (m, 1H), 7.52-7.53 (m, 1H), 6.59 (d, J=9.04 Hz, 1H), 4.50 (s, 4H), 3.46-3.47 (m, 4H), 1.93-1.94 (m, 4H).

MS: 285.0 $(M+2H)^+$.

Preparative Example 46

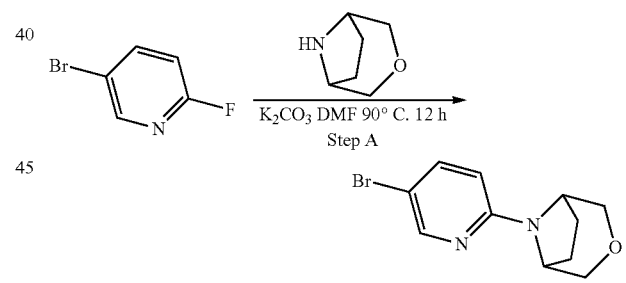

Step A

To a solution of commercially available 5-bromo-2-fluoro-pyridine (0.5 g, 3.34 mmol) and 3-oxa-8-azabicyclo[3.2.1]octane (0.882 g, 5.0133 mmol) in DMF (5 mL) potassium carbonate (0.923 g, 6.6844 mmol) was added and the mixture was heated to 90° C. for 12 h. The reaction mixture was diluted with ethyl acetate (30 mL) and water (30 mL). The organic phase was separated and the aqueous phase was extracted with ethyl acetate two more times. The combined organic phase was dried over $Na_2SO_4$, filtered and the solvents were evaporated under reduced pressure to afford title compound (0.5 g, 67%).

$^1$H-NMR (400 MHz, DMSO-$d_6$) δ 8.17 (d, J=2.12 Hz, 1H), 7.67-7.68 (m, 1H), 6.80 (d, J=8.92 Hz, 1H), 4.42 (s, 2H), 3.60-3.62 (m, 2H), 3.48-3.51 (m, 2H), 1.85-1.86 (m, 4H).

MS: 271.1 $(M+2H)^+$

Preparative example 47

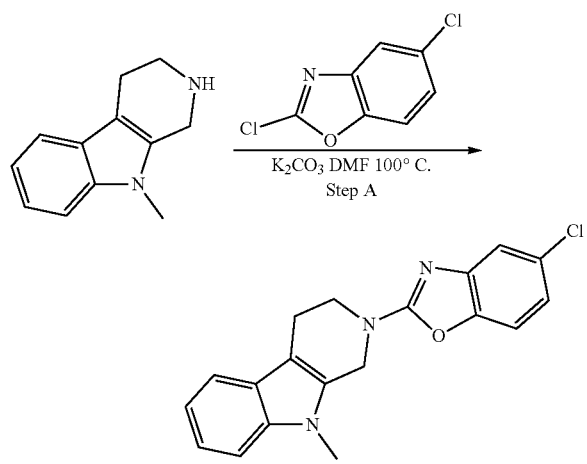

Step A

To a stirred suspension of the title compound from Preparative Example 12 (0.370 g, 0.00199 mol) and commercially available 2,5-dichloro-1,3-benzoxazole (0.336 g, 0.00179 mol) in 15 mL DMF (15 mL) potassium carbonate (0.823 g, 0.00595 mol) was added and the mixture was heated at 100° C. overnight. After completion of reaction by TLC, water was added and a solid was obtained. The solid was filtered and washed with hexane to afford the title compound (0.4 g, crude).

MS: 338.1 (M+H)$^+$

Preparative Example 48

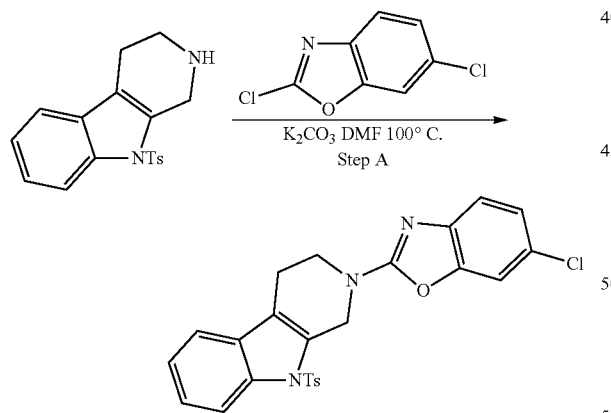

Step A

To a stirred suspension of the title compound from Preparative Example 11 (0.350 g, 0.00107 mol) and commercially available (0.181 g, 0.000965 mol) in 15 mL DMF potassium carbonate (0.445 g, 0.000756 mol) was added and the reaction mixture was heated at 100° C. rovernight. After completion of reaction by TLC, water was added and a solid was obtained. The solid was filtered and washed with hexane to afford the title compound (0.45 g, crude).

MS: 478.1 (M+H)$^+$

Preparative Example 49

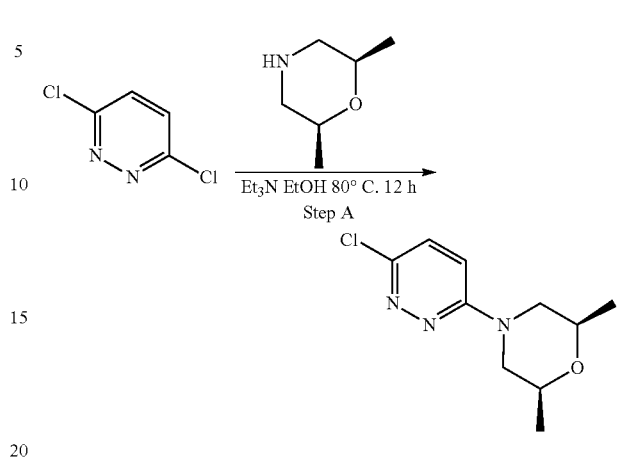

Step A

To a solution of commercially available 3,6-dichloropyridazine (0.500 g, 3.3783 mmol) and (2S,6R)-2,6-dimethylmorpholine (0.505 g, 4.3918 mmol) in ethanol (15 mL) was added triethylamine (0.516 g, 5.0675 mmol) and the reaction was heated at 80° C. for 12 h. The reaction mixture was concentrated under reduced pressure. The crude purified on HP-Sil column (Biotage), by employing a Petroleum ether/ethyl acetate gradient (100/0→70/30) to afford title compound (0.500 g, 64.93%).

$^1$H-NMR (400 MHz, DMSO-d$_6$) δ 7.56 (d, J=9.60 Hz, 1H), 7.40 (d, J=9.60 Hz, 1H), 4.18-4.18 (m, 2H), 3.61-3.62 (m, 2H), 2.49-2.50 (m, 2H), 1.16 (d, J=6.40 Hz, 6H).

MS: 228.1 (M+H)$^+$

Preparative Example 51

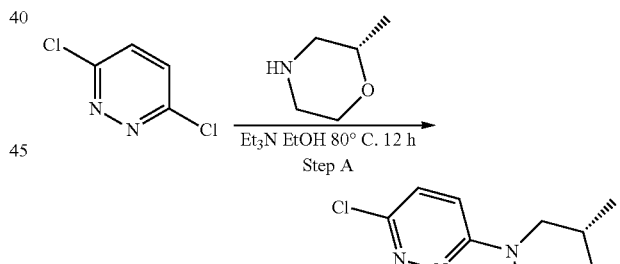

Step A

To a solution of commercially available 3,6-dichloropyridazine (0.500 g, 3.36 mmol) and (2S)-2-methylmorpholine (0.339 g, 3.36 mmol) in ethanol (15 mL) was added triethylamine (0.509 g, 5.03 mmol) and the reaction was heated at 80° C. for 12 h. The reaction mixture was concentrated under reduced pressure. The crude purified on HP-Sil column (Biotage), by employing a Petroleum ether/ethyl acetate gradient (100/0→70/30) to afford title compound (0.250 g, 34.5%).

$^1$H-NMR (400 MHz, DMSO-d$_6$) δ 7.57 (d, J=9.60 Hz, 1H), 7.40 (d, J=9.60 Hz, 1H), 4.08-4.09 (m, 2H), 3.91-3.92 (m, 1H), 3.53-3.54 (m, 2H), 2.90-2.92 (m, 1H), 2.58-2.61 (m, 1H), 1.16 (d, J=6.40 Hz, 3H).

MS: 214.1 (M+H)$^+$.

Preparative Example 52

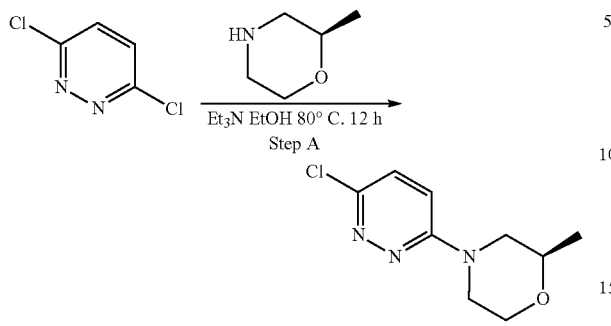

Step A

To a solution of commercially available 3,6-dichloropyridazine (0.500 g, 3.36 mmol) and (2R)-2-methylmorpholine (0.339 g, 3.36 mmol) in ethanol (15 mL) was added triethylamine (0.509 g, 5.03 mmol) and the reaction was heated to 80° C. for 12 h. The reaction mixture was concentrated under reduced pressure. The crude purified on HP-Sil column (Biotage), by employing a Petroleum ether/ethyl acetate gradient (100/0→70/30) to afford title compound (0.250 g, 34.5%).

$^1$H-NMR (400 MHz, DMSO-d$_6$) δ 7.57 (d, J=9.60 Hz, 1H), 7.40 (d, J=9.60 Hz, 1H), 3.91-3.91 (m, 3H), 3.53-3.54 (m, 2H), 2.89-2.90 (m, 1H), 2.64-2.67 (m, 1H), 1.16 (d, J=6.40 Hz, 3H).

MS: 214.2 (M+H)$^+$.

Preparative Example 53

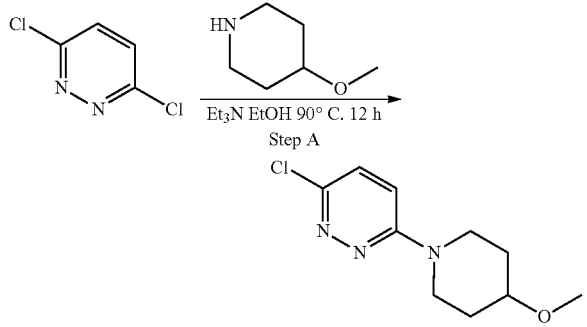

Step A

To a solution of commercially available 3,6-dichloropyridazine (0.230 g, 1.54 mmol) and 4-methoxypiperidine (0.265 g, 2.29 mmol) in ethanol (15 mL) was added triethylamine (0.301 g, 2.29 mmol) and the reaction was heated to 90° C. for 12 h. The reaction mixture was concentrated under reduced pressure. The crude purified on HP-Sil column (Biotage), by employing a Petroleum ether/ethyl acetate gradient (100/0→70/30) to afford title compound (0.335 g, 95.44%).

$^1$H-NMR (400 MHz, DMSO-d$_6$) δ 7.50 (d, J=9.60 Hz, 1H), 7.41 (d, J=9.60 Hz, 1H), 3.92-3.93 (m, 2H), 3.43-3.44 (m, 1H), 3.27-3.27 (m, 5H), 1.88-1.89 (m, 2H), 1.43-1.44 (m, 2H).

MS: 228.1 (M+H)$^+$.

Preparative Example 54

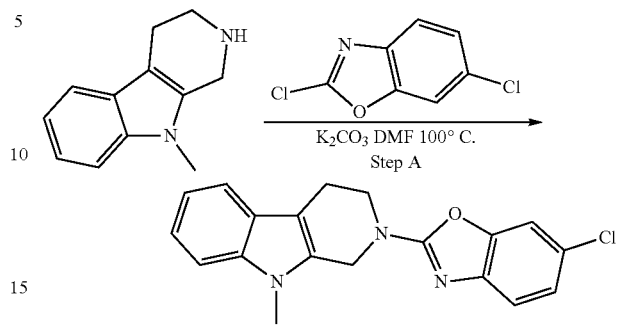

Step A

To a stirred suspension of the title compound from Preparative Example 12 (0.5 g, 2.24 mmol) and commercially available 2,6-dichloro-1,3-benzoxazole (0.43 g, 2.24 mmol) in DMF (15 mL) potassium carbonate (0.93 g, 6.72 mmol) was added and the mixture was heated at 100° C. overnight. After completion of reaction by TLC, add water was added and a solid was obtained solid. The solid was filtered washed with hexane to afford the title compound (0.76 g, crude).

MS: 338.1 (M+H)$^+$

Examples 1-122

The Examples of this invention were prepared following the general procedures for the Buchwald coupling as reported in the Schemes 5, 6 and 7 above. The specific procedures used are:

Procedure 1:

To a stirred solution of the tricyclic amine derivative (0.15 g, 1 eq.) in dry 1,4-dioxane (5 mL), was added the corresponding bromo or chloro derivative (1 eq.) as indicated in Table 1, and sodium tert.-butoxide (3 eq.). The reaction mixture was degassed for 10 min under N$_2$ atmosphere. Then tris(dibenzylideneacetone)dipalladium(0) (Pd$_2$(dba)$_3$; 0.05 eq) and 2-dicyclohexylphosphino-2',6'-diisopropoxybiphenyl (Ru-Phos; 0.1 eq) were added and the reaction mixture was heated to 100° C. until the completion of the reaction. After the completion of the reaction (monitored by LCMS), the reaction mixture was filtered through celite and washed with ethyl acetate. The filtrate was concentrated under reduced pressure to yield the crude product. The crude material was purified by flash column chromatography or preparative HPLC to afford the tosyl protected compound. To a solution of tosyl compound (1.0 eq) in Dioxane:MeOH (1:1, 10 vol), was added NaOtBu (3 eq) and heated to 70° C. for 6 hours. The reaction mixture was concentrated under vacuum and the crude product was column purified to afford desired product. The crude material was purified by flash column chromatography or preparative HPLC to afford the final compounds as indicated in Table 1.

Procedure 2:

To a stirred solution of the tricyclic amine derivative (0.15 g, 1 eq.) in dry 1,4-dioxane (5 mL), was added the corresponding bromo or chloro derivative (1 eq.) as indicated in Table 1, and sodium tert.-butoxide (3 eq.). The reaction mixture was degassed for 10 min under N$_2$ atmosphere. Then tris(dibenzylideneacetone)dipalladium(0) (Pd$_2$(dba)$_3$; 0.05 eq) and 2-dicyclohexylphosphino-2',6'-diisopropoxybiphenyl (Ru-Phos; 0.1 eq) were added and the reaction mixture was heated to 100° C. until the completion of the reaction. After the completion of the reaction (monitored by LCMS), the reaction mixture was filtered through celite and washed with ethyl acetate. The filtrate was concentrated under reduced pressure to yield the crude product. The crude material was purified by flash column chromatography or preparative HPLC to afford the final compounds as indicated in Table 1.

Procedure 3:

Pd(OAc)$_2$ (0.1 eq) and Xantphos (0.3 eq.) were added to a reaction vial and degazed Dioxane (4 ml) was added. The vial was filled with Argon gas and sealed. The suspension was heated at 110° C. for 1 minute then tricyclic amine derivative (70 mg, 1 eq.), bromo or chloro derivative (1.1 eq.) and Cs$_2$CO$_3$ (3.5 eq.) were added and the solution was heated at 100° C. for 18 hours. The reaction mixture was diluted with ethyl acetate (30 mL) and water (30 mL). The organic phase was separated and the aqueous phase was extracted with ethyl acetate two more times. The combined organic phase was dried over Na$_2$SO$_4$, filtered and the solvents were evaporated under reduced pressure. The crude purified on HP-Sil column (Biotage), by employing a DCM/MeOH gradient (100/0→95/05) to to afford the Tosyl protected compound.

Tosyl derivatives (50 mg, 1 eq.), Cs$_2$CO$_3$ (3 eq.) were added into a microwave tube followed by MeOH (Ratio: 1.000, Volume: 4 ml) and degassed THF (Ratio: 2.000, Volume: 8 ml). The reaction mixture was heated at 110° C. for 30 minutes in a microwave reactor and cooled at room temperature. The solvents were removed under reduce pressure and the residue was purified on HP-Sil SNAP cartridges using a Biotage Isolera One purification system by employing a DCM/MeOH gradient (100/0→90/10) to afford the final compounds as indicated in Table 1.

Procedure 4:

To a stirred solution of the tricyclic amine derivative (0.15 g, 1 eq.) in dry 1,4-dioxane (5 mL), was added the corresponding bromo or chloro derivative (1 eq.) as indicated in Table 1, and sodium Cs$_2$CO$_3$ (3 eq.). The reaction mixture was degassed for 10 min under N$_2$ atmosphere. Then Pd(OAc)$_2$; 0.1 eq) and 2-Dicyclohexylphosphino-2',4',6'-triisopropylbiphenyl (XPhos; 0.3 eq) were added and the reaction mixture was heated to 100° C. until the completion of the reaction. After the completion of the reaction (monitored by LCMS), the reaction mixture was filtered through celite and washed with ethyl acetate. The filtrate was concentrated under reduced pressure to yield the crude product. The crude material was purified by flash column chromatography or preparative HPLC to afford the Tosyl protected compound. To a solution of tosyl compound (1.0 eq) in Dioxane:MeOH (1:1, 10 vol), was added NaOtBu (3 eq) and heated to 70° C. for 6 hours. The reaction mixture was concentrated under vacuum and the crude product was column purified to afford desired product. The crude material was purified by flash column chromatography or preparative HPLC to afford the final compounds as indicated in Table 1.

Procedure 5

To a stirred solution of the tricyclic amine derivative (150 mg, 1 eq) in dry dioxane (5 mL), was added the corresponding bromo or chloro derivative (1 eq.) as indicated in Table 1. Sodium Tert-Butoxide (3 eq) was the added and degassed for 10 min under Nitrogen atmosphere. To this reaction mixture was added Ruphos G4 Pd (0.3 eq) and heated to 100° C. until the completion of the reaction. The reaction mixture was filtered through a Celite bed, washed with EtOAc. The filtrate was concentrated and the crude was purified by column chromatography or Prep HPLC to afford the examples compound as indicated in Table 1.

TABLE 1

| Example | Tricyclic amine derivative | Bromo or Chloro derivative | Product Example | 1. Yield; %<br>2. $^1$H-NMR<br>3. MH$^+$ (ESI)<br>4. Synthesis procedure |
|---|---|---|---|---|
| 1 | (structure) | (structure) | (structure) | 1. 11%<br>2. $^1$H-NMR (400 MHz, DMSO-d$_6$) δ = 7.57 (s, 1H), 7.39-7.40 (m, 3H), 7.09-7.11 (m, 1H), 6.98-7.00 (m, 1H), 4.44 (s, 2H), 3.72-3.73 (m, 7H), 3.58-3.60 (m, 2H), 3.48 (bs, 4H), 2.82 (bs, 2H).<br>3. 405.0<br>4. Procedure 2 |
| 2 | (structure) | (structure) | (structure) | 1. 11%<br>2. $^1$H-NMR (400 MHz, DMSO-d$_6$) δ = 7.53 (s, 1H), 7.35-7.37 (m, 3H), 7.09-7.11 (m, 1H), 6.98-7.00 (m, 1H), 4.42 (s, 2H), 3.71 (s, 3H), 3.56-3.57 (m, 2H), 3.11 (s, 6H), 2.82 (bs, 2H).<br>3. 363.2<br>4. Procedure 2 |

TABLE 1-continued

| Example | Tricyclic amine derivative | Bromo or Chloro derivative | Product Example | 1. Yield; %<br>2. ¹H-NMR<br>3. MH⁺ (ESI)<br>4. Synthesis procedure |
|---|---|---|---|---|
| 3 | | | | 1. 19%<br>2. ¹H-NMR (400 MHz, DMSO-d₆) δ = 7.39-7.43 (m, 1H), 7.27-7.31 (m, 2H), 7.20 (d, J = 8.80 Hz, 1H), 6.99 (dd, J = 2.40, 8.40 Hz, 1H), 6.82-6.87 (m, 1H), 4.40 (bs, 2H), 3.69-3.73 (m, 7H), 3.52-3.58 (m, 6H), 2.51-2.81 (m, 2H).<br>3. 407.0<br>4. Procedure 2 |
| 4 | | | | 1. 19%<br>2. ¹H-NMR (400 MHz, DMSO-d₆) δ = 7.39-7.42 (m, 1H), 7.28-7.31 (m, 1H), 6.93-6.98 (m, 2H), 6.82-6.87 (m, 2H), 4.39 (br-s, 2H), 3.68-3.73 (m, 7H), 3.54-3.57 (m, 2H), 2.89-2.91 (m, 4H), 2.78-2.79 (m, 2H).<br>3. 384.2<br>4. Procedure 2 |
| 5 | | | | 1. 19%;<br>2. ¹H-NMR (400 MHz, DMSO-d₆) δ = 10.92 (br-s, 1H), 7.28-7.32 (m, 1H), 7.13-7.16 (m, 1H), 6.83-6.97 (m, 3H), 6.76-6.78 (m, 1H), 4.36 (bs, 2H), 3.71-3.73 (m, 4H), 3.57-3.60 (m, 2H), 2.88-2.90 (m, 4H), 2.73-2.75 (m, 2H).<br>3. 370.2<br>4. Procedure 1 |
| 6 | | | | 1. 20%<br>2. ¹H-NMR (400 MHz, DMSO-d₆) δ = 7.57 (d, J = 2.00 Hz, 1H), 7.44-7.39 (m, 2H), 7.22-7.15 (m, 2H), 6.97-6.91 (m, 1H), 4.43 (s, 2H), 3.74-3.72 (m, 7H), 3.59 (t, J = 5.20 Hz, 2H), 3.49 (t, J = 4.80 Hz, 4H), 2.79 (t, J = 4.80 Hz, 2H).<br>3. 423.2<br>4. Procedure 2 |

TABLE 1-continued

| Example | Tricyclic amine derivative | Bromo or Chloro derivative | Product Example | 1. Yield; %<br>2. ¹H-NMR<br>3. MH⁺ (ESI)<br>4. Synthesis procedure |
|---|---|---|---|---|
| 7 | | | | 1. 24%<br>2. ¹H-NMR (400 MHz, DMSO-d$_6$) δ = 7.61 (d, J = 8.40 Hz, 1H), 7.39-7.43 (m, 1H), 7.28-7.31 (m, 1H), 7.24 (d, J = 2.40 Hz, 1H), 6.97 (dd, J = 2.40, 8.80 Hz, 1H), 6.83-6.87 (m, 1H), 4.46 (bs, 2H), 3.70-3.75 (m, 7H), 3.62-3.64 (m, 2H), 3.50-3.53 (m, 4H), 2.79-2.81 (m, 2H).<br>3. 423.0<br>4. Procedure 2 |
| 8 | | | | 1. 21%<br>2. ¹H-NMR (400 MHz, DMSO-d$_6$) δ = 8.05 (d, J = 2.80 Hz, 1H), 7.49-7.52 (m, 1H), 7.40-7.43 (m, 1H), 7.18-7.21 (m, 1H), 6.91-6.96 (m, 1H), 6.81-6.83 (m, 1H), 4.36 (s, 2H), 3.70-3.72 (m, 7H), 3.48 (t, J = 5.20 Hz, 2H), 3.29-3.32 (m, 4H), 2.75-2.76 (m, 2H).<br>3. 367.1<br>4. Procedure 2 |
| 9 | | | | 1. 29%<br>2. ¹H-NMR (400 MHz, DMSO-d$_6$) δ = 7.40-7.44 (m, 1H), 7.30 (dd, J = 2.00, 10.40 Hz, 1H), 7.04-7.09 (m, 1H), 6.83-6.90 (m, 2H), 6.59-6.62 (m, 1H), 4.41 (bs, 2H), 3.87 (s, 3H), 3.69 (s, 3H), 3.56-3.59 (m, 2H), 2.79-2.82 (m, 2H).<br>3. 329.0<br>4. Procedure 2 |
| 11 | | | | 1. 13%<br>2. ¹H-NMR (400 MHz, DMSO-d$_6$) δ = 7.57 (d, J = 8.40 Hz, 1H), 7.40-7.44 (m, 1H), 7.18-7.22 (m, 2H), 6.91-6.96 (m, 2H), 4.47 (s, 2H), 3.12 (s, 3H), 3.63 (t, J = 5.60 Hz, 2H), 3.13 (s, 6H), 2.79 (d, J = 4.80 Hz, 2H).<br>3. 381.2<br>4. Procedure 2 |

TABLE 1-continued

| Example | Tricyclic amine derivative | Bromo or Chloro derivative | Product Example | 1. Yield; %<br>2. ¹H-NMR<br>3. MH⁺ (ESI)<br>4. Synthesis procedure |
|---|---|---|---|---|
| 12 | | | | 1. 18%<br>2. ¹H-NMR (400 MHz, DMSO-d₆) δ = 7.39-7.42 (m, 1H), 7.26 (d, J = 2.40 Hz, 1H), 7.17-7.20 (m, 1H), 3.52 (d, J = 8.40 Hz, 1H), 6.90-6.96 (m, 2H), 3.12 (s, 2H), 3.70 (s, 3H), 3.54 (t, J = 5.60 Hz, 2H), 3.08 (s, 6H), 2.76 (t, J = 4.80 Hz, 2H).<br>3. 365.1<br>4. Procedure 2 |
| 13 | | | | 1. 12%<br>2. ¹H-NMR (400 MHz, DMSO-d₆) δ = 7.40-7.44 (m, 1H), 7.25 (d, J = 8.64 Hz, 1H), 7.19 (dd, J = 2.48, 9.80 Hz, 1H), 7.06 (d, J = 2.40 Hz, 1H), 6.91-6.96 (m, 1H), 6.77 (dd, J = 2.44, 8.72 Hz, 1H), 4.41 (bs, 2H), 3.72 (s, 3H), 3.55-3.57 (m, 2H), 3.11 (s, 6H), 2.76-2.78 (m, 2H).<br>3. 365.2<br>4. Procedure 2 |
| 14 | | | | 1. 25%<br>2. ¹H-NMR (400 MHz, DMSO-d₆) δ = 7.60 (d, J = 8.80 Hz, 1H), 7.30 (d, J = 8.80 Hz, 1H), 7.23 (s, 1H), 6.93-6.98 (m, 2H), 6.74 (dd, J = 2.00, 8.60 Hz, 1H), 4.45 (br-s, 2H), 3.76 (s, 3H), 3.72-3.76 (m, 4H), 3.69 (s, 3H), 3.62-3.65 (m, 2H), 3.50-3.52 (m, 4H), 2.78-2.80 (m, 2H).<br>3. 435.2<br>4. Procedure 2 |
| 15 | | | | 1. 35%<br>2. ¹H-NMR (400 MHz, DMSO-d₆) δ = 7.56 (d, J = 2.80 Hz, 1H), 7.40 (d, J = 8.80 Hz, 1H), 7.30 (d, J = 8.80 Hz, 1H), 7.16 (dd, J = 2.40, 8.80 Hz, 1H), 6.94 (d, J = 2.40 Hz, 1H), 6.74 (dd, J = 2.40, 8.80 Hz, 1H), 4.41 (br-s, 2H), 3.76 (s, 3H), 3.72-3.74 (m, 4H), 3.68 (s, 3H), 3.57-3.60 (m, 2H), 3.47-3.50 (m, 4H), 2.78-2.80 (m, 2H).<br>3. 435.2<br>4. Procedure 2 |

TABLE 1-continued

| Example | Tricyclic amine derivative | Bromo or Chloro derivative | Product Example | 1. Yield; %  2. ¹H-NMR  3. MH⁺ (ESI)  4. Synthesis procedure |
|---|---|---|---|---|
| 16 | | | | 1. 12%  2. ¹H-NMR (400 MHz, DMSO-d₆) δ = 7.27-7.31 (m, 2H), 7.09 (d, J = 2.40 Hz, 1H), 6.93 (d, J = 2.40 Hz, 1H), 6.82 (dd, J = 2.80, 8.60 Hz, 1H), 6.73 (dd, J = 2.40, 8.80 Hz, 1H), 4.39 (br-s, 2H), 3.76 (s, 3H), 3.71-3.73 (m, 4H), 3.67 (s, 3H), 3.55-3.57 (m, 6H), 2.76-2.79 (m, 2H).  3. 419.2  4. Procedure 2 |
| 17 | | | | 1. 11%  2. ¹H-NMR (400 MHz, DMSO-d₆) δ = 7.56 (d, J = 8.40 Hz, 1H), 7.30 (d, J = 9.20 Hz, 1H), 7.21 (s, 1H), 6.90-6.93 (m, 2H), 6.73 (dd, J = 2.00, 8.80 Hz, 1H), 4.44 (br-s, 2H), 3.76 (s, 3H), 3.69 (s, 3H), 3.61-3.64 (m, 2H), 3.12 (s, 6H), 2.78-2.79 (m, 2H).  3. 393.2  4. Procedure 2 |
| 18 | | | | 1. 19%  2. ¹H-NMR (400 MHz, DMSO-d₆) δ = 7.52 (d, J = 2.00 Hz, 1H), 7.29-7.37 (m, 2H), 7.12 (dd, J = 2.40, 8.80 Hz, 1H), 6.93 (d, J = 2.40 Hz, 1H), 6.73 (dd, J = 2.40, 9.00 Hz, 1H), 4.39 (bs, 2H), 3.76 (s, 3H), 3.67 (s, 3H), 3.55-3.58 (m, 2H), 3.10 (s, 6H), 2.79-2.82 (m, 2H).  3. 393.2  4. Procedure 2 |
| 19 | | | | 1. 13%  2. ¹H-NMR (400 MHz, DMSO-d₆) δ = 7.26-7.31 (m, 2H), 7.14-7.16 (m, 1H), 6.93-6.97 (m, 2H), 6.74 (d, J = 8.80 Hz, 1H), 4.38 (br-s, 2H), 3.76 (s, 3H), 3.67 (s, 3H), 3.55-3.55 (m, 2H), 3.10 (s, 6H), 2.78-2.80 (m, 2H).  3. 377.2  4. Procedure 2 |

TABLE 1-continued

| Example | Tricyclic amine derivative | Bromo or Chloro derivative | Product Example | 1. Yield; %<br>2. ¹H-NMR<br>3. MH⁺ (ESI)<br>4. Synthesis procedure |
|---|---|---|---|---|
| 20 | 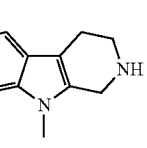 | 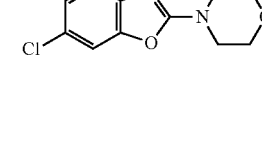 | 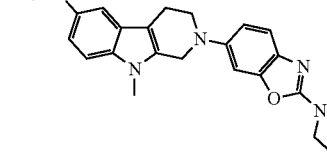 | 1. 15%<br>2. ¹H-NMR (400 MHz, DMSO-d₆) δ = 7.27-7.31 (m, 2H), 7.20 (d, J = 8.80 Hz, 1H), 6.97-7.00 (m, 1H), 3.52 (d, J = 2.00 Hz, 1H), 6.72-6.75 (m, 1H), 3.12 (s, 2H), 3.76 (s, 3H), 3.72 (t, J = 4.80 Hz, 4H), 3.67 (s, 3H), 3.52-3.58 (m, 6H), 2.78 (s, 2H).<br>3. 419.2<br>4. Procedure 2 |
| 21 | 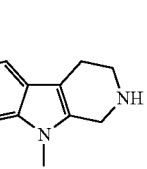 | 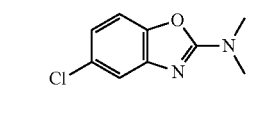 | 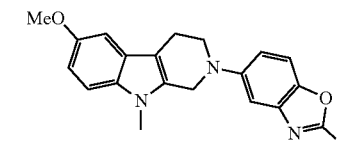 | 1. 22%<br>2. ¹H-NMR (400 MHz, DMSO-d₆) δ = 7.24-7.31 (m, 2H), 7.05 (d, J = 2.12 Hz, 1H), 6.93 (d, J = 2.20 Hz, 1H), 6.72-6.77 (m, 2H), 4.38 (bs, 2H), 3.76 (s, 3H), 3.67 (s, 3H), 3.54-3.57 (m, 2H), 3.11 (s, 6H), 2.77-2.79 (m, 2H).<br>3. 377.1<br>4. Procedure 2 |
| 22 | 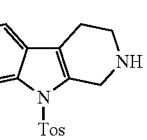 | 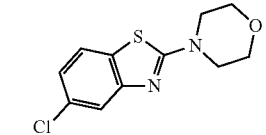 [SMILES: Clc1ccc2sc(N3CCOCC3)nc2c1] | 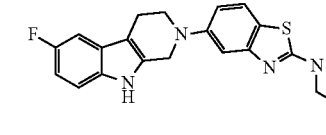 | 1. 13%<br>2. ¹H-NMR (400 MHz, DMSO-d₆) δ = 10.94 (br-s, 1H), 7.60 (d, J = 8.80 Hz, 1H), 7.29-7.32 (m, 1H), 7.11-7.16 (m, 2H), 6.83-6.92 (m, 2H), 3.12 (s, 2H), 3.72 (t, J = 5.20 Hz, 4H), 3.66 (t, J = 5.60 Hz, 2H), 3.51 (t, J = 4.80 Hz, 4H), 2.75 (s, 2H).<br>3. 409.2<br>4. Procedure 1 |
| 23 | 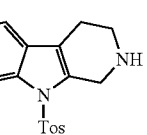 | 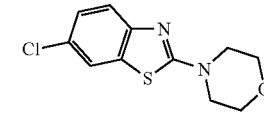 | 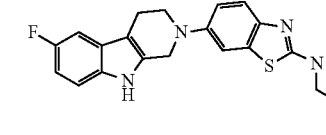 | 1. 11%<br>2. ¹H-NMR (400 MHz, DMSO-d₆) δ = 10.94 (br-s, 1H), 7.49 (s, 1H), 7.39 (d, J = 8.80 Hz, 1H), 7.29-7.32 (m, 1H), 7.16 (d, J = 10.00 Hz, 1H), 7.07-7.09 (m, 1H), 6.87 (t, J = 8.40 Hz, 1H), 4.38 (s, 2H), 3.73 (t, J = 4.80 Hz, 4H), 3.60 (d, J = 4.80 Hz, 2H), 3.48 (t, J = 4.40 Hz, 4H), 2.78 (s, 2H).<br>3. 409.2<br>4. Procedure 1 |

TABLE 1-continued

| Example | Tricyclic amine derivative | Bromo or Chloro derivative | Product Example | 1. Yield; %  2. ¹H-NMR  3. MH⁺ (ESI)  4. Synthesis procedure |
|---|---|---|---|---|
| 24 | | | | 1. 18%  2. ¹H-NMR (400 MHz, DMSO-d₆) δ = 10.94 (br-s, 1H), 7.29-7.32 (m, 1H), 7.14-7.21 (m, 3H), 6.84-6.93 (m, 2H), 4.36 (s, 2H), 3.12 (t, J = 4.80 Hz, 4H), 3.59 (t, J = 5.60 Hz, 2H), 3.53 (t, J = 4.40 Hz, 4H), 2.76 (s, 2H).  3. 393.1  4. Procedure 1 |
| 25 | | | | 1. 23%  2. ¹H-NMR (400 MHz, DMSO-d₆) δ = 10.93 (br-s, 1H), 7.26-7.31 (m, 2H), 7.15 (d, J = 2.00 Hz, 1H), 3.52 (d, J = 2.40 Hz, 1H), 6.83-6.88 (m, 1H), 6.74-6.76 (m, 1H), 4.35 (s, 2H), 3.71 (t, J = 4.80 Hz, 4H), 3.54-3.60 (m, 6H), 2.75 (s, 2H).  3. 393.2  4. Procedure 1 |
| 26 | | | | 1. 17%  2. ¹H-NMR (400 MHz, DMSO-d₆) δ = 10.93 (br-s, 1H), 7.45 (d, J = 2.40 Hz, 1H), 7.33-7.36 (m, 1H), 7.29-7.31 (m, 1H), 7.14-7.17 (m, 1H), 7.03-7.06 (m, 1H), 6.83-6.89 (m, 1H), 4.36 (s, 2H), 3.58 (t, J = 5.60 Hz, 2H), 3.10 (s, 6H), 2.77 (s, 2H).  3. 367.1  4. Procedure 1 |
| 27 | | | | 1. 13%  2. ¹H-NMR (400 MHz, DMSO-d₆) δ = 10.95 (br-s, 1H), 7.29-7.30 (m, 1H), 7.13-7.18 (m, 3H), 6.84-6.86 (m, 2H), 4.34 (s, 2H), 3.55-3.57 (m, 2H), 3.09 (s, 6H), 2.76-2.77 (m, 2H).  3. 351.2  4. Procedure 1 |
| 28 | | | | 1. 23%  2. ¹H-NMR (400 MHz, DMSO-d₆) δ = 10.95 (br-s, 1H), 7.23-7.32 (m, 2H), 7.14-7.16 (m, 1H), 6.96 (s, 1H), 6.84-6.88 (m, 1H), 6.68-6.71 (m, 1H), 4.35 (br-s, 2H), 3.58-3.59 (m, 2H), 3.10 (s, 6H), 2.68-2.75 (m, 2H).  3. 351.2  4. Procedure 1 |

TABLE 1-continued

| Example | Tricyclic amine derivative | Bromo or Chloro derivative | Product Example | 1. Yield; %<br>2. ¹H-NMR<br>3. MH⁺ (ESI)<br>4. Synthesis procedure |
|---|---|---|---|---|
| 29 | | | | 1. 21%<br>2. ¹H-NMR (400 MHz, DMSO-d₆) δ = 7.53 (d, J = 2.40 Hz, 1H), 7.40-7.41 (m, 1H), 7.36 (d, J = 8.80 Hz, 1H), 7.20 (dd, J = 2.40, 9.60 Hz, 1H), 7.13 (dd, J = 2.80, 8.80 Hz, 1H), 6.91-6.91 (m, 1H), 4.41 (s, 2H), 3.71 (s, 3H), 3.56 (t, J = 5.60 Hz, 2H), 3.11 (s, 6H), 2.77-2.79 (m, 2H).<br>3. 381.2<br>4. Procedure 2 |
| 30 | | | | 1. 19%<br>2. ¹H-NMR (400 MHz, DMSO-d₆) δ = 10.57 (br-s, 1H), 7.51 (d, J = 11.60 Hz, 1H), 7.13 (d, J = 10.80 Hz, 1H), 7.03 (s, 1H), 6.81-6.83 (m, 2H), 6.59 (d, J = 10.40 Hz, 1H), 4.32 (s, 2H), 3.66 (br-s, 6H), 3.58 (bs, 3H), 3.42 (br-s, 3H), 2.67 (br-s, 3H).<br>3. 421.1<br>4. Procedure 1 |
| 31 | | | | 1. 27%<br>2. ¹H-NMR (400 MHz, DMSO-d₆) δ = 10.66 (br-s, 1H), 7.49 (d, J = 2.40 Hz, 1H), 7.39 (d, J = 8.80 Hz, 1H), 7.21 (d, J = 8.80 Hz, 1H), 7.06-7.07 (m, 1H), 6.90 (d, J = 2.40 Hz, 1H), 6.66-6.66 (m, 1H), 4.36 (s, 2H), 3.72-3.73 (m, 8H), 3.59-3.60 (m, 2H), 3.47-3.48 (m, 4H), 2.78-2.79 (m, 2H).<br>3. 421.1<br>4. Procedure 1 |
| 32 | | | | 1. 17%<br>2. ¹H-NMR (400 MHz, DMSO-d₆) δ = 10.66 (br-s, 1H), 7.17-7.18 (m, 3H), 6.89-6.89 (m, 2H), 6.66-6.66 (m, 1H), 4.34 (s, 2H), 3.75 (s, 3H), 3.71-3.72 (m, 4H), 3.57-3.59 (m, 2H), 3.52-3.53 (m, 4H), 2.76-2.77 (m, 2H).<br>3. 405.2<br>4. Procedure 1 |

TABLE 1-continued

| Example | Tricyclic amine derivative | Bromo or Chloro derivative | Product Example | 1. Yield; %<br>2. ¹H-NMR<br>3. MH⁺ (ESI)<br>4. Synthesis procedure |
|---|---|---|---|---|
| 33 | (6-methoxy-tetrahydro-β-carboline, N-Tos) | 5-chloro-2-morpholinobenzoxazole | product | 1. 29%<br>2. ¹H-NMR (400 MHz, DMSO-d₆) δ = 10.65 (br-s, 1H), 7.27 (d, J = 8.80 Hz, 1H), 7.20 (d, J = 8.80 Hz, 1H), 6.99 (d, J = 2.40 Hz, 1H), 6.89 (d, J = 2.40 Hz, 1H), 6.73-6.74 (m, 1H), 6.65-6.66 (m, 1H), 4.34 (s, 2H), 3.70-3.71 (m, 4H), 3.55-3.56 (m, 7H), 2.71 (br-s, 2H), 2.51 (br-s, 2H).<br>3. 405.2<br>4. Procedure 1 |
| 34 | (6-methoxy-tetrahydro-β-carboline, N-Tos) | 5-chloro-N,N-dimethylbenzothiazol-2-amine | product | 1. 13%<br>2. ¹H-NMR (400 MHz, DMSO-d₆) δ = 10.66 (br-s, 1H), 7.55 (d, J = 8.80 Hz, 1H), 7.21 (d, J = 8.40 Hz, 1H), 7.08 (d, J = 2.00 Hz, 1H), 6.83-6.84 (m, 2H), 6.65-6.66 (m, 1H), 4.39 (s, 2H), 3.74 (s, 3H), 3.64-3.65 (m, 2H), 3.11 (s, 6H), 2.74-2.75 (m, 2H).<br>3. 379.2<br>4. Procedure 1 |
| 35 | (6-methoxy-tetrahydro-β-carboline, N-Tos) | 6-chloro-N,N-dimethylbenzothiazol-2-amine | product | 1. 11%<br>2. ¹H-NMR (400 MHz, DMSO-d₆) δ = 10.66 (br-s, 1H), 7.45 (d, J = 2.40 Hz, 1H), 7.35 (d, J = 8.80 Hz, 1H), 7.20 (d, J = 8.40 Hz, 1H), 7.03-7.04 (m, 1H), 6.90 (d, J = 2.00 Hz, 1H), 6.66-6.67 (m, 1H), 4.34 (s, 2H), 3.75 (s, 3H), 3.57-3.58 (m, 2H), 3.10 (s, 6H), 2.77-2.78 (m, 2H).<br>3. 379.2<br>4. Procedure 1 |
| 36 | (6-methoxy-tetrahydro-β-carboline, N-Tos) | 6-chloro-N,N-dimethylbenzoxazol-2-amine | product | 1. 29%<br>2. ¹H-NMR (400 MHz, DMSO-d₆) δ = 10.64 (br-s, 1H), 7.11-7.14 (m, 3H), 6.85-6.86 (m, 2H), 6.64-6.65 (m, 1H), 4.31 (s, 2H), 3.74 (s, 3H), 3.54-3.56 (m, 2H), 3.08 (s, 6H), 2.74 (br-s, 2H).<br>3. 363.3<br>4. Procedure 1 |

TABLE 1-continued

| Example | Tricyclic amine derivative | Bromo or Chloro derivative | Product Example | 1. Yield; %<br>2. ¹H-NMR<br>3. MH⁺ (ESI)<br>4. Synthesis procedure |
|---|---|---|---|---|
| 37 | | | | 1. 25%<br>2. ¹H-NMR (400 MHz, DMSO-d₆) δ = 10.85 (br-s, 1H), 7.60 (d, J = 8.80 Hz, 1H), 7.39 (d, J = 7.60 Hz, 1H), 7.33 (d, J = 7.60 Hz, 1H), 7.12 (s, 1H), 7.02-7.04 (m, 1H), 6.97 (d, J = 7.20 Hz, 1H), 6.90-6.92 (m, 1H), 4.43 (s, 2H), 3.67-3.68 (m, 6H), 3.51-3.52 (m, 4H), 2.79 (br-s, 2H).<br>3. 391.2<br>4. Procedure 1 |
| 38 | | | | 1. 27%<br>2. ¹H-NMR (400 MHz, DMSO-d₆) δ = 10.84 (br-s, 1H), 7.49 (d, J = 2.40 Hz, 1H), 7.31-7.41 (m, 3H), 7.02-7.10 (m, 2H), 6.94-6.98 (m, 1H), 4.38 (s, 2H), 3.72-3.74 (m, 4H), 3.60-3.62 (m, 2H), 3.47-3.49 (m, 4H), 2.80-2.82 (m, 2H).<br>3. 391.2<br>4. Procedure 1 |
| 39 | | | | 1. 18%<br>2. ¹H-NMR (400 MHz, DMSO-d₆) δ = 7.18-7.24 (m, 2H), 6.87-6.94 (m, 2H), 6.64-6.69 (m, 2H), 3.52 (s, 2H), 3.74 (s, 3H), 3.12 (t, J = 5.20 Hz, 2H), 3.09 (s, 6H), 2.74 (s, 2H).<br>3. 363.2<br>4. Procedure 1 |
| 40 | | | | 1. 17%<br>2. ¹H-NMR (400 MHz, DMSO-d₆) δ = 10.94 (br-s, 1H), 7.95 (d, J = 2.80 Hz, 1H), 7.41-7.44 (m, 1H), 7.27-7.30 (m, 1H), 7.12-7.15 (m, 1H), 6.79-6.87 (m, 2H), 4.29 (s, 2H), 3.69 (t, J = 5.20 Hz, 4H), 3.49 (t, J = 5.60 Hz, 2H), 3.28 (t, J = 4.80 Hz, 4H), 2.73 (t, J = 5.20 Hz, 2H).<br>3. 353.3<br>4. Procedure 1 |

TABLE 1-continued

| Example | Tricyclic amine derivative | Bromo or Chloro derivative | Product Example | 1. Yield; %<br>2. ¹H-NMR<br>3. MH⁺ (ESI)<br>4. Synthesis procedure |
|---|---|---|---|---|
| 41 | (F-substituted tricyclic amine, N-Tos) | 2-bromo-5-morpholinopyridine | (product) | 1. Yield: 16%<br>2. ¹H-NMR (400 MHz, DMSO-d₆) 10.95 (bs, 1H), 7.86 (d, J = 2.80 Hz, 1H), 7.33-7.36 (m, 1H), 7.27-7.29 (m, 1H), 7.12-7.15 (m, 1H), 3.12 (d, J = 9.20 Hz, 1H), 6.83-6.88 (m, 1H), 4.66 (s, 2H), 3.83 (t, J = 5.60 Hz, 2H), 3.72 (t, J = 4.80 Hz, 4H), 2.97 (t, J = 4.80 Hz, 4H), 2.72 (t, J = 5.20 Hz, 2H).<br>3. 353.2<br>4. Procedure 1 |
| 42 | (F-substituted tricyclic amine, N-Tos) | 5-bromo-N,N-dimethylbenzothiazol-2-amine | (product) | 1. 13%<br>2. ¹H-NMR (400 MHz, DMSO-d₆) δ = 10.94 (br-s, 1H), 7.55 (d, J = 8.40 Hz, 1H), 7.29-7.32 (m, 1H), 7.09-7.16 (m, 2H), 6.83-6.88 (m, 2H), 3.12 (s, 2H), 3.65 (t, J = 5.60 Hz, 2H), 3.11 (s, 6H), 2.76 (d, J = 5.20 Hz, 2H).<br>3. 367.2<br>4. Procedure 1 |
| 43 | (tricyclic amine, N-Tos) | 2-bromo-5-morpholinopyridine | (product) | 1. 21%<br>2. ¹H-NMR (400 MHz, DMSO-d₆) δ = 10.85 (br-s, 1H), 7.86 (d, J = 2.80 Hz, 1H), 7.29-7.31 (m, 3H), 7.00-7.01 (m, 1H), 6.93-6.95 (m, 2H), 4.67 (s, 2H), 3.83-3.84 (m, 2H), 3.71-3.73 (m, 4H), 2.96-2.97 (m, 4H), 2.74-2.76 (m, 2H).<br>3. 335.2<br>4. Procedure 1 |
| 44 | (tricyclic amine, N-Tos) | 5-bromo-2-morpholinopyridine | (product) | 1. 23%<br>2. ¹H-NMR (400 MHz, DMSO-d₆) δ = 10.82 (br-s, 1H), 7.96 (d, J = 2.84 Hz, 1H), 7.30-7.44 (m, 3H), 7.01-7.03 (m, 1H), 6.95-6.97 (m, 1H), 6.80 (d, J = 9.12 Hz, 1H), 4.30 (s, 2H), 3.68-3.70 (m, 4H), 3.48-3.51 (m, 2H), 3.27-3.30 (m, 4H), 2.76-2.77 (m, 2H).<br>3. 335.2<br>4. Procedure 1 |

TABLE 1-continued

| Example | Tricyclic amine derivative | Bromo or Chloro derivative | Product Example | 1. Yield; %  2. ¹H-NMR  3. MH⁺ (ESI)  4. Synthesis procedure |
|---|---|---|---|---|
| 45 | | | | 1. 24%  2. ¹H-NMR (400 MHz, DMSO-d₆) δ = 7.89 (d, J = 2.80 Hz, 1H), 7.35-7.43 (m, 3H), 7.08-7.10 (m, 1H), 6.99-7.03 (m, 2H), 4.69 (s, 2H), 3.83-3.86 (m, 2H), 3.70-3.75 (m, 7H), 3.70-3.72 (m, 7H), 2.97-3.00 (m, 4H), 2.77-2.79 (m, 2H).  3. 349.2  4. Procedure 2 |
| 46 | | | | 1. 28%  2. ¹H-NMR (400 MHz, DMSO-d₆) δ = 8.05 (d, J = 2.80 Hz, 1H), 7.49-7.52 (m, 1H), 7.40-7.43 (m, 2H), 7.09-7.13 (m, 1H), 6.98-7.02 (m, 1H), 6.82 (d, J = 9.20 Hz, 1H), 4.37 (s, 2H), 3.70-3.72 (m, 7H), 3.48-3.51 (m, 2H), 3.29-3.34 (m, 4H), 2.79-2.80 (m, 2H).  3. 349.2  4. Procedure 2 |
| 47 | | | | 1. 14%  2. ¹H-NMR (400 MHz, CD₃OD) δ = 7.76 (s, 1H), 7.20-7.23 (m, 2H), 7.14-7.17 (m, 1H), 6.74-6.79 (m, 2H), 5.22 (d, J = 5.20 Hz, 1H), 4.84-4.87 (m, 1H), 3.78 (t, J = 9.20 Hz, 4H), 3.34-3.38 (m, 1H), 2.95 (t, J = 6.00 Hz, 4H), 2.32-2.49 (m, 3H), 2.02-2.07 (m, 1H), 1.79-1.86 (m, 1H).  3. 379.2  4. Procedure 1 |
| 48 | | | | 1. 13%  2. ¹H-NMR (400 MHz, DMSO-d₆) δ = 10.96 (br-s, 1H), 7.84 (d, J = 1.44 Hz, 1H), 7.45-7.45 (m, 1H), 7.28-7.30 (m, 1H), 7.14-7.15 (m, 1H), 6.84-6.84 (m, 1H), 4.40 (s, 2H), 3.71-3.72 (m, 4H), 3.58-3.60 (m, 2H), 3.15-3.16 (m, 4H), 2.75-2.76 (m, 2H).  3. 371.2  4. Procedure 1 |

TABLE 1-continued

| Example | Tricyclic amine derivative | Bromo or Chloro derivative | Product Example | 1. Yield; %  2. ¹H-NMR  3. MH⁺ (ESI)  4. Synthesis procedure |
|---|---|---|---|---|
| 49 | | | | 1. 28%  2. ¹H NMR (400 MHz, DMSO-d₆) δ 10.97 (s, 1H), 8.34 (d, J = 0.7 Hz, 1H), 7.49 (d, J = 0.9 Hz, 1H), 7.29 (dd, J = 8.8, 4.5 Hz, 1H), 7.14 (dd, J = 9.9, 2.6 Hz, 1H), 6.95-6.71 (m, 1H), 4.74 (s, 2H), 3.90 (t, J = 5.7 Hz, 2H), 3.73 (t, J = 4.9 Hz, 4H), 3.51 (t, J = 4.9 Hz, 4H), 2.76 (d, J = 5.9 Hz, 2H).  3. 410.15  4. Procedure 3 and 5 |
| 50 | | | | 1. 25%  2. ¹H-NMR (400 MHz, DMSO-d₆) δ = 10.93 (br-s, 1H), 7.88 (s, 1H), 7.76 (s, 1H), 7.29-7.30 (m, 1H), 7.17 (d, J = 9.60 Hz, 1H), 6.84-6.87 (m, 2H), 4.47 (s, 2H), 3.74-3.75 (m, 4H), 3.67-3.68 (m, 2H), 3.17-3.18 (m, 4H), 2.77 (br-s, 2H).  3. 353.2  4. Procedure 1 |
| 51 | | | | 1. 17%  2. ¹H-NMR (400 MHz, DMSO-d₆) δ = 10.96 (br-s, 1H), 7.84 (d, J = 1.52 Hz, 1H), 7.46 (dd, J = 2.44, 15.42 Hz, 1H), 7.36-7.38 (m, 1H), 7.11 (dd, J = 2.28, 10.20 Hz, 1H), 6.79-6.80 (m, 1H), 4.38 (s, 2H), 3.71-3.72 (m, 4H), 3.58-3.59 (m, 2H), 3.15-3.16 (m, 4H), 2.75-2.77 (m, 2H).  3. 371.2  4. Procedure 1 |
| 52 | | | | 1. 29%  2. ¹H-NMR (400 MHz, DMSO-d₆) δ = 10.94 (bs, 1H), 7.84 (d, J = 1.52 Hz, 1H), 7.44-7.45 (m, 1H), 7.35-7.37 (m, 1H), 7.08-7.10 (m, 1H), 6.78-6.80 (m, 2H), 4.39 (s, 2H), 3.72-3.73 (m, 4H), 3.56-3.57 (m, 2H), 3.16-3.17 (m, 4H), 2.75-2.78 (m, 2H).  3. 370.2  4. Procedure 1 |

TABLE 1-continued

| Example | Tricyclic amine derivative | Bromo or Chloro derivative | Product Example | 1. Yield; %<br>2. ¹H-NMR<br>3. MH⁺ (ESI)<br>4. Synthesis procedure |
|---|---|---|---|---|
| 53 | | | | 1. 2%<br>2. ¹H NMR (400 MHz, DMSO-d₆) δ 10.96 (s, 1H), 8.19 (d, J = 2.8 Hz, 1H), 8.00 (d, J = 2.8 Hz, 1H), 7.31 (dd, J = 8.7, 4.6 Hz, 1H), 7.15 (td, J = 9.0, 8.2, 2.6 Hz, 1H), 6.87 (td, J = 9.2, 2.6 Hz, 1H), 4.42 (s, 2H), 3.74 (q, J = 5.6, 5.1 Hz, 4H), 3.63 (q, J= 5.6, 4.9 Hz, 2H), 3.59-3.50 (m, 4H), 2.79 (t, J = 5.6 Hz, 2H).<br>3. 410.15<br>4. Procedure 3 |
| 54 | | | | 1. 22%<br>2. ¹H NMR (400 MHz, DMSO-d₆) δ 10.97 (s, 1H), 7.69 (d, J = 8.9 Hz, 1H), 7.30 (dd, J = 8.7, 4.5 Hz, 1H), 7.15 (dd, J = 9.9, 2.6 Hz, 1H), 6.99 (d, J = 8.9 Hz, 1H), 6.86 (td, J = 9.2, 2.6 Hz, 1H), 4.73 (s, 2H), 3.91 (t, J = 5.6 Hz, 2H), 3.72 (dd, J = 5.8, 3.9 Hz, 4H), 3.48 (t, J = 4.9 Hz, 4H), 2.83-2.67 (m, 2H).<br>3. 410.14<br>4. Procedure 3 |
| 55 | | | | 1. 27%<br>2. ¹H-NMR (400 MHz, DMSO-d₆) δ = 10.92 (br-s, 1H), 7.28-7.29 (m, 1H), 7.14 (dd, J = 2.48, 9.86 Hz, 1H), 6.96-6.98 (m, 2H), 6.83-6.83 (m, 3H), 4.29 (s, 2H), 3.71-3.72 (m, 4H), 3.51 (t, J = 5.52 Hz, 2H), 2.94-2.97 (m, 4H), 2.73 (t, J = 5.28 Hz, 2H).<br>3. 352.2<br>4. Procedure 1 |
| 56 | | | | 1. 20%<br>2. ¹H-NMR (400 MHz, DMSO-d₆) δ = 10.92 (br-s, 1H), 7.30 (dd, J = 4.40, 8.80 Hz, 1H), 7.15 (dd, J = 2.40, 9.60 Hz, 1H), 6.97-6.99 (m, 1H), 6.81-6.82 (m, 2H), 6.68 (dd, J = 2.40, 8.80 Hz, 1H), 4.19 (s, 2H), 3.71-3.72 (m, 4H), 3.34-3.35 (m, 2H), 3.03-3.04 (m, 4H), 2.71-2.72 (m, 2H).<br>3. 370.2<br>4. Procedure 1 |

TABLE 1-continued

| Example | Tricyclic amine derivative | Bromo or Chloro derivative | Product Example | 1. Yield; %<br>2. ¹H-NMR<br>3. MH⁺ (ESI)<br>4. Synthesis procedure |
|---|---|---|---|---|
| 57 | | | | 1. 33%<br>2. ¹H-NMR (400 MHz, DMSO-d₆) δ = 10.92 (br-s, 1H), 7.35-7.36 (m, 1H), 7.10 (dd, J = 2.16, 10.22 Hz, 1H), 6.92-6.96 (m, 2H), 6.87-6.89 (m, 2H), 6.79-6.79 (m, 1H), 4.27 (s, 2H), 3.71-3.73 (m, 4H), 3.49-3.50 (m, 2H), 3.08-3.09 (m, 4H), 2.74-2.75 (m, 2H).<br>3. 352.3<br>4. Procedure 4 |
| 58 | | | | 1. 16%<br>2. ¹H-NMR (400 MHz, DMSO-d₆) δ = 10.82 (br-s, 1H), 7.39 (d, J = 7.64 Hz, 1H), 7.32 (d, J = 7.96 Hz, 1H), 7.04 (t, J = 7.64 Hz, 1H), 6.89-6.93 (m, 3H), 6.78 (d, J = 8.72 Hz, 1H), 4.36 (s, 2H), 3.72-3.73 (m, 4H), 3.58-3.59 (m, 2H), 2.89-2.90 (m, 4H), 2.77 (bs, 2H).<br>3. 352.3<br>4. Procedure 1 |
| 59 | | | | 1. 15%<br>2. ¹H-NMR (400 MHz, DMSO-d₆) δ = 10.81 (br-s, 1H), 7.39 (d, J = 7.68 Hz, 1H), 7.31 (d, J = 7.92 Hz, 1H), 7.01-7.03 (m, 1H), 6.96-6.96 (m, 3H), 6.87-6.89 (m, 2H), 4.29 (s, 2H), 3.72-3.73 (m, 4H), 3.51-3.52 (m, 2H), 2.97-2.98 (m, 4H), 2.77 (br-s, 2H).<br>3. 334.2<br>4. Procedure 1 |
| 62 | | | | 1. 8%;<br>2. ¹H-NMR (400 MHz, DMSO-d₆) δ = 10.92 (br-s, 1H), 7.34-7.36 (m, 1H), 7.10 (dd, J = 2.12, 10.16 Hz, 1H), 6.94-6.96 (m, 2H), 6.78-6.79 (m, 3H), 4.26 (s, 2H), 3.48-3.49 (m, 2H), 3.01 (bs, 4H), 2.75 (br-s, 2H), 2.67 (br-s, 2H), 2.33 (br-s, 2H), 2.23 (s, 3H).<br>3. 365.2<br>4. Procedure 4 |

TABLE 1-continued

| Example | Tricyclic amine derivative | Bromo or Chloro derivative | Product Example | 1. Yield; %<br>2. ¹H-NMR<br>3. MH⁺ (ESI)<br>4. Synthesis procedure |
|---|---|---|---|---|
| 67 | (morpholine) | (methyl-tetrahydro-β-carboline-oxazole-chloro) | (methyl-tetrahydro-β-carboline-oxazole-morpholine) | 1. 43.55%<br>2. ¹H-NMR (400 MHz, DMSO-d₆): δ 7.45 (t, J = 7.28 Hz, 2H), 7.20 (d, J = 8.56 Hz, 1H), 7.12-7.13 (m, 2H), 7.02 (t, J = 7.20 Hz, 1H), 6.81-6.82 (m, 1H), 4.88 (s, 2H), 3.95 (t, J = 5.56 Hz, 2H), 3.74-3.75 (m, 4H), 3.71 (s, 3H), 3.05-3.06 (m, 4H), 2.87 (t, J = 5.12 Hz, 2H).<br>3. 389.2<br>4. Procedure 3 |
| 68 | (N-Ts-tetrahydro-β-carboline) | (bromo-pyridazine-morpholine) | (tetrahydro-β-carboline-pyridazine-morpholine) | 1. 12.9%<br>2. ¹H-NMR (400 MHz, DMSO-d₆): δ 10.85 (bs, 1H), δ 7.38 (t, J = 6.00 Hz, 2H), 7.30 (d, J = 8.00 Hz, 1H), 7.23 (d, J = 10.00 Hz, 1H), 7.01-7.02 (m, 1H), 6.96 (t, J = 6.80 Hz, 1H), 4.71 (s, 2H), 3.80 (t, J = 5.60 Hz, 2H), 3.67-3.69 (m, 4H), 3.28-3.29 (m, 4H), 2.74-2.75 (m, 2H).<br>3. 336.1<br>4. Procedure 2 |
| 69 | (N-Ts-tetrahydro-β-carboline) | (bromo-pyridine-hexahydrofuropyrrole) | (tetrahydro-β-carboline-pyridine-hexahydrofuropyrrole) | 1. 61%<br>2. ¹H-NMR (400 MHz, DMSO-d₆): δ 10.89 (s, 1H), 7.92 (d, J = 2.80 Hz, 1H), 7.38-7.39 (m, 2H), 7.31 (d, J = 8.00 Hz, 1H), 7.01-7.01 (m, 1H), 6.93-6.94 (m, 1H), 6.51 (d, J = 8.80 Hz, 1H), 4.26 (s, 2H), 3.83-3.85 (m, 2H), 3.50-3.51 (m, 2H), 3.41-3.43 (m, 4H), 3.25-3.26 (m, 2H), 2.96-2.97 (m, 2H), 2.75-2.76 (m, 2H).<br>3. 361.3<br>4. Procedure 3 |
| 70 | (N-Ts-tetrahydro-β-carboline) | (bromo-pyridine-oxabicyclic) | (tetrahydro-β-carboline-pyridine-oxabicyclic) | 1. 44%<br>2. ¹H-NMR (400 MHz, DMSO-d₆): δ 10.83 (s, 1H), 7.95 (d, J = 2.80 Hz, 1H), 7.39-7.41 (m, 2H), 7.31 (d, J = 8.00 Hz, 1H), 7.03 (t, J = 7.60 Hz, 1H), 6.96 (t, J = 7.20 Hz, 1H), 6.53 (d, J = 8.80 Hz, 1H), 4.29 (s, 2H), 4.23 (d, J = 6.00 Hz, 2H), 4.18 (d, J = 10.40 Hz, 2H), 3.62 (d, J = 10.40 Hz, 2H), 3.49-3.50 (m, 2H), 2.77-2.78 (m, 2H), 2.61-2.63 (m, 1H), 1.78 (d, J = 8.00 Hz, 1H).<br>3. 347.1<br>4. Procedure 3 |

TABLE 1-continued

| Example | Tricyclic amine derivative | Bromo or Chloro derivative | Product Example | 1. Yield; %<br>2. ¹H-NMR<br>3. MH⁺ (ESI)<br>4. Synthesis procedure |
|---|---|---|---|---|
| 71 | | | | 1. 87%<br>2. ¹H-NMR (400 MHz, DMSO-d₆): δ 10.83 (s, 1H), 7.97 (d, J = 2.44 Hz, 1H), 7.45-7.46 (m, 1H), 7.39 (d, J = 7.68 Hz, 1H), 7.31 (d, J = 7.68 Hz, 1H), 7.03 (t, J = 7.64 Hz, 1H), 6.95 (t, J = 7.00 Hz, 1H), 6.61 (d, J = 9.12 Hz, 1H), 4.69 (d, J = 6.28 Hz, 2H), 4.27 (s, 2H), 3.64-3.67 (m, 2H), 3.46-3.49 (m, 4H), 3.08-3.09 (m, 1H), 2.77 (bs, 2H), 1.89 (d, J = 8.40 Hz, 1H).<br>3. 347.3<br>4. Procedure 3 |
| 74 | | | | 1. 50.3%<br>2. ¹H-NMR (400 MHz, DMSO-d₆): δ 10.83 (s, 1H), 7.95 (d, J = 2.64 Hz, 1H), 7.37-7.39 (m, 2H), 7.31 (d, J = 7.96 Hz, 1H), 7.03 (t, J = 7.32 Hz, 1H), 6.95 (t, J = 7.56 Hz, 1H), 6.81 (d, J = 9.16 Hz, 1H), 4.29 (s, 2H), 3.83-3.87 (m, 3H), 3.48-3.49 (m, 4H), 2.76 (bs, 2H), 2.30-2.33 (m, 2H), 1.14 (d, J = 6.16 Hz, 3H).<br>3. 349.3<br>4. Procedure 3 |
| 75 | | | | 1. 52%<br>2. ¹H-NMR (400 MHz, DMSO-d₆): δ 10.83 (s, 1H), 7.96 (s, 1H), 7.30-7.32 (m, 3H), 6.94-6.95 (m, 2H), 6.81 (d, J = 8.00 Hz, 1H), 4.30 (s, 2H), 3.83-3.86 (m, 3H), 3.50-3.55 (m, 4H), 2.66-2.76 (m, 3H), 2.34 (bs, 1H), 1.14 (d, J = 4.00 Hz, 3H).<br>3. 349.3<br>4. Procedure 3 |

TABLE 1-continued

| Example | Tricyclic amine derivative | Bromo or Chloro derivative | Product Example | 1. Yield; %<br>2. ¹H-NMR<br>3. MH⁺ (ESI)<br>4. Synthesis procedure |
|---|---|---|---|---|
| 76 | 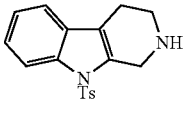 | 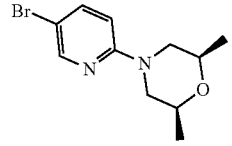 | 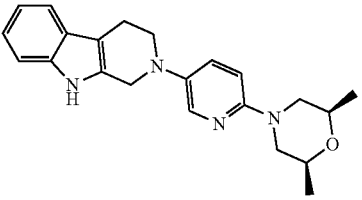 [SMILES: C[C@@H]1CN(c2ccc(N3CCc4c([nH]c5ccccc45)C3)cn2)C[C@H](C)O1] | 1. 38%<br>2. ¹H-NMR (400 MHz, DMSO-d₆): δ 10.83 (s, 1H), 7.95 (d, J = 2.80 Hz, 1H), 7.38-7.40 (m, 2H), 7.31 (d, J = 8.00 Hz, 1H), 7.03 (t, J = 7.60 Hz, 1H), 6.95 (t, J = 7.20 Hz, 1H), 6.81 (d, J = 9.20 Hz, 1H), 4.29 (s, 2H), 3.96 (d, J = 11.60 Hz, 2H), 3.60-3.61 (m, 2H), 3.49 (t, J = 5.60 Hz, 2H), 2.77 (bs, 2H), 2.27 (t, J = 10.80 Hz, 2H), 1.14 (d, J = 6.00 Hz, 6H).<br>3. 363.4<br>4. Procedure 3 |
| 77 | 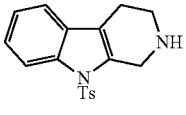 [SMILES: Cc1ccc(S(=O)(=O)n2c3c(c4ccccc42)CCNC3)cc1] | 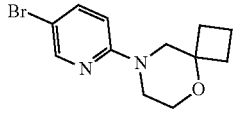 [SMILES: Brc1ccc(N2CCOC3(CCC3)C2)nc1] | 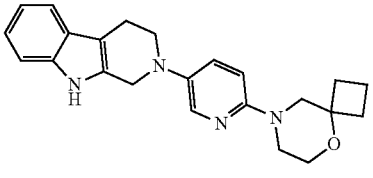 [SMILES: c1ccc2c3c([nH]c2c1)CN(c1ccc(N2CCOC4(CCC4)C2)nc1)CC3] | 1. 55%<br>2. ¹H-NMR (400 MHz, DMSO-d₆): δ 10.83 (s, 1H), 7.96 (d, J = 2.80 Hz, 1H), 7.38-7.40 (m, 2H), 7.31 (d, J = 8.00 Hz, 1H), 6.98-7.01 (m, 2H), 6.97 (d, J = 6.80 Hz, 1H), 4.30 (s, 2H), 3.60-3.61 (m, 2H), 3.50 (t, J = 5.60 Hz, 2H), 3.31 (s, 2H), 3.22-3.23 (m, 2H), 2.77 (t, J = 5.60 Hz, 2H), 1.93-1.93 (m, 4H), 1.68-1.69 (m, 2H).<br>3. 375.2<br>4. Procedure 3 |
| 78 | 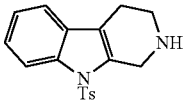 | 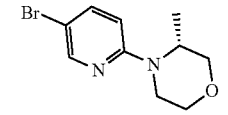 | 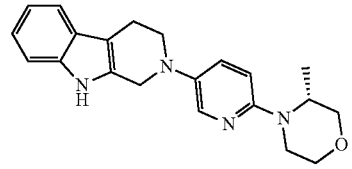 [SMILES: C[C@@H]1COCCN1c1ccc(N2CCc3c([nH]c4ccccc34)C2)cn1] | 1. 54%<br>2. ¹H-NMR (400 MHz, DMSO-d₆): δ 10.83 (s, 1H), 7.96 (d, J = 2.44 Hz, 1H), 7.30-7.32 (m, 3H), 6.93-6.95 (m, 2H), 6.73 (d, J = 9.12 Hz, 1H), 4.13 (s, 2H), 4.09-4.10 (m, 1H), 3.88-3.89 (m, 1H), 3.62-3.64 (m, 3H), 3.45-3.47 (m, 3H), 2.98-3.00 (m, 1H), 2.95-2.97 (m, 2H), 1.04 (d, J = 6.52 Hz, 3H).<br>3. 349.3<br>4. Procedure 3 |

TABLE 1-continued

| Example | Tricyclic amine derivative | Bromo or Chloro derivative | Product Example | 1. Yield; %<br>2. ¹H-NMR<br>3. MH⁺ (ESI)<br>4. Synthesis procedure |
|---|---|---|---|---|
| 79 | 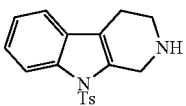 [SMILES: Cc1ccc(S(=O)(=O)n2c3c(c4ccccc42)CCNC3)cc1] | 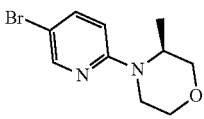 | 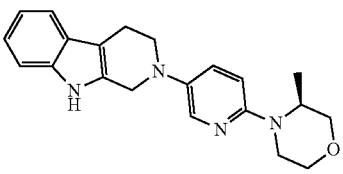 [SMILES: C[C@H]1COCCN1c1ccc(N2CCc3c([nH]c4ccccc34)C2)cn1] | 1. 65%<br>2. ¹H-NMR (400 MHz, DMSO-d₆): δ 10.81 (s, 1H), 7.96 (d, J = 2.80 Hz, 1H), 7.37-7.39 (m, 2H), 7.30 (d, J = 8.00 Hz, 1H), 7.02 (t, J = 7.20 Hz, 1H), 6.95 (t, J = 7.20 Hz, 1H), 6.72 (d, J = 8.80 Hz, 1H), 4.28 (s, 2H), 4.16-4.17 (m, 1H), 3.88-3.89 (m, 1H), 3.61-3.63 (m, 3H), 3.48-3.49 (m, 3H), 2.94-2.96 (m, 1H), 2.76 (bs, 2H), 1.03 (d, J = 6.40 Hz, 3H).<br>3. 349.3<br>4. Procedure 3 |
| 80 | 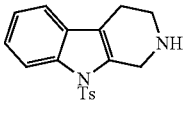 | 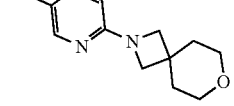 | 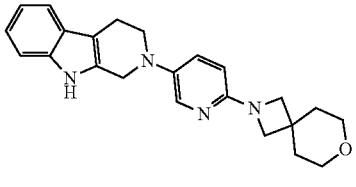 [SMILES: c1ccc2c3c([nH]c2c1)CN(c1ccc(N2CC4(CCOCC4)C2)nc1)CC3] | 1. 57%<br>2. ¹H-NMR (400 MHz, DMSO-d₆): δ 10.81 (s, 1H), 7.89 (d, J = 2.80 Hz, 1H), 7.38-7.39 (m, 2H), 7.31 (d, J = 8.00 Hz, 1H), 7.01-7.01 (m, 1H), 6.96 (t, J = 7.20 Hz, 1H), 6.37 (d, J = 8.80 Hz, 1H), 4.26 (s, 2H), 3.63 (bs, 4H), 3.53-3.54 (m, 4H), 3.45 (t, J = 5.60 Hz, 2H), 2.76 (t, J = 5.20 Hz, 2H), 1.71 (t, J = 5.20 Hz, 4H).<br>3. 375.2<br>4. Procedure 3 |
| 82 | 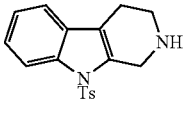 | 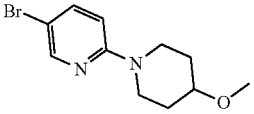 | 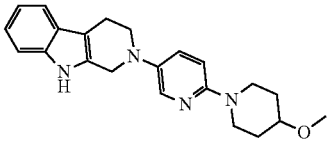 [SMILES: COC1CCN(c2ccc(N3CCc4c([nH]c5ccccc45)C3)cn2)CC1] | 1. 71%<br>2. ¹H-NMR (400 MHz, DMSO-d₆): δ 10.82 (s, 1H), 7.94 (d, J = 2.96 Hz, 1H), 7.38-7.38 (m, 2H), 7.31 (d, J = 7.96 Hz, 1H), 7.01-7.02 (m, 1H), 6.93-6.94 (m, 1H), 6.81 (d, J = 9.12 Hz, 1H), 4.28 (d, J = Hz, 2H), 3.79-3.80 (m, 2H), 3.48 (t, J = 5.60 Hz, 2H), 3.32-3.33 (m, 1H), 3.26 (s, 3H), 2.97-2.99 (m, 2H), 2.75-2.76 (m, 2H), 1.86-1.87 (m, 2H), 1.39-1.40 (m, 2H).<br>3. 363.3<br>4. Procedure 3 |

TABLE 1-continued

| Example | Tricyclic amine derivative | Bromo or Chloro derivative | Product Example | 1. Yield; %  2. $^1$H-NMR  3. MH$^+$ (ESI)  4. Synthesis procedure |
|---|---|---|---|---|
| 83 | | | | 1. 65%  2. $^1$H-NMR (400 MHz, DMSO-d$_6$): δ 10.82 (s, 1H), 7.93 (d, J = 2.76 Hz, 1H), 7.37-7.38 (m, 2H), 7.31 (d, J = 8.04 Hz, 1H), 7.03 (t, J = 7.84 Hz, 1H), 6.95 (t, J = 7.16 Hz, 1H), 6.81 (d, J = 9.12 Hz, 1H), 4.33 (s, 4H), 4.28 (s, 2H), 3.47 (t, J = 5.40 Hz, 2H), 3.30-3.32 (m, 4H), 2.76 (t, J = 5.04 Hz, 2H), 1.80 (t, J = 5.32 Hz, 4H).  3. 375.2  4. Procedure 3 |
| 85 | | | | 1. 69%  2. $^1$H-NMR (400 MHz, DMSO-d$_6$): δ 10.82 (s, 1H), 7.90 (d, J = 2.80 Hz, 1H), 7.38-7.39 (m, 2H), 7.31 (d, J = 8.00 Hz, 1H), 7.03 (t, J = 8.00 Hz, 1H), 6.95 (t, J = 7.20 Hz, 1H), 6.52 (d, J = 9.20 Hz, 1H), 4.71 (s, 1H), 4.60 (s, 1H), 4.26 (s, 2H), 3.74 (d, J = 7.20 Hz, 1H), 3.62 (d, J = 7.20 Hz, 1H), 3.43-3.45 (m, 3H), 3.16 (d, J = 10.00 Hz, 1H), 2.76 (bs, 2H), 1.88 (d, J = 9.60 Hz, 1H), 1.81 (d, J = 9.60 Hz, 1H).  3. 347.3  4. Procedure 3 |
| 86 | | | | 1. 38%  2. $^1$H-NMR (400 MHz, DMSO-d$_6$): 400 MHz, DMSO-d6: δ 10.83 (s, 1H), 7.91 (d, J = 2.84 Hz, 1H), 7.40-7.41 (m, 2H), 7.31 (d, J = 7.96 Hz, 1H), 7.03 (t, J = 7.92 Hz, 1H), 6.95 (t, J = 7.44 Hz, 1H), 6.52 (d, J = 8.96 Hz, 1H), 4.71 (s, 1H), 4.60 (s, 1H), 4.26 (s, 2H), 3.74 (d, J = 7.08 Hz, 1H), 3.62 (d, J = 7.20 Hz, 1H), 3.41-3.43 (m, 3H), 3.15-3.17 (m, 1H), 2.77 (t, J = 5.24 Hz, 2H), 1.88 (d, J = 9.44 Hz, 1H), 1.81 (d, J = 9.60 Hz, 1H).  3. 347.3  4. Procedure 3 |

TABLE 1-continued

| Example | Tricyclic amine derivative | Bromo or Chloro derivative | Product Example | 1. Yield; %<br>2. ¹H-NMR<br>3. MH⁺ (ESI)<br>4. Synthesis procedure |
|---|---|---|---|---|
| 87 | | | | 1. 71%<br>2. ¹H-NMR (400 MHz, DMSO-$d_6$): δ 11.18 (s, 1H), 7.99 (d, J = 2.92 Hz, 1H), 7.43-7.43 (m, 1H), 7.13 (d, J = 8.08 Hz, 1H), 6.96-6.97 (m, 1H), 6.81 (d, J = 9.08 Hz, 1H), 6.70-6.72 (m, 1H), 4.38 (s, 2H), 3.69-3.70 (m, 4H), 3.53 (t, J = 5.60 Hz, 2H), 3.28-3.30 (m, 4H), 2.87 (t, J = 5.12 Hz, 2H).<br>3. 353.2<br>4. Procedure 3 |
| 88 | | | | 1. 19%<br>2. ¹H-NMR (400 MHz, DMSO-$d_6$): δ 11.15 (s, 1H), 7.88 (d, J = 2.92 Hz, 1H), 7.33 (dd, J = 3.04, 9.12 Hz, 1H), 7.12 (d, J = 8.08 Hz, 1H), 6.91-6.93 (m, 2H), 6.69-6.71 (m, 1H), 4.71 (s, 2H), 3.88 (t, J = 5.64 Hz, 2H), 3.71-3.73 (m, 4H), 2.96-2.97 (m, 4H), 2.85 (t, J = 5.44 Hz, 2H).<br>3. 353.3<br>4. Procedure 5 |
| 89 | | | | 1. 45%<br>2. ¹H-NMR (400 MHz, DMSO-$d_6$): δ 11.17 (s, 1H), 7.27 (d, J = 8.68 Hz, 1H), 7.13 (d, J = 8.04 Hz, 1H), 6.97-6.98 (m, 2H), 6.70-6.72 (m, 2H), 4.44 (s, 2H), 3.70-3.71 (m, 4H), 3.55-3.56 (m, 6H), 2.87-2.89 (m, 2H).<br>3. 393.2<br>4. Procedure 2 |
| 90 | | | | 1. 49%<br>2. ¹H-NMR (400 MHz, DMSO-$d_6$): δ 7.24-7.26 (m, 2H), 7.01-7.02 (m, 2H), 6.75-6.76 (m, 2H), 4.45 (s, 2H), 3.65-3.70 (m, 9H), 3.54-3.55 (m, 4H), 2.90 (s, 2H).<br>3. 407.1<br>4. Procedure 2 |
| 91 | | | | 1. 66%<br>2. ¹H-NMR (400 MHz, DMSO-$d_6$): δ 7.23-7.25 (m, 2H), 7.11-7.12 (m, 1H), 6.84-6.85 (m, 3H), 4.41 (s, 2H), 3.88 (s, 3H), 3.71-3.72 (m, 4H), 3.56-3.57 (m, 6H), 2.79 (bs, 2H).<br>3. 407.3<br>4. Procedure 2 |

TABLE 1-continued

| Example | Tricyclic amine derivative | Bromo or Chloro derivative | Product Example | 1. Yield; %<br>2. ¹H-NMR<br>3. MH⁺ (ESI)<br>4. Synthesis procedure |
|---|---|---|---|---|
| 92 | | | | 1. 76.1%<br>2. ¹H-NMR (400 MHz, DMSO-d₆): δ 11.33 (s, 1H), 7.96 (d, J = 3.20 Hz, 1H), 7.42-7.43 (m, 1H), 7.22 (d, J = 7.60 Hz, 1H), 6.87-6.88 (m, 3H), 4.31 (s, 2H), 3.70-3.71 (m, 4H), 3.45-3.47 (m, 2H), 3.28-3.30 (m, 4H), 2.68-2.76 (m, 2H).<br>3. 353.1<br>4. Procedure 3 |
| 93 | | | | 1. 50.0%<br>2. ¹H-NMR (400 MHz, DMSO-d₆): δ 11.32 (s, 1H), 7.28 (d, J = 8.72 Hz, 1H), 7.22 (d, J = 7.60 Hz, 1H), 6.99 (d, J = 2.40 Hz, 1H), 6.87-6.87 (m, 2H), 6.75 (dd, J = 2.44, 8.74 Hz, 1H), 4.36 (s, 2H), 3.70-3.71 (m, 4H), 3.55-3.56 (m, 6H), 2.78 (t, J = 5.44 Hz, 2H).<br>3. 393.1<br>4. Procedure 3 |
| 94 | | | | 1. 17.6%<br>2. ¹H-NMR (400 MHz, DMSO-d₆) δ 8.13 (s, 1H), 7.93 (s, 1H), 7.41 (t, J = 6.80 Hz, 2H), 7.10 (t, J = 7.20 Hz, 1H), 7.00 (t, J = 7.20 Hz, 1H), 4.67 (s, 2H), 3.83 (bs, 2H), 3.70 (s, 3H), 3.33 (bs, 4H), 2.77 (bs, 2H), 2.41 (bs, 4H), 2.19 (s, 3H),<br>3. 363.2<br>4. Procedure 5 |
| 95 | | | | 1. 13.4%<br>2. ¹H-NMR (400 MHz, DMSO-d₆): δ 8.03 (s, 1H), 7.44 (t, J = 7.60 Hz, 3H), 6.98-7.00 (m, 2H), 6.81 (d, J = 8.80 Hz, 1H), 4.36 (s, 2H), 3.69 (s, 3H), 3.47 (t, J = 5.60 Hz, 2H), 3.29 (bs, 4H), 2.73 (bs, 2H), 2.37-2.38 (m, 4H), 2.16 (s, 3H).<br>3. 362.2<br>4. Procedure 5 |

TABLE 1-continued

| Example | Tricyclic amine derivative | Bromo or Chloro derivative | Product Example | 1. Yield; %<br>2. ¹H-NMR<br>3. MH⁺ (ESI)<br>4. Synthesis procedure |
|---|---|---|---|---|
| 96 | | | | 1. 31.8%<br>2. ¹H-NMR (400 MHz, DMSO-d₆): δ 7.49 (d, J = 10.00 Hz, 3H), 7.40-7.41 (m, 1H), 7.30 (d, J = 10.00 Hz, 1H), 7.11 (t, J = 7.60 Hz, 1H), 7.00 (t, J = 7.20 Hz, 1H), 4.78 (s, 2H), 3.85 (t, J = 5.60 Hz, 2H), 3.71-3.72 (m, 7H), 3.33-3.35 (m, 3H), 2.29-2.33 (m, 2H).<br>3. 350.2<br>4. Procedure 5 |
| 97 | | | | 1. 50.3%<br>2. ¹H-NMR (400 MHz, DMSO-d₆): δ 7.41 (t, J = 7.60 Hz, 2H), 7.26 (d, J = 8.68 Hz, 1H), 7.08-7.10 (m, 2H), 7.00 (t, J = 7.12 Hz, 1H), 6.81 (d, J = 8.68 Hz, 1H), 4.42 (s, 2H), 3.71 (s, 3H), 3.57 (bs, 6H), 2.80 (s, 2H), 2.40-2.41 (m, 4H), 2.22 (s, 3H).<br>3. 402.3<br>4. Procedure 3 |
| 98 | | | | 1. 25.7%<br>2. ¹H-NMR (400 MHz, DMSO-d₆): δ 10.83 (s, 1H), 7.39 (d, J = 7.60 Hz, 1H), 7.31 (d, J = 8.00 Hz, 1H), 7.25 (d, J = 8.80 Hz, 1H), 6.94-6.95 (m, 3H), 6.72-6.73 (m, 1H), 4.35 (s, 2H), 3.56-3.57 (m, 6H), 2.78 (s, 2H), 2.40-2.41 (m, 4H), 2.22 (s, 3H).<br>3. 388.2<br>4. Procedure 3 |
| 99 | | | | 1. 21%<br>2. ¹H-NMR (400 MHz, DMSO-d6): δ 10.84 (bs, 1H), 7.39 (d, J = 7.68 Hz, 1H), 7.27-7.29 (m, 2H), 6.94-6.96 (m, 3H), 6.77 (d, J = 7.96 Hz, 1H), 4.37 (s, 2H), 3.70-3.71 (m, 4H), 3.55-3.56 (m, 6H), 2.79 (bs, 2H).<br>3. 375.2<br>4. Procedure 2 |

TABLE 1-continued

| Example | Tricyclic amine derivative | Bromo or Chloro derivative | Product Example | 1. Yield; %<br>2. ¹H-NMR<br>3. MH⁺ (ESI)<br>4. Synthesis procedure |
|---|---|---|---|---|
| 100 | 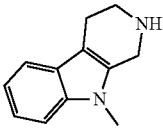 | 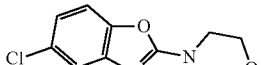 | 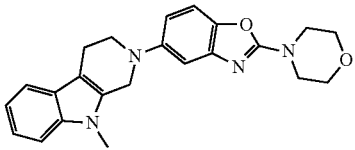 [SMILES: Cn1c2c(c3ccccc31)CCN(c1ccc3oc(N4CCOCC4)nc3c1)C2] | 1. 30.5%<br>2. ¹H-NMR (400 MHz, DMSO-d6): δ 7.42 (t, J = 7.32 Hz, 1H), 7.28 (d, J = 8.72 Hz, 1H), 7.09-7.10 (m, 1H), 7.00 (t, J = 7.28 Hz, 1H), 6.82-6.82 (m, 1H), 4.43 (s, 2H), 3.71-3.73 (m, 7H), 3.55-3.56 (m, 6H), 2.81 (s, 2H).<br>3. 389.2<br>4. Procedure 4 |
| 101 |  | 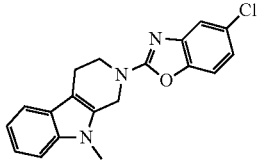 [SMILES: Cn1c2c(c3ccccc31)CCN(c1nc3cc(Cl)ccc3o1)C2] | 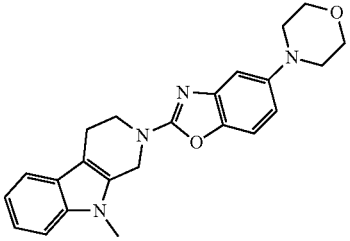 [SMILES: Cn1c2c(c3ccccc31)CCN(c1nc3cc(N4CCOCC4)ccc3o1)C2] | 1. 25.3%<br>2. ¹H-NMR (400 MHz, DMSO-d6): δ 7.44-7.45 (m, 2H), 7.29-7.29 (m, 1H), 7.14 (t, J = 7.20 Hz, 1H), 7.01-7.03 (m, 1H), 6.94-6.94 (m, 1H), 6.65-6.65 (m, 1H), 4.91 (s, 2H), 3.97 (t, J = 5.40 Hz, 2H), 3.71-3.72 (m, 7H), 3.05-3.06 (m, 4H), 2.88 (bs, 2H).<br>3. 389.3<br>4. Procedure 4 |
| 102 |  | 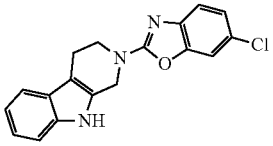 [SMILES: Clc1ccc2nc(N3CCc4c([nH]c5ccccc45)C3)oc2c1] | 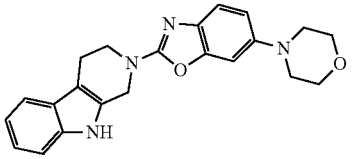 [SMILES: c1ccc2c3c([nH]c2c1)CN(c1nc2ccc(N4CCOCC4)cc2o1)CC3] | 1. 46.7%<br>2. ¹H-NMR (400 MHz, DMSO-d6): δ 10.96 (s, 1H), 7.42 (d, J = 7.76 Hz, 1H), 7.34 (d, J = 8.04 Hz, 1H), 7.18 (d, J = 8.52 Hz, 1H), 7.12-7.13 (m, 1H), 7.06 (t, J = 7.84 Hz, 1H), 6.98 (t, J = 7.16 Hz, 1H), 6.79-6.80 (m, 1H), 4.81 (s, 2H), 3.95 (t, J = 5.60 Hz, 2H), 3.73-3.74 (m, 4H), 3.04-3.05 (m, 4H), 2.86-2.87 (m, 2H).<br>3. 375.2<br>4. Procedure 4 |
| 103 | 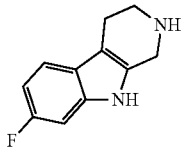 | 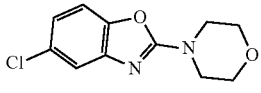 | 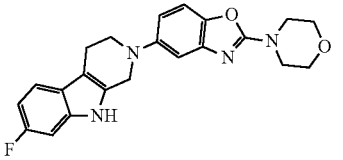 [SMILES: Fc1ccc2c3c([nH]c2c1)CN(c1ccc2oc(N4CCOCC4)nc2c1)CC3] | 1. 33.4%<br>2. ¹H-NMR (400 MHz, DMSO-d6): δ 10.94 (s, 1H), 7.35-7.36 (m, 1H), 7.27 (d, J = 8.68 Hz, 1H), 7.09-7.10 (m, 1H), 7.00 (d, J = 2.24 Hz, 1H), 6.79-6.79 (m, 1H), 6.73-6.74 (m, 1H), 4.34 (s, 2H), 3.70-3.71 (m, 4H), 3.54-3.55 (m, 6H), 2.77 (t, J = 5.08 Hz, 2H).<br>3. 393.3<br>4. Procedure 4 |

TABLE 1-continued

| Example | Tricyclic amine derivative | Bromo or Chloro derivative | Product Example | 1. Yield; % 2. ¹H-NMR 3. MH⁺ (ESI) 4. Synthesis procedure |
|---|---|---|---|---|
| 104 | | | | 1. 7%; 2. ¹H NMR (400 MHz, DMSO-d6): δ 7.38-7.42 (m, 1H), 7.27-7.31 (m, 2H), 7.09 (d, J = 2.40 Hz, 1H), 6.80-6.87 (m, 2H), 4.40 (bs, 2H), 3.70-3.73 (m, 4H), 3.68 (s, 3H), 3.55-3.57 (m, 6H), 2.75-2.79 (m, 2H). 3. 407.2 4 Procedure 2 |
| 105 | | | | 1. 11%; 2. ¹H NMR (400 MHz, DMSO-d6): δ 8.12 (d, J = 3.20 Hz, 1H), 7.85 (d, J = 2.80 Hz, 1H), 7.24-7.24 (m, 1H), 7.09 (d, J = 6.80 Hz, 1H), 6.87-6.88 (m, 1H), 6.76 (d, J = 9.20 Hz, 1H), 3.67-3.69 (m, 9H), 3.30-3.31 (m, 4H), 2.85-2.86 (m, 2H), 1.87 (bs, 2H). 3. 350.2 4. Procedure 2 |
| 107 | | | | 1. 23%; 2. ¹H NMR (400 MHz, DMSO-d6): δ 8.16 (d, J = 1.12 Hz, 1H), 7.94 (d, J = 2.12 Hz, 1H), 7.28-7.28 (m, 1H), 7.16-7.16 (m, 1H), 6.66 (d, J = 8.96 Hz, 1H), 3.93 (bs, 2H), 3.71-3.72 (m, 7H), 3.01-3.02 (m, 4H), 2.89-2.90 (m, 2H), 2.08 (bs, 2H). 3. 368.2 4. Procedure 2 |
| 108 | | | | 1. 28%; 2. ¹H NMR (400 MHz, DMSO-d6): δ 10.94 (bs, 1H), 7.96 (d, J = 3.00 Hz, 1H), 7.42-7.43 (m, 1H), 7.35-7.37 (m, 1H), 7.09-7.09 (m, 1H), 6.79-6.79 (m, 1H), 4.28 (s, 2H), 3.69-3.70 (m, 4H), 3.49 (bs, 2H), 3.28-3.29 (m, 4H), 2.75 (bs, 1H). 3. 353.2 4. Procedure 2 |

TABLE 1-continued

| Example | Tricyclic amine derivative | Bromo or Chloro derivative | Product Example | 1. Yield; %<br>2. ¹H-NMR<br>3. MH⁺ (ESI)<br>4. Synthesis procedure |
|---|---|---|---|---|
| 109 | | | | 1. 29%;<br>2. ¹H NMR (400 MHz, DMSO-d6): δ 10.99 (bs, 1H), 7.86 (d, J = 2.80 Hz, 1H), 7.33-7.34 (m, 2H), 7.08-7.08 (m, 1H), 6.94 (d, J = 9.08 Hz, 1H), 6.78-6.78 (m, 1H), 4.64 (s, 2H), 3.81-3.82 (m, 2H), 3.71-3.73 (m, 4H), 2.96-2.97 (m, 4H), 2.74 (bs, 2H).<br>3. 353.2 |
| 110 | | | | 1. 26%;<br>2. ¹H NMR (400 MHz, DMSO-d6): δ 8.04 (bs, 1H), 7.48-7.49 (m, 1H), 7.38-7.40 (m, 1H), 7.30 (d, J = 10.40 Hz, 1H), 6.81-6.83 (m, 2H), 4.35 (s, 2H), 3.67-3.70 (m, 7H), 3.47-3.48 (m, 2H), 3.30-3.31 (m, 4H), 2.77 (bs, 2H).<br>3. 367.2<br>4. Procedure 2 |
| 111 | | | | 1. 25%;<br>2. ¹H NMR (400 MHz, DMSO-d6): δ 7.88 (d, J = 2.88 Hz, 1H), 7.35-7.35 (m, 2H), 7.28-7.29 (m, 1H), 7.01 (d, J = 9.20 Hz, 1H), 6.81-6.82 (m, 1H), 4.66 (s, 2H), 3.81-3.83 (m, 2H), 3.72-3.73 (m, 4H), 3.68 (s, 3H), 2.97-2.98 (m, 4H), 2.76 (bs, 2H).<br>3. 367.2<br>4. Procedure 2 |
| 112 | | | | 1. 16%<br>2. ¹H-NMR (400 MHz, DMSO-d6): δ 8.63 (d, J = 2.64 Hz, 1H), 7.81 (d, J = 8.80 Hz, 1H), 7.57-7.58 (m, 1H), 7.41-7.43 (m, 2H), 7.13 (t, J = 7.56 Hz, 1H), 7.02 (t, J = 7.28 Hz, 1H), 4.73 (s, 2H), 3.87 (t, J = 5.48 Hz, 2H), 3.73 (s, 3H), 2.85 (bs, 2H).<br>3. 289.2<br>4. Procedure 2 |
| 113 | | | | 1. 12%<br>2. ¹H-NMR (400 MHz, DMSO-d6): δ 10.91 (bs, 1H), 8.54 (d, J = 2.56 Hz, 1H), 7.79 (d, J = 8.84 Hz, 1H), 7.33-7.35 (m, 3H), 6.96-6.97 (m, 2H), 4.66 (s, 2H), 3.89 (t, J = 5.40 Hz, 2H), 2.85 (bs, 2H).<br>3. 275.1<br>4. Procedure 2 |

TABLE 1-continued

| Example | Tricyclic amine derivative | Bromo or Chloro derivative | Product Example | 1. Yield; %<br>2. ¹H-NMR<br>3. MH⁺ (ESI)<br>4. Synthesis procedure |
|---|---|---|---|---|
| 117 | | | | 1. 20%<br>2. ¹H-NMR (400 MHz, DMSO-d₆): δ 10.90 (s, 1H), 7.38-7.39 (m, 2H), 7.27-7.30 (m, 2H), 7.01-7.01 (m, 1H), 6.93-6.93 (m, 1H), 4.72 (s, 2H), 3.78-3.80 (m, 4H), 3.36-3.37 (m, 1H), 3.27 (s, 3H), 3.03-3.04 (m, 2H), 2.75-2.77 (m, 2H), 1.88-1.88 (m, 2H), 1.43-1.44 (m, 2H).<br>3. 364.3<br>4. Procedure 2 |
| 118 | | | | 1. 47%<br>2. ¹H-NMR (400 MHz, DMSO-d₆): 400 MHz, DMSO-d6: δ 10.90 (s, 1H), 7.37-7.39 (m, 2H), 7.27-7.29 (m, 2H), 7.03-7.03 (m, 2H), 4.72 (s, 2H), 3.83-3.84 (m, 5H), 3.58-3.58 (m, 2H), 2.72-2.73 (m, 3H), 2.44-2.46 (m, 1H), 1.15-1.16 (m, 3H).<br>3. 350.1<br>4. Procedure 2 |
| 119 | | | | 1. 11%<br>2. ¹H-NMR (400 MHz, DMSO-d₆): δ 10.89 (s, 1H), 7.43 (d, J = 9.60 Hz, 1H), 7.38 (d, J = 7.60 Hz, 1H), 7.27-7.29 (m, 2H), 7.01-7.01 (m, 1H), 6.93-6.93 (m, 1H), 4.64 (s, 2H), 3.88-3.89 (m, 5H), 3.58-3.58 (m, 2H), 2.75-2.76 (m, 3H), 2.43-2.44 (m, 1H), 1.15 (d, J = 6.40 Hz, 3H).<br>3. 350.2<br>4. Procedure 2 |
| 120 | | | | 1. 30%<br>2. ¹H-NMR (400 MHz, DMSO-d₆): δ 10.90 (s, 1H), 7.37-7.39 (m, 2H), 7.27-7.30 (m, 2H), 6.95-6.95 (m, 2H), 4.73 (s, 2H), 3.95-3.97 (m, 2H), 3.81-3.83 (m, 2H), 3.62-3.63 (m, 2H), 2.77-2.78 (m, 2H), 2.33-2.35 (m, 2H), 1.14 (d, J = 6.00 Hz, 6H).<br>3. 364.3<br>4. Procedure 2 |

TABLE 1-continued

| Example | Tricyclic amine derivative | Bromo or Chloro derivative | Product Example | 1. Yield; %<br>2. ¹H-NMR<br>3. MH⁺ (ESI)<br>4. Synthesis procedure |
|---|---|---|---|---|
| 121 | F-tricyclic amine with Tos | Br-quinoline-morpholine | F-tricyclic-quinoline-morpholine product | 1. 38%<br>2. ¹H-NMR (400 MHz, DMSO-$d_6$): δ 10.95 (s, 1H), 7.88 (d, 1H), 7.57 (d, 1H), 7.33 (dd, 1H), 7.18 (m, 2H), 6.98-6.77 (m, 3H), 4.54 (s, 2H), 3.78 (t, 2H), 3.72 (t, 4H), 3.60 (t, 4H), 2.79 (t, 2H).<br>3. 403.21<br>4. Procedure 3 |
| 122 | F-tricyclic amine with Tos | Br-quinoline-morpholine | F-tricyclic-quinoline-morpholine product | 1. 25%<br>2. ¹H-NMR (400 MHz, DMSO-$d_6$): δ 10.96 (s, 1H), 7.96 (d, 1H), 7.53 (s, 2H), 7.31 (dd, 1H), 7.25-7.03 (m, 3H), 6.87 (t, 1H), 4.45 (s, 2H), 3.70 (m, 6H), 3.56 (m, 4H), 2.89-2.68 (m, 2H).<br>3. 403.19<br>4. Procedure 3 |

Example 123

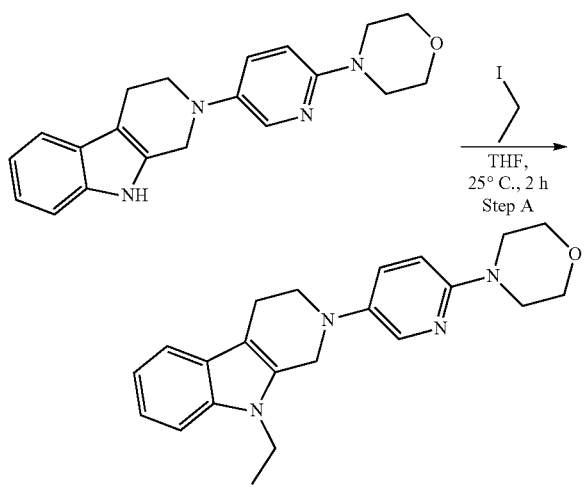

Step A

To a solution of Example 44 in THF (15.0 mL), sodium hydride (60%) (0.0412 g, 1.79 mmol) was added slowly at 0° C. then stirred it for 1 hr at 25° C. Ethyl Iodide (0.305 g, 0.00179 mol) in 15.0 mL THF was added slowly at 0° C. then stirred it for 2 hr at 25° C. The reaction mixture was monitored by LCMS, the reaction mixture was diluted with water (50.0 mL). The organic phase was separated and the aqueous phase was extracted with ethyl acetate two more time. The combined organic phase was dried over $Na_2SO_4$, filtered and the solvents were evaporated under reduced pressure. The crude purified on HP-Sil column (biotage) by employing a Ethyl Acetate/Petroluem Ether (50/50) gradient to afford title compound as an off white solid.

¹H-NMR (400 MHz, DMSO-$d_6$): δ 8.05 (d, J=2.88 Hz, 1H), 7.49-7.50 (m, 1H), 7.42 (d, J=8.20 Hz, 2H), 7.08-7.08 (m, 1H), 6.97-6.97 (m, 1H), 6.81 (d, J=9.08 Hz, 1H), 4.38 (s, 2H), 4.18 (q, J=7.08 Hz, 2H), 3.69-3.70 (m, 4H), 3.50 (t, J=5.60 Hz, 2H), 3.29-3.30 (m, 4H), 2.78 (t, J=5.52 Hz, 2H), 1.26 (t, J=7.12 Hz, 3H).

MS: 363.2 (M+H)⁺.

HCl Salt of Compounds of the Present Invention

General Procedure

To a solution of an Example compound (0.1 g) in dry DCM (10 mL), cooled to 0° C., was added 1M HCl in ether (5 eq) or 4M HCl in Dioxane (5 eq) and stirred for 15 minutes. The reaction mixture was concentrated under vacuum and triturated with diethylether to afford desired product as indicated in Table 2

EXAMPLES

Following the hydrochloride salt procedure as described in the general procedure above, the following compounds were prepared.

TABLE 2

| Example | Starting Free Base | Product | 1. Yield  2. ¹H-NMR  3. MH⁺ (ESI) |
|---|---|---|---|
| 123 HCl | | ·HCl | 1. 83%  2. ¹H-NMR (400 MHz, DMSO-d6): δ 8.21 (d, J = 8.36 Hz, 1H), 7.63 (bs, 1H), 7.37-7.40 (m, 3H), 6.99-7.01 (m, 2H), 4.53 (s, 2H), 4.20-4.22 (m, 2H), 3.74-3.75 (m, 4H), 3.57-3.58 (m, 6H), 2.83 (s, 2H), , 1.28 (t, J = 7.16 Hz, 3H).  3. 363.2 |
| 108 HCl | | ·HCl | 1. 65%  2. ¹H-NMR (400 MHz, DMSO-d₆) δ 10.83 (bs, 1H), 7.92-7.93 (m, 1H), 7.41-7.43 (m, 1H), 7.35-7.37 (m, 1H), 7.05-7.07 (m, 1H), 6.77-6.79 (m, 1H), 4.25 (s, 2H), 3.68-3.69 (m, 4H), 3.52 (bs, 2H), 3.25-3.27 (m, 4H), 2.83 (bs, 1H).  3. 353.1 |
| 109 HCl | | ·HCl | 1. 85%  2. ¹H-NMR (400 MHz, DMSO-d₆) δ 10.85 (bs, 1H), 7.91-7.93 (m, 1H), 7.40-7.42 (m, 1H), 7.36-7.37 (m, 1H), 7.03-7.05 (m, 1H), 6.77-6.79 (m, 1H), 4.27 (s, 2H), 3.65-3.67 (m, 4H), 3.57 (bs, 2H), 3.25-3.27 (m, 4H), 2.85 (bs, 1H).  3. 353.1 |
| 110 HCl | | ·HCl | 1. 82%  2. ¹H-NMR (400 MHz, DMSO-d6): 400 MHz, DMSO-d6: δ 8.20 (d, J = 7.88 Hz, 1H), 7.62 (s, 1H), 7.38-7.41 (m, 3H), 6.83-6.84 (m, 1H), 4.48 (s, 2H), 3.69-3.73 (m, 7H), 3.56-3.59 (m, 6H), 2.82 (s, 2H).  3. 367.2 |
| 111 HCl | | ·HCl | 1. 79%  2. ¹H-NMR (400 MHz, DMSO-d6): δ 8.08 (d, J = 8.72 Hz, 1H), 7.60 (d, J = 9.64 Hz, 1H), 7.44-7.46 (m, 2H), 7.31-7.32 (m, 1H), 6.85-6.86 (m, 1H), 4.93 (s, 2H), 4.02 (t, J = 5.16 Hz, 2H), 3.70 (bs, 7H), 3.11 (bs, 4H), 2.87 (s, 2H).  3. 367.2 |
| 80 HCl | | ·HCl | 1. 74%  2. ¹H-NMR (400 MHz, DMSO-d6): δ 10.91 (s, 1H), 8.14-8.15 (m, 1H), 7.40 (d, J = 7.72 Hz, 1H), 7.33 (d, J = 7.96 Hz, 1H), 7.05 (t, J = 7.60 Hz, 2H), 6.90-6.92 (m, 2H), 4.37 (bs, 2H), 3.97 (bs, 3H), 3.53-3.54 (m, 7H), 2.79 (s, 2H), 1.77-1.78 (m, 4H).  3. 375.2 |

TABLE 2-continued

| Example | Starting Free Base | Product | 1. Yield<br>2. ¹H-NMR<br>3. MH⁺ (ESI) |
|---|---|---|---|
| 69 HCl | 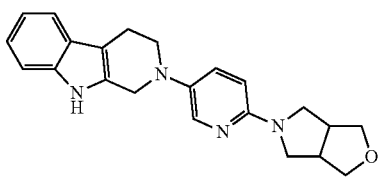 [SMILES: c1ccc2c3c([nH]c2c1)CN(c1ccc(N2CC4COCC4C2)nc1)CC3] |  | 1. 87%<br>2. ¹H-NMR (400 MHz, DMSO-d6): δ 10.93 (s, 1H), 8.17-8.18 (m, 1H), 7.33-7.35 (m, 3H), 7.11-7.13 (m, 1H), 6.99-7.03 (m, 2H), 4.38 (s, 2H), 3.73-3.75 (m, 4H), 3.59-3.61 (m, 4H), 3.48-3.49 (m, 2H), 3.12-3.13 (m, 2H), 2.80 (s, 2H).<br>3. 361.3 |
| 86 HCl | 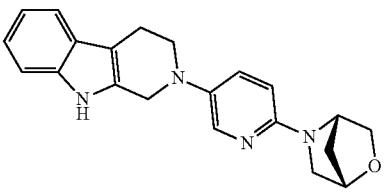 [SMILES: c1ccc2c3c([nH]c2c1)CN(c1ccc(N2C[C@@H]4C[C@H]2CO4)nc1)CC3] | 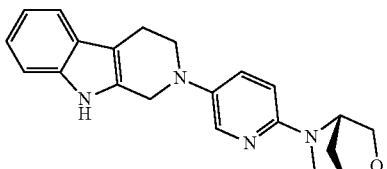 | 1. 89%<br>2. ¹H-NMR (400 MHz, DMSO-d6): δ 10.93 (s, 1H), 8.16-8.17 (m, 1H), 7.41 (d, J = 7.68 Hz, 1H), 7.34 (d, J = 7.72 Hz, 2H), 7.21 (d, J = 9.84 Hz, 1H), 7.05 (t, J = 7.96 Hz, 1H), 6.97 (t, J = 7.44 Hz, 1H), 5.17 (s, 1H), 4.78 (s, 1H), 4.38 (s, 2H), 3.74-3.76 (m, 2H), 3.59-3.60 (m, 3H), 3.39-3.41 (m, 1H), 2.81 (s, 2H), 1.98 (s, 2H).<br>3. 347.1 |
| 85 HCl | 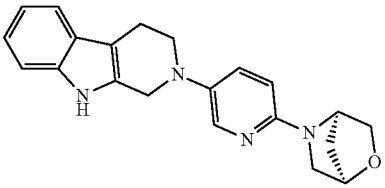 [SMILES: c1ccc2c3c([nH]c2c1)CN(c1ccc(N2C[C@H]4C[C@@H]2CO4)nc1)CC3] | 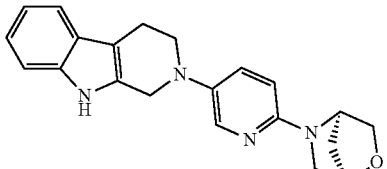 | 1. 78%<br>2. ¹H-NMR (400 MHz, DMSO-d6): δ 10.92 (s, 1H), 8.16-8.17 (m, 1H), 7.41 (d, J = 8.00 Hz, 1H), 7.34 (d, J = 8.00 Hz, 2H), 7.21 (d, J = 9.60 Hz, 1H), 7.03-7.04 (m, 1H), 6.95-6.95 (m, 1H), 5.17 (s, 1H), 4.79 (s, 1H), 4.39 (s, 2H), 3.75-3.77 (m, 2H), 3.59-3.60 (m, 3H), 3.39-3.41 (m, 1H), 2.81-2.82 (m, 2H), 1.99 (s, 2H).<br>3. 347.1 |
| 82 HCl | 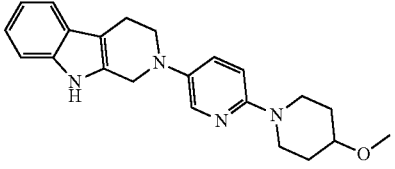 [SMILES: COC1CCN(c2ccc(N3CCc4c([nH]c5ccccc45)C3)cn2)CC1] | 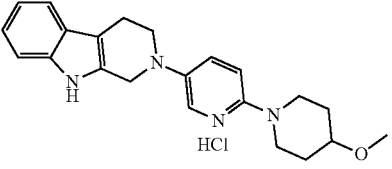 [SMILES: COC1CCN(c2ccc(N3CCc4c([nH]c5ccccc45)C3)cn2)CC1 ; Cl] | 1. 78%<br>2. ¹H-NMR (400 MHz, DMSO-d6): δ 10.92 (s, 1H), 8.16-8.17 (m, 1H), 7.41 (d, J = 8.00 Hz, 1H), 7.34 (d, J = 8.00 Hz, 2H), 7.21 (d, J = 9.60 Hz, 1H), 7.03-7.04 (m, 1H), 6.95-6.95 (m, 1H), 5.17 (s, 1H), 4.79 (s, 1H), 4.39 (s, 2H), 3.75-3.77 (m, 2H), 3.59-3.60 (m, 3H), 3.39-3.41 (m, 1H), 2.81-2.82 (m, 2H), 1.99 (s, 2H).<br>3. 347.1 |
| 44 HCl | 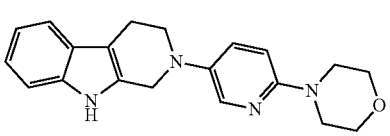 | 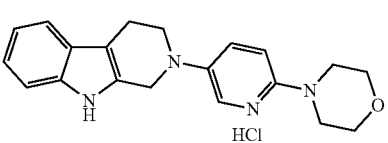 [SMILES: c1ccc2c3c([nH]c2c1)CN(c1ccc(N2CCOCC2)nc1)CC3 ; Cl] | 1. 88%<br>2. ¹H-NMR (400 MHz, DMSO-d6): δ 10.98 (s, 1H), 8.18-8.19 (m, 1H), 7.34-7.35 (m, 4H), 6.96-6.98 (m, 2H), 4.46 (s, 2H), 3.61-3.62 (m, 10H), 2.84 (s, 2H).<br>3. 335.3 |
| 46 HCl | 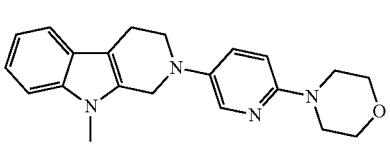 [SMILES: Cn1c2c(c3ccccc31)CCN(c1ccc(N3CCOCC3)nc1)C2] | 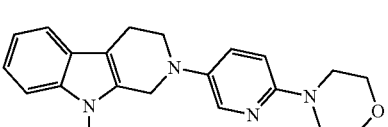 | 1. 85%<br>2. ¹H-NMR (400 MHz, DMSO-d6): δ 8.24-8.24 (m, 1H), 7.67 (s, 1H), 7.39-7.41 (m, 3H), 7.12 (t, J = 7.20 Hz, 1H), 7.01 (t, J = 7.20 Hz, 1H), 4.52 (s, 2H), 3.62-3.64 (m, 13H), 2.85 (bs, 2H).<br>3. 349.3 |

TABLE 2-continued

| Example | Starting Free Base | Product | 1. Yield<br>2. ¹H-NMR<br>3. MH⁺ (ESI) |
|---|---|---|---|
| 45 HCl | | | 1. 78%<br>2. ¹H-NMR (400 MHz, DMSO-d₆): δ 8.07 (bs, 1H), 7.61-7.63 (m, 1H), 7.43-7.45 (m, 3H), 7.15 (t, J = 7.76 Hz, 1H), 7.04 (t, J = 7.00 Hz, 1H), 4.95 (s, 2H), 4.02-4.03 (m, 2H), 3.71-3.72 (m, 7H), 3.11-3.12 (m, 4H), 2.89-2.90 (m, 2H).<br>3. 349.2 |
| 83 HCl | | | 1. 88%<br>2. ¹H-NMR (400 MHz, DMSO-d6): δ 10.91 (s, 1H), 8.16 (d, J = 8.28 Hz, 1H), 7.33-7.35 (m, 4H), 7.05 (t, J = 7.04 Hz, 1H), 6.97 (t, J = 7.08 Hz, 1H), 4.41 (s, 2H), 3.72 (bs, 2H), 3.63 (s, 6H), 3.40 (bs, 2H), 2.81 (bs, 2H), 1.56-1.58 (m, 4H).<br>3. 375.2 |
| 79 HCl | | | 1. 81%<br>2. ¹H-NMR (400 MHz, DMSO-d6): δ 10.94 (s, 1H), 8.16 (d, J = 9.04 Hz, 1H), 7.60 (s, 1H), 7.42 (d, J = 7.72 Hz, 1H), 7.34 (d, J = 8.00 Hz, 2H), 7.06 (t, J = 7.24 Hz, 1H), 6.98 (t, J = 7.56 Hz, 1H), 4.45 (s, 2H), 3.97-4.00 (m, 1H), 3.66-3.67 (m, 4H), 3.32-3.38 (m, 4H), 2.84 (s, 2H), 1.19-1.21 (m, 3H).<br>3. 349.3 |
| 76 HCl | | | 1. 69%<br>2. ¹H-NMR (400 MHz, DMSO-d6): δ 10.92 (s, 1H), 8.15 (d, J = 7.68 Hz, 1H), 7.52 (bs, 1H), 7.41 (d, J = 7.56 Hz, 2H), 7.34 (d, J = 7.96 Hz, 1H), 7.06 (t, J = 7.68 Hz, 1H), 6.97 (t, J = 7.16 Hz, 1H), 4.44 (s, 2H), 4.08-4.11 (m, 2H), 3.66 (bs, 4H), 2.83 (bs, 2H), 2.65-2.67 (m, 2H), 1.16 (d, J = 6.16 Hz, 6H).<br>3. 363.2 |
| 75 HCl | | | 1. 85%<br>2. ¹H-NMR (400 MHz, DMSO-d6): δ 10.90 (s, 1H), 8.09 (bs, 1H), 7.59 (bs, 1H), 7.41 (d, J = 7.60 Hz, 1H), 7.34 (d, J = 8.00 Hz, 2H), 7.06 (t, J = 7.20 Hz, 1H), 6.98 (t, J = 7.60 Hz, 1H), 4.44 (s, 2H), 4.04-4.07 (m, 1H), 3.94-3.96 (m, 2H), 3.88-3.91 (m, 4H), 3.03-3.05 (m, 1H), 2.68-2.73 (m, 3H), 1.16 (d, J = 6.00 Hz, 3H).<br>3. 349.2 |
| 74 HCl | | | 1. 79%<br>2. ¹H-NMR (400 MHz, DMSO-d6): δ 10.90 (s, 1H), 8.10 (bs, 1H), 7.53 (bs, 1H), 7.41 (d, J = 7.60 Hz, 1H), 7.34 (d, J = 8.00 Hz, 2H), 7.06 (t, J = 7.20 Hz, 1H), 6.98 (t, J = 8.00 Hz, 1H), 4.44 (s, 2H), 3.94-3.96 (m, 3H), 3.38-3.40 (m, 4H) 2.68-2.68 (m, 4H), , 1.16 (d, J = 6.40 Hz, 3H).<br>3. 349.3 |

TABLE 2-continued

| Example | Starting Free Base | Product | 1. Yield<br>2. ¹H-NMR<br>3. MH⁺ (ESI) |
|---|---|---|---|
| 71 HCl | (structure) | (structure) HCl | 1. 82%<br>2. ¹H-NMR (400 MHz, DMSO-d6): δ 10.93 (s, 1H), 8.09 (s, 1H), 7.41-7.43 (m, 3H), 7.34 (d, J = 8.00 Hz, 1H), 7.06 (t, J = 6.80 Hz, 1H), 6.98 (t, J = 7.20 Hz, 1H), 4.44-4.47 (m, 2H), 4.00-4.10 (m, 4H), 3.65-3.66 (m, 4H), 2.83 (bs, 2H), 2.03-2.04 (m, 2H).<br>3. 347.1 |
| 105 HCl | (structure) | (structure) 2 X HCl | 1. 71%<br>2. ¹H-NMR (400 MHz, DMSO-d6): 400 MHz, DMSO-d6: δ 8.23 (s, 1H), 7.96 (s, 1H), 7.35 (d, J = 10.80 Hz, 3H), 7.01-7.02 (m, 1H), 3.59-3.68 (m, 13H), 2.91 (bs, 2H), 1.91 (bs, 2H).<br>3. 350.1 |
| 107 HCl | (structure) | (structure) 2 X HCl | 1. 82%<br>2. ¹H-NMR (400 MHz, DMSO-d6): δ 8.24 (s, 1H), 8.00 (d, J = 9.20 Hz, 1H), 7.60 (s, 1H), 7.39 (t, J = 7.60 Hz, 1H), 7.20 (d, J = 9.60 Hz, 1H), 3.91-3.98 (m, 2H), 3.74-3.76 (m, 7H), 3.16 (s, 4H), 2.96-2.97 (m, 2H), 2.06 (bs, 2H).<br>3. 368.3 |

Biological Assay Description

Full-Length Tau (flTau) Disaggregation Assay by Thioflavin T (ThT)

The longest isoform of human Tau (2N4R; 441 amino acids) was expressed in bacteria and purified. For the Tau disaggregation assay by ThT, 35 μM of recombinant full-length (fl)Tau in PBS were aggregated for 24 hours at 37° C. in presence of 50 μM of heparin (Sigma-Aldrich) and 10 mM of DTT (Sigma-Aldrich) under shaking at 750 RPM. Compounds were dissolved in anhydrous dimethyl sulfoxide (DMSO, Sigma-Aldrich) to reach a concentration of 10 mM. flTau aggregates and serial dilutions of compounds were mixed together in PBS (volume 50 μL) to a final concentration of 2 μM of flTau aggregates and from 160 to 0.04 μM of compounds. The mixture was incubated for 30 minutes at room temperature (RT), then 40 μL of this mixture were transferred into a black 384-well plate assay (Perkin-Elmer) and mixed with 10 μL of 100 μM ThT in 250 mM glycine (both from Sigma-Aldrich) in PBS. Fluorescence (relative fluorescence units; RFU) was measured in monoplicate or duplicate on a Tecan reader (excitation: 440 nm; emission: 485 nm). Percentage of flTau disaggregation was then calculated and the half maximal effective concentration ($EC_{50}$) was determined using GraphPad Prism version 5 (GraphPad Software) assuming a one-binding site fitting model.

Tau K18 Disaggregation Assay by ThT

The Tau K18 fragment, encompassing amino acids 244 to 372 of the longest isoform (2N4R) of human Tau441, was expressed in bacteria and purified or bought from SignalChem. For the K18 disaggregation assay by ThT, 35 μM of recombinant K18 in PBS were aggregated for 24 hours at 37° C. in presence of 50 μM of heparin (Sigma-Aldrich) and 10 mM of DTT (Sigma-Aldrich) under shaking at 750 RPM. Compounds were dissolved in anhydrous dimethyl sulfoxide (DMSO, Sigma-Aldrich) to reach a concentration of 10 mM. K18 aggregates and serial dilutions of compounds were mixed together in PBS (volume 50 μL) to a final concentration of 2 μM of K18 aggregates and from 160 to 0.04 μM of compounds. The mixture was incubated for 30 minutes at room temperature (RT), then 40 μL of this mixture were transferred into a black 384-well plate assay (Perkin-Elmer) and mixed with 10 μL of 100 μM ThT in 250 mM glycine (both from Sigma-Aldrich) in PBS. Fluorescence (relative fluorescence units; RFU) was measured in monoplicate or duplicate on a Tecan reader (excitation: 440 nm; emission: 485 nm). Percentage of K18 disaggregation was then calculated and half maximal effective concentration (E050) was determined using GraphPad Prism version 5 (GraphPad Software) assuming a one-binding site fitting model.

The following example compounds were measured:

| Examples | Tau K18 disaggregation $EC_{50}$ (μM) | flTau disaggregation $EC_{50}$ (μM) |
|---|---|---|
| 1 | | +++ |
| 2 | | +++ |
| 6 | | +++ |
| 7 | | +++ |
| 8 | | +++ |
| 9 | | +++ |
| 11 | | +++ |
| 12 | | +++ |
| 13 | | +++ |
| 14 | | +++ |
| 15 | | +++ |
| 16 | | +++ |
| 17 | | +++ |
| 18 | | +++ |
| 19 | | +++ |
| 20 | +++ | |
| 21 | +++ | |
| 22 | +++ | |
| 23 | +++ | |

-continued

| Examples | Tau K18 disaggregation EC$_{50}$ (μM) | flTau disaggregation EC$_{50}$ (μM) |
|---|---|---|
| 24 | +++ | |
| 25 | +++ | |
| 26 | +++ | |
| 27 | +++ | |
| 28 | +++ | |
| 29 | +++ | |
| 30 | +++ | |
| 31 | +++ | |
| 32 | +++ | |
| 33 | ++ | |
| 34 | +++ | |
| 35 | +++ | |
| 36 | +++ | |
| 37 | ++ | |
| 38 | +++ | |
| 39 | +++ | |
| 40 | +++ | |
| 41 | +++ | |
| 42 | +++ | |
| 43 | +++ | |
| 44 | +++ | |
| 45 | +++ | |
| 46 | +++ | |
| 47 | ++ | |
| 48 | +++ | |
| 49 | +++ | |
| 50 | ++ | |
| 51 | ++ | |
| 52 | +++ | |
| 53 | +++ | |
| 54 | +++ | |
| 55 | +++ | |
| 56 | +++ | |
| 57 | +++ | |
| 58 | +++ | |
| 59 | +++ | |
| 62 | ++ | |
| 67 | +++ | |
| 68 | +++ | |
| 70 | +++ | |
| 76 | +++ | |
| 77 | +++ | |
| 78 | +++ | |
| 86 | +++ | |
| 87 | +++ | |
| 88 | +++ | |
| 89 | +++ | |
| 90 | +++ | |
| 91 | +++ | |
| 92 | +++ | |
| 93 | +++ | |
| 94 | ++ | |
| 95 | + | |
| 96 | +++ | |
| 97 | ++ | |
| 98 | + | |
| 99 | +++ | |
| 100 | +++ | |
| 101 | +++ | |
| 102 | +++ | |
| 103 | +++ | |
| 104 | | +++ |
| 112 | +++ | |
| 113 | +++ | |
| 117 | +++ | |
| 118 | +++ | |
| 119 | +++ | |
| 120 | +++ | |
| 121 | ++ | |
| 122 | +++ | |
| 80 HCl | ++ | |
| 69 HCl | +++ | |
| 86 HCl | +++ | |
| 85 HCl | ++ | |
| 82 HCl | +++ | |
| 107 HCl | + | |
| 123 HCl | +++ | |
| 108 HCl | +++ | |
| 109 HCl | +++ | |
| 110 HCl | +++ | |
| 111 HCl | +++ | |
| 44 HCl | +++ | |
| 46 HCl | ++ | |
| 45 HCl | +++ | |
| 83 HCl | + | |
| 79 HCl | ++ | |
| 76 HCl | +++ | |
| 75 HCl | +++ | |
| 74 HCl | +++ | |
| 71 HCl | ++ | |
| 105 HCl | + | |

Legend:
+++ EC$_{50}$ < 10 uM;
++ EC$_{50}$ 10 < x < 25 uM;
+ EC$_{50}$ 25 < x < 50 uM.

Reduction of Intracellular Tau Aggregation

A human neuroblastoma cell line overexpressing the full-length form of human Tau carrying the P301L mutation was cultured in complete medium [DMEM-F12 4.5 g/L Glutamax (Invitrogen), 15% FBS (Biochrom), 1% Peni/Strep (Invitrogen) supplemented with 2.5 μg/ml of G418 (Sigma-Aldrich) selection antibiotic]. The day before the experiment 5×10$^5$ cells/well were plated in a 6 well plate in 3 mL of complete medium. The next day, cells were incubated with DMSO or a compound of the present invention at 5 μM for additional 24 h at 37° C. After incubation, cells were trypsinized, resuspended in 100 μl of homogenization buffer [25 mM Tris-HCl pH 7.4, 150 mM NaCl, 1 mM EDTA, 1 mM EGTA containing phosphatase inhibitors (30 mM NaF, 0.2 mM Na$_3$VO$_4$, 1 nM okadaic acid, 1 mM PMSF, 5 mM Na$_4$P$_2$O$_7$) and protease inhibitor cocktail (Complete™, Roche)], and then physically lysed with three rapid cycles of freezing and thawing. Samples were then directly tested in the AlphaLISA assay.

Phosphorylated, aggregated, and total Tau were quantified by AlphaLisa using the following antibody pairs:
HT7-Acceptor beads+biotin (BT)-Tau13-Donor beads: Total Tau
HT7-Acceptor beads+biotin (BT)-HT7-Donor beads: Aggregated human Tau The Tau13 (Abcam) was biotinylated using EZ-Link® NHS-PEO Solid Phase biotinylation kit (Thermo Scientific), while the HT7-biotin was from a commercial source (Thermo Scientific).

For each antibody pairs the concentration of acceptor beads and biotinylated antibodies was optimized. All samples were first tested in a dilution series in PBS in order to identify the linear range and optimal dilution for each sample and assay. For the final protocol, the following reagents were added in a 384-well white OptiPlate (PerkinElmer):
5 μL of test diluted sample
20 μL of the mixture biotin-mAb acceptor beads at the following final concentrations:
HT7-BT at 1.25 nM in combination with HT7-Acc beads at 10 μg/ml
Tau13-BT at 5 nM in combination with HT7-Acc beads at 2.5 μg/ml After incubation of this mixture at room temperature for 1 h, 25 μL of Streptavidin Donor beads (Perkin Elmer) at 25 μg/mL were added in the dark. Plates were analyzed after 30 min incubation using the EnSpire Alpha instrument and EnSpire Workstation version 3.00. Data for aggregated Tau were normalized to total Tau and then expressed as percentage of the DMSO-treated cells.

The following example compounds were measured:

| Example | % Reduction of intracellular Tau aggregation |
|---|---|
| 12 | + |
| 21 | + |
| 38 | + |
| 43 | ++ |
| 44 | +++ |
| 45 | ++ |
| 46 | ++ |

Legend:
+++ % > 50;
++ % 50 < x < 25;
+ % 25 < x < 0

Reduction of Intracellular Tau Misfolding by Immunocytochemistry

A human neuroblastoma cell line overexpressing the full-length form of human Tau carrying the P301L mutation were cultured in complete medium [DMEM-F12 4.5 g/L Glutamax (Invitrogen), 15% FBS (Biochrom), 1% Peni/Strep (Invitrogen) supplemented with 2.5 μg/ml of G418 (Sigma-Aldrich) selection antibiotic].

To induce the accumulation of intracellular misfolded Tau, cells were in vitro differentiated from neuroblastoma cells to neuronal-like cells. For this, cells were plated in 96-well plate at a density of 2500 cells/well in 100 μl complete medium supplemented with 10 μM retinoic acid (RA; Sigma, R2625) for 1 week. Every 2 to 3 days, medium was changed and fresh retinoic acid was added. To assess the capability of the compounds of this invention to reduce the levels of misfolded intracellular Tau, compounds were dispensed on the cells at concentrations between of 0.1 and 10 nM for 24 hours. After the incubation with the compounds cells were fixed in 4% PFA for 15 min and washed 3 times in PBS. Then cells were blocked in 10% neat goat serum (NGS), 0.25% Triton X-100 in PBS for 2 h at room temperature. Permeabilized fixed cells were then incubated overnight in 5% NGS/0.25% Triton X-100 in PBS with monoclonal anti-mouse MC1 antibody (provided by Prof. Peter Davies, Albert Einstein College of Medicine, New York, USA) diluted 1:4000 to detect misfolded Tau and polyclonal anti-rabbit total Tau (Abcam; ab64193), and diluted 1:400 to detect total Tau. Following the incubation with primary antibodies, cells were washed 3 times in PBS and then incubated 30 min with secondary Antibodies Goat anti-mouse FITC (Abcam ab6785) and goat anti-rabbit Alexa Fluor 594 (Abcam 150080). Cells were then washed 3 times in PBS and images acquired with Incucyte. The signal for misfolded Tau was normalized to total Tau signal and the reduction of Tau misfolding was expressed as percentage compare to vehicle treated cells. Data are mean of at least 3 pictures/well. When evaluated for its capability to reduce intracellular Tau misfolding Example 44 showed potency at low nM concentration as shown in FIG. 1.

Full-Length Tau (flT) Inhibiton of Aggregation Assay by ThT

The isoform of human Tau (2N4R; 441 amino acids) was purchased from Biotechne (USA). The protein was expressed in bacteria E. coli, purified and concentrated in PBS to a final concentration of 50 μM.

To induce Tau aggregation, 4 μM of monomeric flTau was incubated for 72 hours at 37° C. under agitation cycles consisting of both orbital shaking and mixing function using the Hula Mixer (Life Technologies) with Tau paired-helical filaments (PHF) enriched from the post-mortem brain of one Alzheimer's disease (AD) patient obtained from an external source (Tissue Solutions) diluted 1:200. The enrichment procedure was modified from Jicha et al, 1997 (Journal of Neuroscience Research 48:128-132 (1997)) and Rostagno and Ghiso, 2009 (Current protocols in cell biology (2009), Chapter 3, Unit 3.33 3.33.1-33). Briefly, around 9 g of the AD human brain sample were thawed on ice and homogenized with 50 ml of homogenization buffer [0.75 M NaCl in RAB buffer (100 mM 2-(N-morpholino) ethanesulfonic acid (MES), 1 mM EGTA, 0.5 mM MgSO4, 2 mM DTT, pH 6.8) supplemented with protease inhibitors (Complete; Roche 11697498001)] in a glass Dounce homogenizer. The homogenate was then incubated at 4° C. for 20 min to let depolymerize any residual microtubules, before being transferred into polycarbonate centrifuge bottles (16×76 mm; Beckman 355603) and centrifuged at 11,000 g (12,700 RPM) in an ultracentrifuge (Beckman, XL100K) for 20 min at 4° C. using the pre-cooled 70.1 rotor (Beckman, 342184). Pellets were kept on ice. Supernatants were pooled into polycarbonate bottles and centrifuged again at 100,000 g (38,000 RPM) for 1 hour at 4° C. in the 70.1 Ti rotor to isolate PHF-rich pellets, whereas soluble Tau remained in the supernatants. The pellets from the first and second centrifugations were resuspended in 120 mL of extraction buffer [10 mM Tris-HCl pH 7.4, 10% sucrose, 0.85 M NaCl, 1% protease inhibitor (Calbiochem 539131), 1 mM EGTA, 1% phosphatase inhibitor (Sigma P5726 and P0044)]. The solution was then transferred into polycarbonate centrifuge bottles (16×76 mm; Beckman 355603) and centrifuged at 15,000 g (14,800 RPM) in an ultracentrifuge (Beckman, XL100K) for 20 min at 4° C. using the 70.1 Ti rotor. In the presence of 10% sucrose and at low speed centrifugation, most PHF remained in the supernatant whereas intact or fragmented NFTs and larger PHF aggregates were pelleted. The pellets were discarded. 20% Sarkosyl (Sigma L7414-10ML) was added to the supernatants to a final concentration of 1% and stirred at room temperature for 1 h. This solution was then centrifuged in polycarbonate bottles at 100,000 g (38,000 RPM) for 1 h at 4° C. in the 70.1 Ti rotor, and the pellets containing PHF-rich material were resuspended in a total final volume of 1.5 mL of PBS, aliquoted and stored at −80° C.

To test the capability of compounds of this invention to inhibit Tau aggregation, serial dilution of compounds in DMSO were added to the monomeric flTau/PHF mix prior incubation. After incubation, 40 μl of the mixture was transferred into a black 384-well plate assay (Perkin-Elmer) and mixed with 10 μl of 100 μM ThT in 250 mM glycine (both from Sigma-Aldrich, Buchs, Switzerland) in PBS. Fluorescence was measured in monoplicate on a Tecan reader Spark using filter (excitation at 448 nm/BW 7 nm, emission at 485 nm/BW 20 nm). A dose response type of curve was obtained out to two independent experiments each with technical duplicates and the IC50 was calculated using GraphPad Prism 7.03.

IC50 values of the inhibition of flTau aggregation with Example 44 and Example 46 are indicated in the table below:

| Example | IC50 (uM) |
|---------|-----------|
| 44 | 0.39 |
| 46 | 1.2 |

The invention claimed is:

1. A compound of formula (I):

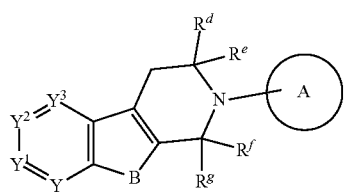

(I)

or stereoisomers, racemic mixtures, tautomers, pharmaceutically acceptable salts, thereof;
wherein
A is selected from the group consisting of

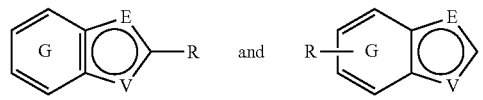

wherein

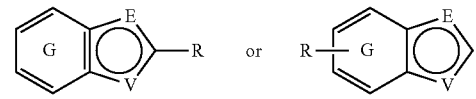

can be attached to the N atom at any available position;
B is $NR^a$;
E and V are independently selected from the group consisting of N, $NR^5$, O and S;
G is selected from the group consisting of a benzene ring and a pyridine ring;
Y, $Y^1$, $Y^2$ and $Y^3$ are CZ;
Z is independently selected from the group consisting of H, halogen, O-alkyl, alkyl and CN;
R is independently selected from the group consisting of

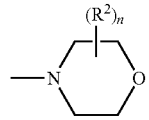

and —$NR^3R^4$;
$R^a$ is selected from the group consisting of H and alkyl;
$R^d$, $R^e$, $R^f$, and $R^g$ are H;
$R^2$ is independently selected from the group consisting of alkyl and —O-alkyl, wherein if two $R^2$ are geminal they can be joined to form a 3 to 6-membered ring;

$R^3$ and $R^4$ are independently selected from the group consisting of H and alkyl;
$R^5$ is selected from the group consisting of H and alkyl; and
n is 0, 1, 2, 3 or 4.

2. The compound according to claim 1, which is a compound of formula

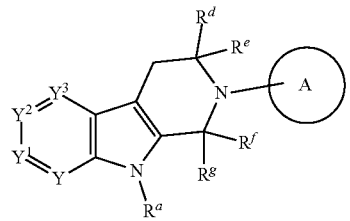

(Ia)

wherein A, $R^a$, $R^d$, $R^e$, $R^f$, $R^g$, Y, $Y^1$, $Y^2$ and $Y^3$ are as defined in claim 1.

3. A compound selected from the group consisting of:

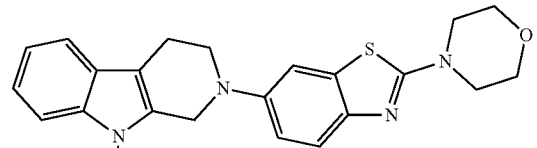

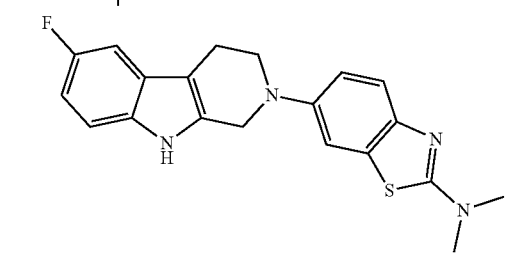

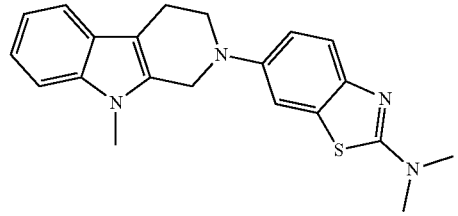

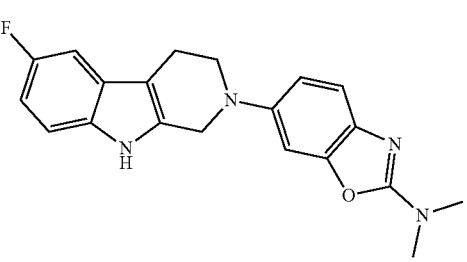

171
-continued
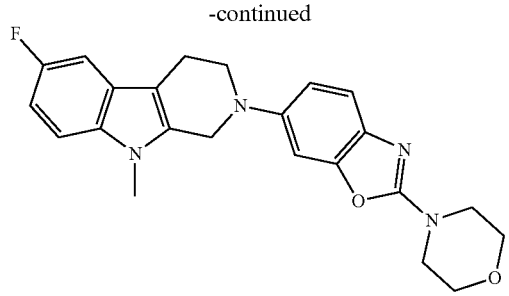
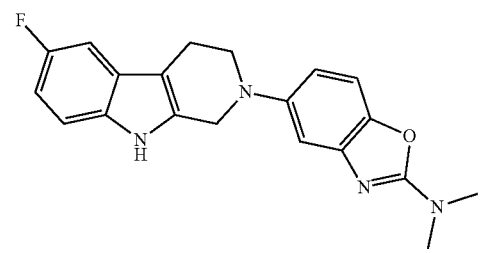
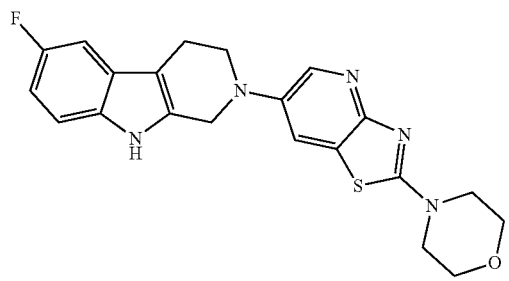
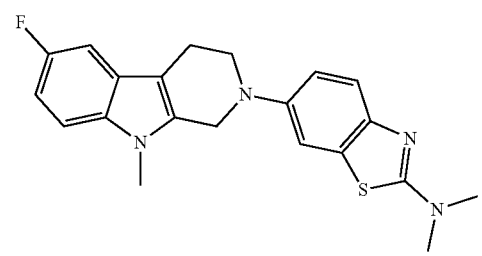
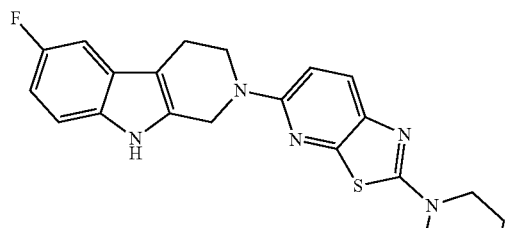
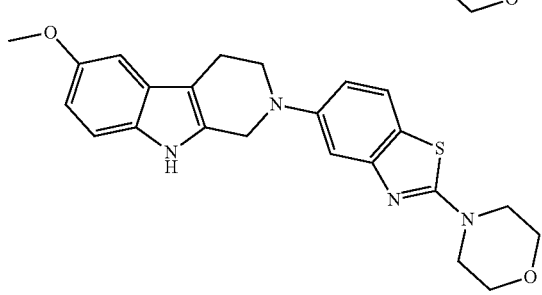
172
-continued
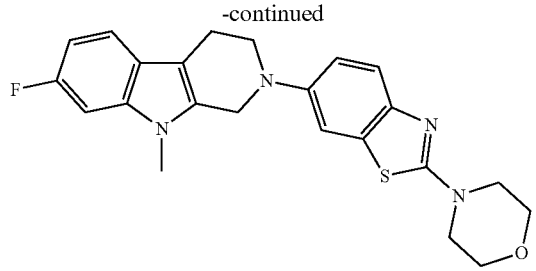
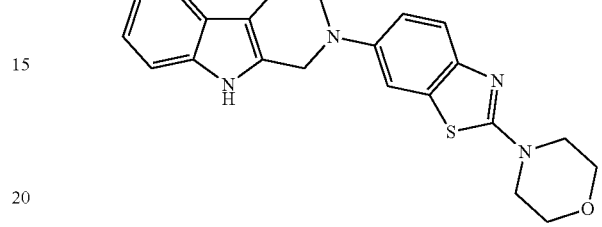
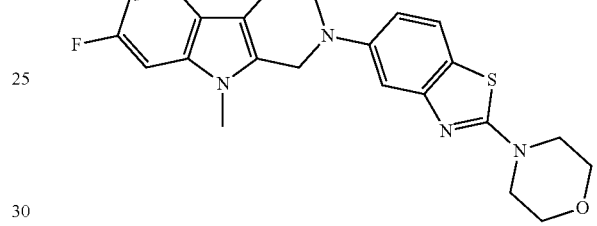
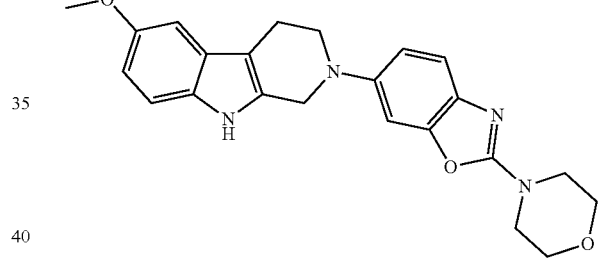
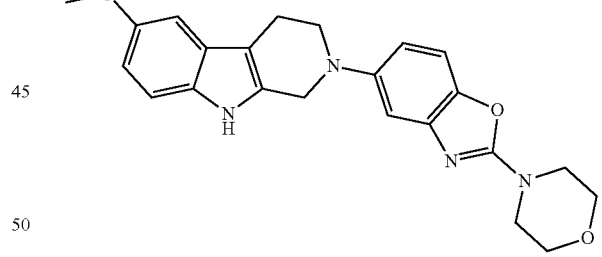
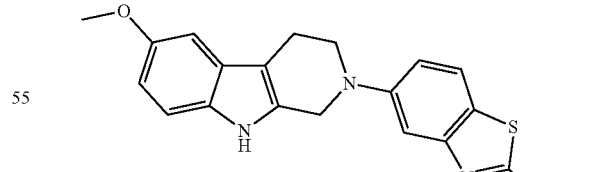
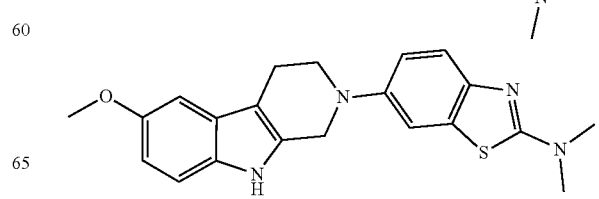

173
-continued
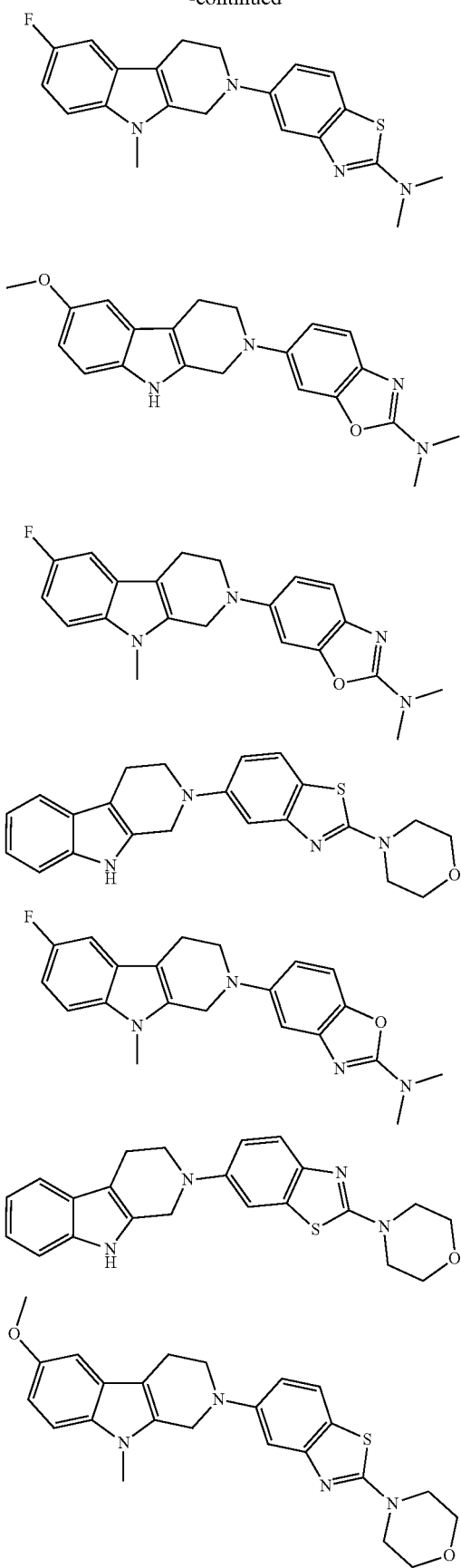
174
-continued
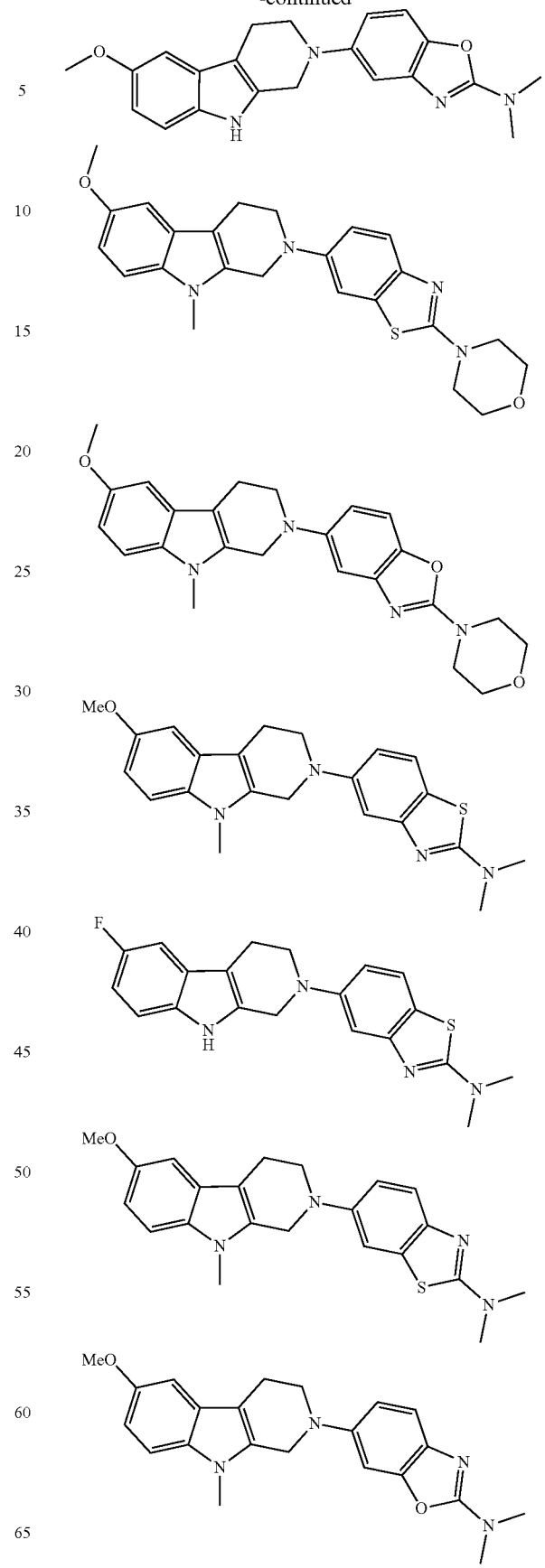

-continued

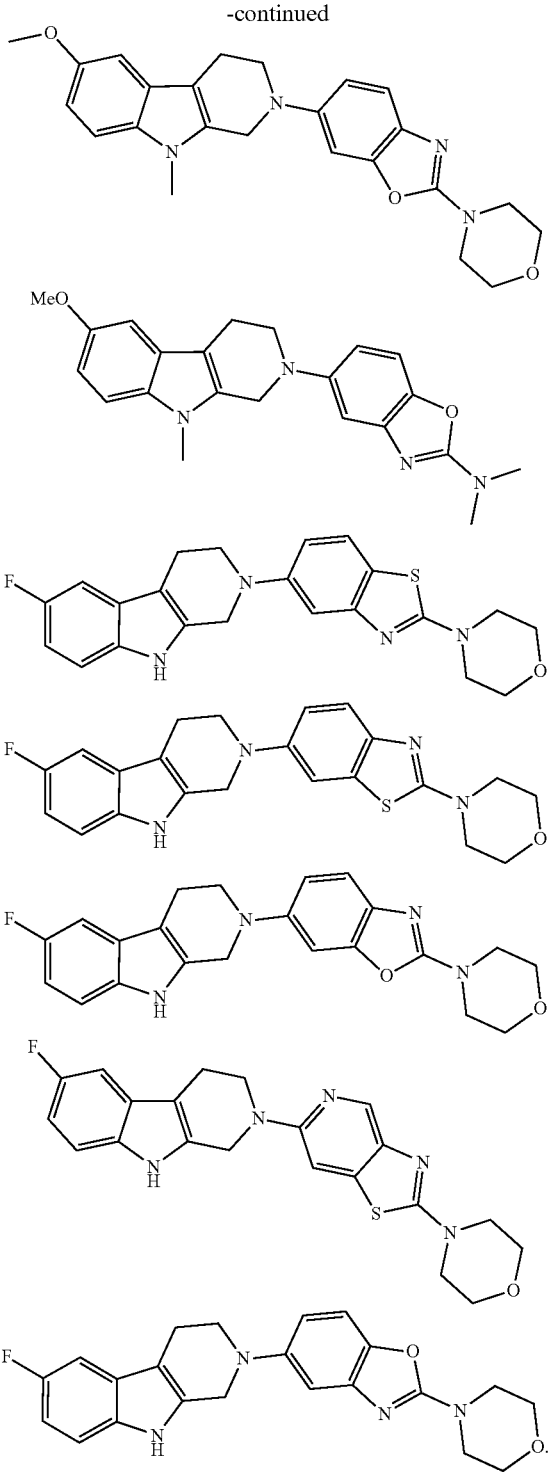

4. A pharmaceutical composition comprising a compound as defined in claim 1 and optionally a pharmaceutically acceptable carrier or excipient.

5. A method of decreasing Tau aggregation, the method comprising administering an effective amount of a compound as defined in claim 1 to a subject in need thereof.

6. A method of preventing the formation of Tau aggregates and/or of inhibiting Tau aggregation, the method comprising administering an effective amount of a compound as defined in claim 1 to a subject in need thereof.

7. A method of interfering intracellularly with Tau aggregates, the method comprising administering an effective amount of a compound as defined in claim 1 to a subject in need thereof.

8. A mixture comprising a compound as defined in claim 1 and at least one further biologically active compound selected from a therapeutic agent different from the compound as defined in claim 1, a pharmaceutically acceptable carrier, a diluent or an excipient.

9. The mixture according to claim 8, wherein the further biologically active compound is a compound used in the treatment of amyloidosis.

10. The mixture according to claim 8, wherein the further biologically active compound is selected from the group consisting of compounds against oxidative stress, anti-apoptotic compounds, metal chelators, inhibitors of DNA repair such as pirenzepine and metabolites, 3-amino-1-propanesulfonic acid (3APS), 1,3-propanedisulfonate (1,3PDS), α-secretase activators, β- and γ-secretase inhibitors, Tau proteins, neurotransmitter, β-sheet breakers, attractants for amyloid beta clearing/depleting cellular components, inhibitors of N-terminal truncated amyloid beta including pyroglutamated amyloid beta 3-42, anti-inflammatory molecules, or cholinesterase inhibitors (ChEIs) such as tacrine, rivastigmine, donepezil, and/or galantamine, M1 agonists, other drugs including any amyloid or Tau modifying drug and nutritive supplements, an antibody, including any functionally equivalent antibody or functional parts thereof or a vaccine.

11. The mixture according to claim 8, wherein the compound and/or the further biologically active compound is/are present in a therapeutically effective amount.

12. A compound of the formula:

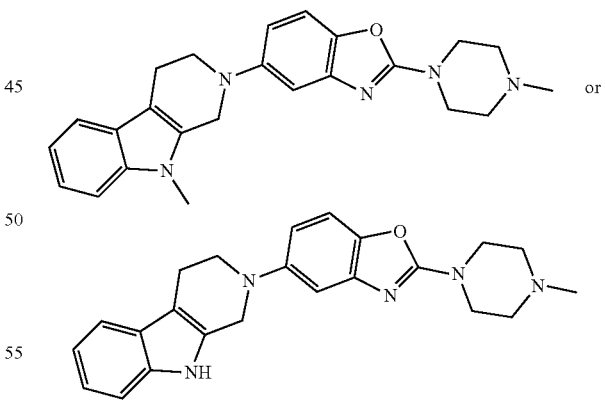

or a pharmaceutically acceptable salt thereof.

* * * * *